US011066413B2

(12) United States Patent
Wang et al.

(10) Patent No.: US 11,066,413 B2
(45) Date of Patent: Jul. 20, 2021

(54) AMINOPYRIMIDINE FIVE-MEMBERED HETEROCYCLIC COMPOUND, AND INTERMEDIATE, PREPARATION METHOD, PHARMACEUTICAL COMPOSITION AND APPLICATION THEREOF

(71) Applicant: GUANGZHOU MAXINOVEL PHARMACEUTICALS CO., LTD., Guangzhou (CN)

(72) Inventors: Yuguang Wang, Guangzhou (CN); Nong Zhang, Guangzhou (CN); Tianzhi Wu, Guangzhou (CN)

(73) Assignee: GUANGZHOU MAXINOVEL PHARMACEUTICALS CO., LTD., Guangdong (CN)

( * ) Notice: Subject to any disclaimer, the term of this patent is extended or adjusted under 35 U.S.C. 154(b) by 0 days.

(21) Appl. No.: 16/491,459

(22) PCT Filed: Mar. 7, 2018

(86) PCT No.: PCT/CN2018/078248
§ 371 (c)(1),
(2) Date: Sep. 5, 2019

(87) PCT Pub. No.: WO2018/161910
PCT Pub. Date: Sep. 13, 2018

(65) Prior Publication Data
US 2020/0048270 A1    Feb. 13, 2020

(30) Foreign Application Priority Data

Mar. 7, 2017 (CN) .......................... 201710132426.6

(51) Int. Cl.
C07D 491/044   (2006.01)
C07D 473/00    (2006.01)
C07D 487/04    (2006.01)
A61K 31/519    (2006.01)

(52) U.S. Cl.
CPC ....... *C07D 491/044* (2013.01); *C07D 473/00* (2013.01); *C07D 487/04* (2013.01)

(58) Field of Classification Search
CPC . C07D 491/044; C07D 473/00; C07D 487/04
See application file for complete search history.

(56) References Cited

U.S. PATENT DOCUMENTS

2011/0124634 A1   5/2011  Sun et al.
2013/0237537 A1   9/2013  Hull, III et al.

FOREIGN PATENT DOCUMENTS

| CN | 102098918 A | 6/2011 |
| CN | 105025899 A | 11/2015 |
| WO | 2004016605 A1 | 2/2004 |
| WO | 2009139834 A1 | 11/2009 |
| WO | 2015027431 A1 | 3/2015 |
| WO | 2016081290 A1 | 5/2016 |
| WO | 2016119707 A1 | 8/2016 |

OTHER PUBLICATIONS

STN Reg No. 1350040-46-8, entered into STN on Dec. 7, 2011 (Year: 2011).*
STN Reg No. 1782196-21-7, entered into STN on Jun. 17, 2015 (Year: 2015).*
STN Reg No. 1319021-98-2, entered into STN on Dec. 5, 2011 (Year: 2011).*
Su Y. et al., "Cooperation of adenosine and prostaglandin E2(PGE2) in amplification of cAMP-PKA signaling and immunosuppression", Cancer Immunol Immunother, 2008, vol. 57, No. 11, p. 1611-1623.
Chu Y.Y. et al., "Characterization of the rat A2a adenosine receptor gene", DNA and Cell Biology, 1996, vol. 15, No. 4, p. 329-337.
Desai A. et al., "Adenosine A2a receptor stimulation increases angiogenesis by down-regulating production of the antiangiogenic matrix protein thrombospondin 1", Mol. Pharmacol., 2005, vol. 67, No. 5, p. 1406-1413.
Lokshin A. et al., "Adenosine-mediated inhibition of the cytotoxic activity and cytokine production by activated natural killer cells", Cancer Res, 2006, vol. 66, No. 15, p. 7758-7765.
Hoskin D.W. et al., "Inhibition of T cell and natural killer cell function by adenosine and its contribution to immune evasion by tumor cells (Review)", Int.J.Oncol., 2008, vol. 32, No. 3, p. 527-535.
Deaglio S. et al., "Adenosine generation catalyzed by CD39 and CD73 expressed on regulatory T cells mediated immune suppression", J. Exp. Med., 2007, vol. 204, No. 6, p. 1257-1265.
International Search Report and Written Opinion of PCT/CN2018/078248 dated Jun. 8, 2018.

(Continued)

*Primary Examiner* — Karen Cheng
(74) *Attorney, Agent, or Firm* — Dilworth IP, LLC

(57) ABSTRACT

Disclosed in the present invention is an aminopyrimidine five-membered heterocyclic compound, and an intermediate, preparation method, pharmaceutical composition and application thereof. The aminopyrimidine five-membered heterocyclic compound provided by the present invention has a significant antagonistic effect on adenosine A2A receptors, and may be used as an antagonist for adenosine A2A receptors to effectively relieve or treat immune tolerance, diseases of the central nervous system, inflammatory diseases and like related diseases, while the preparation method is simple.

23 Claims, No Drawings

(56) References Cited

OTHER PUBLICATIONS

Gangjee et al., "Design, Synthesis, and X-ray Crystal Structure of a Potent Dual Inhibitor of Thymidylate Synthase and Dihydrofolate Reductase as an Antitumor Agent", J. Med. Chem. 2000, 43, 3837-3851.
Mizar et al., "Three-component synthesis of 5:6 and 6:6 fused pyrimidines using KF-alumina as a catalyst", Tetrahedron Letters 49 (2008) 5283-5285.
Extended European Search Report, European Application No. 18763276.5. dated Feb. 26, 2020, 10 pages.
Compound with RN of 1349021-98-2 in database Registry, publication date: Dec. 5, 2011.
The first Office Action of counterpart Chinese application 201810187065.X dated Mar. 3. 2021.

\* cited by examiner

AMINOPYRIMIDINE FIVE-MEMBERED HETEROCYCLIC COMPOUND, AND INTERMEDIATE, PREPARATION METHOD, PHARMACEUTICAL COMPOSITION AND APPLICATION THEREOF

The present disclosure claims the priority to Chinese Patent Application CN201710132426.6, filed on Mar. 7, 2017, the contents of which are incorporated herein by their entireties.

FIELD OF INVENTION

The present disclosure relates to an aminopyrimidine five-membered heterocyclic compound, an intermediate, a preparation method, a pharmaceutical composition and a use thereof.

PRIOR ARTS

Immune regulation is an important mean for the body to maintain a stable internal environment and resist external harmful stimuli. Adenosine, acting as an important transmitter and tempering of the body, may be increased significantly when metabolic block and cell damages appeared, and activates the adenosine receptors to exert biological effects, therefore participates in the immune regulation of the body. Recent studies have shown that activation of adenosine A2A receptors can play an important role in immunomodulation in many pathological processes such as ischemia, hypoxia, inflammation, trauma, transplantation, etc., this may be related to the high expression levels of A2A receptors in various immune cells such as T cells, B cells, mononuclear macrophage and neutrophil (Su Y., et al., *Cancer Immunol Immuno Ther.*, 2008, 57 (11), 1611-1623). The adenosine A2A receptor is one of the four known adenosine receptors (A1, A2A, A2B and A3), belonging to the G-protein coupled receptor family, and mostly coupled with the Gs and Gα protein. The adenosine A2A receptor is widely distributed in the body, mainly expressed in the corpus striatum of the central nervous system, and also expressed in the peripheral, heart, liver, lung, kidney and other tissues (Chu Y. Y., et al., *Biol*, 1996, 15 (4), 329-337).

In recent years, studies have found that adenosine A2A receptor antagonists play an increasingly important role in the immunotherapy of tumors. Under normal circumstances, the body can rely on the complete immune mechanism to effectively monitor and reject cancerous cells, for example: in cellular immunity, T lymphocytes, antibody-dependent cytotoxic cells (K cells), NK cells and macrophages all have killing effect to tumors. However, in the cases that the function of the cancerous cells themselves or the above-mentioned immune cells changes, they may escape from the elimination of the immune system, and malignant to form a tumor. The activation of adenosine A2A receptor can promote the body to produce immune tolerance, and closely participate in the formation of "immune escape" or "immunosuppression" of tumor cells, which creates favorable conditions for the occurrence and development of tumors. (Desai A., et al., *Mol. Pharmacol.*, 2005, 67 (5), 1406-1413; Lokshin A., et al., *Cancer Res*, 2006, 66 (15), 7758-7765; Hoskin D. W., et al., *Int. J. Oncol.*, 2008, 32 (3), 527-535; Deaglio S., et al., *J. Exp. Med.*, 2007, 204 (6), 1257-1265). The A2A receptor antagonist can inhibit the activation of adenosine A2A receptor, thereby avoiding the body producing immune tolerance, and ultimately affecting the growth of tumor cells, having the effect of anti-tumor.

Although adenosine A2A receptor antagonists have very good prospects, and have been researched and developed by many pharmaceutical companies and research institutes in the past two decades, but so far, no drug has been approved for marketing as various technical reasons.

Content of the Present Invention

The technical problem to be solved by the present disclosure is to fill the gap in current market for the adenosine A2A receptor antagonist drug, thereby providing an aminopyrimidine five-membered heterocyclic compound, an intermediate thereof, a preparation method, a pharmaceutical composition and a use thereof. The aminopyrimidine five-membered heterocyclic compound provided by the present disclosure has obvious antagonistic effect on adenosine A2A receptor, and can serve as an adenosine A2A receptor antagonist to effectively mitigate or treat immune tolerance, central nervous system diseases, inflammatory diseases and other related diseases; meanwhile the preparation method therefor is simple.

The present disclosure provides an aminopyrimidine five-membered heterocyclic compound represented by formula I-1, a pharmaceutically acceptable salt, a tautomer, an enantiomer or a diastereomer or a prodrug thereof:

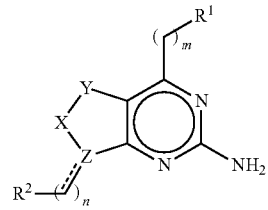

I-1 wherein, "=====" represents for a single bond or a double bond;

when "=====" is a single bond, Z is N or CR$^5$; R$^5$ is H, D or C$_1$-C$_{20}$ alkyl;

when "=====" is double bond, Z is C;

X is O, CO or NR$^3$;

Y is CO, CH$_2$ and NR$^4$;

each of R$^1$ and R$^2$ is independently substituted or unsubstituted C$_1$-C$_{20}$ alkyl, substituted or unsubstituted C$_6$-C$_{30}$ aryl or substituted or unsubstituted C$_2$-C$_{30}$ heteroaryl;

the C$_2$-C$_{30}$ heteroaryl in the substituted or unsubstituted C$_2$-C$_{30}$ heteroaryl refers to C$_2$-C$_{30}$ heteroaryl comprising 1-4 heteroatoms which is selected from the group consisting of N, O and S;

the substituent in the substituted C$_1$-C$_{20}$ alkyl, the substituted C$_6$-C$_{30}$ aryl or the substituted C$_2$-C$_{30}$ heteroaryl is selected from one or more (e.g., two) of the group consisting of halogen, C$_1$-C$_{20}$ alkyl, halogenated C$_1$-C$_{20}$ alkyl, oxo, hydroxyl, amino, amindo

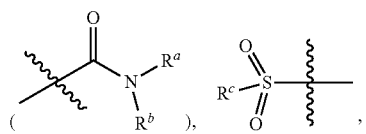

cyano, C$_1$-C$_{20}$ alkoxyl, halogenated C$_1$-C$_{20}$ alkoxyl and C$_1$-C$_{20}$ alkylthio; when the number of the substituent is more than one, the substituent may be the same or different;

wherein, each of $R^a$ and $R^b$ is independently H or $C_1$-$C_{20}$ alkyl; $R^c$ is $C_1$-$C_{20}$ alkyl (e.g., methyl);

$R^3$ is H, $C_1$-$C_{20}$ alkyl or $C_3$-$C_{30}$ cycloalkyl;

$R^4$ is H, $C_1$-$C_{20}$ alkyl or $C_3$-$C_{30}$ cycloalkyl;

m is 0, 1, 2 or 3;

n is 0, 1, 2 or 3.

In the present disclosure, in the aminopyrimidine five-membered heterocyclic compound represented by formula I-1, in $R^1$ and $R^2$, the $C_1$-$C_{20}$ alkyl in the substituted or unsubstituted $C_1$-$C_{20}$ alkyl, the $C_1$-$C_{20}$ alkyl and the halogenated $C_1$-$C_{20}$ alkyl, and the $C_1$-$C_{20}$ alkyl in $R^3$, $R^4$ and $R^5$ can be $C_1$-$C_{10}$ alkyl (e.g., $C_1$-$C_4$ alkyl, also e.g., methyl, ethyl, n-propyl, iso-propyl, n-butyl, iso-butyl or tert-butyl).

In the present disclosure, in the aminopyrimidine five-membered heterocyclic compound represented by formula I-1, the substituted or unsubstituted $C_6$-$C_{30}$ aryl can be substituted or unsubstituted $C_6$-$C_{20}$ aryl (e.g., substituted or unsubstituted phenyl, substituted or unsubstituted naphthyl, substituted or unsubstituted anthryl, or substituted or unsubstituted phenanthryl).

In the present disclosure, in the aminopyrimidine five-membered heterocyclic compound represented by formula I-1, the substituted or unsubstituted $C_2$-$C_{30}$ heteroaryl can be substituted or unsubstituted 5-membered heteroaryl or 6-membered heteroaryl, preferably substituted or unsubstituted 5-membered heteroaryl, e.g., substituted or unsubstituted furyl, substituted or unsubstituted thienyl, substituted or unsubstituted pyridinyl, or substituted or unsubstituted pyranyl.

In the present disclosure, in the aminopyrimidine five-membered heterocyclic compound represented by formula I-1, the substituted or unsubstituted $C_2$-$C_{30}$ heteroaryl can be substituted or unsubstituted $C_2$-$C_{30}$ heteroaryl comprising 1-4 heteroatoms which is selected from the group consisting of N, O and S (e.g., the heteroatom is O, the number of the heteroatom is 1).

In the present disclosure, the substituted or unsubstituted $C_2$-$C_{20}$ heteroaryl may be substituted or unsubstituted $C_2$-$C_{10}$ heteroaryl (e.g., substituted or unsubstituted $C_2$-$C_5$ heteroaryl, or substituted or unsubstituted $C_4$-$C_5$ heteroaryl (e.g., substituted or unsubstituted furyl, thienyl, pyridinyl or pyranyl)).

In the present disclosure, in the aminopyrimidine five-membered heterocyclic compound represented by formula I-1, the $C_1$-$C_{20}$ alkoxyl in $C_1$-$C_{20}$ alkoxyl or the halogenated $C_1$-$C_{20}$ alkoxyl may be $C_1$-$C_{10}$ alkoxyl (e.g., $C_1$-$C_4$ alkoxyl, also e.g., methoxyl, ethoxy, n-propoxy, iso-propoxy, n-butoxy, iso-butoxy or tert-butoxy).

In the present disclosure, in the aminopyrimidine five-membered heterocyclic compound represented by formula I-1, the $C_1$-$C_{20}$ alkylthio may be $C_1$-$C_{10}$ alkylthio (e.g., $C_1$-$C_4$ alkylthio, also e.g., methylthio, ethylthio, n-propylthio, iso-propylthio, n-butylthio, iso-butylthio or tert-butylthio).

In the present disclosure, in the aminopyrimidine five-membered heterocyclic compound represented by formula I-1, the halogen may be F, Cl, Br or I, preferably F.

In the present disclosure, in the aminopyrimidine five-membered heterocyclic compound represented by formula I-1, the $C_3$-$C_{30}$ cycloalkyl may be $C_3$-$C_{10}$ cycloalkyl (e.g. $C_3$-$C_6$ cycloalkyl, also e.g., cyclopropyl, cyclobutyl, cyclopentyl or cyclohexyl).

In the present disclosure, the number of the halogen in the halogenated $C_1$-$C_{20}$ alkyl may be one or more (e.g., 2 or 3).

The halogenated $C_1$-$C_{20}$ alkyl is preferably

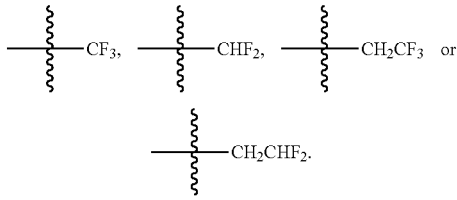

In the present disclosure, the number of the halogen in the halogenated $C_1$-$C_{20}$ alkoxyl may be one or more (e.g., 2 or 3).

The halogenated $C_1$-$C_{20}$ alkoxyl is preferably

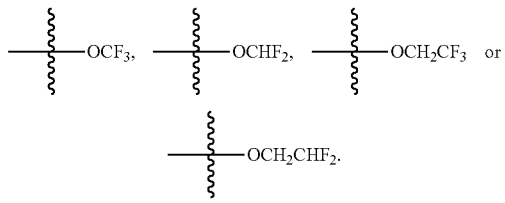

Preferably, when Z is $CR^5$, $R^5$ is H or D.

Preferably, the substituent in the substituted $C_1$-$C_{20}$ alkyl, the substituted $C_6$-$C_{30}$ aryl or the substituted $C_2$-$C_{30}$ heteroaryl is selected from one or more of the group consisting of halogen, $C_1$-$C_{20}$ alkyl, halogenated $C_1$-$C_{20}$ alkyl, amino, amido

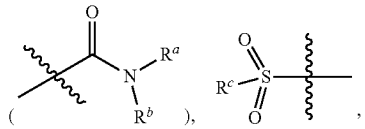

cyano, $C_1$-$C_{20}$ alkoxyl, halogenated $C_1$-$C_{20}$ alkoxyl and $C_1$-$C_{20}$ alkylthio.

Preferably, $R^1$ is

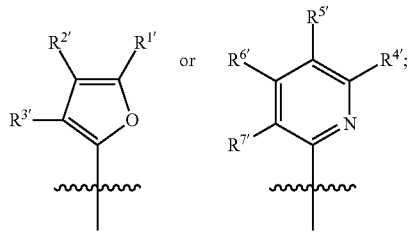

wherein, $R^{1'}$, $R^{2'}$, $R^{3'}$, $R^{4'}$, $R^{5'}$, $R^{6'}$ and $R^{7'}$ are the same or different, and each of which is independently H, D, halogen or $C_1$-$C_{20}$ alkyl; the halogen and $C_1$-$C_{20}$ alkyl are as defined above; e.g., $R^1$ is

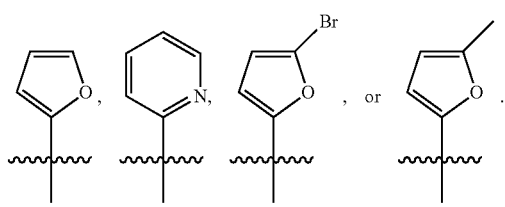

Preferably, $R^2$ is

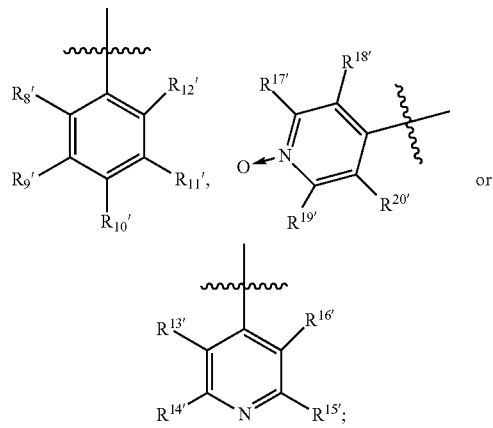

wherein, $R^{8'}$, $R^{9'}$, $R^{10'}$, $R^{11'}$, $R^{12'}$, $R^{13'}$, $R^{14'}$, $R^{15'}$, $R^{16'}$, $R^{17'}$, $R^{18'}$, $R^{19'}$ and $R^{20'}$ are the same or different, and each of which is independently H, D, halogen, cyano, amido

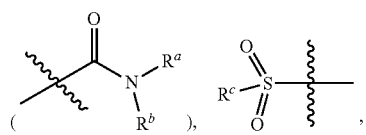

$C_1$-$C_{20}$ alkyl, halogenated $C_1$-$C_{20}$ alkyl, $C_1$-$C_{20}$ alkoxyl or halogenated $C_1$-$C_{20}$ alkoxyl; the $C_1$-$C_{20}$ alkyl, the halogenated $C_1$-$C_{20}$ alkyl, the $C_1$-$C_{20}$ alkoxyl or the halogenated $C_1$-$C_{20}$ alkoxyl is as defined above; e.g., $R^2$ is

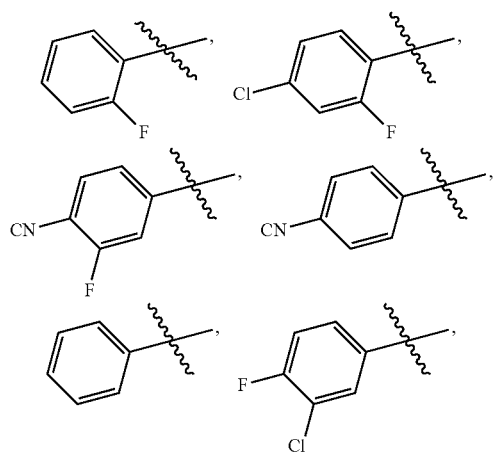

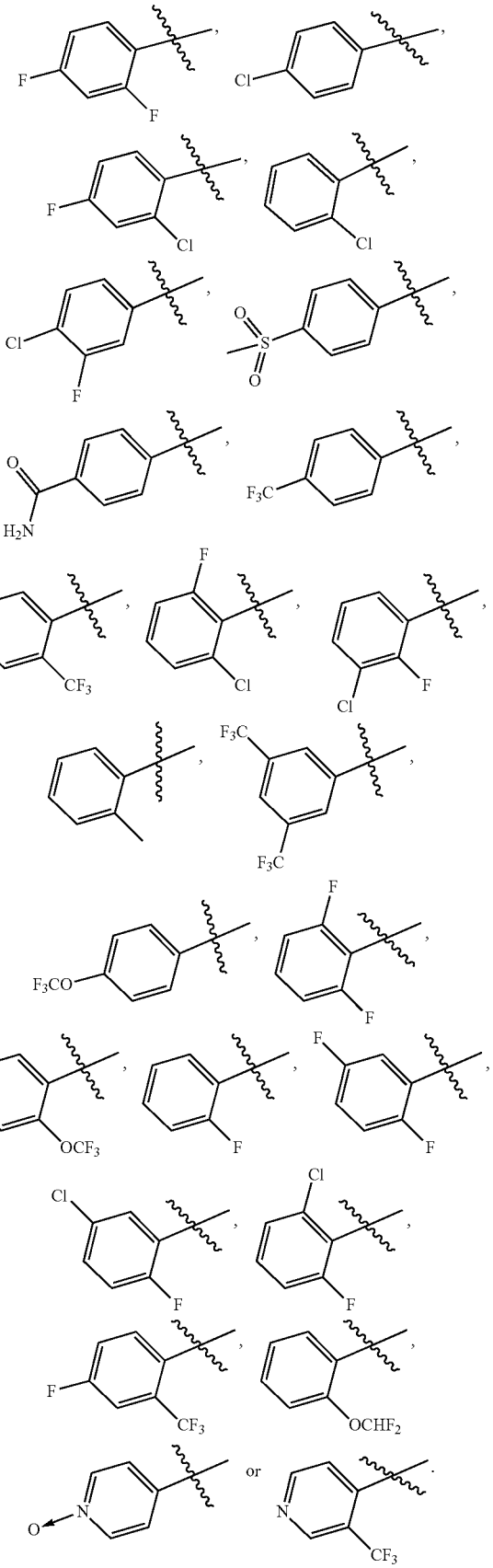

Preferably, m is 0 or 1.
Preferably, n is 0 or 1.
Preferably, when X is NR$^3$, R$^3$ is H or C$_1$-C$_{20}$ alkyl; e.g., R$^3$ is methyl.
Preferably, when Y is NR$^4$, R$^4$ is H or C$_1$-C$_{20}$ alkyl; e.g., R$^4$ is methyl.
Preferably, the

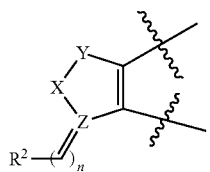

in the formula I-1 is

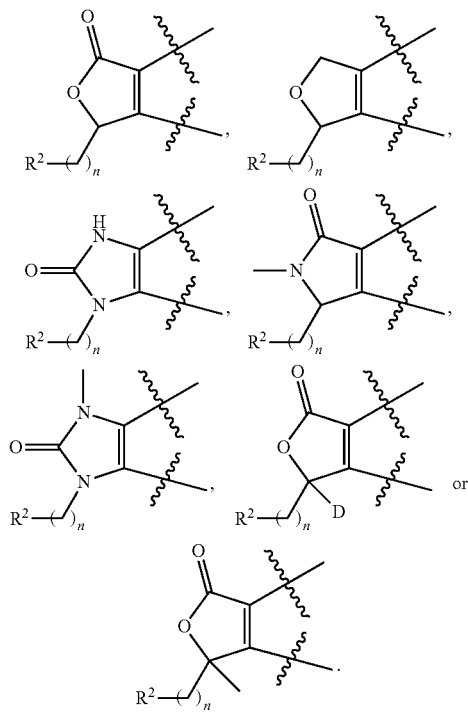

In a preferred embodiment of the present disclosure, in the aminopyrimidine five-membered heterocyclic compound represented by formula I-1:
"═" represents for a single bond or a double bond;
when "═" is a single bond, Z is N or CR$^5$; R$^5$ is H, D or C$_1$-C$_{20}$ alkyl;
when "═" is double bond, Z is C;
X is O, CO or NR$^3$; R$^3$ is H or C$_1$-C$_{20}$ alkyl;
Y is CO, CH$_2$ and NR$^4$; R$^4$ is H or C$_1$-C$_{20}$ alkyl;
each of R$^1$ and R$^2$ is independently substituted or unsubstituted C$_6$-C$_{30}$ aryl or substituted or unsubstituted C$_2$-C$_{30}$ heteroaryl;
m is 0, 1, 2 or 3;
n is 0, 1, 2 or 3;
the substituents in the substituted C$_6$-C$_{30}$ aryl and the substituted C$_2$-C$_{30}$ heteroaryl are as defined above.
In another preferred embodiment of the present disclosure, in the aminopyrimidine five-membered heterocyclic compound represented by formula I-1,
"═" represents for a single bond or a double bond;
when "═" is a single bond, Z is N or CR$^5$; R$^5$ is H, D or C$_1$-C$_{20}$ alkyl;
when "═" is double bond, Z is C;
X is O, CO or NR$^3$; R$^3$ is C$_1$-C$_{20}$ alkyl;
Y is CO, CH$_2$ and NR$^4$; R$^4$ is H or C$_1$-C$_{20}$ alkyl;
each of R$^1$ and R$^2$ is independently substituted or unsubstituted C$_6$-C$_{20}$ aryl (e.g., substituted or unsubstituted phenyl, substituted or unsubstituted naphthyl, substituted or unsubstituted anthryl, or substituted or unsubstituted phenanthryl) or substituted or unsubstituted C$_2$-C$_{20}$ heteroaryl comprising 1-4 heteroatoms which is selected from the group consisting of N, O and S (e.g., the heteroatom is O, the number of the heteroatom is 1);
m is 0, 1, 2 or 3;
n is 0, 1, 2 or 3;
the substituents in the substituted C$_6$-C$_{20}$ aryl and the substituted C$_2$-C$_{20}$ heteroaryl are as defined above.
In a further preferred embodiment of the present disclosure, in the aminopyrimidine five-membered heterocyclic compound represented by formula I-1,
"═" represents fo a single bond or a double bond;
when "═" is a single bond, Z is N or CR$^5$; R$^5$ is H, D or C$_1$-C$_{20}$ alkyl;
when "═" is double bond, Z is C;
X is O, CO or NR$^3$; R$^3$ is C$_1$-C$_{20}$ alkyl;
Y is CO, CH$_2$ and NR$^4$; R$^4$ is H or C$_1$-C$_{20}$ alkyl;
R$^2$ is substituted or unsubstituted C$_6$-C$_{20}$ aryl (e.g., substituted or unsubstituted phenyl, substituted or unsubstituted naphthyl, substituted or unsubstituted anthryl, or substituted or unsubstituted phenanthryl) or substituted or unsubstituted C$_2$-C$_{20}$ heteroaryl comprising 1-4 heteroatoms which is selected from the group consisting of N, O and S (e.g., the heteroatom is O, the number of the heteroatom is 1);
R$^1$ is substituted or unsubstituted C$_2$-C$_{20}$ heteroaryl comprising 1-4 heteroatoms which is selected from the group consisting of N, O and S (e.g., the heteroatom is O, the number of the heteroatom is 1);
m is 0, 1, 2 or 3;
n is 0, 1, 2 or 3;
the substituents in the substituted C$_6$-C$_{20}$ aryl and the substituted C$_2$-C$_{20}$ heteroaryl are as defined above.
In a further preferred embodiment of the present disclosure, in the aminopyrimidine five-membered heterocyclic compound represented by formula I-1,
"═" represents for a single bond or a double bond;
when "═" is a single bond, Z is N or CR$^5$; R$^5$ is H or D;
when "═" is double bond, Z is C;
X is O, CO or NR$^3$; R$^3$ is C$_1$-C$_{20}$ alkyl;
Y is CO, CH$_2$ and NR$^4$; R$^4$ is H or C$_1$-C$_{20}$ alkyl;
R$^2$ is substituted or unsubstituted C$_6$-C$_{20}$ aryl (e.g., substituted or unsubstituted phenyl, substituted or unsubstituted naphthyl, substituted or unsubstituted anthryl, or substituted or unsubstituted phenanthryl), or, substituted or unsubstituted furyl, thienyl, pyridinyl or pyranyl, e.g., substituted or unsubstituted pyridinyl;
R$^1$ is substituted or unsubstituted furyl, substituted or unsubstituted thienyl, substituted or unsubstituted pyridinyl or, substituted or unsubstituted pyranyl, e.g., substituted or unsubstituted furyl;
m is 0 or 1;
n is 0 or 1;
the substituents in the substituted C$_6$-C$_{20}$ aryl, the substituted furyl, the substituted thienyl, the substituted pyridinyl and the substituted pyranyl are as defined above.

In a further preferred embodiment of the present disclosure, in the aminopyrimidine five-membered heterocyclic compound represented by formula I-1, " " represents for a single bond or a double bond;

when " " is a single bond, Z is N or CR$^5$; R$^5$ is H or D;

when " " is double bond, Z is C;

X is O, CO or NR$^3$; R$^3$ is C$_1$-C$_{20}$ alkyl;

Y is CO, CH$_2$ and NR$^4$; R$^4$ is H or C$_1$-C$_{20}$ alkyl;

R$^1$ is

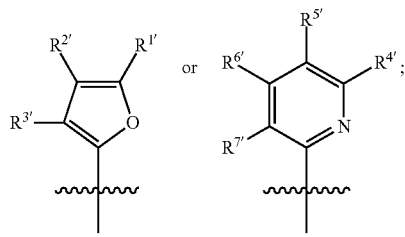

R$^2$ is

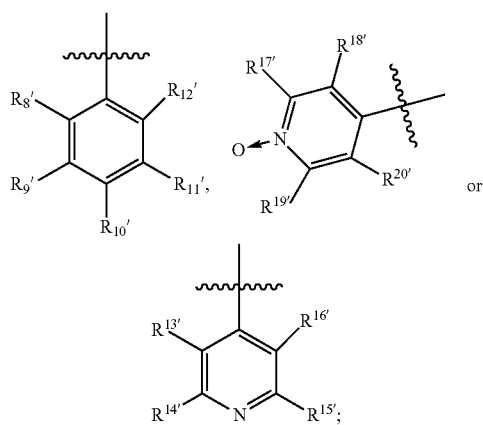

m is 0 or 1;
n is 0 or 1;
all of the substituents are as defined above.

In a further preferred embodiment of the present disclosure, in the aminopyrimidine five-membered heterocyclic compound represented by formula I-1, " " represents for a single bond or a double bond;

when " " is a single bond, Z is N or CR$^5$; R$^5$ is H or D;

when " " is double bond, Z is C;

X is O, CO or NR$^3$; R$^3$ is C$_1$-C$_{20}$ alkyl;

Y is CO, CH$_2$ and NR$^4$; R$^4$ is H or C$_1$-C$_{20}$ alkyl;

R$^1$ is

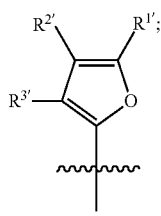

R$^2$ is

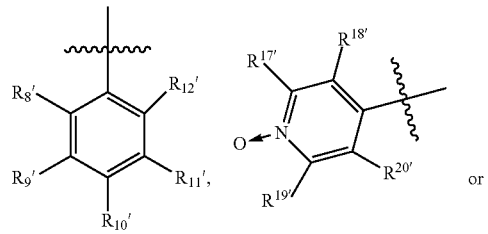

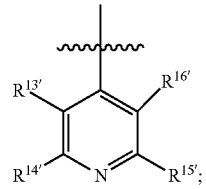

m is 0 or 1;
n is 0 or 1;
all of the substituents are as defined above.

In a further preferred embodiment of the present disclosure, in the aminopyrimidine five-membered heterocyclic compound represented by formula I-1, " " represents for a single bond or a double bond;

when " " is a single bond, Z is N or CR$^5$; R$^5$ is H or D;

when " " is a double bond, Z is C;

X is O, CO or NR$^3$; R$^3$ is C$_1$-C$_{20}$ alkyl;

Y is CO, CH$_2$ and NR$^4$; R$^4$ is H or C$_1$-C$_{20}$ alkyl;

R$^1$ is

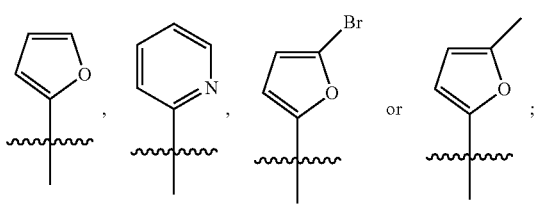

R$^2$ is

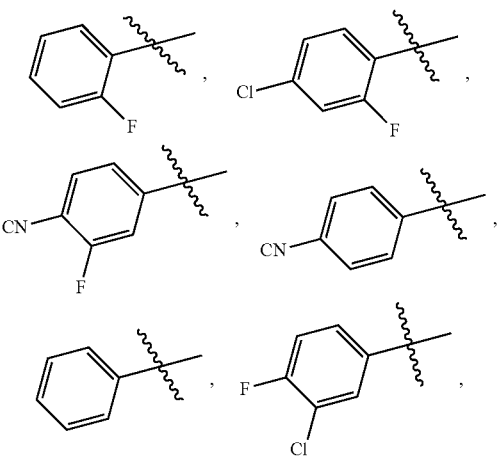

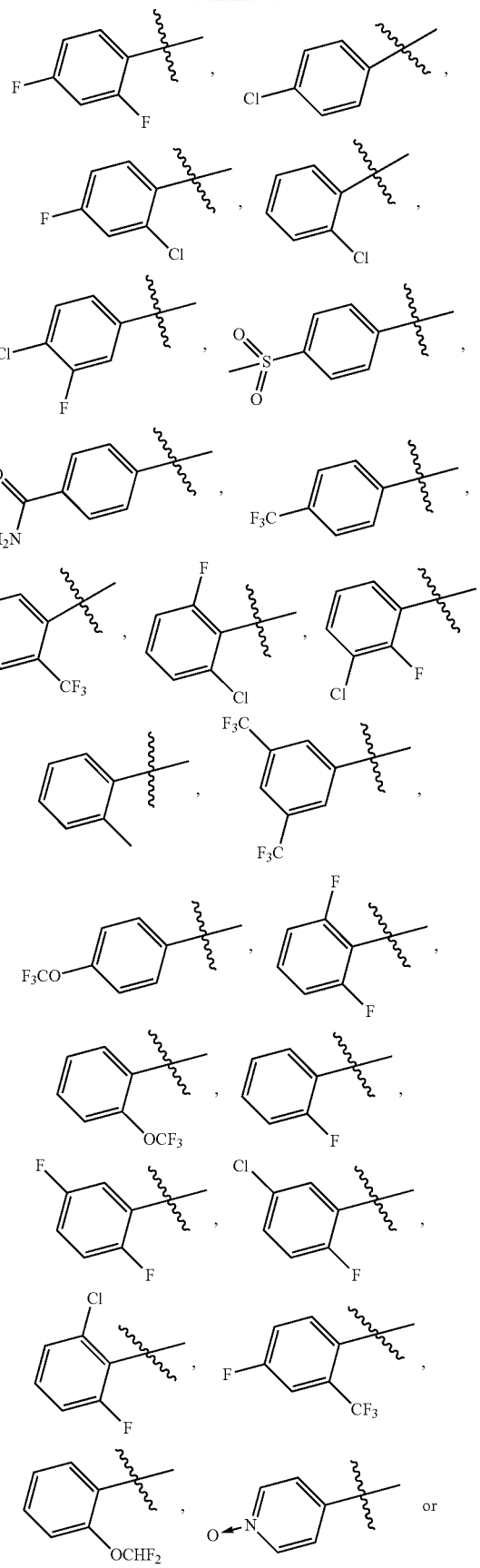

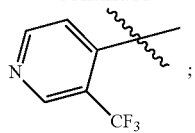

m is 0 or 1;
n is 0 or 1;
all of the substituents are as defined above.

In a further preferred embodiment of the present disclosure, in the aminopyrimidine five-membered heterocyclic compound represented by formula I-1, "====" represents for a single bond or a double bond;

when "====" is a single bond, Z is N or CR⁵; R⁵ is H or D;

when "====" is a double bond, Z is C;

X is O, CO or NR³; R³ is $C_1$-$C_{20}$ alkyl;

Y is CO, CH₂ and NR⁴; R⁴ is H or $C_1$-$C_{20}$ alkyl;

R¹ is

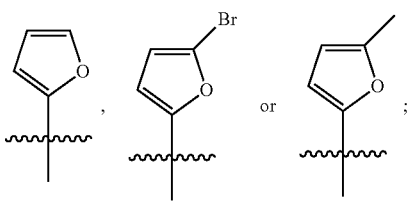

R² is

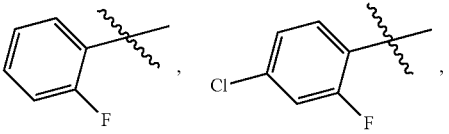

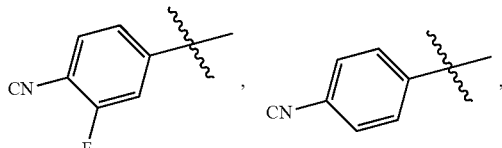

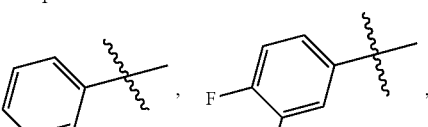

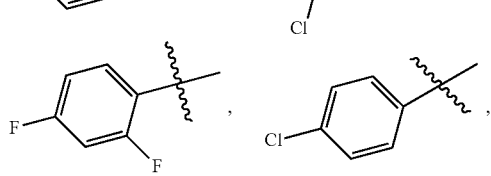

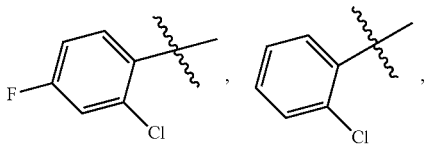

-continued
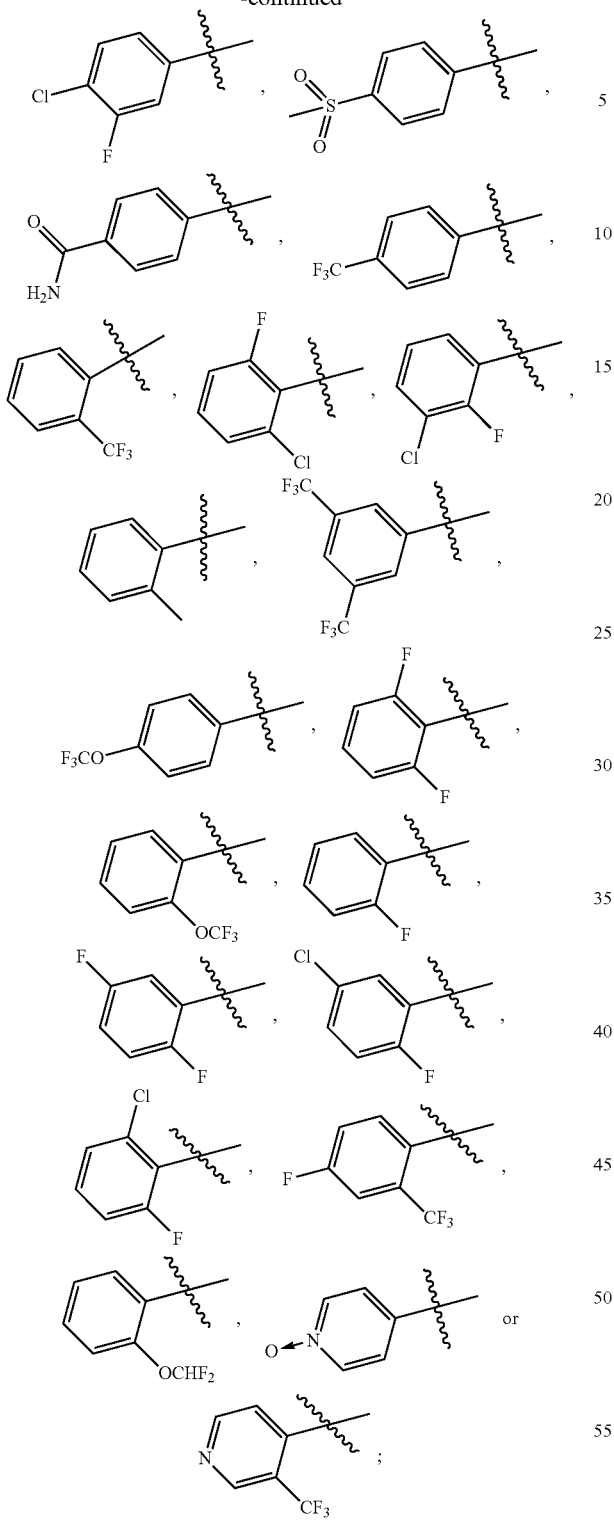
m is 0 or 1;
n is 0 or 1;
all of the substituents are as defined above.
More preferably, the aminopyrimidine five-membered heterocyclic compound represented by formula I-1 can be any one of the following compound:
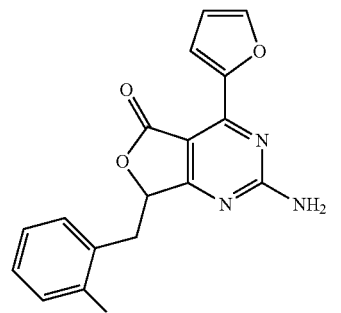
1
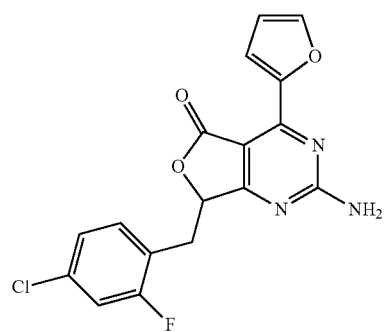
2
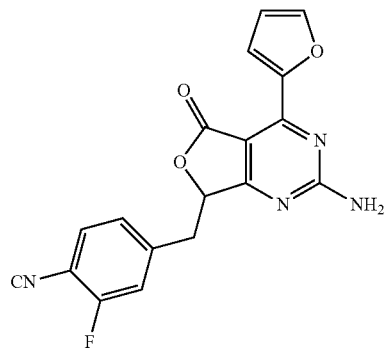
3
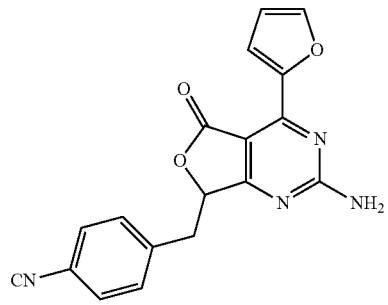
4
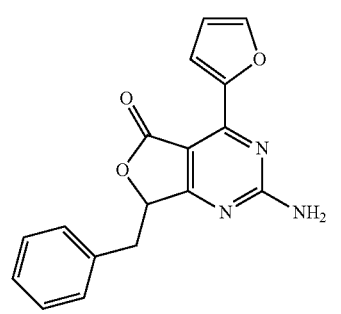
5

-continued
6
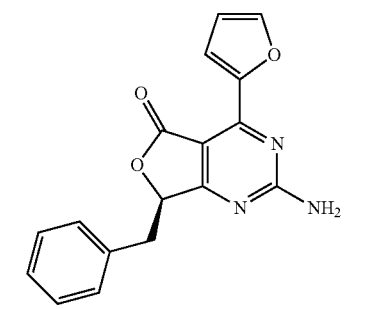
7
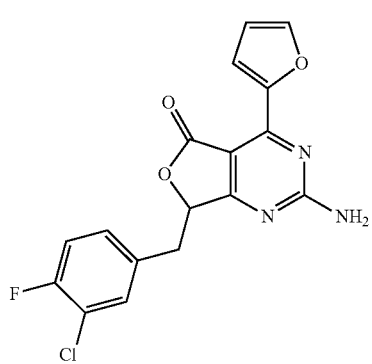
8
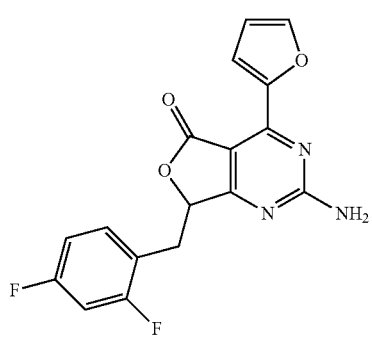
9
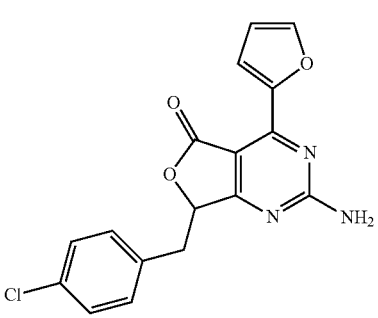
10
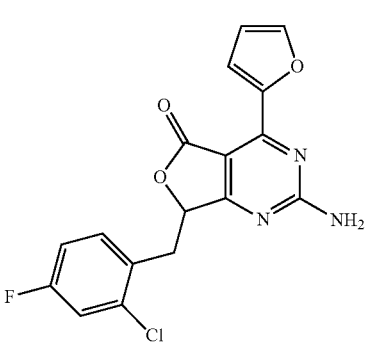
-continued
11
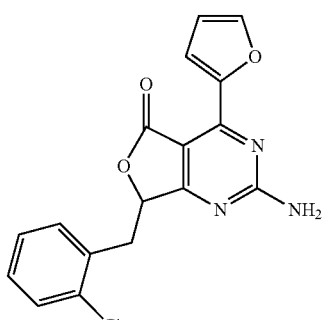
12
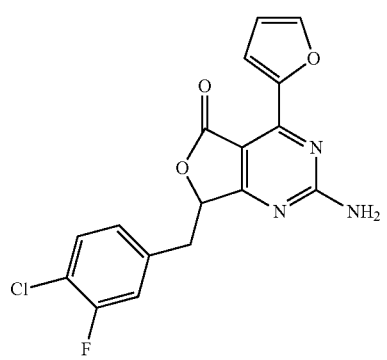
13
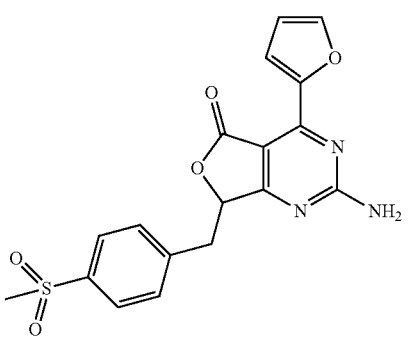
14
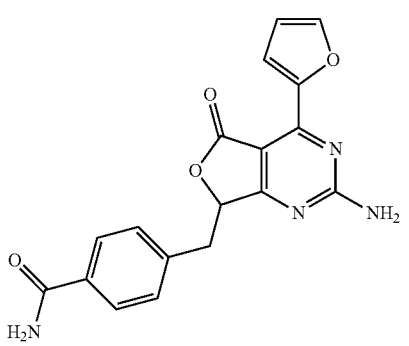

-continued
15
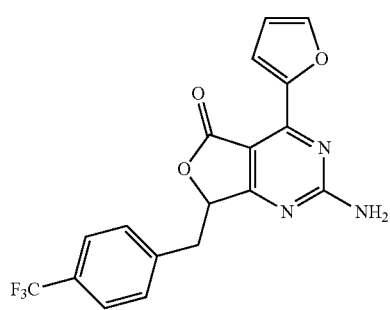
16
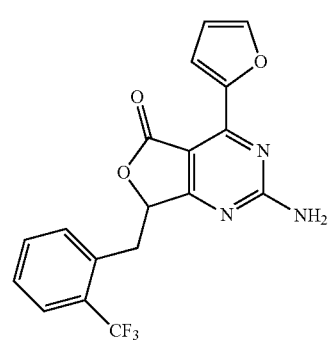
17
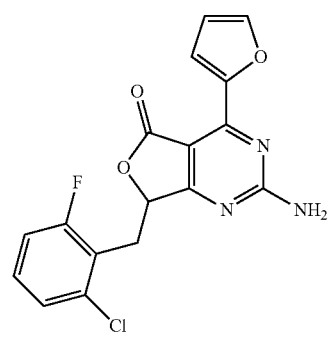
18
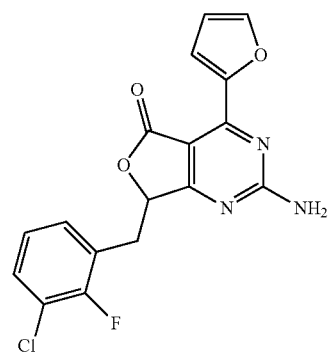
19
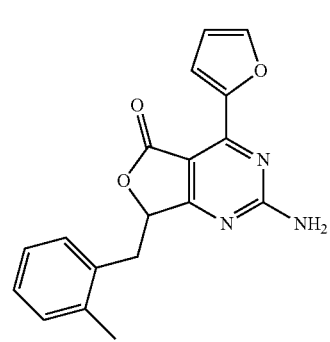
-continued
20
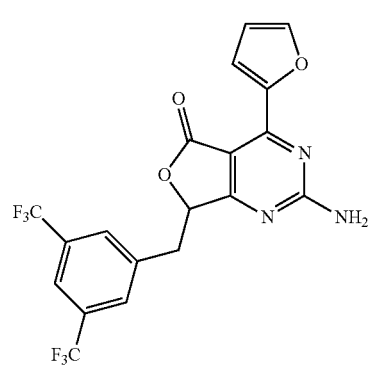
21
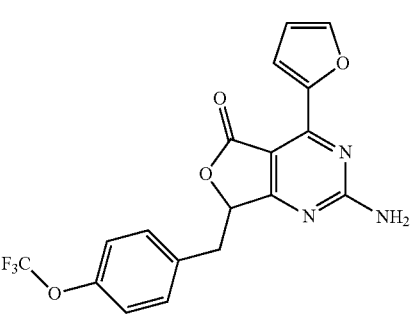
22
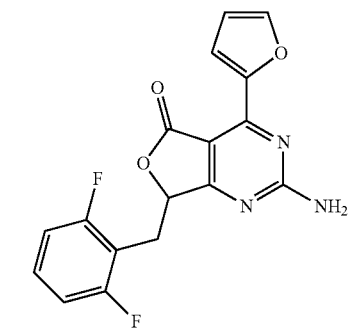
23
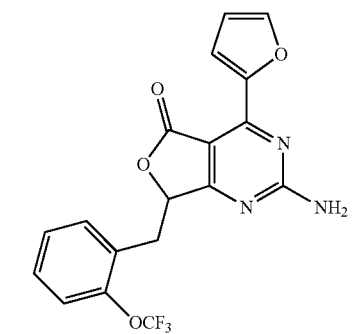

24
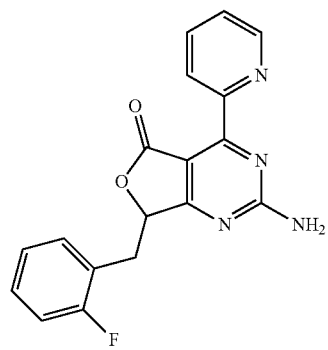
25
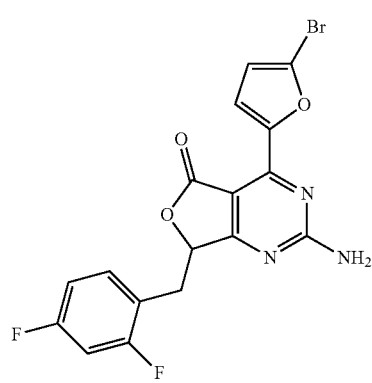
26
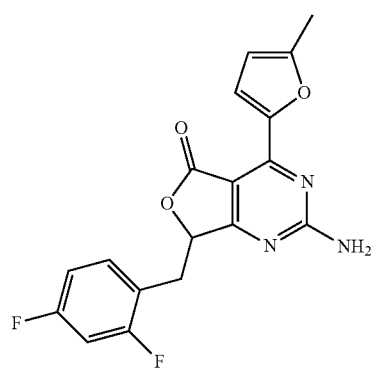
27
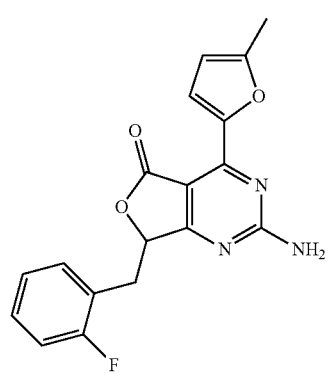
28
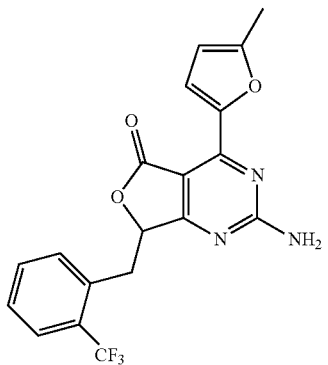
29
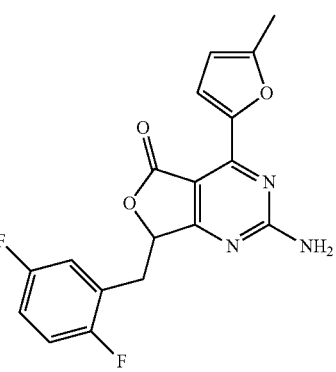
30
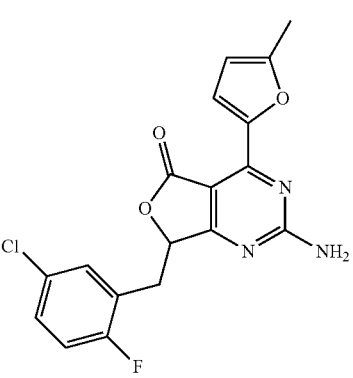
31
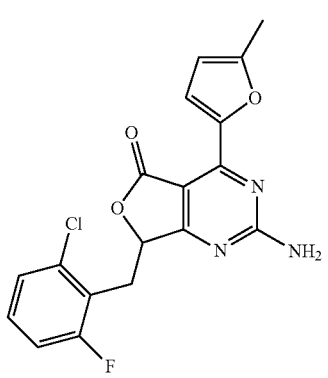

-continued
32
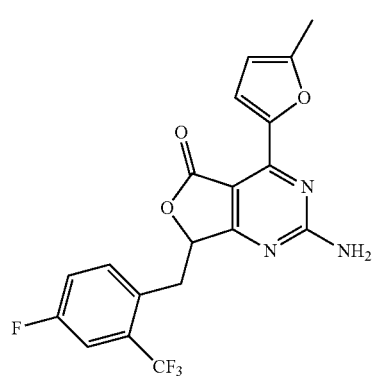
33
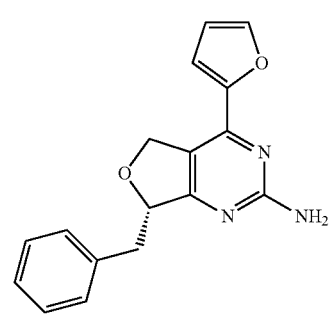
34
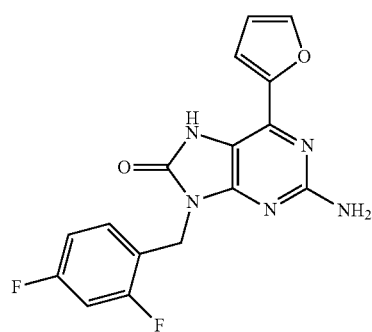
35
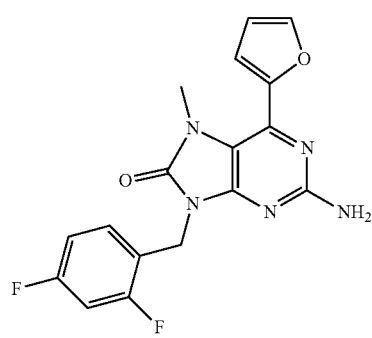
36
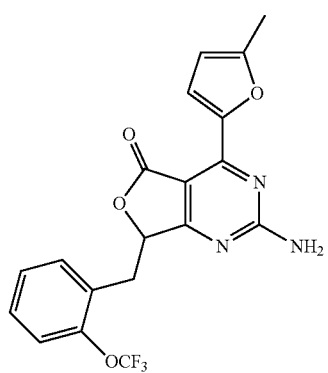
37
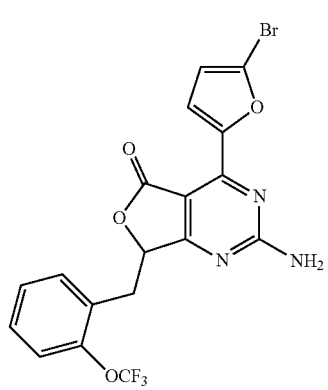
38
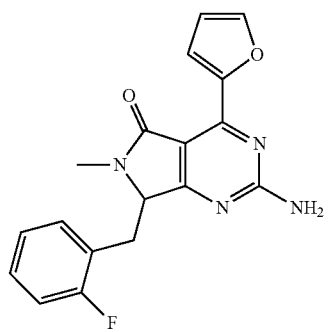
39
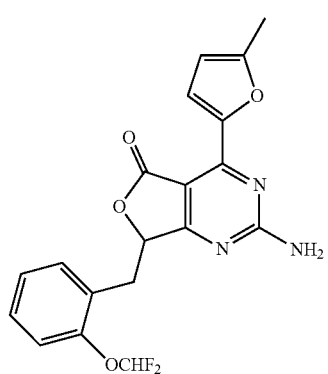

40
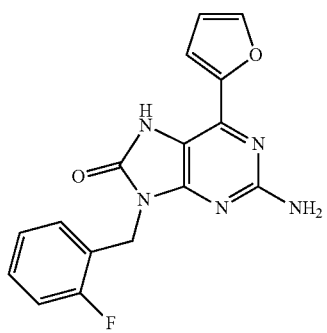
41
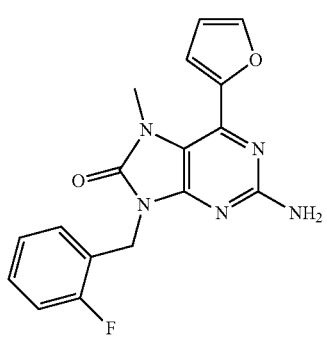
42
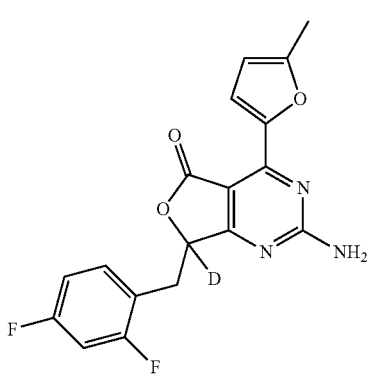
43
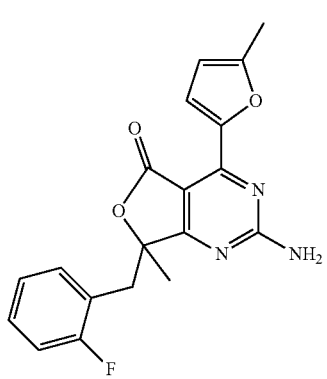
44
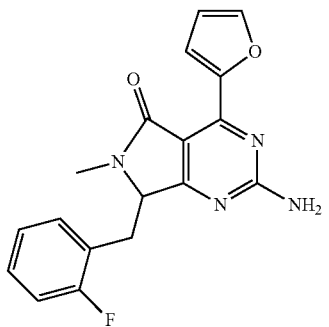
45
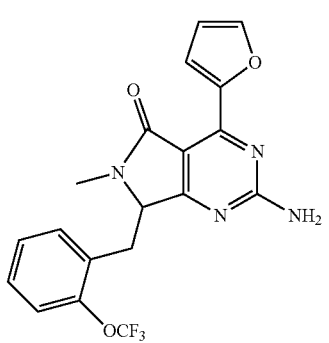
46
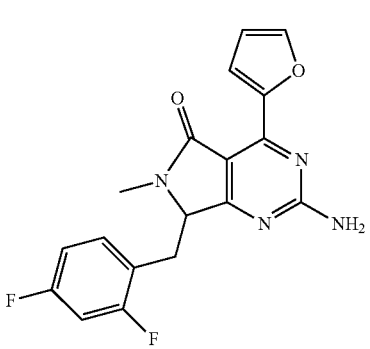
47
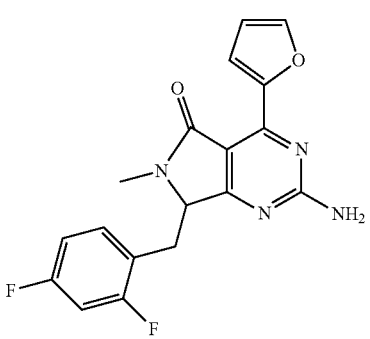

48
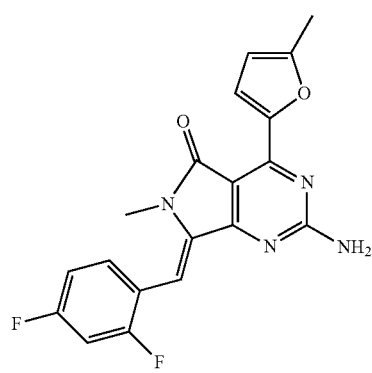
49
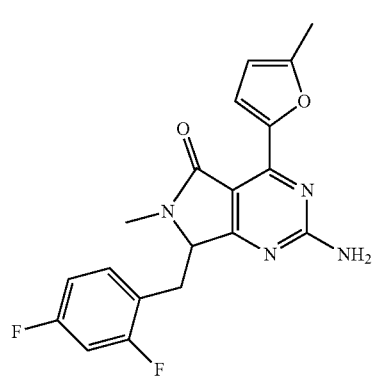
50
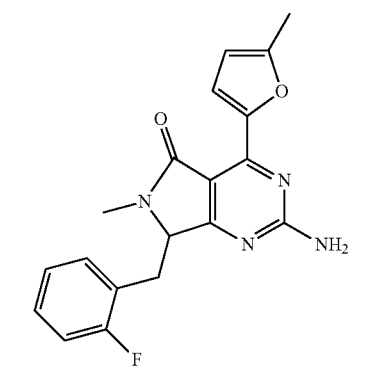
51
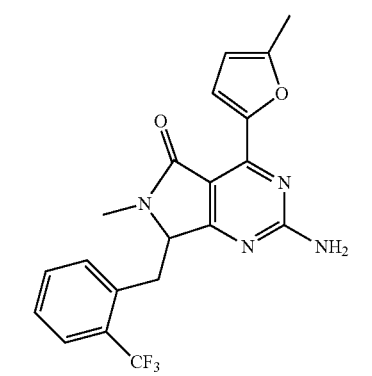
52
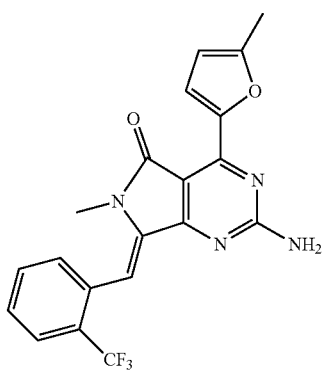
53
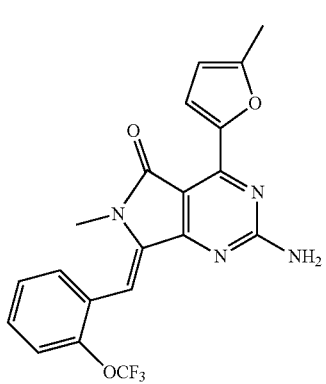
54
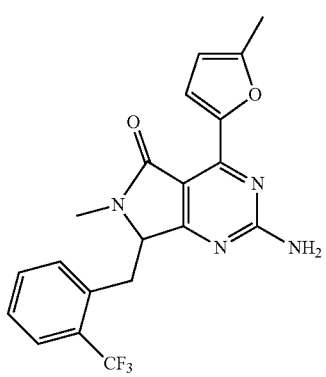
55
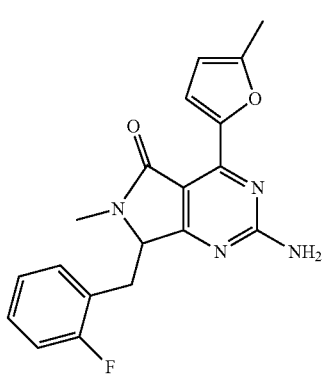

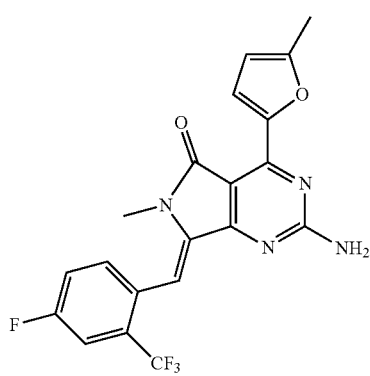

56

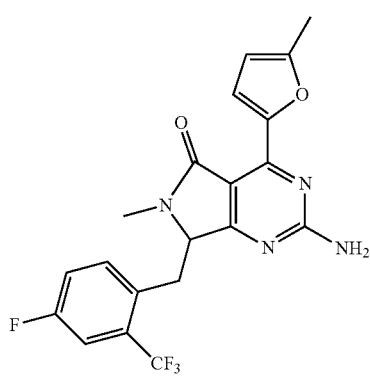

57

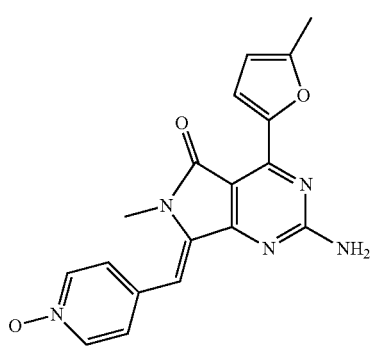

58

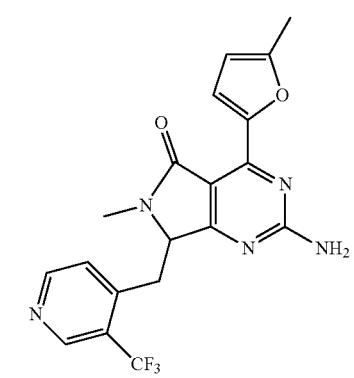

59

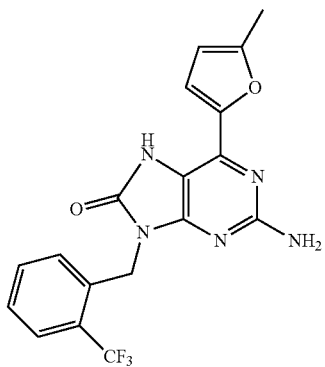

60

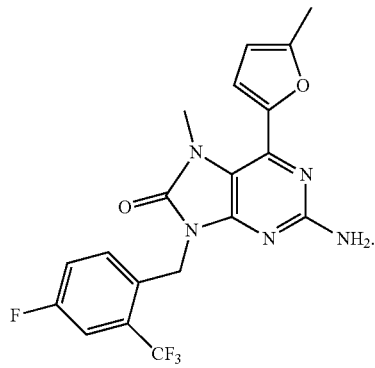

61

The present disclosure also provides a method for preparing the aminopyrimidine five-membered heterocyclic compound represented by formula I-1, which comprises the following steps: in an organic solvent, carrying out a nucleophilic substitution reaction on a compound represented by formula I-A-1 and a aminating agent as shown below, to obtain the aminopyrimidine five-membered heterocyclic compound represented by formula I-1;

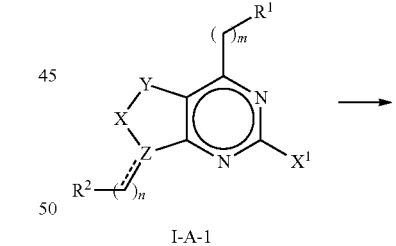

I-A-1

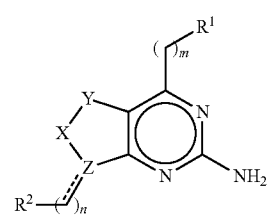

I-1 wherein, X, Y, Z, $R^1$, $R^2$, m and n are as defined above, $X^1$ is halogen (preferred F, Cl, Br or I) or substituted sulfonyl (preferred methylsulfonyl).

In the method for preparing the aminopyrimidine five-membered heterocyclic compound represented by formula I-1, the condition of the nucleophilic substitution reaction may be common conditions of the one in the organic synthesis field, and is preferably as follows in the present disclosure: the organic solvent can be that commonly used for such a reaction in the art, preferably an ether solvent. The ether solvent is preferably tetrahydrofuran. The amount of the organic solvent used can not be specifically limited as long as it does not affect the progress of the reaction. The aminating reagent can be that commonly used in the art, preferably a solution of aqueous ammonia or ammonia in methanol. The molar concentration of the solution of ammonia in methanol is preferably 5.0 mol/L to 10.0 mol/L (e.g., 7.0 mol/L). The amount of the aminating agent used can not be specifically limited as long as it does not affect the progress of the reaction, and generally, is a common amount of such a reaction in the art. The amount of the compound represented by formula I-A-1 and the aminating reagent can be a common one for such a reaction in the art. The temperature for the nucleophilic substitution reaction can be a common one for such a reaction in the art, preferably 10° C.-40° C. The progress of the nucleophilic substitution reaction can be monitored by a common detection method (e.g., TLC, HPLC, GC or HNMR, etc.) in the art, and generally the disappearance of the compound represented by formula I-A-1 is regarded as the end point of the reaction. The reaction duration is preferably 2-10 hours (e.g., 3 hours).

After the nucleophilic substitution reaction is complete, a post-treatment operation may be further included. The post-treatment method can be a common one in the field of organic synthesis. The present disclosure preferably comprises the following steps: subjecting the reaction solution after completion of the nucleophilic substitution reaction to a solid-liquid separation (preferably concentration under reduced pressure), and purifying by column chromatography (the column chromatography conditions can be routinely selected according to TLC conditions).

Furthermore, the compound obtained by the above method can further be used to prepare other target compounds of the present disclosure by modifying the peripheral positions referring to the related methods disclosed in the embodiments.

The present disclosure also provides a use of one or more of the aminopyrimidine five-membered heterocyclic compound represented by formula I-1, the pharmaceutically acceptable salt, the tautomer, the enantiomer, the diastereomer and the prodrug thereof, in manufacturing a medicament for preventing, mitigating and/or treating related diseases caused by adenosine A2A receptor.

The present disclosure also provides a use of one or more of the aminopyrimidine five-membered heterocyclic compound represented by formula I-1, the pharmaceutically acceptable salt, the tautomer, the enantiomer, the diastereomer and the prodrug thereof in preparing an A2A receptor antagonist.

The related diseases caused by the adenosine A2A receptor generally include central nervous system diseases, immune tolerance diseases, and inflammatory diseases.

The central nervous system diseases include Parkinson's disease, Alzheimer's disease, depression, schizophrenia, epilepsy, and Huntington's disease, etc.

The immune tolerance diseases include organ transplant rejection and tumors. The tumors include, for example, myelofibrosis, hematoma (such as leukemia, lymphoma, etc.) and solid tumors (such as kidney cancer, liver cancer, stomach cancer, lung cancer, breast cancer, prostate cancer, pancreatic cancer, thyroid cancer, ovarian cancer, glioblastoma, skin cancer and melanoma etc.) etc.

The inflammatory diseases include acute inflammatory diseases such as pneumonia, hepatitis, nephritis, myocarditis, septicopyemia and the like, as well as chronic inflammatory diseases such as arthritis, asthma, atherosclerosis and the like.

The present disclosure also provides a pharmaceutical composition, comprising a prophylactically, mitigating and/or therapeutically effective amount of one or more of the aminopyrimidine five-membered heterocyclic compound represented by formula I-1, the pharmaceutically acceptable salt, the tautomer, the enantiomer, the diastereomer and the prodrug thereof, and one or more of pharmaceutically acceptable carriers and/or diluents.

The pharmaceutical composition of the present disclosure can be in form for oral administration or in form of sterile injectable aqueous solution, and the oral or injectable composition can be prepared according to any method known in the art for preparing a pharmaceutical composition.

The pharmaceutical composition of the present disclosure can be used in combination with one or more clinically used chemotherapeutic agents and/or targeting agents, which may be formulated into a single dosage form, particularly a liposomal dosage, by any suitable ratio according to methods conventional in the art for treating various neoplastic diseases.

The present disclosure provides an aminopyrimidine five-membered heterocyclic compound represented by formula I, a pharmaceutically acceptable salt, a tautomer, an enantiomer or a diastereomer or a prodrug thereof:

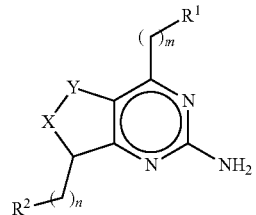

Wherein
X is selected from O, $CH_2$ or $NR^3$;
Y is selected from O, CO or $CH_2$;
each of $R^1$ and $R^2$ is independently selected from substituted or unsubstituted $C_1$-$C_{20}$ alkyl, substituted or unsubstituted $C_6$-$C_{30}$ aryl or substituted or unsubstituted $C_2$-$C_{30}$ heteroaryl;
the $C_2$-$C_{30}$ heteroaryl in the substituted or unsubstituted $C_2$-$C_{30}$ heteroaryl refers to a $C_2$-$C_{30}$ heteroaryl comprising 1-4 heteroatoms which is selected from the group consisting of N, O and S;
the substituent in the substituted $C_1$-$C_{20}$ alkyl, the substituted $C_6$-$C_{30}$ aryl or the substituted $C_2$-$C_{30}$ heteroaryl is selected from one or more of the group consisting of halogen, $C_1$-$C_{20}$ alkyl, hydroxyl, amino, amindo

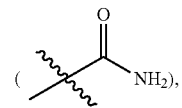

cyano, $C_1$-$C_{20}$ alkoxyl, and $C_1$-$C_{20}$ alkylthio; when the number of the substituent is more than one, the substituent may be the same or different;

$R^3$ is H, $C_1$-$C_{20}$ alkyl or $C_3$-$C_{30}$ cycloalkyl;

m is 0, 1, 2 or 3;

n is 0, 1, 2 or 3.

In the aminopyrimidine five-membered heterocyclic compound represented by formula I, the $C_1$-$C_{20}$ alkyl in the substituted or unsubstituted $C_1$-$C_{20}$ alkyl, and the $C_1$-$C_{20}$ alkyl is preferably $C_1$-$C_{10}$ alkyl. The $C_1$-$C_{10}$ alkyl is preferably $C_1$-$C_4$ alkyl. The $C_1$-$C_4$ alkyl is preferably methyl, ethyl, n-propyl, iso-propyl, n-butyl, iso-butyl or tert-butyl.

In the aminopyrimidine five-membered heterocyclic compound represented by formula I, the substituted or unsubstituted $C_6$-$C_{30}$ aryl is preferably substituted or unsubstituted $C_6$-$C_{20}$ aryl. The substituted or unsubstituted $C_6$-$C_{20}$ aryl is preferably substituted or unsubstituted phenyl, substituted or unsubstituted naphthyl, substituted or unsubstituted anthryl, or substituted or unsubstituted phenanthryl.

In the aminopyrimidine five-membered heterocyclic compound represented by formula I, the substituted or unsubstituted $C_2$-$C_{30}$ heteroaryl is preferably substituted or unsubstituted $C_2$-$C_{20}$ heteroaryl comprising 1-4 heteroatoms which is selected from the group consisting of N, O and S (e.g., the heteroatom is O, the number of the heteroatom is 1). The substituted or unsubstituted $C_2$-$C_{20}$ heteroaryl may be substituted or unsubstituted $C_2$-$C_{10}$ heteroaryl (preferably substituted or unsubstituted $C_2$-$C_5$ heteroaryl, or substituted or unsubstituted $C_3$-$C_5$ heteroaryl). The substituted or unsubstituted $C_2$-$C_{10}$ heteroaryl is preferably substituted or unsubstituted furyl.

In the aminopyrimidine five-membered heterocyclic compound represented by formula I, the $C_1$-$C_{20}$ alkoxyl is preferably $C_1$-$C_{10}$ alkoxyl. The $C_1$-$C_{10}$ alkoxyl is preferably $C_1$-$C_4$ alkoxyl. The $C_1$-$C_4$ alkoxyl is preferably methoxyl, ethoxy, n-propoxy, iso-propoxy, n-butoxy, iso-butoxy or tert-butoxy.

In the aminopyrimidine five-membered heterocyclic compound represented by formula I, the $C_1$-$C_{20}$ alkylthio is preferably $C_1$-$C_{10}$ alkylthio. The $C_1$-$C_{10}$ alkylthio is preferably $C_1$-$C_4$ alkylthio. The $C_1$-$C_4$ alkylthio is preferably methylthio, ethylthio, n-propylthio, iso-propylthio, n-butylthio, iso-butylthio or tert-butylthio.

In the aminopyrimidine five-membered heterocyclic compound represented by formula I, the halogen is preferably F, Cl, Br or I, more preferably F.

In the aminopyrimidine five-membered heterocyclic compound represented by formula I, the $C_3$-$C_{30}$ cycloalkyl is preferably $C_3$-$C_{10}$ cycloalkyl. The $C_3$-$C_{10}$ cycloalkyl is preferably $C_3$-$C_6$ cycloalkyl. The $C_3$-$C_6$ cycloalkyl is preferably cyclopropyl, cyclobutyl, cyclopentyl or cyclohexyl.

In a preferred embodiment of the present disclosure, the aminopyrimidine five-membered heterocyclic compound represented by formula I is preferably represented by formula II-1 or II-2:

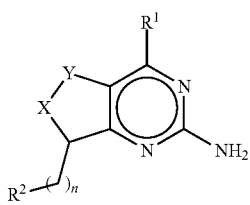

II-1

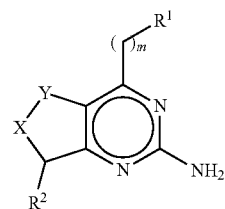

II-2 wherein, X, Y, $R^1$, $R^2$, m and n are as defined above.

The aminopyrimidine five-membered heterocyclic compound represented by formula I is preferably selected from the group consisting of

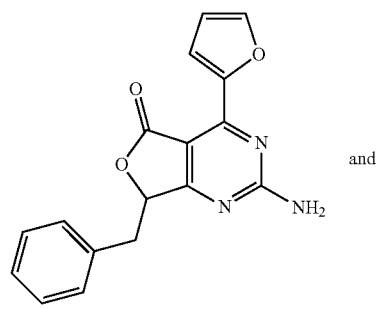

and

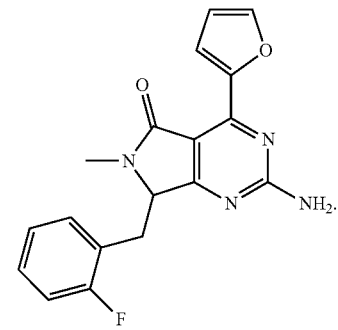

The present disclosure also provides a method for preparing the aminopyrimidine five-membered heterocyclic compound represented by formula I, which comprises the following steps: in an organic solvent, carrying out a nucleophilic substitution reaction on a compound represented by formula I-A and a aminating agent as shown below, to obtain the aminopyrimidine five-membered heterocyclic compound represented by formula I;

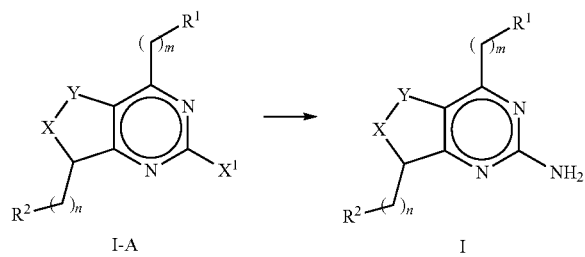

I-A          I

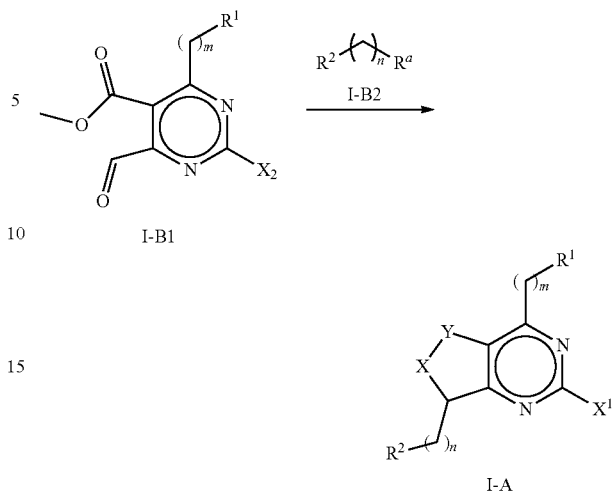

I-B1 wherein, X, Y, $R^1$, $R^2$, m and n are as defined above, $X^1$ is halogen (preferred F, Cl, Br or I).

In the method for preparing the aminopyrimidine five-membered heterocyclic compound represented by formula I, the condition of the nucleophilic substitution reaction may be any common conditions of the one in the organic synthesis field, and is preferably as follows in the present disclosure: the organic solvent can be that commonly used for such a reaction in the art, preferably an ether solvent. The ether solvent is preferably tetrahydrofuran. The amount of the organic solvent used can not be specifically limited as long as it does not affect the progress of the reaction. The aminating reagent can be that commonly used in the art, preferably a solution of aqueous ammonia or ammonia in methanol. The molar concentration of the solution of ammonia in methanol is preferably 5.0 mol/L to 10.0 mol/L (e.g., 7.0 mol/L). The amount of the aminating agent used can not be specifically limited as long as it does not affect the progress of the reaction, and generally, is a common amount of such a reaction in the art. The amount of the compound represented by formula I-A and the aminating reagent can be a common one for such a reaction in the art. The temperature for the nucleophilic substitution reaction can be a common one for such a reaction in the art, preferably 10° C.-40° C. The progress of the nucleophilic substitution reaction can be monitored by a common detection method (e.g., TLC, HPLC, GC or HNMR, etc.) in the art, and generally the disappearance of the compound represented by formula I-A is regarded as the end point of the reaction. The reaction duration is preferably 2-10 hours (e.g., 3 hours).

After the nucleophilic substitution reaction is complete, a post-treatment operation may be further included. The post-treatment method can be a common one in the field of organic synthesis. The present disclosure preferably comprises the following steps: subjecting the reaction solution after completion of the nucleophilic substitution reaction to a solid-liquid separation (preferably concentration under reduced pressure), and purifying by column chromatography (the column chromatography conditions can be routinely selected according to TLC conditions).

Furthermore, the compound obtained by the above method can further be used to prepare other target compounds of the present disclosure by modifying the peripheral positions referring to the related methods disclosed in the embodiments.

The method for preparing the aminopyrimidine five-membered heterocyclic compound represented by formula I, can further comprises the following steps: in an organic solvent, carrying out a cyclization reaction on a compound represented by formula I-B1 and a compound represented by formula I-B2 as shown below, to obtain the compound represented by formula I-A;

I-A wherein, in formula I-B1, I-B2 and I-A, $R^1$, $R^2$, m and n are as defined above, X is O, Y is CO; in formula I-B2, $R^a$ is ZnBr, ZnCl, ZnI, MgBr, MgCl, MgI or Li.

In the method for preparing the compound represented by formula I-A, the condition of the cyclization reaction may be any common conditions of the one in the organic synthesis field, and is preferably as follows in the present disclosure: the organic solvent is preferably an ether solvent. The ether solvent is preferably tetrahydrofuran. The amount of the organic solvent used can not be specifically limited as long as it does not affect the progress of the reaction. The amount of the compound represented by formula I-B1 and the compound represented by formula I-B2 can be a common one for such a reaction in the art, the molar ratio thereof is preferably 1:1-1:5, more preferably 1:1-1:2. The temperature for the cyclization reaction is preferably 10° C.-40° C. (room temperature). The progress of the cyclization reaction can be monitored by a common detection method (e.g., TLC, HPLC, GC or HNMR, etc.) in the art. The cyclization reaction duration is preferably 10-24 hours, more preferably 12-16 hours.

The cyclization reaction is preferably carried out under gas atmosphere, more preferably under nitrogen atmosphere.

The cyclization reaction is preferably carried out by adding the organic solution of the compound represented by formula I-B2 into the organic solution of the compound represented by formula I-B1. The organic solvent in the organic solution herein is as defined above.

After the cyclization reaction is complete, a post-treatment operation may be further included. The post-treatment method can be a common one in the field of organic synthesis. The present disclosure preferably comprises the following steps: subjecting the reaction solution after completion of the cyclization reaction to a solid-liquid separation (preferably concentration under reduced pressure), and purifying the resulting solid by column chromatography (the column chromatography conditions can be routinely selected according to TLC conditions).

The present disclosure further provides a compound represented by formula I-A:

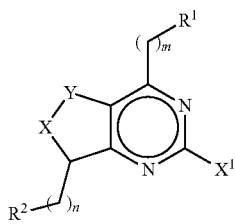

I-A wherein, X, Y, $R^1$, $R^2$, m and n are as defined above, $X^1$ is halogen (preferred F, Cl, Br or I) or substituted sulfonyl (preferred methylsulfonyl), the substituent in the substituted sulfonyl is $C_1$-$C_{20}$ alkyl, e.g., $C_1$-$C_4$ alkyl, also e.g., methyl.

The present disclosure also provides a use of one or more of the aminopyrimidine five-membered heterocyclic compound represented by formula I, the pharmaceutically acceptable salt, the tautomer, the enantiomer, the diastereomer and the prodrug thereof, in manufacturing a medicament for preventing, mitigating and/or treating the related diseases caused by adenosine A2A receptor.

The related diseases caused by the adenosine A2A receptor generally include central nervous system diseases, immune tolerance diseases, and inflammatory diseases.

The central nervous system diseases include Parkinson's disease, Alzheimer's disease, depression, schizophrenia, epilepsy, and Huntington's disease, etc.

The immune tolerance diseases include organ transplant rejection and tumors. The tumors include, for example, myelofibrosis, hematoma (such as leukemia, lymphoma, etc.) and solid tumors (such as kidney cancer, liver cancer, stomach cancer, lung cancer, breast cancer, prostate cancer, pancreatic cancer, thyroid cancer, ovarian cancer, glioblastoma, skin cancer and melanoma etc.) etc.

The inflammatory diseases include acute inflammatory diseases such as pneumonia, hepatitis, nephritis, myocarditis, septicopyemia and the like, as well as chronic inflammatory diseases such as arthritis, asthma, atherosclerosis and the like.

The present disclosure also provides a pharmaceutical composition, comprising a prophylactically, mitigating and/or therapeutically effective amount of one or more of the aminopyrimidine five-membered heterocyclic compound represented by formula I, the pharmaceutically acceptable salt, the tautomer, the enantiomer, the diastereomer and the prodrug thereof, and one or more of pharmaceutically acceptable carriers and/or diluents.

The pharmaceutical composition of the present disclosure can be in form for oral administration or in form of sterile injectable aqueous solution, and the oral or injectable composition can be prepared according to any method known in the art for preparing a pharmaceutical composition.

The pharmaceutical composition of the present disclosure can be used in combination with one or more clinically used chemotherapeutic agents and/or targeting agents, which may be formulated into a single dosage form, particularly a liposomal dosage, by any suitable ratio according to methods conventional in the art for treating various neoplastic diseases.

The present disclosure also provides an intermediate for the aminopyrimidine five-membered heterocyclic compound represented by formula I-1, the pharmaceutically acceptable salt, the tautomer, the enantiomer, the diastereomer and the prodrug thereof, which is selected from the group consisting of

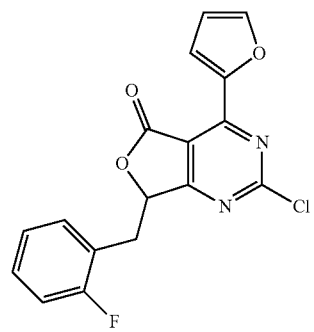

1-a

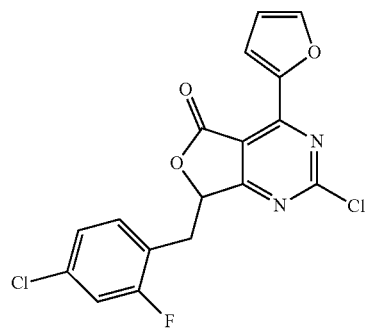

2-a

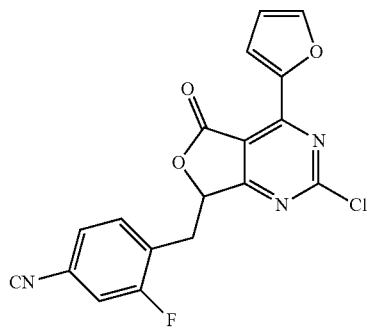

3-a

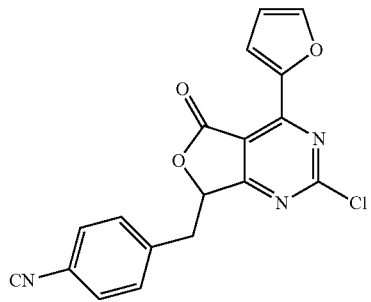

4-a

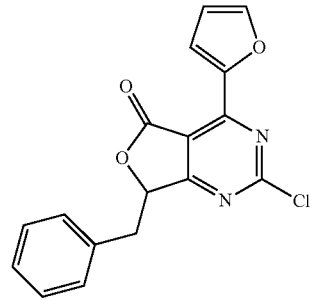

5-a

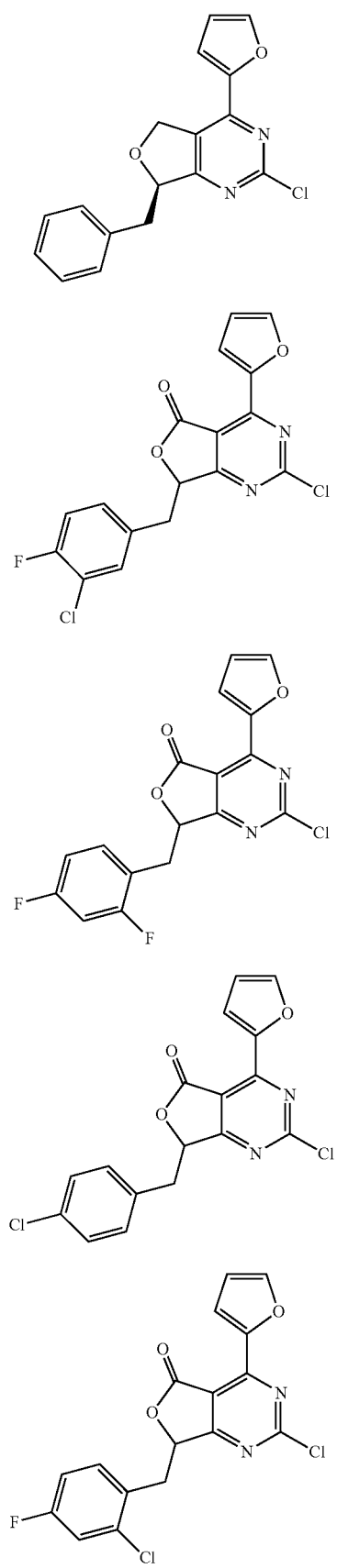
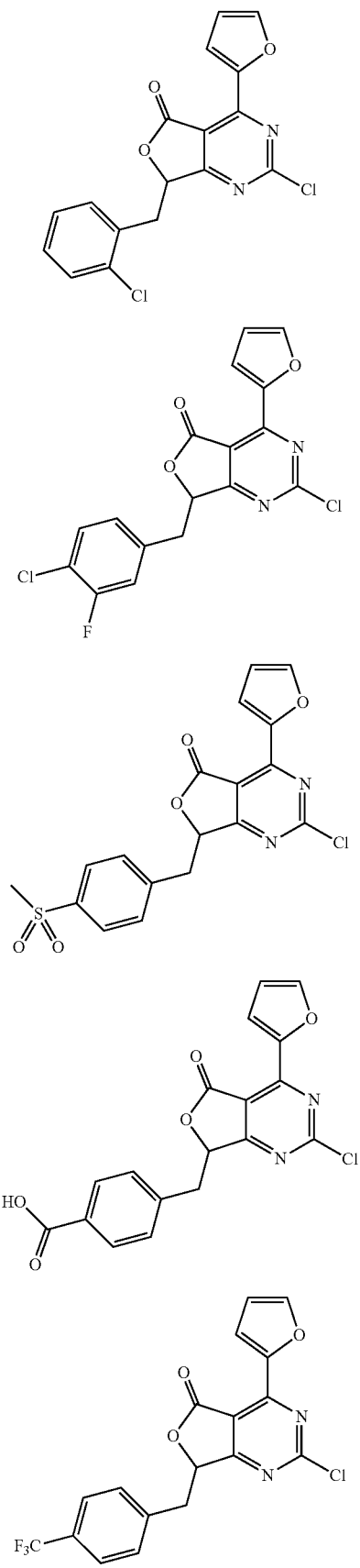

| 16-a | 20-a |
|---|---|
| 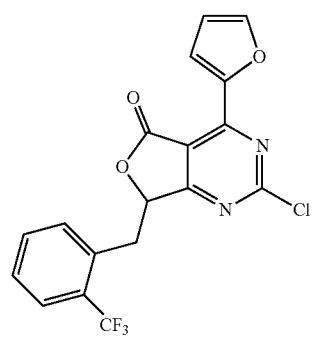 | 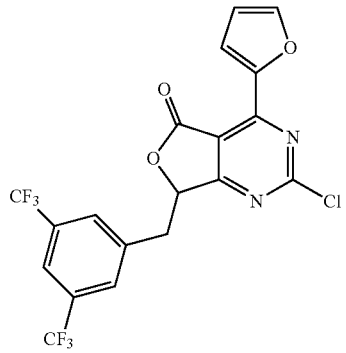 |
| 17-a | 21-a |
| 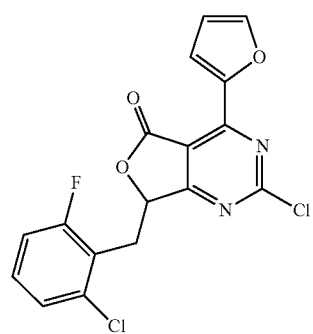 | 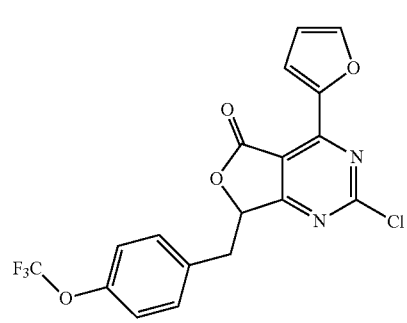 |
| 18-a | 22-a |
| 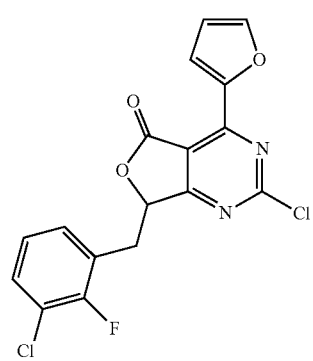 | 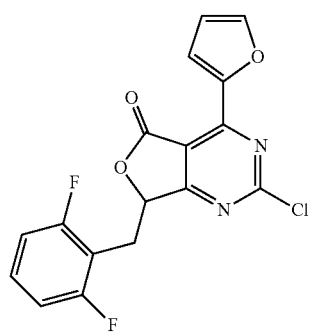 |
| 19-a | 23-a |
| 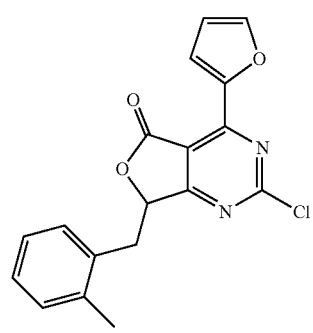 | 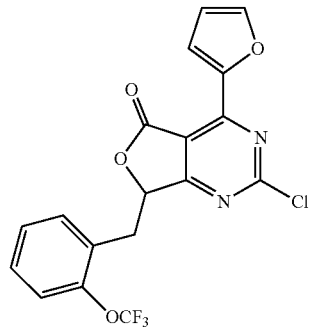 |

24-a
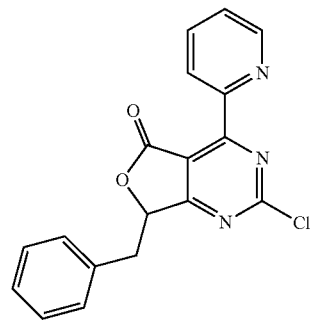
26-a
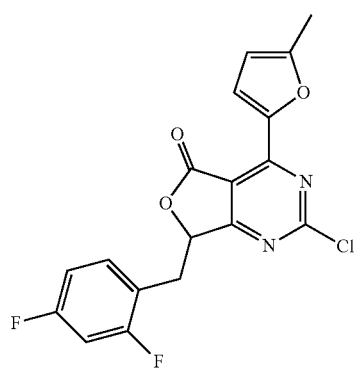
27-a
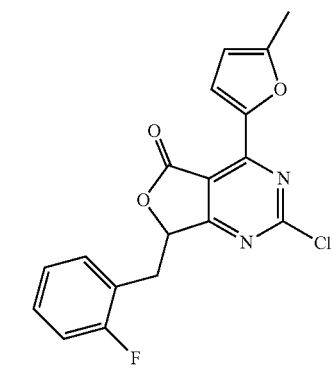
28-a
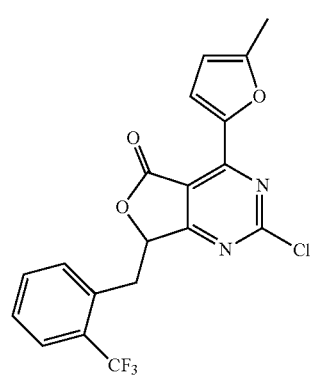
29-a
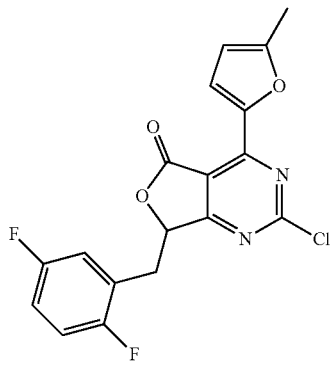
30-a
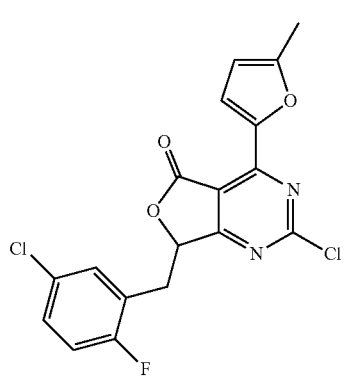
31-a
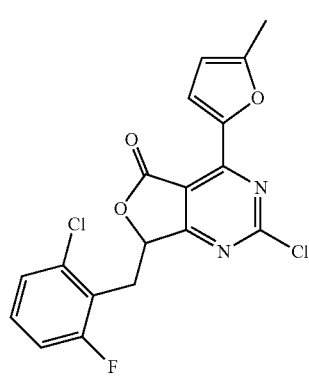
32-a
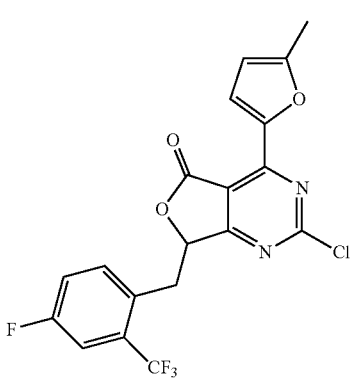

33-b
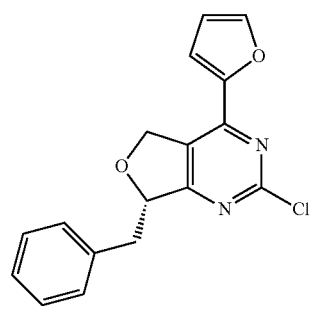
34-a
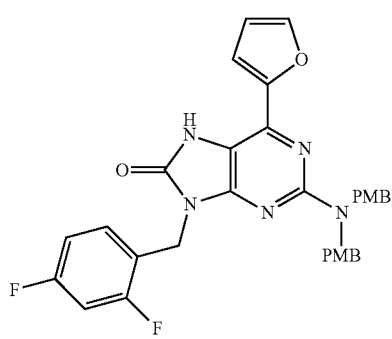
35-a
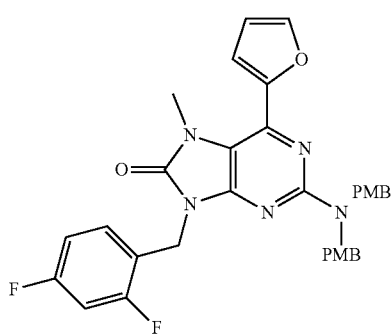
36-a
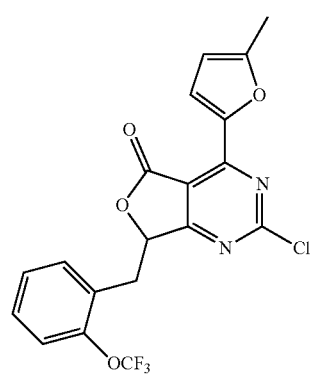
38-a
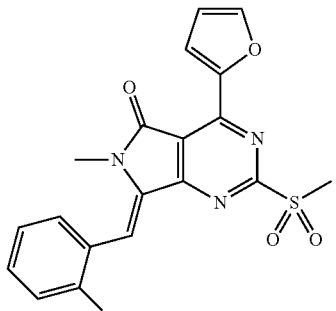
39-a
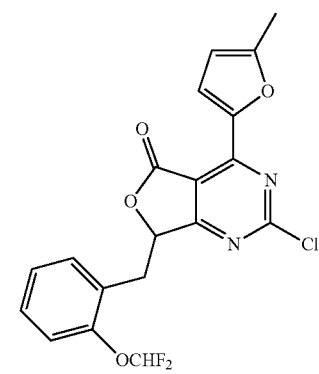
40-a
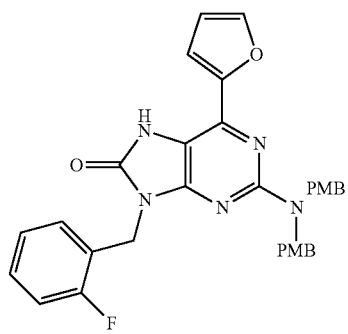
41-a
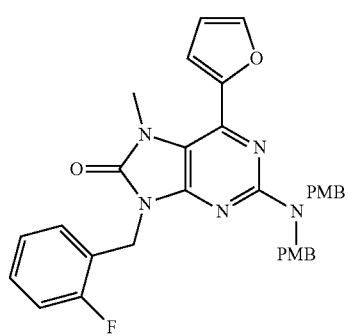

45
-continued
43-a
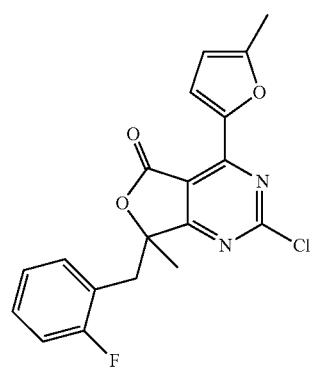
44-a
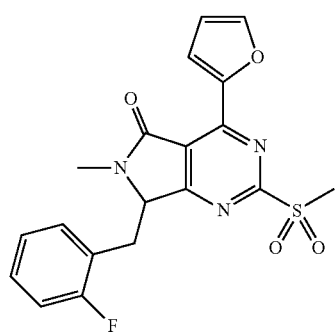
45-a
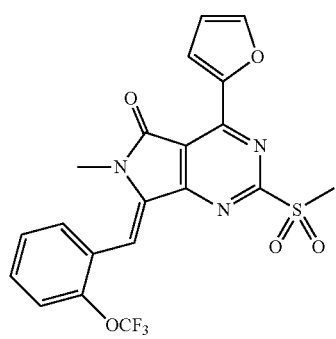
46-a
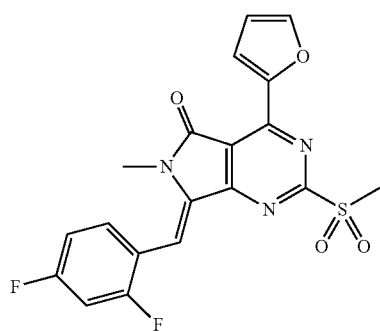
46
-continued
48-a
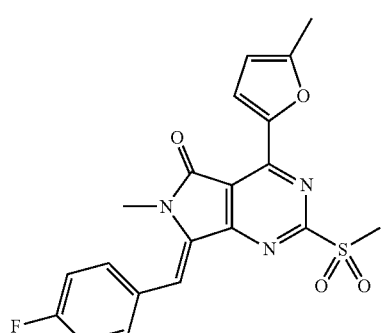
50-a
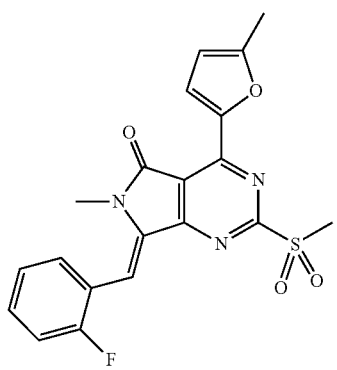
51-a
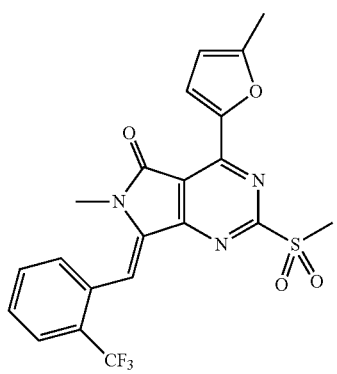
52-a
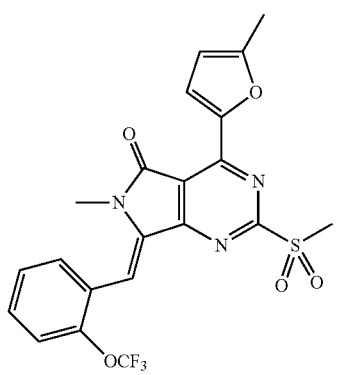

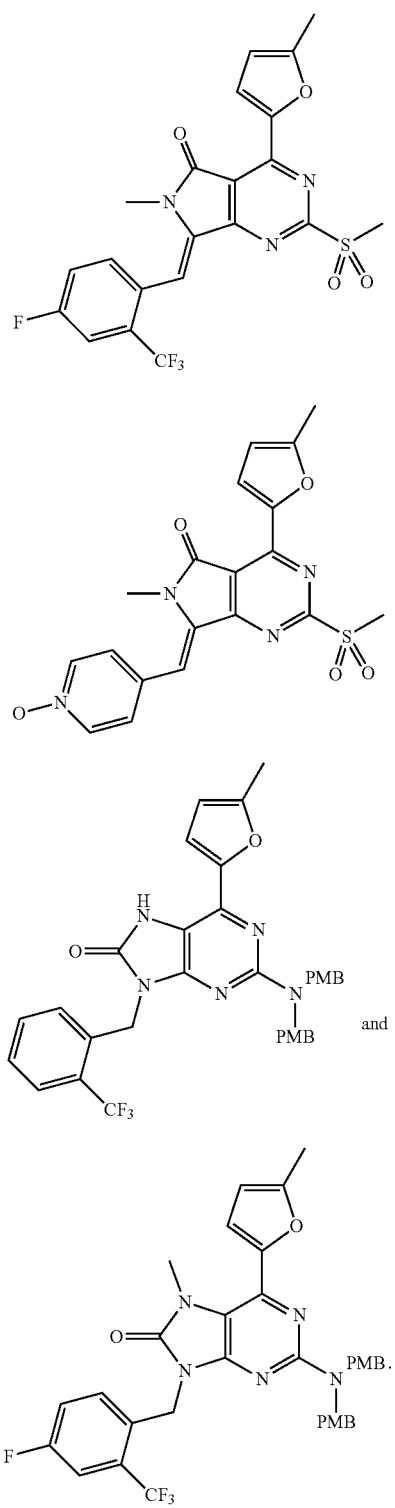

Unless otherwise indicated, the following terms and phrases used herein are intended to have the following meanings:

the term "alkyl" (including when used alone and contained in other groups) refers to linear and branched saturated aliphatic hydrocarbon group comprising 1-20 carbon atoms (preferably 1 to 10 carbon atoms, more preferably 1 to 8 carbon atoms), such as methyl, ethyl, n-propyl, isopropyl, n-butyl, tert-butyl, isobutyl, pentyl, hexyl, heptyl, octyl, decyl, decyl, 4,4-dimethylpentyl, 2,2,4-trimethylpentyl, undecyl, dodecyl, and various isomers thereof and the like.

The term "cycloalkyl" (including when used alone and contained in other groups) refers to saturated or partially unsaturated cyclic hydrocarbon group (including 1 or 2 double bonds, but none of which has a fully conjugated π-electron system) comprising 1-3 ring, which includes monocycloalkyl, bicycloalkyl, and tricycloalkyl, and which contains 3-20 ring-forming carbon atoms, preferably 3-10 carbon atoms, e.g., cyclopropyl, cyclobutyl, cyclopentyl, cyclohexyl, cycloheptyl, cyclooctyl, cyclodecane, cyclododecyl, cyclohexenyl and the like.

The term "aryl" (including when used alone and contained in other groups) represents for any stable monocyclic or bicyclic carbon ring that may contain up to 7 atoms in each ring wherein at least one ring is an aromatic ring. Examples of the aryl unit include phenyl, naphthyl, tetrahydronaphthyl, 2,3-indanyl, biphenyl, phenanthryl, anthryl or acenaphthyl. It could be understood that in the case where the aryl substituent is a bicyclic substituent and one of the rings is a non-aromatic ring, the linkage is carried out through an aromatic ring.

The term "heteroaryl" (including when used alone and contained in other groups) represents for a stable monocyclic or bicyclic ring that may contain up to 7 atoms in each ring, wherein at least one ring is an aromatic ring and contains 1-4 heteroatoms selected from the group consisting of O, N and S. Heteroaryl groups within the scope of this definition include, but are not limited to, acridyl, carbazolyl, oxinolinyl, quinoxalinyl, pyrazolyl, indolyl, benzotriazolyl, furyl, thienyl, benzothienyl, benzofuranyl, quinolyl, isoquinolyl, oxazolyl, isoxazolyl, indolyl, pyrazinyl, pyridazinyl, pyridyl, pyrimidinyl, pyrrolyl and tetrahydroquinoline. As defined above for "heterocycloalkyl", "heteroaryl" is also understood to include any N-oxide derivative of the nitrogen-containing heteroaryl. In the case where the heteroaryl substituent is a bicyclic substituent and one ring is a non-aromatic ring or does not contain a heteroatom, it should be understood that the linkage is carried out by an aromatic ring or by a heteroatom comprising a ring, respectively.

The term "alkoxy" (including when used alone and contained in other groups) represents cyclic or acyclic alkyl group containing the said number of carbon atoms that are attached through an oxygen bridge. Thus, "alkoxy" includes the definitions of the above alkyl and cycloalkyl.

The term "oxo" refers to the case where an oxygen atom directly serves as a substituent of a carbon atom or a nitrogen atom, for example, forming a carbonyl group with carbon atoms or forming an oxynitride with nitrogen atoms, or the like.

The term "halogen" means fluorine, chlorine, bromine, iodine or astatine.

The term "hydroxy" means —OH.
The term "amino" means —NH$_2$.
The term "amido" means

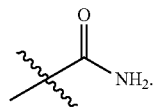

The term "alkylthio" means —S—.
The term "cyano" means —CN.

The term "prophylactically, mitigating and/or therapeutically effective amount" as used herein refers to an amount of the compound that is sufficient to effectively prevent, mitigate and/or treat a disease or condition described herein when administered to a subject. While the amount of the compound that constitutes the "prophylactically, mitigating and/or therapeutically effective amount" would vary depending on the compound, the condition and severity of the disease, and the age of the subject to be treated, it can be determined in a conventional manner by those skilled in the art.

As used herein, where a particular salt, pharmaceutical composition, composition and excipient, etc. is mentioned as a "pharmaceutically acceptable", it is meant that the salt, pharmaceutical composition, composition and excipient, etc. are generally non-toxic, safe, and suitable for use by a subject, preferably a mammalian subject, more preferably a human subject.

The term "pharmaceutically acceptable salt" as used herein represents for a pharmaceutically acceptable organic or inorganic salt of the compound. Exemplary salts include, but are not limited to, sulfates, citrates, acetates, oxalates, chlorides, bromides, iodides, nitrates, hydrogen sulfates, phosphates, acid phosphates, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methane sulfonate, ethane sulfonate, benzene sulfonate, p-toluenesulfonate and pamoate (i.e., 1-1-methylene-bis (2-hydroxy-3-naphthoate)).

The term "prodrug" as used herein, refers to the derivative of compound comprising a biologically reactive functional group such that under biological conditions (in vitro or in vivo), the bioreactive functional group can crack from the compound or otherwise reacted to provide the compound. Typically, the prodrug is inactive, or at least less active than the compound itself, such that the compound does not exert its activity until cracking from the biologically reactive functional group. The bioreactive functional group can be hydrolyzed or oxidized under biological conditions to provide the compound. For example, a prodrug can comprise a biohydrolyzable group. Examples of biohydrolyzable groups include, but are not limited to, biohydrolyzable phosphates, biohydrolyzable esters, biohydrolyzable amides, biohydrolyzable carbonates, biohydrolyzable carbamates, and biohydrolyzable acyl urea.

The compound of the present disclosure may contain one or more asymmetric centers ("stereoisomers"). As used herein, the term "stereoisomer" refers to the cis- and trans-isomers, the R- and S-enantiomers, and the diastereomers. These stereoisomers can be prepared by asymmetric synthesis or chiral separation (for example, separation, crystallization, thin layer chromatography, column chromatography, gas chromatography and high performance liquid chromatography). These stereoisomers may also be derived from diastereomers, which was obtained by reaction of enantiomers or racemates mixture with a suitable chiral compound and then crystallized or treated with any other suitable conventional method.

In the present disclosure, the room temperature is 10-40° C.

Without departing from conventional knowledge in the art, the preferred embodiments of the present disclosure may be obtained by arbitrarily combination of the above preferred conditions.

The reagents and raw materials of the present disclosure are commercially available.

The present invention possesses positive effects of:

The aminopyrimidine five-membered heterocyclic compound of the present disclosure has obvious antagonistic activity on adenosine A2A receptor, and can serves as an A2A receptor antagonist to effectively mitigate or treat immune tolerance, central nervous system diseases, inflammatory diseases and other related diseases, meanwhile the preparation method therefor is simple.

DETAILED DESCRIPTION OF THE PREFERRED EMBODIMENT

The following examples further illustrate the present invention, but the present invention is not limited thereto. The experimental methods in the following examples which have not been precisely specificated are selected according to conventional methods and conditions, or according to the product description.

The compound structure was determined by nuclear magnetic resonance (NMR) or mass spectrometry (MS), the NMR spectrum was obtained by a Bruker Avance-500 instrument using deuterated dimethyl sulfoxide, deuterated chloroform and deuterated methanol as solvent, and TMS was used for internal standard.

Mass spectra were obtained by liquid chromatography-mass spectrometry (LC-MS) employing Agilent Technologies 6110 with ESI ion source.

The microwave reaction was carried out in an Explorer automatic microwave synthesizer manufactured by CEM Corporation of the United States, the magnetron frequency was 2450 MHz and the continuous microwave output power was 300 W.

The instrument used for high performance liquid phase preparation was Gilson 281, and the preparative column used was Xbridge, 21.2×250 mm C18, 10 μm.

Embodiment 1

2-amino-7-(2-fluorobenzyl)-4-(furan-2-yl)-5H,7H-furo[3,4-d]pyrimidin-5-one (Compound 1)

Synthetic Route

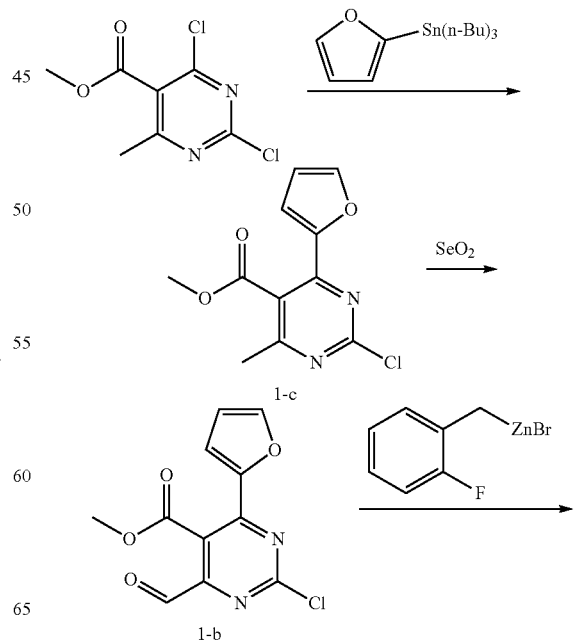

-continued

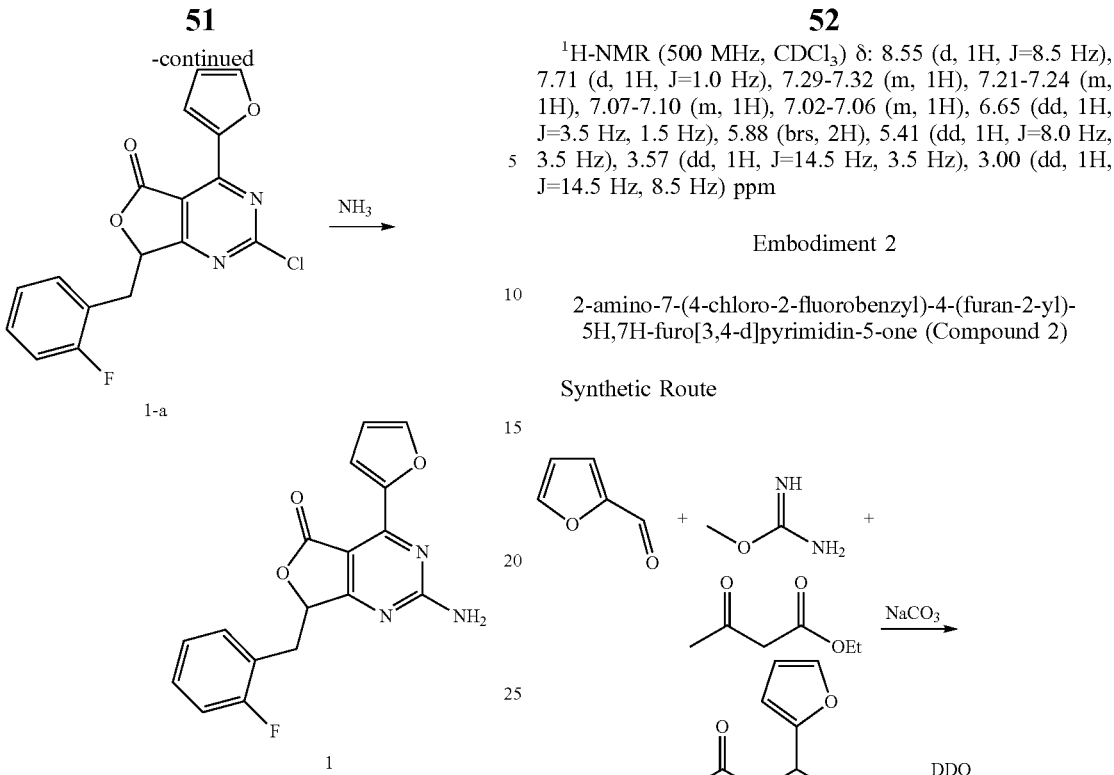

Synthesis of Compound 1-c

The mixture of 2,4-dichloro-6-methyl-pyrimidin-5-methyl formate (940 mg, 4.25 mmol), 2-furyl tributylstannane (1.42 g, 4.0 mmol), palladium tetrakis(triphenylphosphine) (260 mg, 0.22 mmol), and tetrahydrofuran (30 mL) was stirred at 60° C. for 16 hours under nitrogen atmosphere. After cooling down to room temperature, the reaction mixture was concentrated under reduced pressure, and the residue was purified by silica gel chromatography (PE/DCM=3/1) to give a white solid 1-c (870 mg, yield: 81%).

LC-MS (ESI): m/z=253[M+H]$^+$.

Synthesis of Compound 1-b

The mixture of compound 1-c (800 mg, 3.2 mmol), selenium dioxide (880 mg, 8.0 mmol) and dioxane (20 mL) was heated at reflux for 8 hours. After cooling down to room temperature, the mixture was concentrated under reduced pressure, and the residue was purified by silica gel chromatography (DCM) to give the compound 1-b (280 mg, yield: 33%).

LC-MS (ESI): m/z=267[M+H]$^+$.

Synthesis of Compound 1-a

Under nitrogen atmosphere, 0.5 M o-fluorobenzylzinc bromide in tetrahydrofuran solution (4.0 mL, 2.0 mmol) was added into the compound 1-b (267 mg, 1.0 mmol) in 10 mL tetrahydrofuran solution. The mixture was stirred under room temperature for 16 hours. The mixture was concentrated under reduced pressure, and the residue was purified by silica gel chromatography (PE/EtOAc=5/1) to give the compound 1-a (220 mg, yield: 64%). LC-MS (ESI): m/z=345[M+H]$^+$.

Synthesis of Compound 1

7.0 M ammonia in methanol solution (2 mL) was added into compound 1-a (60 mg, 0.17 mmol) in tetrahydrofuran (10 mL) solution, and then stirred at room temperature for 3 hours. The reaction solution was then concentrated, and the residue was purified by silica gel chromatography (PE: EtOAc=2:1) to give the compound 1 (35 mg, yield: 63%). LC-MS (ESI): m/z=326[M+H]$^+$.

$^1$H-NMR (500 MHz, CDCl$_3$) δ: 8.55 (d, 1H, J=8.5 Hz), 7.71 (d, 1H, J=1.0 Hz), 7.29-7.32 (m, 1H), 7.21-7.24 (m, 1H), 7.07-7.10 (m, 1H), 7.02-7.06 (m, 1H), 6.65 (dd, 1H, J=3.5 Hz, 1.5 Hz), 5.88 (brs, 2H), 5.41 (dd, 1H, J=8.0 Hz, 3.5 Hz), 3.57 (dd, 1H, J=14.5 Hz, 3.5 Hz), 3.00 (dd, 1H, J=14.5 Hz, 8.5 Hz) ppm Embodiment 2

2-amino-7-(4-chloro-2-fluorobenzyl)-4-(furan-2-yl)-5H,7H-furo[3,4-d]pyrimidin-5-one (Compound 2)

Synthetic Route

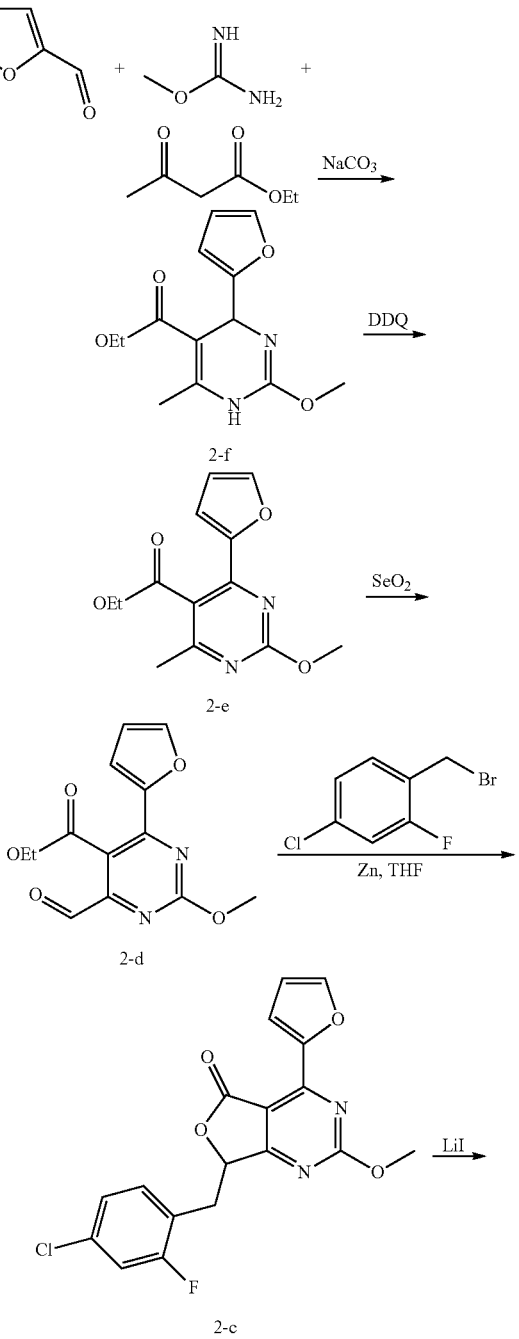

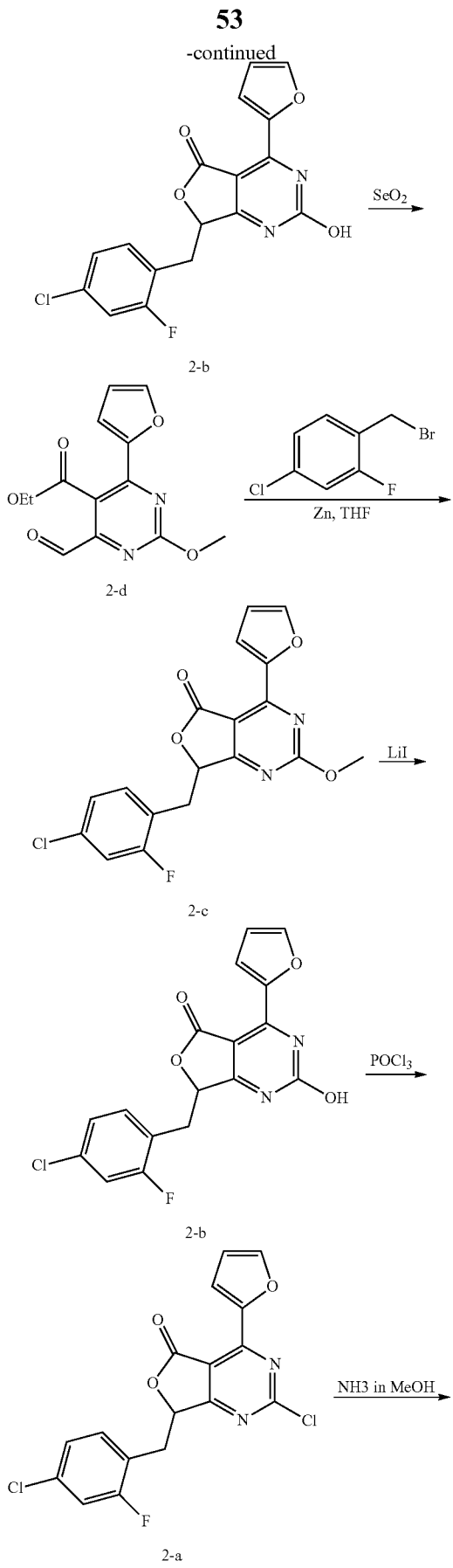

Synthesis of the Compound 2-f

Furfural (9.6 g, 0.1 mol), O-methylisothiourea sulfate (20.64 g, 0.12 mol) and ethyl acetoacetate (14.3 g, 0.11 mol) were dissolved in anhydrous N,N-dimethylformamide (200 mL), sodium dicarbonate (33.6 g, 0.4 mmol) was added thereto. The reaction mixture was heated to 70° C. under nitrogen atmosphere, stirred for 3 hours and cooled down to room temperature. After addition of saturated brine (300 mL), a large amount of yellow suspended solids appeared, EtOAc (500 mL×2) was used for extraction, the organic phases were combined and washed by water (200 mL) and saturated brine (100 mL), dried over anhydrous sodium sulfate, then concentrated under reduced pressure, and the residue was purified by silica gel chromatography (PE:EtOAc=6-3:1) to give a pale yellow solid 2-f (15.0 g, yield: 57%). LC-MS (ESI): m/z=265.1[M+H]$^+$.

Synthesis of the Compound 2-e

Compound 2-f (14.0 g, 53 mmol) was dissolved in DCM (200 mL), and 2,3-dichloro-5,6-dicyano-p-benzoquinone (12.0 g, 53.0 mmol) was added at room temperature while stirring. The reaction mixture was stirred overnight. The reaction mixture was filtered, the residue was washed by DCM (50 mL), the filtrate was combined, then concentrated under reduced pressure, and the residue was purified by silica gel chromatography (PE:EtOAc=5-2:1) to give the pale yellow crystal 2-e (8.5 g, yield: 61%). LC-MS (ESI): m/z=263.0[M+H]$^+$.

Synthesis of the Compound 2-d

Compound 2-e (1.31 g, 5.0 mmol) was dissolved in dioxane (30 mL), selenium dioxide (1.11 g, 10.0 mmol) and glacial acetic acid (2 mL) were added at room temperature, the mixture was heated to 120° C. and stirred for 10 hours. After cooling down to room temperature, the mixture was concentrated under reduced pressure, the residue was purified by silica gel chromatography (PE:EtOAc=6-2:1) to give a pink solid 2-d (450 mg, yield: 33%).

LC-MS (ESI): m/z=277.0[M+H]$^+$.

Synthesis of the Compound 2-c 2-d (140 mg, 0.5 mmol), 2-fluoro-4-chlorobenzyl bromide (450 mg, 2.0 mmol), zinc powder (130 mg, 2.0 mmol) and dry tetrahydrofuran (10 mL) were added into a 100 mL three-neck flask at 55° C., then reacted under nitrogen atmosphere for 2 hours. When the reaction mixture was cooled down to room temperature, saturated ammonium chloride (20 mL) solution was added. Then the product was extracted with EtOAc (30 mL×3), washed by saturated brine (30 mL), and dried over anhydrous sodium sulfate. After concentration under reduced pressure, the residue was purified by silica gel chromatography (PE:EtOAc=8:1) to give a white solid product 2-c (160 mg, yield: 86%).

LC-MS (ESI): m/z=375[M+H]$^+$.

Synthesis of the Compound 2-b 2-c (160 mg, 0.42 mmol), lithium iodide (374 mg, 2.81 mmol) and pyridine (8 mL) was added into a 100 mL single neck flask. The mixture was refluxed under nitrogen atmosphere for 5 hours. After cooling down to room temperature, the reaction mixture was then concentrated under reduced pressure, and the residue was purified by silica gel chromatography (DCM:MeOH=30:1) to give a white solid product 2-b (138 mg, yield: 86%).

LC-MS (ESI): m/z=361[M+H]$^+$.

Synthesis of the Compound 2-a 2-b (100 mg, 0.28 mmol) and phosphorus oxychloride (3 mL) was added into a 25 mL single neck flask. The mixture was refluxed under nitrogen atmosphere for 2 hours. After cooling down to room temperature, the reaction mixture was then concentrated under reduced pressure, the residue was diluted by adding EtOAc (20 mL), and washed by ice water (20 mL) and saturated brine (20 mL) successively, dried over anhydrous sodium sulfate. After concentration under reduced pressure, the obtained solid crude product 2-a was used directly in the next step.

Synthesis of the Compound 2

Compound 2-a was dissolved in tetrahydrofuran (5 mL), then 7.0 M ammonia in methanol solution (2 mL, 14 mmol) was added thereto. The mixture was stirred to react at room temperature for 1 hour. After concentration under reduced pressure, the residue was purified by silica gel chromatography (PE:EtOAc=1:1) to give a pale yellow solid product 2 (15 mg, two steps yield: 14.8%).

LC-MS (ESI): m/z=360[M+H]$^+$.

$^1$H NMR (500 MHz, DMSO-d$_6$) δ: 8.27 (d, J=3.5 Hz, 1H), 8.09 (s, br., 1H), 8.03 (d, J=1.0 Hz, 1H), 7.94 (s, br., 1H), 7.42 (dd, J=2.0 Hz, 10.0 Hz, 1H), 7.36 (t, J=8.0 Hz, 1H), 7.26 (dd, J=2.0 Hz, 8.5 Hz, 1H), 6.77 (dd, J=2.0 Hz, 3.5 Hz, 1H), 5.53 (dd, J=3.5 Hz, 8.5 Hz, 1H), 3.39 (dd, J=3.5 Hz, 15.0 Hz, 1H), 3.01 (dd, J=8.5 Hz, 15.0 Hz, 1H) ppm Embodiment 3

4-{[2-amino-4-(furan-2-yl)-5-oxo-5H,7H-furo[3,4-d]pyrimidin-7-yl]methyl-2-fluorobenzonitrile (Compound 3)

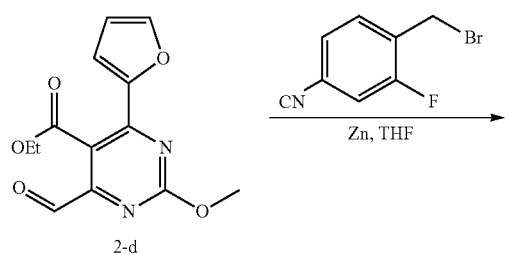

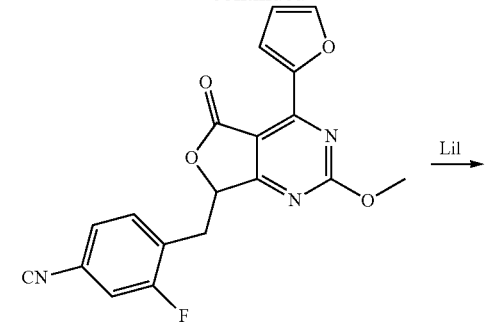

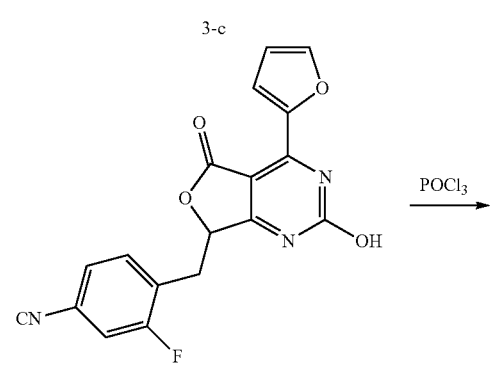

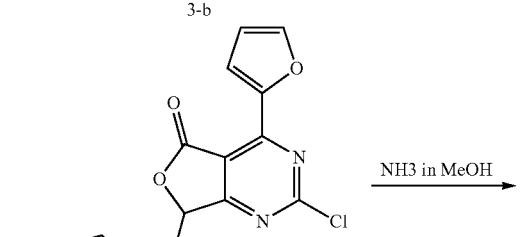

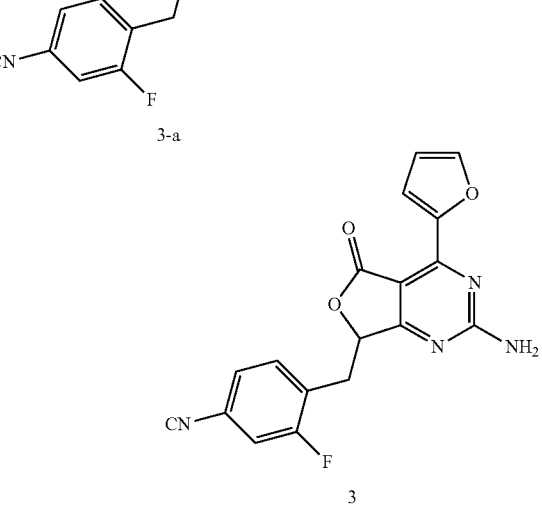

Synthesis of the Compound 3-c 2-d (200 mg, 0.72 mmol), 2-fluoro-4-cyanobenzyl bromide (428 mg, 2.0 mmol), zinc powder (130 mg, 2.0 mmol) and dry tetrahydrofuran (10 mL) were added into 100 mL three-neck flask, the mixture was reacted at 55° C. for 2 hours under nitrogen atmosphere. When the reaction mixture was cooled down to room temperature, saturated ammonium chloride solution (20 mL) was added, and then extracted with EtOAc (30 mL×3). The combined organic phases were washed by saturated brine (30 mL), dried over anhydrous sodium sulfate, then concentrated under reduced pressure, and the residue was purified by silica gel chromatography (PE:EtOAc=10:1) to give a white solid product 3-c (160 mg, yield: 61%). LC-MS (ESI): m/z=366[M+H]$^+$.

Synthesis of the Compound 3-b 3-c (160 mg, 0.44 mmol), lithium iodide (245 mg, 1.76 mmol) and pyridine (10 mL) were added into a 100 mL single neck flask. The mixture was refluxed to react under nitrogen atmosphere for 5 hours, then concentrated under reduced pressure, and the residue was purified by silica gel chromatography (DCM:EtOAc=10:1) to give a white solid product 3-b (140 mg, yield: 90%).

LC-MS (ESI): m/z=352[M+H]$^+$.

Synthesis of the Compound 3-a 3-b (140 mg, 0.4 mmol) and phosphorus oxychloride (3 mL) were added into a 25 mL single neck flask. The mixture was refluxed to react under nitrogen atmosphere for 2 hours. After concentration under reduced pressure, the residue was diluted by adding EtOAc (20 mL), and washed by water (20 mL) and saturated brine (20 mL) successively, dried over anhydrous sodium sulfate. After concentration under reduced pressure, the obtained solid crude product 3-a was used directly in the next step without further purification.

Synthesis of the Compound 3

Compound 3-a was dissolved in tetrahydrofuran (10 mL), then 7 N ammonia in methanol solution (2 mL, 14 mmol) was added. The mixture was stirred to react at room temperature for 2 hours, then concentrated under reduced pressure, and the residue was purified by silica gel chromatography (PE:EtOAc=1:1) to give a pale yellow solid product 3 (15 mg, two steps yield: 10.6%).

LC-MS (ESI): m/z=351[M+H]$^+$.

$^1$H NMR (500 MHz, d$_6$-DMSO) δ: 8.27 (d, J=3.5 Hz, 1H), 8.11 (brs, 1H), 8.03 (s, 1H), 7.92 (brs, 1H), 7.89 (t, J=7.5 Hz, 1H), 7.50 (d, J=10.0 Hz, 1H), 7.34 (d, J=8.0 Hz, 1H), 6.78 (dd, J=1.5 Hz, 3.5 Hz, 1H), 5.67 (dd, J=3.5 Hz, 8.5 Hz, 1H), 3.45 (dd, J=3.5 Hz, 15.0 Hz, 1H), 3.14 (dd, J=8.5 Hz, 15.0 Hz, 1H) ppm.

Embodiment 4

4-{[2-amino-4-(furan-2-yl)-5-oxo-5H,7H-furo[3,4-d]pyrimidin-7-yl]methylbenzonitrile (Compound 4)

Synthetic Route

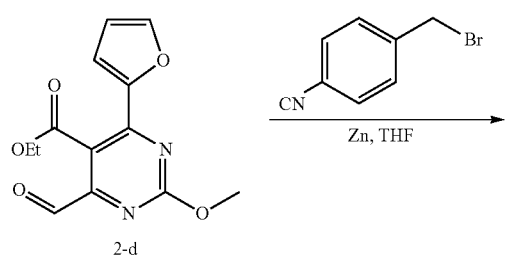

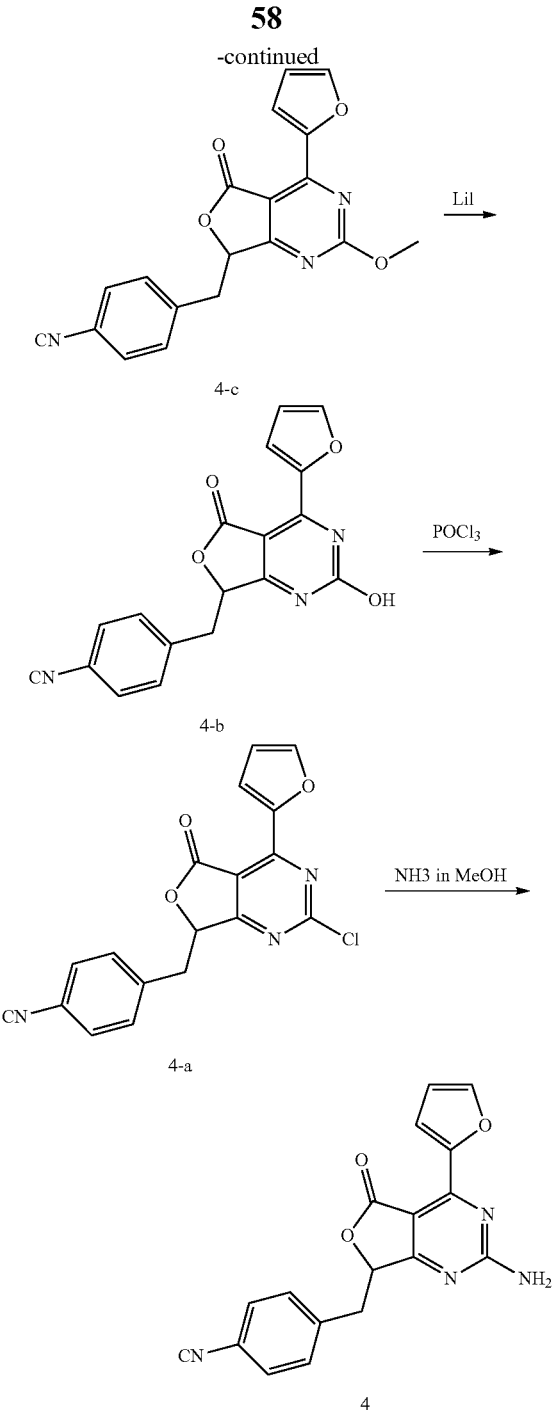

Synthesis of the Compound 4-c

Zinc powder (213 mg, 3.26 mmol) was added into anhydrous tetrahydrofuran (50 mL) and heated to 55° C., then 4-cyanobenzyl bromide (636 mg, 3.26 mmol) was added. The mixture was heated to 60° C., compound 2-d (300 mg, 1.08 mmol) was added, and continued stirring for 1 hour. After cooling down to room temperature, saturated ammonium chloride solution (50 mL) was added, then extracted with EtOAc (50 mL×2), the organic phase washed by saturated brine (50 mL), dried over anhydrous sodium sulfate, then concentrated under reduced pressure, and the residue was purified by silica gel chromatography (PE:EtOAc=5:1) to give a yellow oily product 4-c (300 mg, yield: 80%).

LC-MS (ESI): m/z=348[M+1]$^+$.

Synthesis of the Compound 4-b

Compound 4-c (300 mg, 0.86 mmol) was dissolved in pyridine (15 mL), lithium iodide (347 mg, 2.6 mmol) was added at room temperature, then the reaction mixture was stirred at 110° C. for 12 hours. After cooling down to room temperature, the reaction mixture was then concentrated under reduced pressure, and the residue was purified by silica gel chromatography (EtOAc:MeOH=5:1) to give a black oily product 4-b (220 mg, yield: 76%).

LC-MS (ESI): m/z=333[M+1]$^+$.

Synthesis of the Compound 4-a

Compound 4-b (220 mg, 0.66 mmol) was dissolved in phosphorus oxychloride (15 mL), N,N-dimethylaniline (0.22 mL) was added under room temperature, the reaction mixture was reacted at 110° C. for 2 hours, after cooling down to room temperature, the reaction mixture was then concentrated under reduced pressure to remove phosphorus oxychloride, the residue was added into ice water (50 mL), extracted with DCM (50 mL×3), the organic phase was washed by saturated brine (50 mL), dried over anhydrous sodium sulfate, then the solution was concentrated under reduced pressure to give the compound 4-a (90 mg, yield: 76%).

The product was used directly in the next step without further purification.

LC-MS (ESI): m/z=352[M+1]$^+$.

Synthesis of the Compound 4

Compound 4-a (90 mg, 0.26 mmol) was dissolved in tetrahydrofuran (10 mL), 7.0 M ammonia in methanol solution (3 mL) was added at room temperature, after stirring for 15 mins, the reaction mixture was then concentrated under reduced pressure, and the residue was purified by silica gel chromatography (DCM:EtOAc=20:1) to give the compound 4 (7 mg, yield: 8%).

LC-MS (ESI): m/z=333[M+1]$^+$.

$^1$H-NMR (400 MHz, CDCl$_3$) δ: 8.51-8.49 (d, J=2.8 Hz, 1H), 7.71 (s, 1H), 7.57-7.55 (d, J=6.8 Hz, 2H), 7.38-7.26 (d, J=6.8 Hz, 2H), 6.65-6.64 (m, 1H), 5.40-5.38 (m, 1H), 3.54-3.50 (m, 1H), 3.18-3.14 (m, 1H) ppm Embodiment 5

2-amino-7-benzyl-4-(furan-2-yl)-5H,7H-furo[3,4-d]pyrimidin-5-one (Compound 5)

Synthetic Route

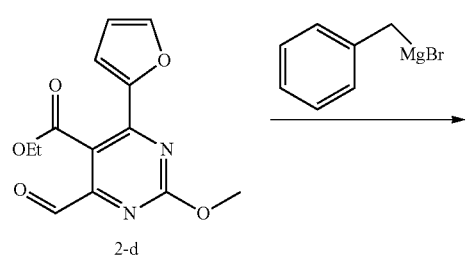

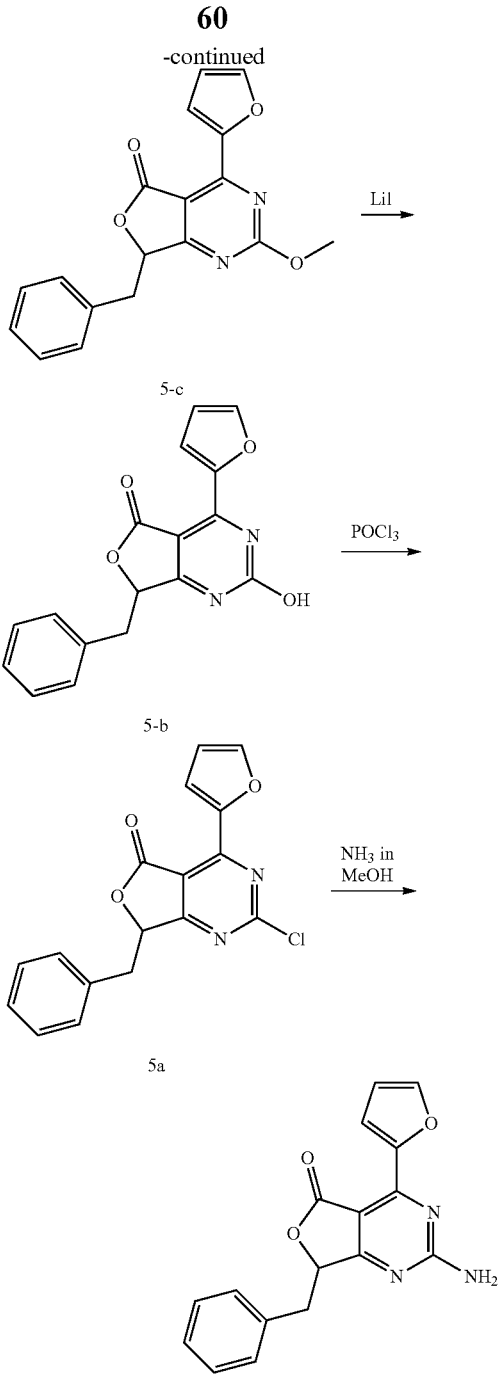

Synthesis of the Compound 5-c

At room temperature, Compound 2-d (450 mg, 1.63 mmol) was dissolved in anhydrous tetrahydrofuran (20 mL), 1.0 M benzylmagnesium bromide in tetrahydrofuran solution (1.95 mL, 1.95 mmol) was added dropwise into the reaction solution at −78° C. and under nitrogen atmosphere. After the completion of the reaction, the cooling device was removed, the reaction was slowly heated to room temperature, continued stirring for 16 hours. Saturated ammonium chloride solution (20 mL) was added and extracted with EtOAc (50 mL×2), the organic phases were combined and washed by water (30 mL) and saturated brine (20 mL), dried over anhydrous sodium sulfate. After concentration under reduced pressure, the residue was purified by silica gel chromatography (PE:EtOAc=6-3:1) to give a colorless viscous 5-c (320 mg, yield: 61%).

LC-MS (ESI): m/z=323.0[M+H]+.

Synthesis of the Compound 5-b

Compound 5-c (320 mg, 1.0 mmol) was dissolved in pyridine (10 mL), lithium iodide (670 mg, 5.0 mmol) was added into the reaction mixture at room temperature. The reaction mixture was heated to 120° C. and stirred for 16 hours, then cooled down to room temperature. After concentration under reduced pressure, the residue was purified by silica gel chromatography (EtOAc:MeOH=100:1-5:1) to give a yellow solid 5-b (260 mg, yield: 84%).

LC-MS (ESI): m/z=309.1[M+1]+.

Synthesis of the Compound 5-a

Compound 5-b (260 mg, 0.84 mmol) was dissolved in phosphorus oxychloride (10 mL), the reaction mixture was heated to 120° C. and stirred for 3 hours, then cooled down to room temperature. After concentration under reduced pressure, the residue was added into the mixture of ice and water (30 mL), and extracted with EtOAc (50 mL×2), the organic phases was combined and washed by water (30 mL) and saturated brine (20 mL), dried over anhydrous sodium sulfate. Then the solution was concentrated under reduced pressure to give a brown crude product 5-a (200 mg, yield: 72.8%), which was used directly in the next step.

LC-MS (ESI): m/z=327.0[M+H]+.

Synthesis of the Compound 5

Compound 5-a (200 mg, 0.61 mmol) was dissolved in tetrahydrofuran (15 mL), 7.0 M ammonia in methanol solution (5 mL) was added, and stirred at room temperature for 2 hours. After concentration under reduced pressure, the residue was purified by HPLC (mobile phase: water (10 mM ammonium bicarbonate), acetonitrile; gradient: 25%-55% (initial mobile phase was 25% water-75% acetonitrile, at the end the mobile phase was 55% water-45% acetonitrile, the % refers to volume percentage)) to give a white solid 5 (5 mg, yield: 2.6%).

LC-MS (ESI): m/z=308.0[M+H]+.

$^1$H-NMR: (400 MHz, CD$_3$OD) δ:8.54 (d, J=2.4 Hz, 1H), 7.71 (s, 1H), 7.30-7.20 (m, 5H), 6.66-6.64 (dd, J$_1$=2.0 Hz, J$_2$=2.8 Hz, 1H), 5.87 (s, br., 2H), 5.42-5.40 (dd, J$_1$=3.2 Hz, J$_2$=6.0 Hz, 1H), 3.51-3.47 (dd, J$_1$=2.4 Hz, J$_2$=10.4 Hz, 1H), 3.14-3.09 (dd, J$_1$=2.4 Hz, J$_2$=11.6 Hz, 1H) ppm.

Embodiment 6

(R)-7-benzyl-4-(furan-2-yl)-5,7-dihydrofuro[3,4-d]pyrimidin-2-amine (Compound 6)

Synthetic Route

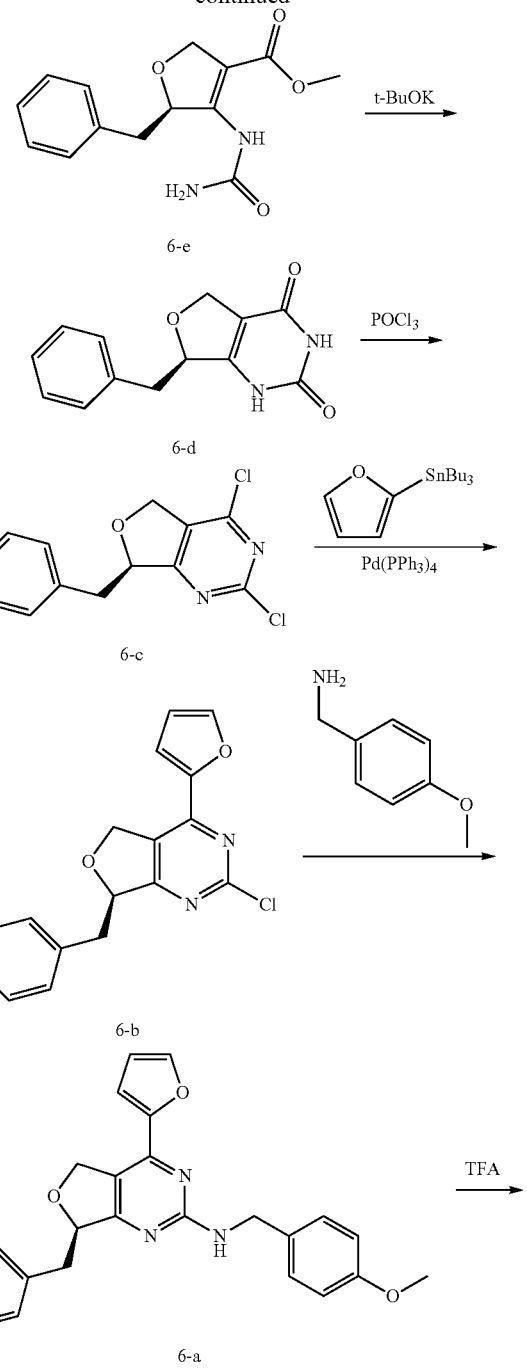

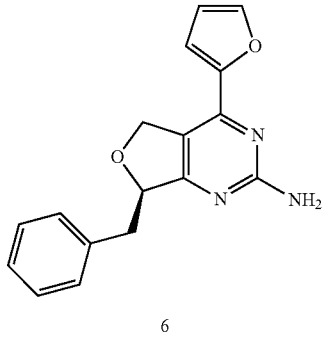

Synthesis of the Compound 6-f

Sodium hydride (480 mg, 12 mmol) was suspended in anhydrous tetrahydrofuran (20 mL), (S)-3-phenyl-2-hydracrylic acid (1.08 g, 6 mmol) was added dropwise at 0° C. After the completion of the addition, the reaction was continued stirring for 30 mins at 0° C., followed by adding of methyl acrylate (0.74 g, 9 mmol). After stirring for 3 hours at room temperature, the reaction was quenched by 0.5 M hydrochloric acid (30 mL), and extracted with EtOAc (30 mL×3). The organic phases were combined and washed by saturated brine (50 mL), dried over anhydrous sodium sulfate. After concentration under reduced pressure, the residue was purified by silica gel chromatography (PE:EtOAc=10:1) to give a colorless liquid product 6-f (600 mg, yield: 43%).

Synthesis of the Compound 6-e

Urea (460 mg, 7.68 mmol) and 35% concentrated hydrochloric acid (0.5 mL) were added into compound 6-f (600 mg, 2.56 mmol) in ethanol (20 mL) solution, and was heated and refluxed for reaction for 4 hours, then was cooled down to room temperature, and concentrated under reduced pressure, the residue was added into EtOAc (40 mL), and then washed by water (40 mL) and saturated brine (40 mL) successively, dried over anhydrous sodium sulfate. After concentration under reduced pressure, the residue was purified by silica gel chromatography (PE:EtOAc=1:2) to give a pale yellow solid product 6-e (320 mg, yield: 45%).

LC-MS (ESI): m/z=277[M+1]$^+$.

Synthesis of the Compound 6-d

Compound 6-e (320 mg, 1.16 mmol) was dissolved in ethanol (10 mL) and tetrahydrofuran (5 mL) solution, potassium tert-butoxide (190 mg, 1.70 mmol) was added. The reaction mixture was stirred for 2 hours at 60° C., then cooled down to room temperature. After concentration under reduced pressure, the residue was dissolve by adding water (6 mL), 1 M hydrochloric acid was added dropwise until pH<2, a white solid was precipitated. After filtration, the residue was dried in vacuum to give a white solid 6-d (226 mg, yield: 80%).

$^1$HNMR (500 MHz, DMSO-d$_6$) δ:11.57 (s, 1H), 11.02 (s, 1H), 7.26-7.29 (m, 2H), 7.19-7.22 (m, 3H), 5.17-5.20 (m, 1H), 4.56-4.58 (m, 1H), 4.41-4.44 (m, 1H), 3.13-3.17 (m, 1H), 2.89-2.93 (m, 1H) ppm.

Synthesis of the Compound 6-c

Compound 6-d (220 mg, 0.9 mmol) was suspended in phosphorus oxychloride (2 mL), N,N-dimethylaniline (2 drops) was added. The reaction mixture was stirred for 2 hours at 110° C., then cooled down to room temperature. After concentration under reduced pressure, EtOAc (20 mL) was added into the residue, and washed by ice water (20 mL) and saturated brine (20 mL) successively. After concentration under reduced pressure, the residue was purified by silica gel chromatography (PE:EtOAc=10:1) to give a white solid 6-c (130 mg, yield: 51%).

LC-MS (ESI): m/z=281[M+1]$^+$.

Synthesis of the Compound 6-b

Compound 6-c (130 mg, 0.46 mmol) was dissolved in dry tetrahydrofuran (10 mL), 2-(tributylstannyl)furane (249 mg, 0.67 mmol), lithium chloride (210 mg, 5 mmol) and palladium tetrakis(triphenyl)phosphine (21 mg, 0.2 mmol). Under nitrogen atmosphere the mixture was stirred for 6 hours at 55° C., then cooled down to room temperature. After concentration under reduced pressure, the residue was purified by silica gel chromatography (PE:EtOAc=10:1) to give a pale yellow solid 6-b (117 mg, yield: 81%).

LC-MS (ESI): m/z=313[M+1]$^+$.

Synthesis of the Compound 6-a

Compound 6-b (110 mg, 0.35 mmol) was dissolved in dioxane (10 mL), then p-methoxybenzylamine (141 mg, 1.0 mmol) and di(isopropyl)ethylamine (271 mg, 2.1 mmol) were added. The reaction mixture was heated and refluxed for 4 hours, then cooled down to room temperature. After concentration under reduced pressure, the residue was purified by silica gel chromatography (PE:EtOAc=10:1-3:1) to give a pale yellow solid 6-a (84 mg, yield: 58%).

LC-MS (ESI): m/z=414[M+1]$^+$.

Synthesis of the Compound 6

Compound 6-a (84 mg, 0.2 mmol) was added into trifluoroacetic acid (10 mL), the reaction mixture was heated and refluxed for 6 hours, then cooled down to room temperature. After concentration under reduced pressure, the residue was washed by saturated dicarbonate water solution (20 mL), then extracted with EtOAc (20 mL×3). The organic phases were combined and then concentrated under reduced pressure, and the residue was purified by silica gel chromatography (PE:EtOAc=10:1-3:1) to give a yellow solid 6 (30 mg, yield: 50%).

LC-MS (ESI): m/z=294[M+1]$^+$.

$^1$HNMR (500 MHz, CDCl$_3$) δ: 7.60 (s, 1H), 7.19-7.26 (m, 5H), 7.08 (d, J=3.5 Hz, 1H), 6.55-6.57 (m, 1H), 5.35 (brs, 2H), 5.21-5.23 (m, 1H), 5.16 (d, J=12.5 Hz, 1H), 5.08 (dd, J=12.5 Hz, 2.5 Hz, 1H), 3.30 (dd, J=14 Hz, 4.0 Hz, 1H), 2.96-3.01 (m, 1H) ppm Embodiment 7

2-amino-7-(3-chloro-4-fluorobenzyl)-4-(furan-2-yl)-5H,7H-furo[3,4-d]pyrimidin-5-one (Compound 7)

Synthetic Route

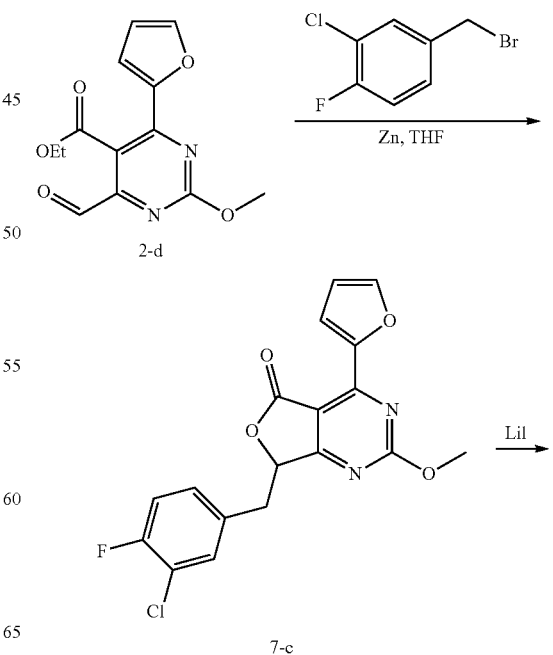

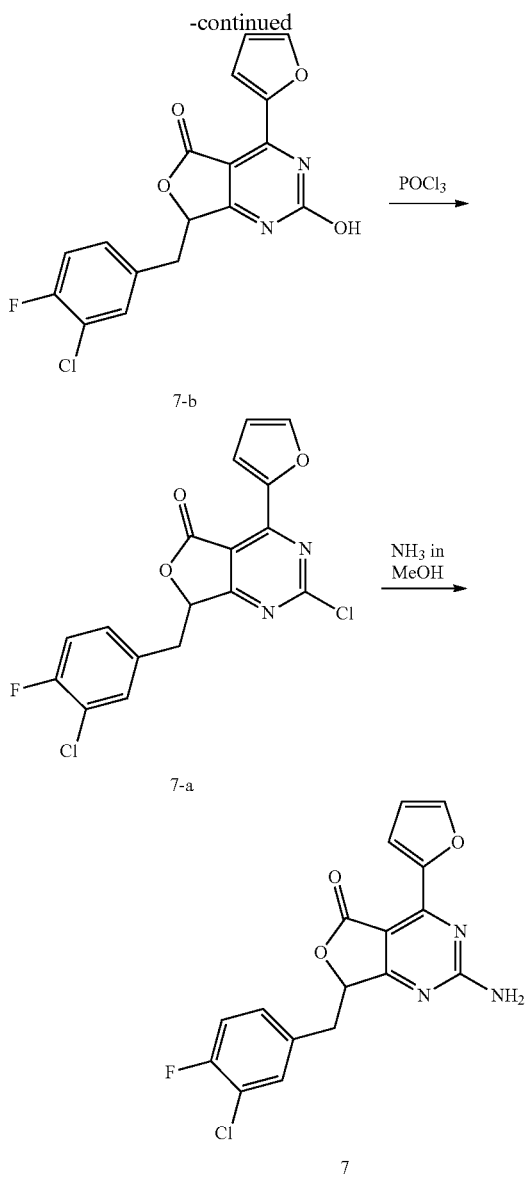

Synthesis of the Compound 7-c

At room temperature, compound 2-d (552 mg, 2.0 mmol) was dissolved in anhydrous tetrahydrofuran (30 mL), zinc powder (390 mg, 6.0 mmol) and 4-fluoro-3-chlorobenzyl bromide (892 mg, 4.0 mmol) were added into the reaction solution. The reaction mixture was slowly heated to 60° C., stirred for 2 hours. After cooling down to room temperature, saturated ammonium chloride solution (50 mL) was added to quench the reaction. After extraction with EtOAc (50 mL×2), the organic phases were combined and washed successively by water (30 mL) and saturated brine (20 mL), dried over anhydrous sodium sulfate. After concentration under reduced pressure, the residue was purified by silica gel chromatography (PE:EtOAc=6:1) to give a white solid 7-c (450 mg, yield: 61%).

LC-MS (ESI): m/z=375.0[M+1]$^+$.

Synthesis of the Compound 7-b

Compound 7-c (450 mg, 1.2 mmol) was dissolved in pyridine (15 mL), lithium iodide (806 mg, 6.0 mmol) was added at room temperature. The reaction mixture was stirred for 16 hours at 120° C. and then cooled down to room temperature. After concentration under reduced pressure, the residue was purified by silica gel chromatography (EtOAc:MeOH=100:1-5:1) to give a pale yellow solid 7-b (300 mg, yield: 69%).

LC-MS (ESI): m/z=361.0[M+1]$^+$.

Synthesis of the Compound 7-a

Compound 7-b (300 mg, 0.83 mmol) was dissolved in phosphorus oxychloride (15 mL), the reaction mixture was stirred for 3 hours at 120° C. and then cooled down to room temperature. After concentration under reduced pressure, the residue was added into a mixture of ice and water (100 mL), and extracted with EtOAc (50 mL×2), the organic phases were combined and washed by water (30 mL) and saturated brine (20 mL), dried over anhydrous sodium sulfate. Then the solution was concentrated under reduced pressure to give a brown solid 7-a (200 mg, yield: 63.8%). The product was used directly in the next step without further purification.

LC-MS (ESI): m/z=378.9[M+1]$^+$.

Synthesis of the Compound 7

Compound 7-a (200 mg, 0.53 mmol) was dissolved in tetrahydrofuran (10 mL), ammonia in methanol solution (10 mL) was added at room temperature and stirred for 2 hours. The reaction solution was then concentrated, the residue was added into methanol (10 mL), then treated with ultrasound for 1 min, followed by filtration. The residue was dried in vacuum to give a white solid 7 (48 mg, yield: 25%).

LC-MS (ESI): m/z=360.0[M+H]$^+$.

$^1$H NMR: (400 MHz CD$_3$OD) δ: 8.55 (d, J=2.8 Hz, 1H), 7.73 (s, 1H), 7.34-7.32 (m, 1H), 7.17-7.13 (m, 1H), 7.05 (t, J=6.8 Hz, 1H), 6.68-6.66 (m, 1H), 5.80 (bs, 1H), 5.37-5.35 (m, 1H), 3.46-3.41 (dd, J$_1$=2.8 Hz, J$_2$=11.6 Hz, 1H), 3.10-3.04 (dd, J$_1$=6.4 Hz, J$_2$=12.0 Hz, 1H) ppm.

Embodiment 8

2-amino-7-(2,4-difluorobenzyl)-4-(furan-2-yl)-5H,7H-furo[3,4-d]pyrimidin-5-one (Compound 8)

Synthetic Route

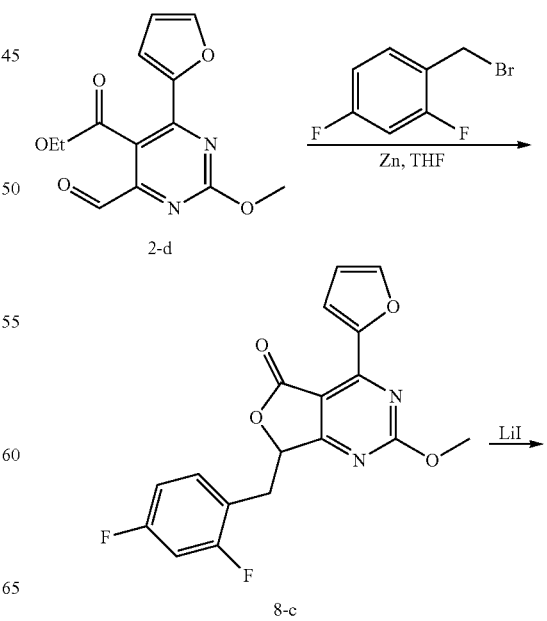

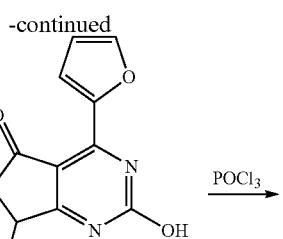

8-b

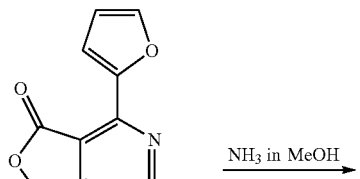

8-a

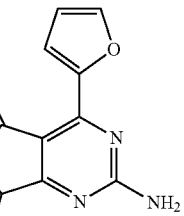

8

Synthesis of the Compound 8-c

At room temperature, Compound 2-d (6.75 g, 32.6 mmol) was dissolved in anhydrous tetrahydrofuran (200 mL), zinc powder (2.13 g, 32.6 mmol) was added into the reaction solution. The reaction mixture was heated to 55° C., then 2,4-difluorobenzyl bromide (3.0 g, 10.8 mmol) was added and stirred for 1 hour. After cooling down to room temperature, saturated ammonium chloride solution (100 mL) was added to quench the reaction. After extraction with EtOAc (100 mL×2), the organic phases were combined and washed successively by water (100 mL) and saturated brine (100 mL), dried over anhydrous sodium sulfate. After concentration under reduced pressure, the residue was purified by silica gel chromatography (PE:EtOAc=5:1) to give a yellow solid 8-c (3.4 g, yield: 87%).

LC-MS (ESI): m/z=359.0[M+1]⁺.

Synthesis of the Compound 8-b

Compound 8-c (3.4 g, 9.5 mmol) was dissolved in dioxane (35 mL), concentrated hydrochloric acid (4 mL) was added at room temperature, the mixture was stirred at 100° C. for 4 hours, then cooled down to room temperature. The reaction solution was then concentrated, and the residue was purified by silica gel chromatography (EtOAc:MeOH=20:1) to give a brown solid 8-b (3.0 g, yield: 92%).

LC-MS (ESI): m/z=345.0[M+1]⁺.

Synthesis of the Compound 8-a

Compound 8-b (3.0 g, 8.7 mmol) was dissolved in phosphorus oxychloride (35 mL), and N,N-dimethylaniline (0.5 mL) was added. The reaction mixture was stirred at 125° C. for 2 hours and then cooled down to room temperature, then concentrated under reduced pressure, the residue was added into a mixture of ice and water (300 mL), and extracted with EtOAc (100 mL×2), the organic phases were combined and washed by water (100 mL) and saturated brine (100 mL), dried over anhydrous sodium sulfate. After concentration under reduced pressure, the residue was purified by silica gel chromatography (PE:EtOAc=10:1) to give a yellow solid 8-a (1.3 g, yield: 41%).

LC-MS (ESI): m/z=363.0[M+1]⁺.

Synthesis of the Compound 8

Compound 8-a (1.3 g, 3.59 mmol) was dissolved in tetrahydrofuran (30 mL), ammonia in methanol solution (6 mL) was added at room temperature, and stirred for 1 hour. The reaction mixture was then concentrated under reduced pressure, the residue was added into methanol (20 mL) and stirred for 15 mins, followed by filtration. The residue was dried in vacuum to give a compound 8 (910 mg, yield: 76%).

LC-MS (ESI): m/z=344.0[M+H]⁺.

¹H NMR (400 MHz, CDCl₃) δ:8.54-8.53 (d, J=2.8 Hz, 1H), 7.71 (s, 1H), 7.29-7.28 (m, 1H), 6.83-6.74 (m, 2H), 6.66-6.65 (m, 1H), 5.82 (s, 2H), 5.3-5.35 (m, 1H), 3.53-3.51 (m, 1H), 3.02-2.97 (m, 1H) ppm Embodiment 9

2-amino-7-(4-chlorobenzyl)-4-(furan-2-yl)-5H,7H-furo[3,4-d]pyrimidin-5-one (Compound 9)

Synthetic Route

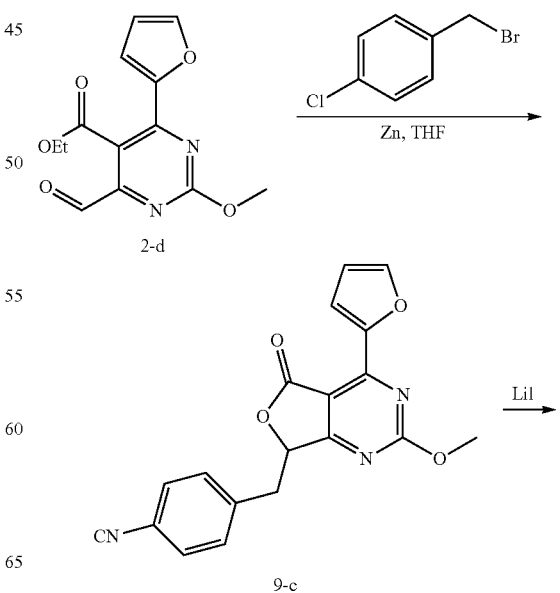

9-c

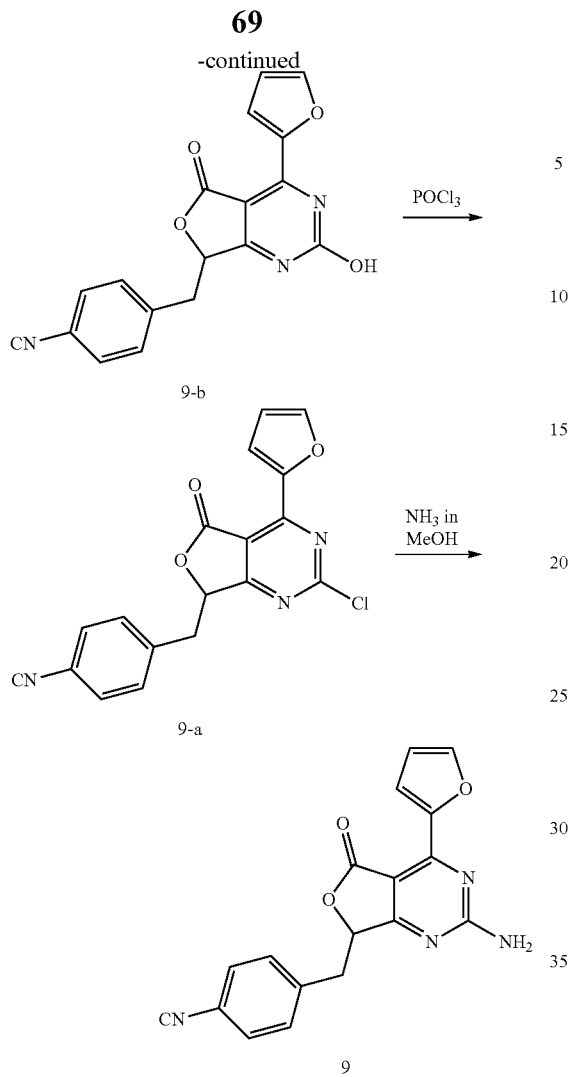

Synthesis of the Compound 9-c

At room temperature, compound 2-d (276 mg, 1.0 mmol) was dissolved in anhydrous tetrahydrofuran (20 mL), zinc powder (260 mg, 4.0 mmol) and 4-chlorobenzyl bromide (412 mg, 2.0 mmol) were added into the reaction solution. The reaction mixture was heated to 60° C. and stirred for 2 hours. After cooling down to room temperature, saturated ammonium chloride solution (20 mL) was added to quench the reaction. After extraction with EtOAc (50 mL×2), the organic phases were combined and washed successively by water (50 mL) and saturated brine (50 mL), dried over anhydrous sodium sulfate. After concentration under reduced pressure, the residue was purified by silica gel chromatography (PE:EtOAc=6:1) to give a yellow solid 9-c (310 mg, yield: 87%).

LC-MS (ESI): m/z=357.0[M+1]$^+$.

Synthesis of the Compound 9-b

Compound 9-c (310 mg, 0.87 mmol) was dissolved in pyridine (30 mL), lithium iodide (583 mg, 4.35 mmol) was added at room temperature. The reaction mixture was stirred for 16 hours at 120° C. and then cooled down to room temperature. After concentration under reduced pressure, the residue was purified by silica gel chromatography (EtOAc:MeOH=100-5:1) to give a brown solid 9-b (200 mg, yield: 67%).

LC-MS (ESI): m/z=342.9[M+1]$^+$.

Synthesis of the Compound 9-a

Compound 9-b (200 mg, 0.58 mmol) was dissolved in phosphorus oxychloride (20 mL), the reaction mixture was stirred for 3 hours at 120° C. and then cooled down to room temperature. After concentration under reduced pressure, the residue was added into a mixture of ice and water (100 mL), and extracted with EtOAc (50 mL×2), the organic phases was combined and washed by water (30 mL) and saturated brine (20 mL), dried over anhydrous sodium sulfate. Then the solution was concentrated under reduced pressure to give a brown solid 9-a (100 mg, yield: 46.5%). The product was used directly in the next step without further purification.

LC-MS (ESI): m/z=360.9[M+1]$^+$.

Synthesis of the Compound 9

Compound 9-a (100 mg, 0.27 mmol) was dissolved in tetrahydrofuran (10 mL), ammonia in methanol solution (5 mL) was added at room temperature, and stirred for 1 hour. The reaction mixture was then concentrated under reduced pressure, methanol (20 mL) was added into the residue, then treated with ultrasound for 1 min, followed by filtration. The residue was dried in vacuum to give a compound 9 (15 mg, yield: 16%).

LC-MS (ESI): m/z=342.0[M+H]$^+$.

$^1$H NMR (400 MHz CDCl$_3$) δ: 8.53 (d, J=3.2 Hz, 1H), 7.72 (s, 1H), 7.28-7.20 (m, 4H), 6.66 (d, J=1.6 Hz, 1H), 5.80 (bs, 2H), 5.39-5.37 (m, 1H), 3.47-3.43 (dd, J$_1$=3.2 Hz, J$_2$=12.0 Hz, 1H), 3.13-3.08 (dd, J$_1$=5.2 Hz, J$_2$=11.6 Hz, 1H) ppm

Embodiment 10

2-amino-7-(2-chloro-4-fluorobenzyl)-4-(furan-2-yl)-5H,7H-furo[3,4-d]pyrimidin-5-one (Compound 10)

Synthetic Route

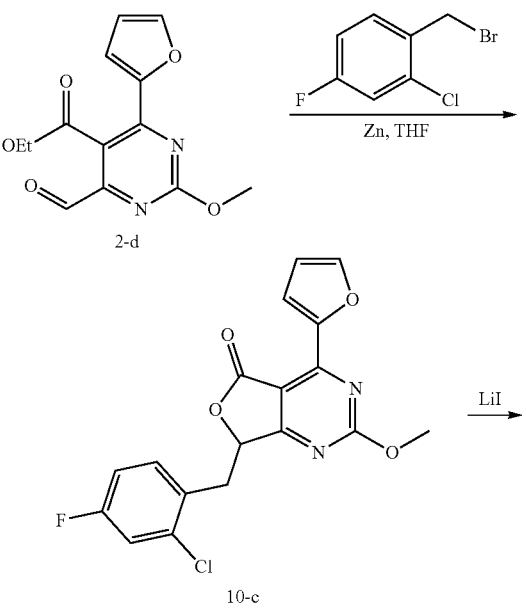

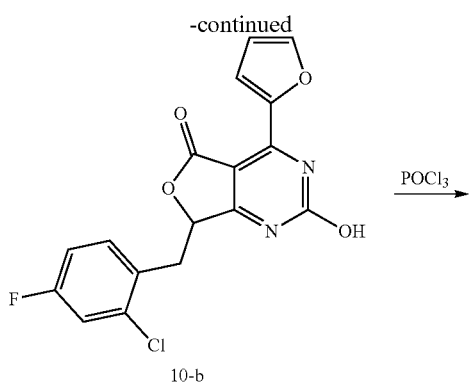

10-b

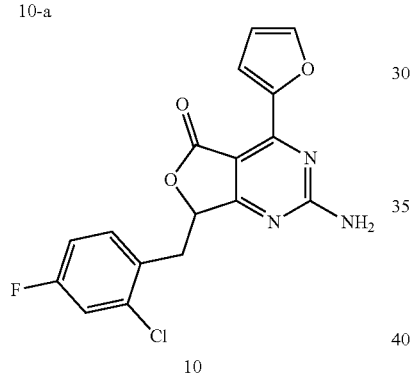

10-a

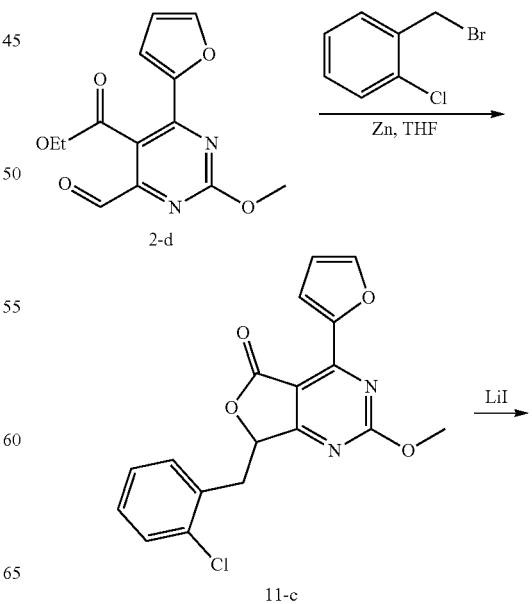

10

Synthesis of the Compound 10-c

At room temperature, 4-fluoro-2-chlorobenzyl bromide (729 mg, 3.26 mmol) was dissolved in anhydrous tetrahydrofuran (20 mL), zinc powder (213 mg, 3.26 mmol) was added. The reaction mixture was heated to 55° C., then compound 2-d (300 mg, 1.08 mmol) was added and stirred for 1 hour. After cooling down to room temperature, saturated ammonium chloride solution (50 mL) was added to quench the reaction. After extraction with EtOAc (50 mL×2), the organic phases were combined and washed successively by water (50 mL) and saturated brine (50 mL), dried over anhydrous sodium sulfate. After concentration under reduced pressure, the residue was purified by silica gel chromatography (PE:EtOAc=5:1) to give a white solid 10-c (200 mg, yield: 50%).

LC-MS (ESI): m/z=375[M+1]$^+$.

Synthesis of the Compound 10-b

Compound 10-c (200 mg, 0.53 mmol) was dissolved in pyridine (15 mL), lithium iodide (358 mg, 2.07 mmol) was added at room temperature. The reaction mixture was stirred for 4 hours at 125° C. and then cooled down to room temperature. After concentration under reduced pressure, the residue was purified by silica gel chromatography (EtOAc: MeOH=50:1) to give a yellow solid 10-b (150 mg, yield: 79%).

LC-MS (ESI): m/z=361[M+1]$^+$.

Synthesis of the Compound 10-a

Compound 10-b (150 mg, 0.42 mmol) was dissolved in phosphorus oxychloride (15 mL), N,N-dimethylaniline (0.02 mL) was then added. The reaction mixture was stirred for 2 hours at 125° C. and then cooled down to room temperature, then concentrated under reduced pressure, the residue was added into a mixture of ice and water (100 mL), and extracted with EtOAc (100 mL×2), the organic phases were combined and washed by water (50 mL) and saturated brine (50 mL), dried over anhydrous sodium sulfate. Then the solution was concentrated under reduced pressure to give a yellow solid 10-a (100 mg, yield: 61.9%). The product was used directly in the next step without further purification.

LC-MS (ESI): m/z=379.0[M+1]$^+$.

Synthesis of the Compound 10

Compound 10-a (100 mg, 0.26 mmol) was dissolved in tetrahydrofuran (10 mL), ammonia in methanol solution (1 mL) was added at room temperature, and stirred for 15 mins. The reaction mixture was then concentrated under reduced pressure, and the residue was purified by silica gel chromatography (DCM:EtOAc=20:1) to give the compound 10 (27 mg, yield: 28%).

LC-MS (ESI): m/z=360.0[M+H]$^+$.

$^1$H NMR (400 MHz, DMSO-d$_6$) δ: 8.30 (s, 1H), 8.09-8.04 (m, 3H), 7.50-7.46 (m, 2H), 7.26-7.25 (m, 1H), 6.79 (s, 1H), 5.54-5.17 (m, 1H), 3.51-3.48 (m, 1H), 3.07-3.03 (m, 1H) ppm Embodiment 11

2-amino-7-(2-chlorobenzyl)-4-(furan-2-yl)-5H,7H-furo[3,4-d]pyrimidin-5-one (Compound 11)

Synthetic Route

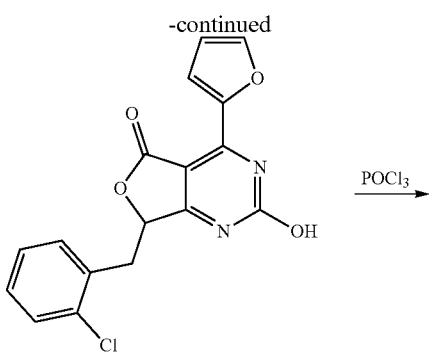

11-b

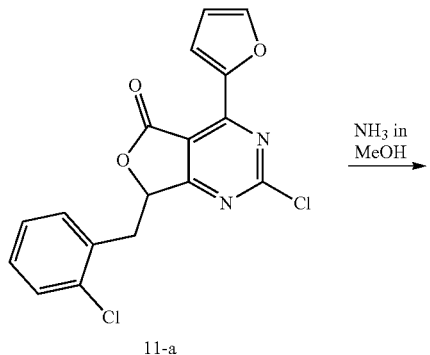

11-a

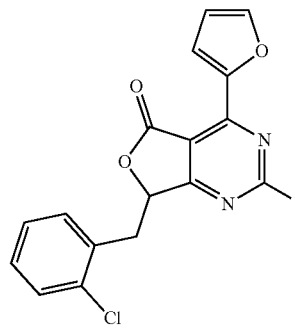

11

Synthesis of the Compound 11-c

At room temperature, compound 2-d (276 mg, 1.0 mmol) was dissolved in anhydrous tetrahydrofuran (20 mL), zinc powder (260 mg, 4.0 mmol) and 2-chlorobenzyl bromide (412 mg, 2.0 mmol) were added into the reaction solution. The reaction mixture was heated to 60° C. and stirred for 2 hours. After cooling down to room temperature, saturated ammonium chloride solution (20 mL) was added to quench the reaction. After extraction with EtOAc (50 mL×2), the organic phases were combined and washed successively by water (50 mL) and saturated brine (50 mL), dried over anhydrous sodium sulfate. After concentration under reduced pressure, the residue was purified by silica gel chromatography (PE:EtOAc=6:1) to give a yellow solid 11-c (320 mg, yield: 89%).

LC-MS (ESI): m/z=357.0[M+1]$^+$.

Synthesis of the Compound 11-b

Compound 11-c (320 mg, 0.89 mmol) was dissolved in pyridine (20 mL), lithium iodide (602 mg, 4.5 mmol) was added at room temperature. The reaction mixture was stirred for 16 hours at 120° C. and then cooled down to room temperature. After concentration under reduced pressure, the residue was purified by silica gel chromatography (EtOAc: MeOH=100-5:1) to give a brown solid 11-b (190 mg, yield: 62%).

LC-MS (ESI): m/z=343[M+1]$^+$.

Synthesis of the Compound 11-a

Compound 11-b (190 mg, 0.55 mmol) was dissolved in phosphorus oxychloride (10 mL), the reaction mixture was stirred for 3 hours at 120° C. and then cooled down to room temperature. After concentration under reduced pressure, the residue was added into a mixture of ice and water (100 mL), and extracted with EtOAc (50 mL×2), the organic phases were combined and washed by water (30 mL) and saturated brine (20 mL), dried over anhydrous sodium sulfate. Then the solution was concentrated under reduced pressure to give a brown solid 11-a (70 mg, yield: 36.3%). The product was used directly in the next step without further purification.

LC-MS (ESI): m/z=360.9[M+1]$^+$.

Synthesis of the Compound 11

Compound 11-a (70 mg, 0.19 mmol) was dissolved in tetrahydrofuran (5 mL), ammonia in methanol solution (3 mL) was added at room temperature, and stirred for 1 hour. The reaction mixture was then concentrated under reduced pressure, methanol (20 mL) was added into the residue, then treated with ultrasound for 1 min, followed by filtration. The residue was dried in vacuum to give a compound 11 (15 mg, yield: 22%).

LC-MS (ESI): m/z=342.0[M+H]$^+$.

$^1$H NMR (400 MHz, CDCl$_3$) δ: 8.60 (d, J=2.4 Hz, 1H), 7.71 (s, 1H), 7.43-7.39 (m, 2H), 7.28-7.24 (m, 2H), 6.68 (d, J=2.0 Hz, 1H), 5.86 (s, br., 2H), 5.50-5.48 (m, 1H), 3.75-3.71 (dd, J$_1$=2.8 Hz, J$_2$=12.0 Hz, 1H), 3.03-2.98 (dd, J$_1$=7.6 Hz, J$_2$=11.6 Hz, 1H) ppm Embodiment 12

2-amino-7-(4-chloro-3-fluorobenzyl)-4-(furan-2-yl)-5H,7H-furo[3,4-d]pyrimidin-5-one (Compound 12)

Synthetic Route

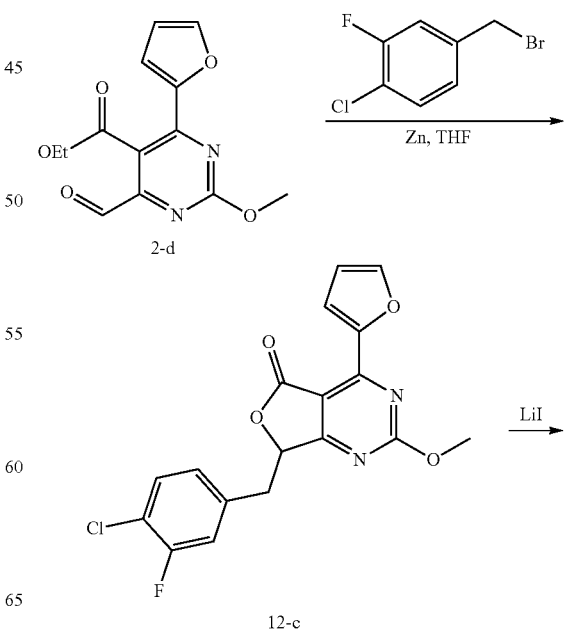

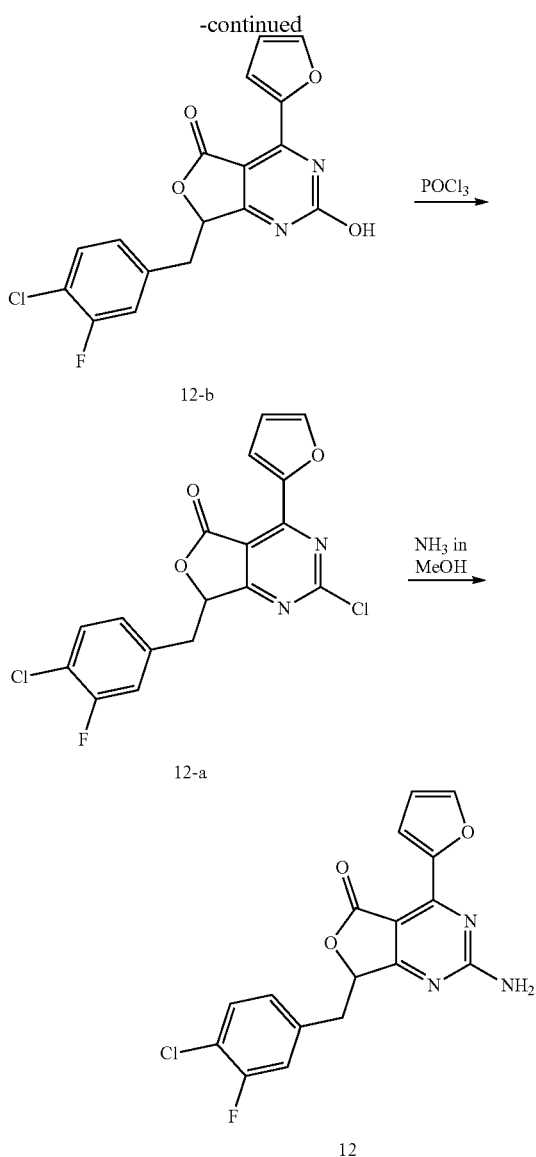

Synthesis of the Compound 12-c

Compound 2-d (552 mg, 2.0 mmol) was dissolved in anhydrous tetrahydrofuran (30 mL) at room temperature, zinc powder (390 mg, 6.0 mmol) and 3-fluoro-4-chlorobenzyl bromide (892 mg, 4.0 mmol) was added into the reaction solution. The reaction mixture was heated to 60° C. and stirred for 2 hours. After cooling down to room temperature, saturated ammonium chloride solution (20 mL) was added to quench the reaction. After extraction with EtOAc (50 mL×2), the organic phases were combined and washed successively with water (50 mL) and saturated brine (50 mL), dried over anhydrous sodium sulfate. After concentration under reduced pressure, the residue was purified by silica gel chromatography (PE:EtOAc=6:1) to give a pale yellow solid 12-c (650 mg, yield: 86%).

LC-MS (ESI): m/z=375.0[M+1]$^+$.

Synthesis of the Compound 12-b

Compound 12-c (600 mg, 1.6 mmol) was dissolved in pyridine (15 mL), lithium iodide (1.07 g, 8.0 mmol) was added at room temperature. The reaction mixture was stirred for 16 hours at 120° C. and then cooled down to room temperature. After concentration under reduced pressure, the residue was purified by silica gel chromatography (EtOAc:MeOH=100-5:1) to give a brown solid 12-b (450 mg, yield: 78%).

LC-MS (ESI): m/z=361[M+1]$^+$.

Synthesis of the Compound 12-a

Compound 12-b (450 mg, 1.25 mmol) was dissolved in phosphorus oxychloride (15 mL), the reaction mixture was stirred for 3 hours at 120° C. and then cooled down to room temperature. After concentration under reduced pressure, the residue was added into a mixture of ice and water (100 mL), and extracted with EtOAc (50 mL×2), the organic phases was combined and washed by water (30 mL) and saturated brine (20 mL), dried over anhydrous sodium sulfate. Then the solution was concentrated under reduced pressure to give a brown solid 12-a (400 mg, yield: 84.6%).

The product was used directly in the next step without further purification.

LC-MS (ESI): m/z=379[M+1]$^+$.

Synthesis of the Compound 12

Compound 12-a (400 mg, 1.05 mmol) was dissolved in tetrahydrofuran (15 mL), ammonia in methanol solution (10 mL) was added at room temperature, and stirred for 1 hour. The reaction mixture was then concentrated under reduced pressure, methanol (20 mL) was added into the residue, then treated with ultrasound for 1 min, followed by filtration. The residue was dried in vacuum to give a compound 12 (5 mg, yield: 2%).

LC-MS (ESI): m/z=360.0[M+H]$^+$.

$^1$H NMR (400 MHz, CDCl$_3$) δ: 8.54 (d, J=2.4 Hz, 1H), 7.73 (s, 1H), 7.31-7.28 (m, 1H), 7.09-7.00 (m, 2H), 6.67-6.66 (m, 1H), 5.88 (s, br., 2H), 5.39-5.36 (m, 1H), 3.47-3.43 (dd, J$_1$=2.0 Hz, J$_2$=12.0 Hz, 1H), 3.12-3.07 (dd, J$_1$=6.0 Hz, J$_2$=12.0 Hz, 1H) ppm Embodiment 13

2-amino-4-(furan-2-yl)-7-(4-methylsulfonylbenzyl)-5H,7H-furo[3,4-d]pyrimidin-5-one (Compound 13)

Synthetic Route

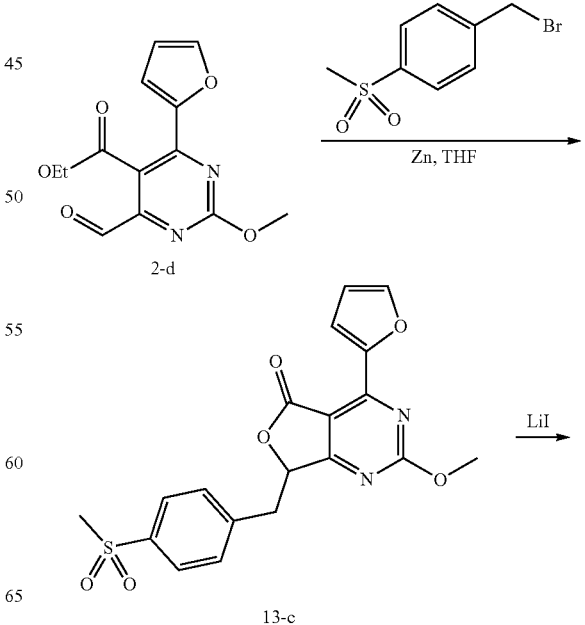

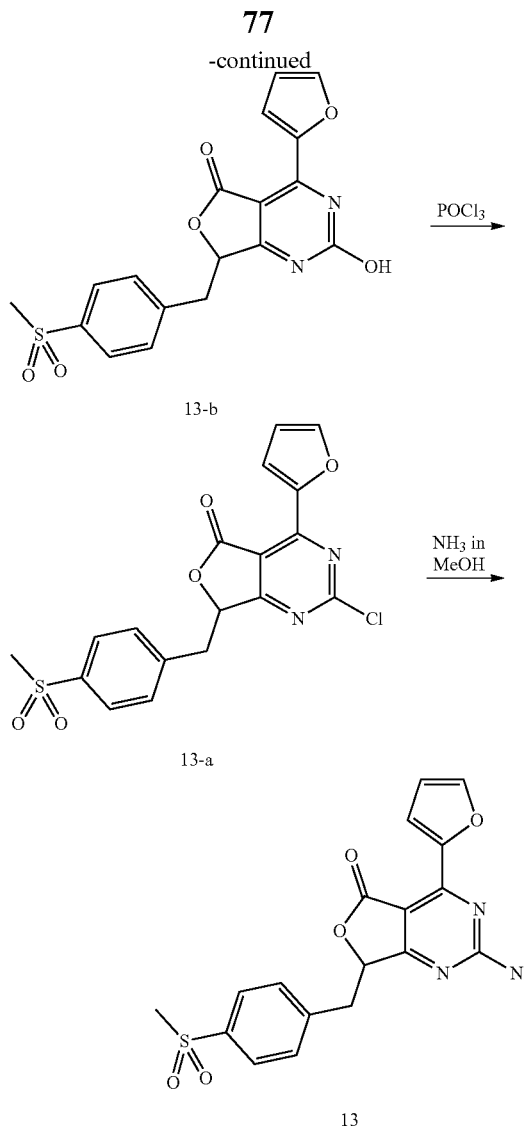

MeOH=5:1) to give a yellow solid 13-b (200 mg, yield: 61%).

LC-MS (ESI): m/z=387[M+1]⁺.

Synthesis of the Compound 13-a

Compound 13-b (200 mg, 0.52 mmol) was dissolved in phosphorus oxychloride (15 mL), and then added N,N-dimethylaniline (0.02 mL). The reaction mixture was stirred for 2 hours at 125° C. and then cooled down to room temperature, then concentrated under reduced pressure, the residue was added into a mixture of ice and water (100 mL), and extracted with EtOAc (100 mL×2), the organic phases were combined and washed by water (50 mL) and saturated brine (50 mL), dried over anhydrous sodium sulfate. Then the solution was concentrated under reduced pressure to give a yellow solid 13-a (200 mg, yield: 95.2%). The product was used directly in the next step without further purification.

LC-MS (ESI): m/z=405[M+1]⁺.

Synthesis of the Compound 13

Compound 13-a (200 mg, 0.52 mmol) was dissolved in tetrahydrofuran (10 mL), ammonia in methanol solution (1 mL) was added at room temperature, and stirred for 15 mins. The reaction mixture was then concentrated under reduced pressure, and the residue was purified by silica gel chromatography (DCM:EtOAc=20:1) to give the compound 13 (50 mg, yield: 23%).

LC-MS (ESI): m/z=386[M+H]⁺.

$^1$H NMR (400 MHz, DMSO-$d_6$) δ: 8.26-8.25 (d, J=3.2 Hz, 1H), 8.11-7.93 (m, 3H), 7.87-7.86 (d, J=6.8 Hz, 2H), 7.56-7.54 (d, J=6.4 Hz, 2H), 6.78-6.77 (m, 1H), 5.66-5.64 (m, 1H), 3.48-3.44 (m, 1H), 3.19 (s, 3H), 3.15-3.10 (m, 1H) ppm Embodiment 14

4-((2-amino-4-(furan-2-yl)-5-oxo-5H,7H-furo[3,4-d]pyrimidin-7-yl)methyl)benzamide (Compound 14)

Synthetic Route

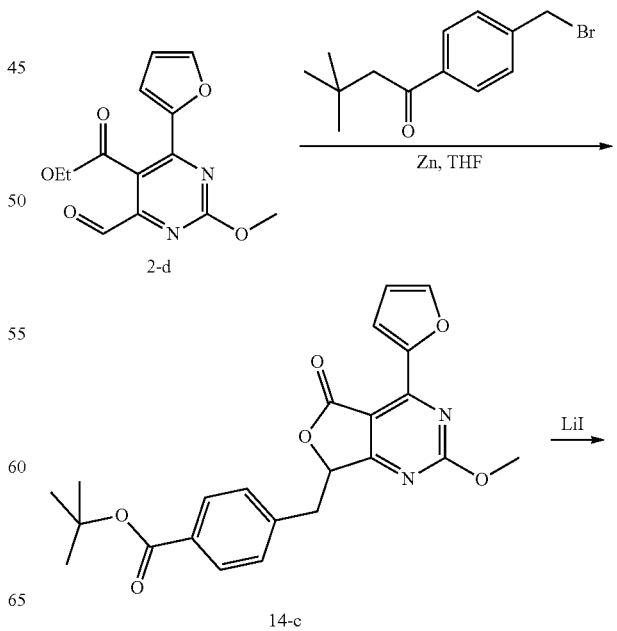

Synthesis of the Compound 13-c

At room temperature, 4-methylsulfonyl benzyl bromide (809 mg, 3.26 mmol) was dissolved in anhydrous tetrahydrofuran (20 mL), zinc powder (213 mg, 3.26 mmol) was added. The reaction mixture was heated to 55° C., compound 2-d (300 mg, 1.08 mmol) was added and stirred for 1 hour. After cooling down to room temperature, saturated ammonium chloride solution (50 mL) was added to quench the reaction. After extraction with EtOAc (50 mL×2), the organic phases were combined and washed successively by water (50 mL) and saturated brine (50 mL), dried over anhydrous sodium sulfate. After concentration under reduced pressure, the residue was purified by silica gel chromatography (PE:EtOAc=5:1) to give a white solid 13-c (340 mg, yield: 78%).

LC-MS (ESI): m/z=401[M+1]⁺.

Synthesis of the Compound 13-b

Compound 13-c (340 mg, 0.85 mmol) was dissolved in pyridine (15 mL), lithium iodide (569 mg, 4.25 mmol) was added at room temperature. The reaction mixture was stirred for 4 hours at 125° C. and then cooled down to room temperature. After concentration under reduced pressure, the residue was purified by silica gel chromatography (EtOAc:

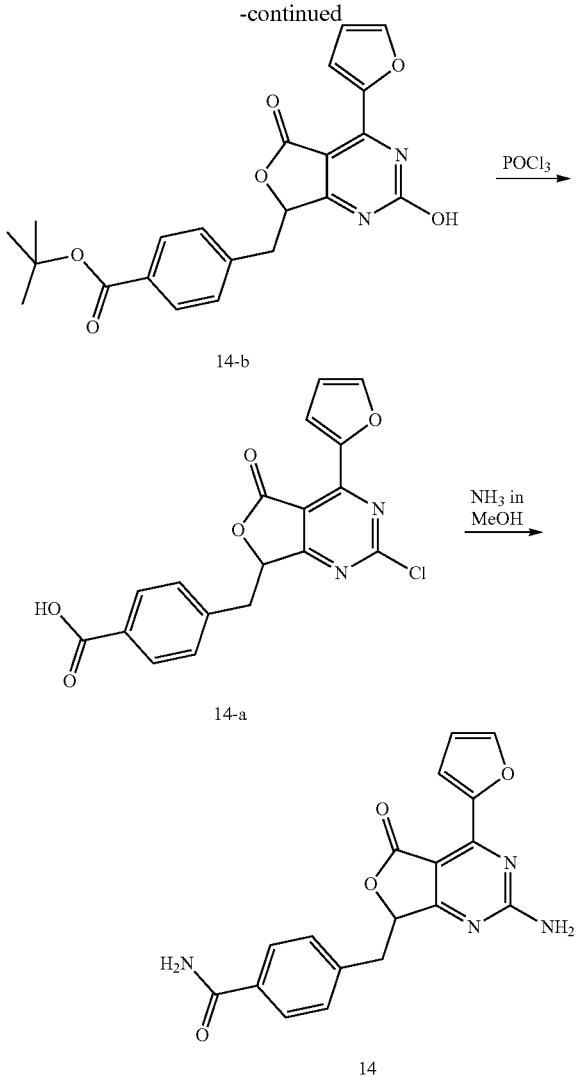

Synthesis of the Compound 14-a

Compound 14-b (190 mg, 0.45 mmol) was dissolved in phosphorus oxychloride (15 mL), the reaction mixture was stirred at 120° C. for 3 hours, cooled down to room temperature. The reaction solution was then concentrated, the residue was added into a mixture of ice and water (50 mL), and extracted with EtOAc (50 mL×2), the organic phases were combined and washed with water (30 mL) and saturated brine (20 mL), dried over anhydrous sodium sulfate. After concentration under reduced pressure, the residue was dissolved in methanol (20 mL), then the solution was concentrated under reduced pressure to give a brown crude product 14-a (200 mg), the product was used directly in the next step without further purification.

LC-MS (ESI): m/z=384.9[M+H]$^+$.

Synthesis of the Compound 14

Compound 14-b (200 mg) was dissolved in tetrahydrofuran (5 mL), ammonia in methanol solution (10 mL) was added at room temperature and continued stirring for 16 hours. After concentration under reduced pressure, the residue was purified by HPLC (mobile phase: water (10 mM ammonium bicarbonate), acetonitrile; gradient: 25%-55% (initial mobile phase was 25% water-75% acetonitrile, at the end the mobile phase was 55% water-45% acetonitrile, the % refers to volume percentage)) to give a pale yellow solid 14 (7 mg, yield: 4.4%).

LC-MS (ESI): m/z=351 [M+H]$^+$.

$^1$H NMR: (400 MHz, DMSO-d$_6$) δ: 8.24 (d, J=2.4 Hz, 1H), 8.09 (s, 1H), 7.93 (s, 1H), 7.91 (s, 1H), 7.78 (d, J=6.8 Hz, 1H), 7.31 (s, 1H), 7.29 (d, J=6.8 Hz, 1H), 6.77-6.75 (q, 1H), 5.65-5.62 (q, 1H), 3.43-3.39 (dd, J$_1$=2.8 Hz, J$_2$=11.6 Hz, 1H), 3.13-3.05 (dd, J$_1$=6.0 Hz, J$_2$=11.6 Hz, 1H) ppm Embodiment 15

2-amino-4-(furan-2-yl)-7-((4-(trifluoromethyl)phenyl)methyl-5H,7H-furo[3,4-d]pyrimidin-5-one (Compound 15)

Synthetic Route

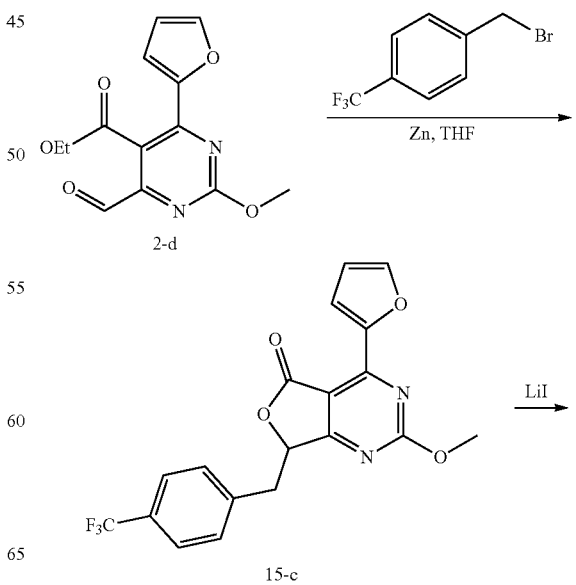

Synthesis of the Compound 14-c

Compound 2-d (276 mg, 1.0 mmol) was dissolved in anhydrous tetrahydrofuran (20 mL) at room temperature, zinc powder (325 mg, 5.0 mmol) and 4-bromomethyl tert-butyl benzoate (325 mg, 1.2 mmol) were added into the reaction solution. The reaction mixture was slowly heated to 60° C., stirred for 2 hours then cooled down to room temperature. Saturated ammonium chloride (20 mL) was added to quench the reaction. After extraction with EtOAc (50 mL×2), the organic phases were combined and washed successively by water (30 mL) and saturated brine (20 mL), dried over anhydrous sodium sulfate, then concentrated under reduced pressure, and the residue was purified by silica gel chromatography (PE:EtOAc=6:1-3:1) to give a yellow solid 14-c (390 mg, yield: 92%).

LC-MS (ESI): m/z=423.0[M+H]$^+$.

Synthesis of the Compound 14-b

Compound 14-c (390 mg, 0.92 mmol) was dissolved in pyridine (20 mL), lithium iodide (619 mg, 4.62 mmol) was added at room temperature. The reaction mixture was stirred at 120° C. for 16 hours, cooled down to room temperature. The reaction solution was then concentrated, and the residue was purified by silica gel chromatography (EtOAc:MeOH=100:1-5:1) to give a brown solid 14-b (190 mg, yield: 50%). LC-MS (ESI): m/z=409.0[M+1]$^+$.

-continued

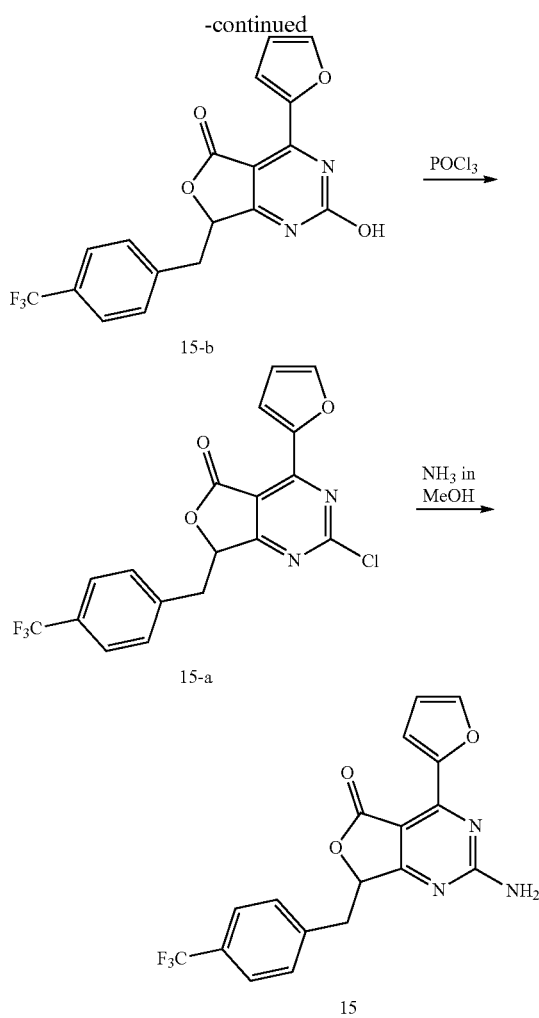

Synthesis of the Compound 15-c

At room temperature, 4-trifluoromethyl benzyl bromide (780 mg, 3.26 mmol) was dissolved in anhydrous tetrahydrofuran (20 mL), zinc powder (213 mg, 3.26 mmol) was added. The reaction mixture was heated to 55° C., then compound 2-d (300 mg, 1.08 mmol) was added and stirred for 1 hour. After cooling down to room temperature, saturated ammonium chloride solution (50 mL) was added to quench the reaction. After extraction with EtOAc (50 mL×2), the organic phases were combined and washed successively by water (50 mL) and saturated brine (50 mL), dried over anhydrous sodium sulfate. After concentration under reduced pressure, the residue was purified by silica gel chromatography (PE:EtOAc=5:1) to give a white solid 15-c (330 mg, yield: 78%).

LC-MS (ESI): m/z=391[M+1]$^+$.

Synthesis of the Compound 15-b

Compound 15-c (330 mg, 0.85 mmol) was dissolved in pyridine (15 mL), lithium iodide (566 mg, 4.23 mmol) was added at room temperature. The reaction mixture was stirred at 125° C. for 4 hours and then cooled down to room temperature. After concentration under reduced pressure, the residue was purified by silica gel chromatography (EtOAc:MeOH=5:1) to give a yellow solid 15-b (300 mg, yield: 93%).

LC-MS (ESI): m/z=377[M+1]$^+$.

Synthesis of the Compound 15-a

Compound 15-b (300 mg, 0.77 mmol) was dissolved in phosphorus oxychloride (15 mL), and N,N-dimethylaniline (0.02 mL) was added. The reaction mixture was stirred at 125° C. for 2 hours and then cooled down to room temperature, then concentrated under reduced pressure, the residue was added into a mixture of ice and water (100 mL), and extracted with EtOAc (100 mL×2), the organic phases was combined and washed by water (50 mL) and saturated brine (50 mL), dried over anhydrous sodium sulfate. Then the solution was concentrated under reduced pressure to give a yellow solid 15-a (300 mg, yield: 95.6%). The product was used directly in the next step without further purification.

LC-MS (ESI): m/z=395[M+1]$^+$.

Synthesis of the Compound 15

Compound 15-a (300 mg, 0.76 mmol) was dissolved in tetrahydrofuran (15 mL), ammonia in methanol solution (1 mL) was added at room temperature, and stirred for 15 mins. The reaction mixture was then concentrated under reduced pressure, and the residue was purified by silica gel chromatography (DCM:EtOAc=15:1) to give the compound 15 (53 mg, yield: 19%).

LC-MS (ESI): m/z=376[M+H]$^+$.

$^1$H NMR (400 MHz, CDCl$_3$) δ: 8.51-8.50 (d, J=2.8 Hz, 1H), 7.703-7.701 (m, 1H), 7.56-7.52 (m, 2H), 7.39-7.37 (m, 2H), 6.64-6.63 (m, 1H), 5.87 (s, 2H), 5.39-5.37 (m, 1H), 3.53-3.51 (m, 1H), 3.16-3.12 (m, 1H) ppm Embodiment 16

2-amino-4-(furan-2-yl)-7-((2-(trifluoromethyl)phenyl)methyl)-5H,7H-furo[3,4-d]pyrimidin-5-one (Compound 16)

Synthetic Route

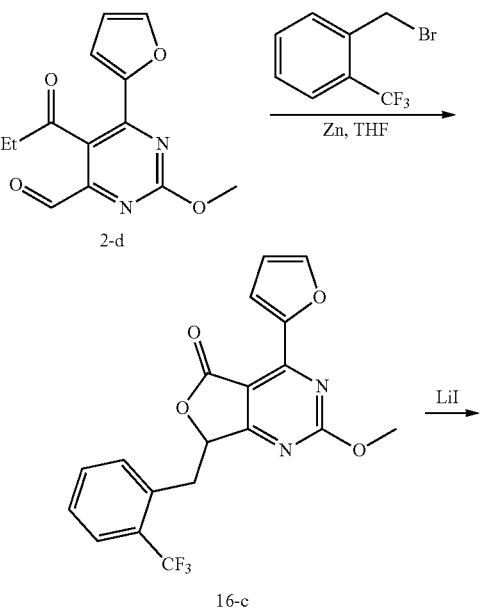

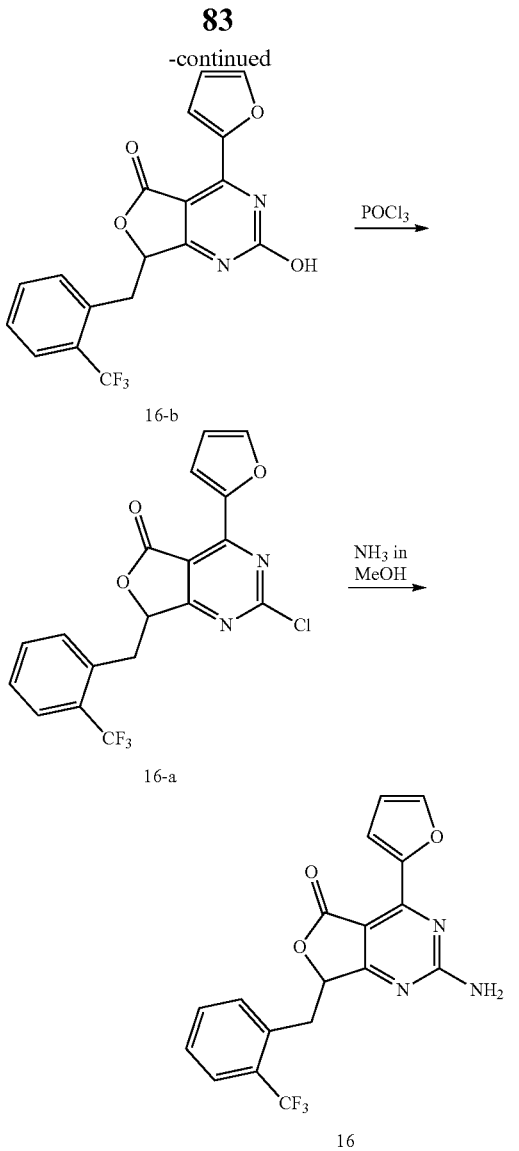

Synthesis of the Compound 16-c

At room temperature, 2-trifluoromethyl benzyl bromide (780 mg, 3.26 mmol) was dissolved in anhydrous tetrahydrofuran (20 mL), zinc powder (213 mg, 3.26 mmol) was added. The reaction mixture was heated to 55° C., then compound 2-d (300 mg, 1.08 mmol) was added and stirred for 1 hour. After cooling down to room temperature, saturated ammonium chloride solution (50 mL) was added to quench the reaction. After extraction with EtOAc (50 mL×2), the organic phases were combined and washed successively by water (50 mL) and saturated brine (50 mL), dried over anhydrous sodium sulfate. After concentration under reduced pressure, the residue was purified by silica gel chromatography (PE:EtOAc=5:1) to give a white solid 16-c (260 mg, yield: 61.7%).

LC-MS (ESI): m/z=391[M+1]$^+$.

Synthesis of the Compound 16-b

Compound 16-c (260 mg, 0.67 mmol) was dissolved in pyridine (15 mL), lithium iodide (446 mg, 3.33 mmol) was added at room temperature. The reaction mixture was stirred at 125° C. for 4 hours and then cooled down to room temperature. After concentration under reduced pressure, the residue was purified by silica gel chromatography (EtOAc:MeOH=5:1) to give a yellow solid 16-b (210 mg, yield: 84%).

LC-MS (ESI): m/z=377[M+1]$^+$.

Synthesis of the Compound 16-a

Compound 16-b (210 mg, 0.55 mmol) was dissolved in phosphorus oxychloride (15 mL), and N,N-dimethylaniline (0.02 mL) was added. The reaction mixture was stirred at 125° C. for 2 hours and then cooled down to room temperature, then concentrated under reduced pressure, the residue was added into a mixture of ice and water (100 mL), and extracted with EtOAc (100 mL×2), the organic phases were combined and washed by water (50 mL) and saturated brine (50 mL), dried over anhydrous sodium sulfate. Then the solution was concentrated under reduced pressure to give a yellow solid 16-a (200 mg, yield: 92.2%). The product was used directly in the next step without further purification.

LC-MS (ESI): m/z=395[M+1]$^+$.

Synthesis of the Compound 16

Compound 16-a (200 mg, 0.51 mmol) was dissolved in tetrahydrofuran (15 mL), ammonia in methanol solution (1 mL) was added at room temperature, and stirred for 15 mins. The reaction mixture was then concentrated under reduced pressure, and the residue was purified by silica gel chromatography (DCM:EtOAc=15:1) to give the compound 16 (5 mg, yield: 2.6%).

LC-MS (ESI): m/z=376[M+H]$^+$.

$^1$H NMR (400 MHz, CDCl$_3$) δ: 8.59-8.58 (d, J=2.8 Hz, 1H), 7.72-7.69 (m, 2H), 7.59-7.53 (m, 2H), 7.42-7.39 (t, J=5.6 Hz, 1H), 6.67-6.66 (m, 1H), 5.82 (s, 2H), 5.35-5.33 (m, 1H), 3.77-3.74 (d, J=12.4 Hz, 1H), 2.98-2.93 (m, 1H) ppm Embodiment 17

2-amino-7-((2-chloro-6-fluorophenyl)methyl)-4-(furan-2-yl)-5H,7H-furo[3,4-d]pyrimidin-5-one (Compound 17)

Synthetic Route

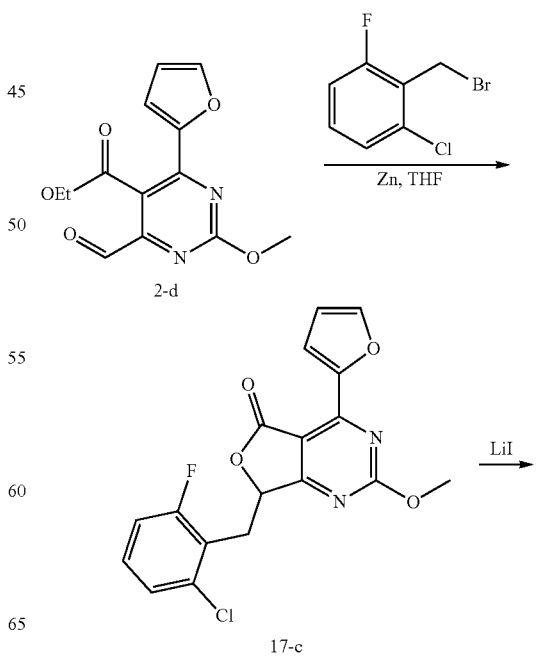

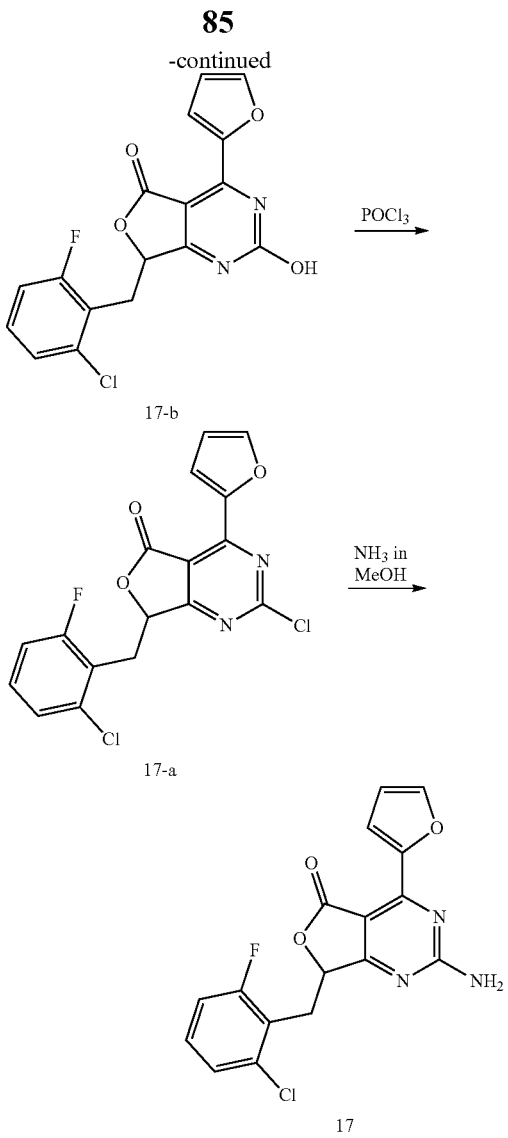

Synthesis of the Compound 17-c

At room temperature, 2-chloro-6-fluorobenzyl bromide (780 mg, 3.26 mmol) was dissolved in anhydrous tetrahydrofuran (20 mL), zinc powder (213 mg, 3.26 mmol) was added. The reaction mixture was heated to 55° C., compound 2-d (300 mg, 1.08 mmol) was added and stirred for 1 hour. After cooling down to room temperature, saturated ammonium chloride solution (50 mL) was added to quench the reaction. After extraction with EtOAc (50 mL×2), the organic phases were combined and washed successively by water (50 mL) and saturated brine (50 mL), dried over anhydrous sodium sulfate. After concentration under reduced pressure, the residue was purified by silica gel chromatography (PE:EtOAc=5:1) to give a white solid 17-c (300 mg, yield: 74%).

LC-MS (ESI): m/z=375[M+1]$^+$.

Synthesis of the Compound 17-b

Compound 17-c (300 mg, 0.8 mmol) was dissolved in pyridine (15 mL), lithium iodide (537 mg, 4.0 mmol) was added at room temperature. The reaction mixture was stirred at 125° C. for 4 hours and then cooled down to room temperature. After concentration under reduced pressure, the residue was purified by silica gel chromatography (EtOAc: MeOH=15:1) to give a yellow solid 17-b (260 mg, yield: 89%).

LC-MS (ESI): m/z=361[M+1]$^+$.

Synthesis of the Compound 17-a

Compound 17-b (260 mg, 0.72 mmol) was dissolved in phosphorus oxychloride (15 mL), and N,N-dimethylaniline (0.02 mL) was added. The reaction mixture was stirred at 125° C. for 2 hours and then cooled down to room temperature, then concentrated under reduced pressure, the residue was added into a mixture of ice and water (100 mL), and extracted with EtOAc (100 mL×2), the organic phases were combined and washed by water (50 mL) and saturated brine (50 mL), dried over anhydrous sodium sulfate. Then the solution was concentrated under reduced pressure to give a yellow solid 17-a (130 mg, yield: 47.7%). The product was used directly in the next step without further purification.

LC-MS (ESI): m/z=379[M+1]$^+$.

Synthesis of Compound 17

Compound 17-a (130 mg, 0.34 mmol) was dissolved in tetrahydrofuran (15 mL), ammonia in methanol solution (1 mL) was added at room temperature, and stirred for 15 mins. The reaction mixture was then concentrated under reduced pressure, and the residue was purified by silica gel chromatography (DCM:EtOAc=15:1) to give the compound 17 (50 mg, yield: 40.8%).

LC-MS (ESI): m/z=360[M+H]$^+$.

$^1$HNMR (400 MHz, CDCl$_3$) δ: 8.60-8.59 (d, J=2.8 Hz, 1H), 7.72 (s, 1H), 7.24-7.22 (m, 2H), 7.05-7.01 (m, 1H), 6.67-6.45 (m, 1H), 5.82 (s, 2H), 5.44-5.43 (m, 1H), 3.53-3.49 (m, 1H), 3.27-3.22 (m, 1H) ppm Embodiment 18

2-amino-7-((3-chloro-2-fluorophenyl)methyl)-4-(furan-2-yl)-5H,7H-furo[3,4-d]pyrimidin-5-one (Compound 18)

Synthetic Route

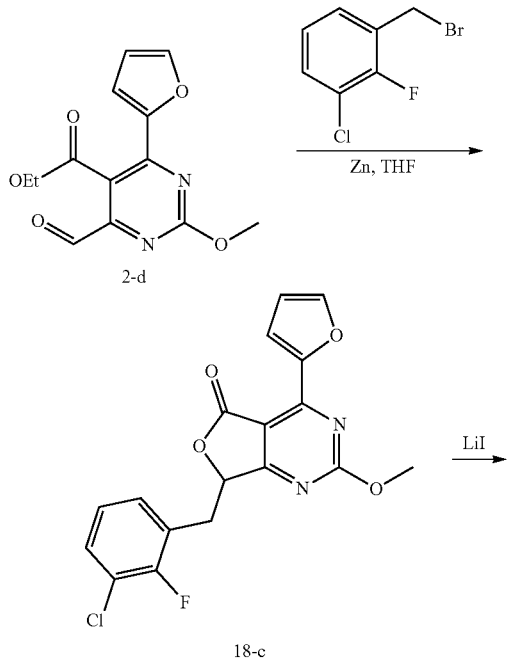

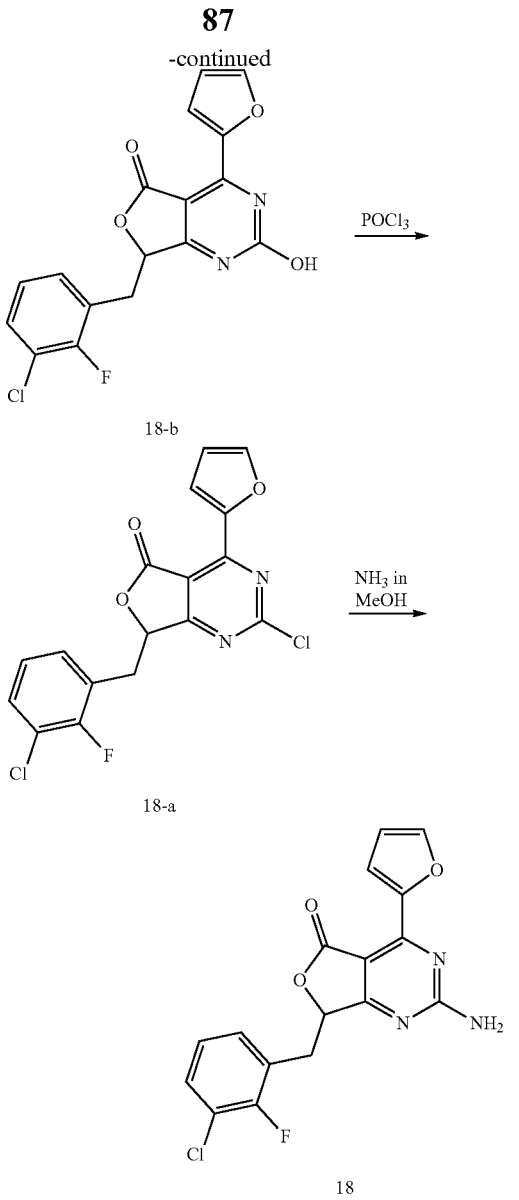

18-b 18-a

18

Synthesis of the Compound 18-c

At room temperature, 3-chloro-2-fluorobenzyl bromide (761 mg, 3.26 mmol) was dissolved in anhydrous tetrahydrofuran (20 mL), zinc powder (213 mg, 3.26 mmol) was added. The reaction mixture was heated to 55° C., compound 2-d (300 mg, 1.08 mmol) was added and stirred for 1 hour. After cooling down to room temperature, saturated ammonium chloride solution (50 mL) was added to quench the reaction. After extraction with EtOAc (50 mL×2), the organic phases were combined and washed successively by water (50 mL) and saturated brine (50 mL), dried over anhydrous sodium sulfate. After concentration under reduced pressure, the residue was purified by silica gel chromatography (PE:EtOAc=5:1) to give a white solid 18-c (310 mg, yield: 76%).

LC-MS (ESI): m/z=375[M+1]$^+$.

Synthesis of the Compound 18-b

Compound 18-c (310 mg, 0.83 mmol) was dissolved in pyridine (15 mL), lithium iodide (555 mg, 4.14 mmol) was added at room temperature. The reaction mixture was stirred at 125° C. for 4 hours and then cooled down to room temperature. After concentration under reduced pressure, the residue was purified by silica gel chromatography (EtOAc:MeOH=15:1) to give a yellow solid 18-b (265 mg, yield: 88%).

LC-MS (ESI): m/z=361[M+1]$^+$.

Synthesis of the Compound 18-a

Compound 18-b (265 mg, 0.74 mmol) was dissolved in phosphorus oxychloride (15 mL), and N,N-dimethylaniline (0.02 mL) was added. The reaction mixture was stirred at 125° C. for 2 hours and then cooled down to room temperature, then concentrated under reduced pressure, the residue was added into a mixture of ice and water (100 mL), and extracted with EtOAc (100 mL×2), the organic phases were combined and washed by water (50 mL) and saturated brine (50 mL), dried over anhydrous sodium sulfate. Then the solution was concentrated under reduced pressure to give a yellow solid 18-a (140 mg, yield: 50%). The product was used directly in the next step without further purification.

LC-MS (ESI): m/z=379[M+1]$^+$.

Synthesis of the Compound 18

Compound 18-a (140 mg, 0.37 mmol) was dissolved in tetrahydrofuran (15 mL), ammonia in methanol solution (1 mL) was added at room temperature, and stirred for 15 mins. The reaction mixture was then concentrated under reduced pressure, and the residue was purified by silica gel chromatography (DCM:EtOAc=15:1) to give the compound 18 (35 mg, yield: 26.3%).

LC-MS (ESI): m/z=360[M+H]$^+$.

$^1$H NMR (400 MHz, CDCl$_3$) δ: 8.55-8.51 (d, J=2.8 Hz, 1H), 7.13 (s, 1H), 7.32-7.29 (m, 1H), 7.24-7.21 (m, 1H), 7.05-7.01 (t, J=6.4 Hz, 1H), 6.65-6.64 (m, 1H), 5.87 (s, 2H), 5.40-5.34 (m, 1H), 3.59-3.55 (m, 1H), 3.03-2.99 (m, 1H) ppm Embodiment 19

2-amino-7-((2-methylphenyl)methyl)-4-(furan-2-yl)-5H,7H-furo[3,4-d]pyrimidin-5-one (Compound 19)

Synthetic Route

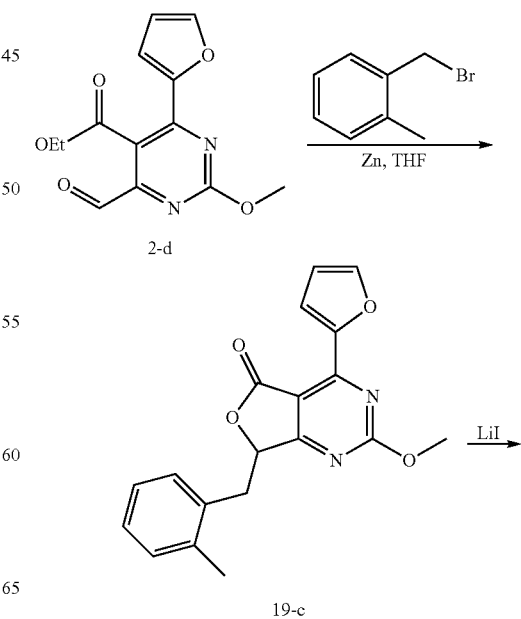

2-d 19-c

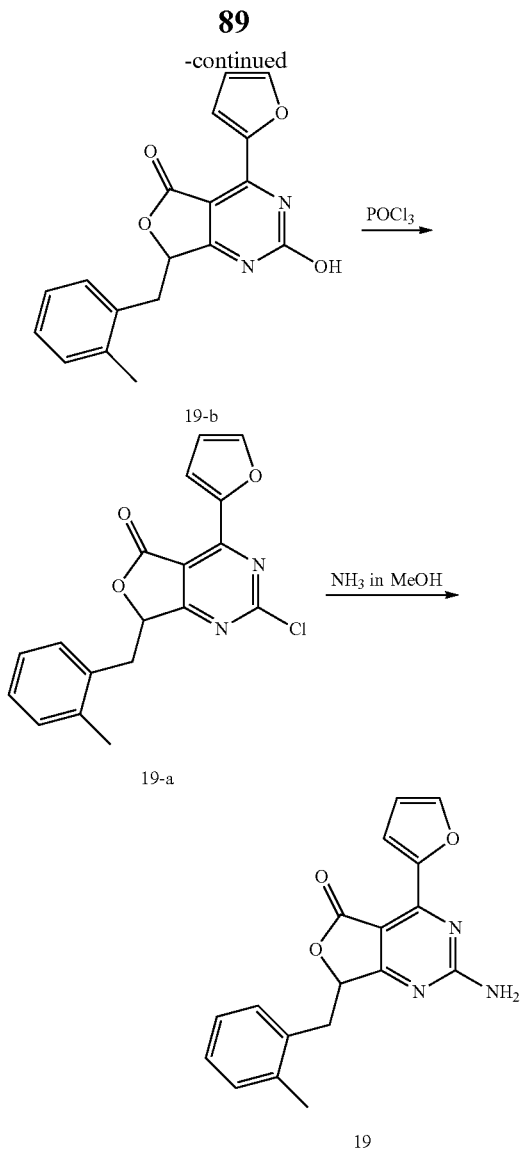

19-b 19-a

19

Synthesis of the Compound 19-c

At room temperature, compound 2-d (276 mg, 1.0 mmol) was dissolved in anhydrous tetrahydrofuran (20 mL), zinc powder (325 mg, 5.0 mmol) and 2-methyl benzyl bromide (370 mg, 2.0 mmol) were added into the reaction solution. The reaction mixture was heated to 60° C. and stirred for 2 hours. After cooling down to room temperature, saturated ammonium chloride solution (20 mL) was added to quench the reaction. After extraction with EtOAc (50 mL×2), the organic phases was combined and washed successively by water (50 mL) and saturated brine (50 mL), dried over anhydrous sodium sulfate. After concentration under reduced pressure, the residue was purified by silica gel chromatography (PE:EtOAc=6:1) to give a pale yellow solid 19-c (300 mg, yield: 89%).

LC-MS (ESI): m/z=337[M+1]$^+$.

Synthesis of the Compound 19-b

Compound 19-c (200 mg, 0.59 mmol) was dissolved in pyridine (15 mL), lithium iodide (399 mg, 2.97 mmol) was added at room temperature. The reaction mixture was stirred at 120° C. for 16 hours and then cooled down to room temperature. After concentration under reduced pressure, the residue was purified by silica gel chromatography (EtOAc:MeOH=100-5:1) to give a brown solid 19-b (170 mg, yield: 90%).

LC-MS (ESI): m/z=323[M+1]$^+$.

Synthesis of the Compound 19-a

Compound 19-b (170 mg, 0.54 mmol) was dissolved in phosphorus oxychloride (10 mL), the reaction mixture was stirred at 120° C. for 3 hours and then cooled down to room temperature. After concentration under reduced pressure, the residue was added into a mixture of ice and water (100 mL), and extracted with EtOAc (50 mL×2), the organic phases was combined and washed by water (30 mL) and saturated brine (20 mL), dried over anhydrous sodium sulfate. Then the solution was concentrated under reduced pressure to give a brown solid 19-a (110 mg, yield: 53.8%). The product was used directly in the next step without further purification.

LC-MS (ESI): m/z=379[M+1]$^+$.

Synthesis of the Compound 19

Compound 19-a (110 mg, 0.29 mmol) was dissolved in tetrahydrofuran (5 mL), ammonia in methanol solution (5 mL) was added at room temperature, and stirred for 1 hour. The reaction mixture was then concentrated under reduced pressure, the residue was added into methanol (3 mL), then treated with ultrasound for 1 min, followed by filtration. The residue was dried in vacuum to give a compound 19 (35 mg, yield: 34%).

LC-MS (ESI): m/z=322.0[M+H]$^+$.

$^1$H NMR (400 MHz, CDCl$_3$) δ: 8.57 (d, J=1.6 Hz, 1H), 7.73 (s, 1H), 7.28-7.26 (m, 1H), 7.18-7.14 (m, 3H), 6.67 (d, J=1.6 Hz, 1H), 5.85 (s, br., 2H), 5.42-5.39 (m, 1H), 3.53-3.49 (dd, J$_1$=6.8 Hz, J$_2$=12.0 Hz, 1H), 3.07-3.02 (dd, J$_1$=6.0 Hz, J$_2$=18.8 Hz, 1H), 2.42 (s, 3H) ppm Embodiment 20

2-amino-7-((3,5-di(trifluoromethyl)phenyl)methyl)-4-(furan-2-yl)-5H,7H-furo[3,4-d]pyrimidin-5-one (Compound 20)

Synthetic Route

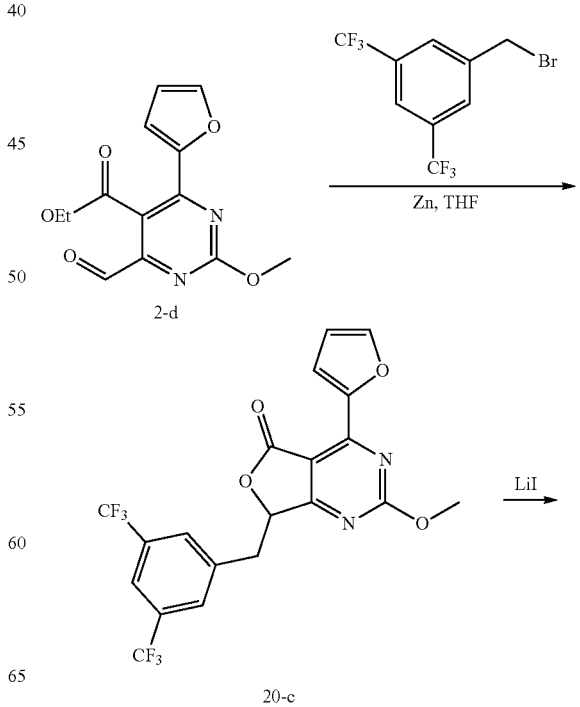

20-c

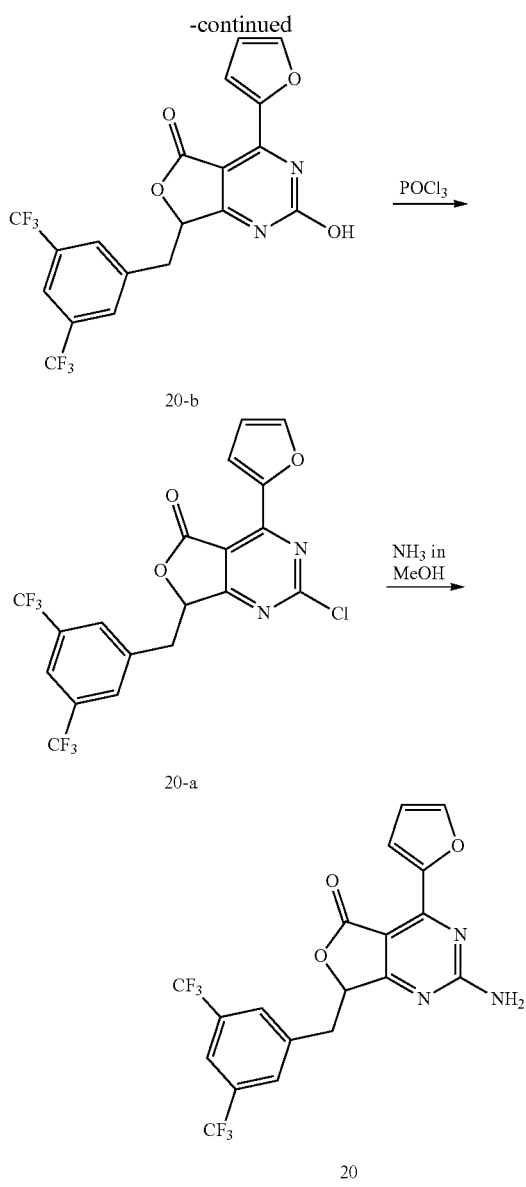

20-b 20-a

20

Synthesis of the Compound 20-c

At room temperature, 3,5-di(trifluoromethyl)benzyl bromide (1.0 g, 3.26 mmol) was dissolved in anhydrous tetrahydrofuran (20 mL), zinc powder (213 mg, 3.26 mmol) was added. The reaction mixture was heated to 55° C., compound 2-d (300 mg, 1.08 mmol) was added and stirred for 1 hour. After cooling down to room temperature, saturated ammonium chloride solution (50 mL) was added to quench the reaction. After extraction with EtOAc (50 mL×2), the organic phases was combined and washed successively by water (50 mL) and saturated brine (50 mL), dried over anhydrous sodium sulfate. After concentration under reduced pressure, the residue was purified by silica gel chromatography (PE:EtOAc=5:1) to give a white solid 20-c (350 mg, yield: 70%).

LC-MS (ESI): m/z=459[M+1]$^+$.

Synthesis of the Compound 20-b

Compound 20-c (350 mg, 0.76 mmol) was dissolved in pyridine (15 mL), lithium iodide (409 mg, 3.05 mmol) was added at room temperature. The reaction mixture was stirred at 125° C. for 4 hours and then cooled down to room temperature. After concentration under reduced pressure, the residue was purified by silica gel chromatography (EtOAc:MeOH=10:1) to give a yellow solid 20-b (300 mg, yield: 88%).

LC-MS (ESI): m/z=445[M+1]$^+$.

Synthesis of the Compound 20-a

Compound 20-b (300 mg, 0.67 mmol) was dissolved in phosphorus oxychloride (15 mL), and N,N-dimethylaniline (0.02 mL) was added. The reaction mixture was stirred at 125° C. for 2 hours and then cooled down to room temperature, then concentrated under reduced pressure, the residue was added into a mixture of ice and water (100 mL), and extracted with EtOAc (100 mL×2), the organic phases were combined and washed by water (50 mL) and saturated brine (50 mL), dried over anhydrous sodium sulfate. Then the solution was concentrated under reduced pressure to give a yellow solid 20-a (180 mg, yield: 58%). The product was used directly in the next step without further purification.

LC-MS (ESI): m/z=463[M+1]$^+$.

Synthesis of the Compound 20

Compound 20-a (8140 mg, 0.39 mmol) was dissolved in tetrahydrofuran (15 mL), ammonia in methanol solution (2 mL) was added at room temperature, and stirred for 15 mins. The reaction mixture was then concentrated under reduced pressure, and the residue was purified by silica gel chromatography (DCM:EtOAc=15:1) to give the compound 20 (107 mg, yield: 61.9%).

LC-MS (ESI): m/z=444[M+H]$^+$.

$^1$H NMR (400 MHz, CDCl$_3$) δ: 8.51-8.50 (d, J=2.8 Hz, 1H), 7.75 (m, 3H), 7.72-7.71 (m, 1H), 6.66-6.65 (m, 1H), 5.77 (s, 2H), 5.41-5.38 (m, 1H), 3.60-3.56 (m, 1H), 3.24-3.19 (m, 1H) ppm Embodiment 21

2-amino-7-((4-(trifluoromethoxyl)phenyl)methyl)-4-(furan-2-yl)-5H,7H-furo[3,4-d]pyrimidin-5-one (Compound 21)

Synthetic Route

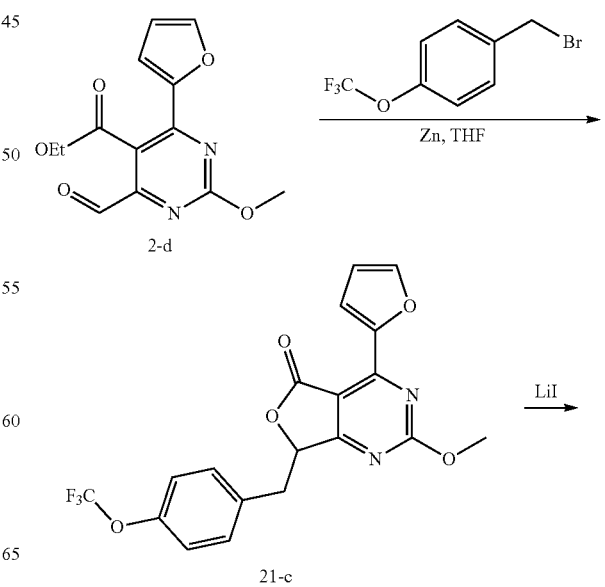

21-c

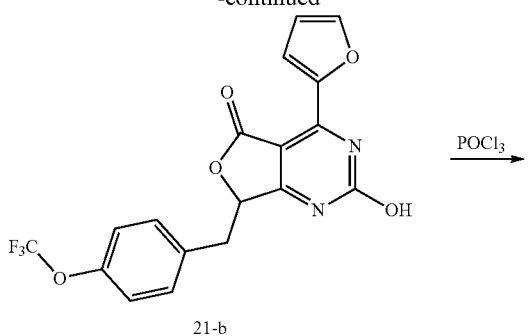

21-b

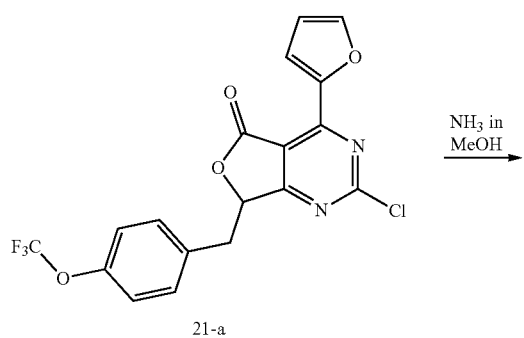

21-a

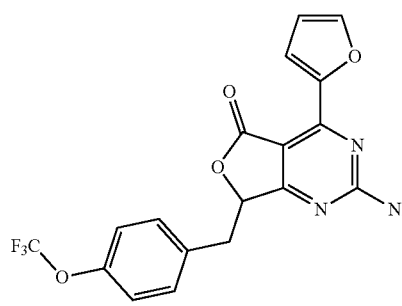

21

Synthesis of the Compound 21-c

At room temperature, compound 2-d (276 mg, 1.0 mmol) was dissolved in anhydrous tetrahydrofuran (25 mL), zinc powder (325 mg, 5.0 mmol) and 4-trifluoromethoxylbenzyl bromide (510 mg, 2.0 mmol) were added into the reaction solution. The reaction mixture was heated to 60° C. and stirred for 2 hours. After cooling down to room temperature, saturated ammonium chloride solution (20 mL) was added to quench the reaction. After extraction with EtOAc (50 mL×2), the organic phases were combined and washed successively by water (50 mL) and saturated brine (50 mL), dried over anhydrous sodium sulfate. After concentration under reduced pressure, the residue was purified by silica gel chromatography (PE:EtOAc=6:1) to give a pale yellow solid 21-c (400 mg, yield: 98%). LC-MS (ESI): m/z=407[M+1]$^+$.

Synthesis of the Compound 21-b

Compound 21-c (400 mg, 0.99 mmol) was dissolved in pyridine (20 mL), lithium iodide (670 mg, 5.0 mmol) was added at room temperature. The reaction mixture was stirred at 120° C. for 16 hours and then cooled down to room temperature. After concentration under reduced pressure, the residue was purified by silica gel chromatography (EtOAc: MeOH=100-5:1) to give a brown solid 21-b (350 mg, yield: 90%). LC-MS (ESI): m/z=393[M+1]$^+$.

Synthesis of the Compound 21-a

Compound 21-b (350 mg, 0.90 mmol) was dissolved in phosphorus oxychloride (10 mL), the reaction mixture was stirred at 120° C. for 3 hours and then cooled down to room temperature. After concentration under reduced pressure, the residue was added into a mixture of ice and water (100 mL), and extracted with EtOAc (50 mL×2), the organic phases were combined and washed by water (30 mL) and saturated brine (20 mL), dried over anhydrous sodium sulfate. After concentration under reduced pressure, the residue was purified by silica gel chromatography (EtOAc:MeOH=100:1-5:1) to give a pale yellow solid 21-a (90 mg, yield: 24.3%). LC-MS (ESI): m/z=410.9[M+1]$^+$.

Synthesis of the Compound 21

Compound 21-a (90 mg, 0.22 mmol) was dissolved in tetrahydrofuran (5 mL), ammonia in methanol solution (5 mL) was added at room temperature, and stirred for 1 hour. The reaction mixture was then concentrated under reduced pressure, the residue was added methanol (3 mL), then treated with ultrasound for 1 min, followed by filtration. The residue was dried in vacuum to give a compound 21 (10 mg, yield: 12%). LC-MS (ESI): m/z=391.9[M+H]$^+$.

$^1$H NMR (400 MHz, CDCl$_3$) δ: 8.53 (d, J=2.8 Hz, 1H), 7.72 (s, 1H), 7.32-7.28 (m, 2H), 7.14-7.12 (m, 2H), 6.66 (d, J=1.6 Hz, 1H), 5.80 (s, br., 2H), 5.40-5.37 (m, 1H), 3.51-3.47 (dd, J$_1$=2.8 Hz, J$_2$=11.6 Hz, 1H), 3.13-3.08 (dd, J$_1$=10.0 Hz, J$_2$=11.6 Hz, 1H) ppm Embodiment 22

2-amino-7-((2,6-difluorophenyl)methyl)-4-(furan-2-yl)-5H,7H-furo[3,4-d]pyrimidin-5-one (Compound 22)

Synthetic Route

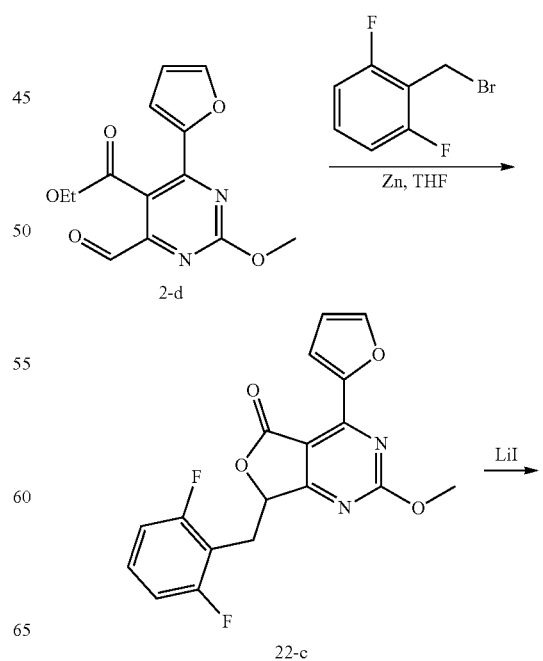

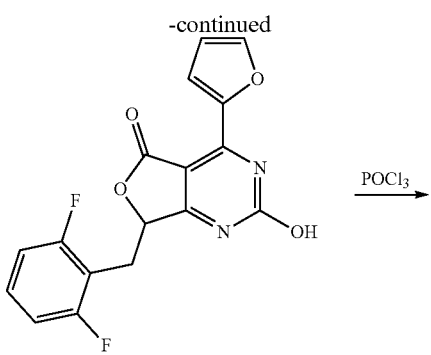

22-b

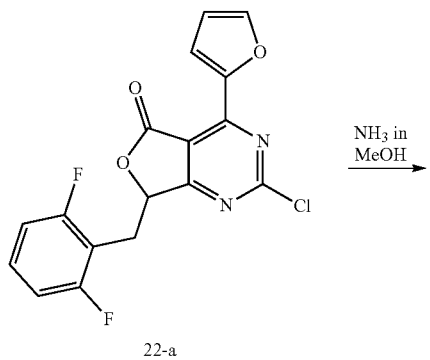

22-a

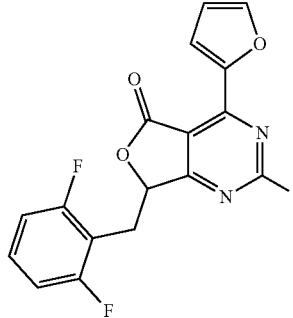

22

Synthesis of the Compound 22-c

At room temperature, compound 2-d (276 mg, 1.0 mmol) was dissolved in anhydrous tetrahydrofuran (20 mL), zinc powder (325 mg, 5.0 mmol) and 2,6-difluorobenzyl bromide (414 mg, 2.0 mmol) were added into the reaction solution. The reaction mixture was heated to 60° C. and stirred for 2 hours. After cooling down to room temperature, saturated ammonium chloride solution (20 mL) was added to quench the reaction. After extraction with EtOAc (50 mL×2), the organic phases were combined and washed successively by water (50 mL) and saturated brine (50 mL), dried over anhydrous sodium sulfate. After concentration under reduced pressure, the residue was purified by silica gel chromatography (PE:EtOAc=6:1) to give a pale yellow solid 22-c (320 mg, yield: 89%).

LC-MS (ESI): m/z=358.9[M+1]$^+$.

Synthesis of the Compound 22-b

Compound 22-c (280 mg, 0.78 mmol) was dissolved in pyridine (15 mL), lithium iodide (628 mg, 4.69 mmol) was added at room temperature. The reaction mixture was stirred at 120° C. for 16 hours and then cooled down to room temperature. After concentration under reduced pressure, the residue was purified by silica gel chromatography (EtOAc:MeOH=100-5:1) to give a brown solid 22-b (200 mg, yield: 75%).

LC-MS (ESI): m/z=344.9[M+1]$^+$.

Synthesis of the Compound 22-a

Compound 22-b (200 mg, 0.58 mmol) was dissolved in phosphorus oxychloride (15 mL), the reaction mixture was stirred at 120° C. for 3 hours and then cooled down to room temperature. After concentration under reduced pressure, the residue was added into a mixture of ice and water (100 mL), and extracted with EtOAc (50 mL×2), the organic phases were combined and washed by water (30 mL) and saturated brine (20 mL), dried over anhydrous sodium sulfate. After concentration under reduced pressure, the residue was purified by silica gel chromatography (PE:EtOAc=30:1) to give a yellow solid 22-a (110 mg, yield: 52%).

LC-MS (ESI): m/z=363[M+1]$^+$.

Synthesis of the Compound 22

Compound 22-a (110 mg, 0.3 mmol) was dissolved in tetrahydrofuran (5 mL), ammonia in methanol solution (5 mL) was added at room temperature, and stirred for 1 hour. The reaction mixture was then concentrated under reduced pressure, the residue was added into methanol (3 mL), then treated with ultrasound for 1 min, followed by filtration. The residue was dried in vacuum to give a compound 22 (35 mg, yield: 33%). LC-MS (ESI): m/z=344[M+H]$^+$.

$^1$H NMR (400 MHz, CDCl$_3$) δ: 8.60 (d, J=3.2 Hz, 1H), 7.74 (s, 1H), 7.28-7.23 (m, 2H), 6.95-6.91 (m, 2H), 6.68-6.67 (m, 1H), 5.85 (s, br., 2H), 5.43-5.40 (m, 1H), 3.47-3.43 (dd, J$_1$=3.2 Hz, J$_2$=11.2 Hz, 1H), 3.17-3.12 (dd, J$_1$=7.6 Hz, J$_2$=11.6 Hz, 1H) ppm Embodiment 23

2-amino-7-((2-(trifluoromethoxyl)phenyl)methyl)-4-(furan-2-yl)-5H,7H-furo[3,4-d]pyrimidin-5-one (Compound 23)

Synthetic Route

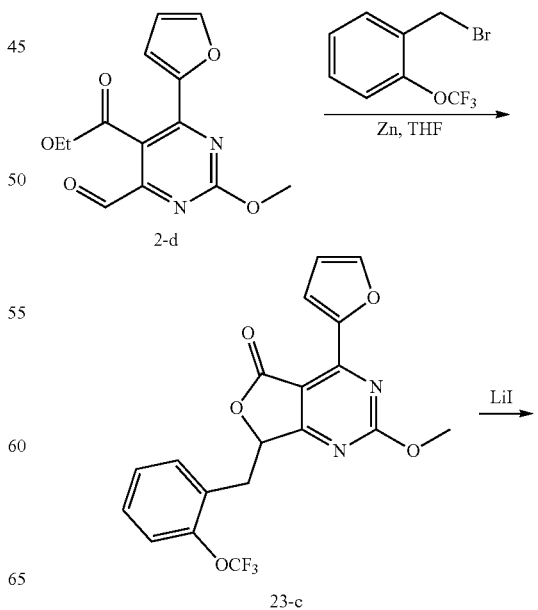

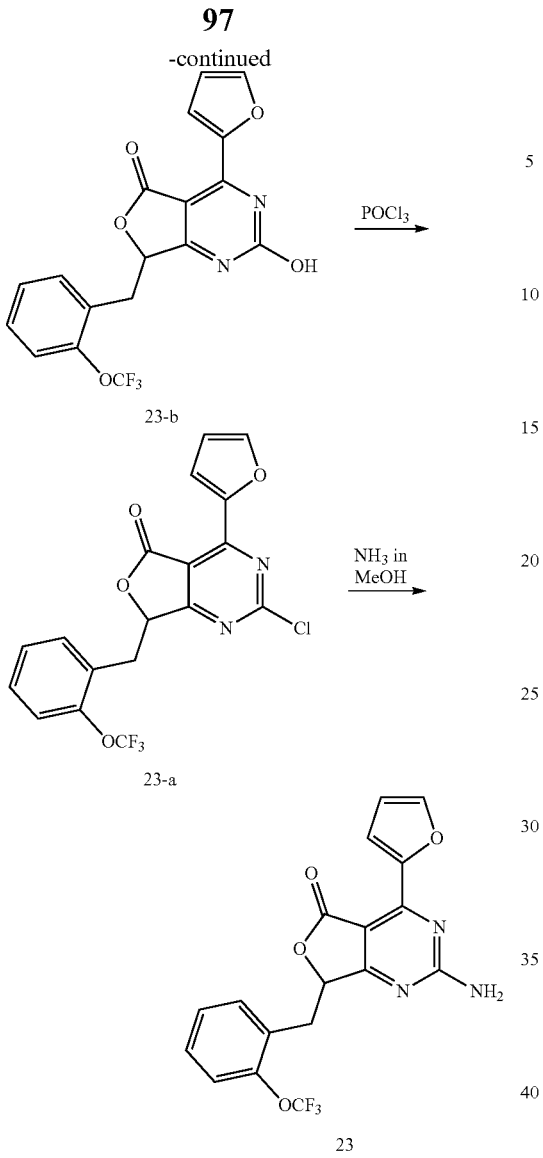

Synthesis of the Compound 23-c

At room temperature, compound 2-d (276 mg, 1.0 mmol) was dissolved in anhydrous tetrahydrofuran (20 mL), zinc powder (325 mg, 5.0 mmol) and 2-trifluoromethoxylbenzyl bromide (510 mg, 2.0 mmol) were added into the reaction solution. The reaction mixture was heated to 60° C. and stirred for 2 hours. After cooling down to room temperature, saturated ammonium chloride solution (20 mL) was added to quench the reaction. After extraction with EtOAc (50 mL×2), the organic phases were combined and washed successively by water (50 mL) and saturated brine (50 mL), dried over anhydrous sodium sulfate. After concentration under reduced pressure, the residue was purified by silica gel chromatography (PE:EtOAc=6:1) to give a pale yellow solid 23-c (370 mg, yield: 91%). LC-MS (ESI): m/z=406.9[M+1]$^+$.

Synthesis of the Compound 23-b

Compound 23-c (370 mg, 0.91 mmol) was dissolved in pyridine (20 mL), lithium iodide (610 mg, 4.5 mmol) was added at room temperature. The reaction mixture was stirred at 120° C. for 16 hours and then cooled down to room temperature. After concentration under reduced pressure, the residue was purified by silica gel chromatography (EtOAc:MeOH=100-5:1) to give a brown solid 23-b (280 mg, yield: 78%). LC-MS (ESI): m/z=393[M+1]$^+$.

Synthesis of the Compound 23-a

Compound 23-b (280 mg, 0.71 mmol) was dissolved in phosphorus oxychloride (15 mL), the reaction mixture was stirred at 120° C. for 3 hours and then cooled down to room temperature. After concentration under reduced pressure, the residue was added into a mixture of ice and water (100 mL), and extracted with EtOAc (50 mL×2), the organic phases were combined and washed by water (30 mL) and saturated brine (20 mL), dried over anhydrous sodium sulfate. After concentration under reduced pressure, the residue was purified by silica gel chromatography (PE:EtOAc=30:1) to give a yellow solid 23-a (120 mg, yield: 41%). LC-MS (ESI): m/z=410.9[M+1]$^+$.

Synthesis of the Compound 23

Compound 23-a (120 mg, 0.29 mmol) was dissolved in tetrahydrofuran (5 mL), ammonia in methanol solution (5 mL) was added at room temperature, and stirred for 1 hour. The reaction mixture was then concentrated under reduced pressure, the residue was added into methanol (3 mL), then treated with ultrasound for 1 min, followed by filtration. The residue was dried in vacuum to give a compound 23 (50 mg, yield: 43%).

LC-MS (ESI): m/z=391.9[M+H]$^+$.

$^1$H NMR (400 MHz, CDCl$_3$) δ: 8.57 (d, J=2.8 Hz, 1H), 7.73 (s, 1H), 7.47-7.45 (m, 1H), 7.35-7.260 (m, 3H), 6.68-6.67 (m, 1H), 5.84 (s, br., 2H), 5.43-5.40 (m, 1H), 3.64-3.60 (dd, J$_1$=2.8 Hz, J$_2$=11.6 Hz, 1H), 3.06-3.01 (dd, J$_1$=6.8 Hz, J$_2$=11.6 Hz, 1H) ppm

Embodiment 24

2-amino-7-benzyl-4-(pyridin-2-yl)-5H,7H-furo[3,4-d]pyrimidin-5-one (Compound 24)

Synthetic Route

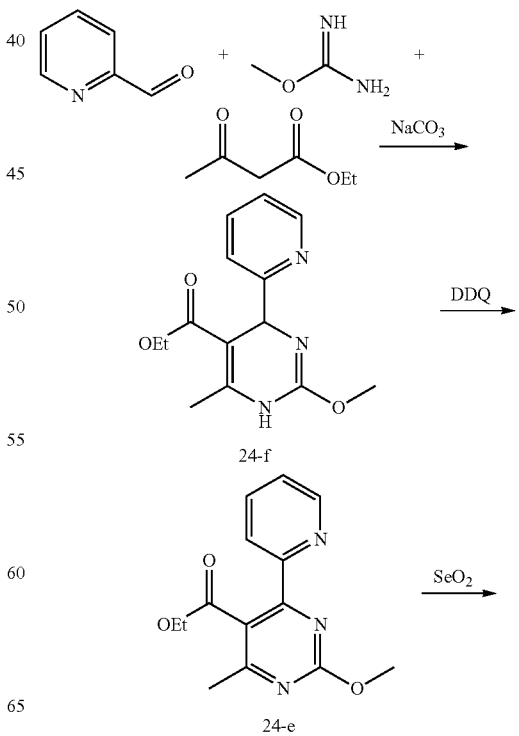

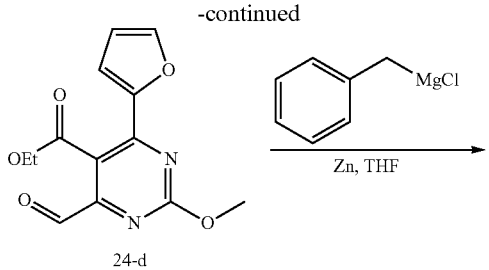
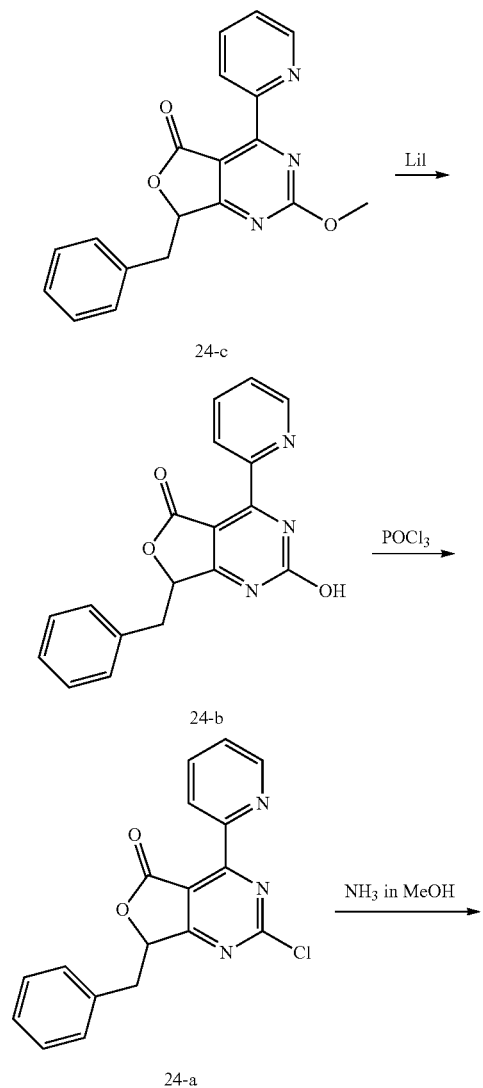

Synthesis of the Compound 24-f

2-Pyridine carboxaldehyde (5.0 g, 46.7 mmol), O-methylisothiourea sulfate (9.64 g, 56.0 mmol) and ethyl acetoacetate (6.67 g, 51.3 mmol) were dissolved in anhydrous N,N-dimethylformamide (100 mL), then sodium dicarbonate (15.7 g, 186.8 mmol) was added into the solution. The reaction mixture was heated to 70° C. under nitrogen atmosphere, stirred for 3 hours and then cooled down to room temperature. After addition of saturated brine (200 mL), a large amount of yellow suspended solids appeared, EtOAc (500 mL×2) was used for extraction, the organic phases were combined and washed by water (200 mL) and saturated brine (100 mL), dried over anhydrous sodium sulfate, then concentrated under reduced pressure, and the residue was purified by silica gel chromatography (PE:EtOAc=10:1) to give a white solid 24-f (10.2 g, yield: 79%).

LC-MS (ESI): m/z=276.3[M+H]$^+$.

Synthesis of the Compound 24-e

Compound 24-f (10.0 g, 36.3 mmol) was dissolved in DCM (100 mL), 2,3-dichloro-5,6-dicyanobenzoquinone (9.08 g, 40.0 mmol) was added while stirring at room temperature. The reaction mixture was stirred overnight. The reaction mixture was filtered, the residue was washed by DCM (50 mL), the filtrate was combined, then concentrated under reduced pressure, and the residue was purified by silica gel chromatography (PE:EtOAc=5-2:1) to give a grey crystal 24-e (6.5 g, yield: 65%). LC-MS (ESI): m/z=274.3 [M+H]$^+$.

Synthesis of the Compound 24-d

Compound 24-e (6.5 g, 23.8 mmol) was dissolved in dioxane (100 mL), selenium dioxide (3.96 g, 35.7 mmol) and glacial acetic acid (2 mL) were added at room temperature, the mixture was heated to 120° C. and stirred for 10 hours. After cooling down to room temperature, the mixture was concented under reduced pressure, the residue was purified by silica gel chromatography (PE:EtOAc=3:1) to give a pink solid 24-d (1.8 g, yield: 26%).

LC-MS (ESI): m/z=288.1[M+H]$^+$.

Synthesis of the Compound 24-c

At −78° C. and under nitrogen atmosphere, benzylmagnesium chloride in tetrahydrofuran solution (1.0 M, 1.5 mL, 1.5 mmol) was added into compound 24-d (287 mg, 1.0 mmol) in anhydrous tetrahydrofuran (10 mL) solution, the reaction mixture was slowly warmed to room temperature, stirred for 16 hours. Saturated ammonium chloride solution (20 mL) was added. The mixture was extracted with EtOAc (30 mL×3), washed by saturated brine (30 mL), dried over anhydrous sodium sulfate. After concentration under reduced pressure, the residue was purified by silica gel chromatography (PE:EtOAc=6:1) to give a grey solid product 24-c (230 mg, yield: 69%). LC-MS (ESI): m/z=334[M+H]$^+$.

Synthesis of the Compound 24-b 24-c (310 mg, 0.93 mmol), lithium iodide (623 mg, 4.6 mmol) and pyridine (15 mL) were added into a 100 mL single neck flask. The reaction mixture was stirred at 120° C. for 16 hours and then cooled down to room temperature. After concentration under reduced pressure, the residue was purified by silica gel chromatography (EtOAc:MeOH=100-10:1) to give a yellow solid 24-b (280 mg, yield: 94%).

LC-MS (ESI): m/z=320[M+1]$^+$.

Synthesis of the Compound 24-a

Compound 24-b (280 mg, 0.87 mmol) was dissolved in phosphorus oxychloride (15 mL), the reaction mixture was stirred at 120° C. for 3 hours and then cooled down to room temperature. After concentration under reduced pressure, the residue was added into a mixture of ice and water (100 mL), and extracted with EtOAc (50 mL×2), the organic phases were combined and washed by water (30 mL) and saturated brine (20 mL), dried over anhydrous sodium sulfate. After concentration under reduced pressure, the residue was purified by silica gel chromatography (PE:EtOAc=30:1) to give a yellow solid 24-a (180 mg, yield: 62%).

LC-MS (ESI): m/z=338[M+1]$^+$.

Synthesis of the Compound 24

Compound 24-a (180 mg, 0.53 mmol) was dissolved in tetrahydrofuran (5 mL), 7.0 M ammonia in methanol solution (5 mL, 35 mmol) was added at room temperature, and stirred for 1 hour. The reaction mixture was then concentrated under reduced pressure, the residue was added into methanol (3 mL), then treated with ultrasound for 1 min, followed by filtration. The residue was dried in vacuum to give a compound 24 (45 mg, yield: 27%).

LC-MS (ESI): m/z=319[M+H]$^+$.

$^1$H NMR (400 MHz, CDCl$_3$) δ: 8.86 (d, J=3.6 Hz, 1H), 8.11 (d, J=6.4 Hz, 1H), 7.89-7.85 (m, 1H), 7.47-7.45 (m, 1H), 7.26-7.21 (m, 5H), 5.95 (s, br., 2H), 5.49-5.47 (m, 1H), 3.54-3.50 (dd, J$_1$=3.2 Hz, J$_2$=11.6 Hz, 1H), 3.19-3.14 (dd, J$_1$=6.4 Hz, J$_2$=12.0 Hz, 1H) ppm Embodiment 25

2-amino-4-(5-bromofuran-2-yl)-7-((2,4-difluorophenyl)methyl)-5H,7H-furo[3,4-d]pyrimidin-5-one (Compound 25)

Synthetic Route

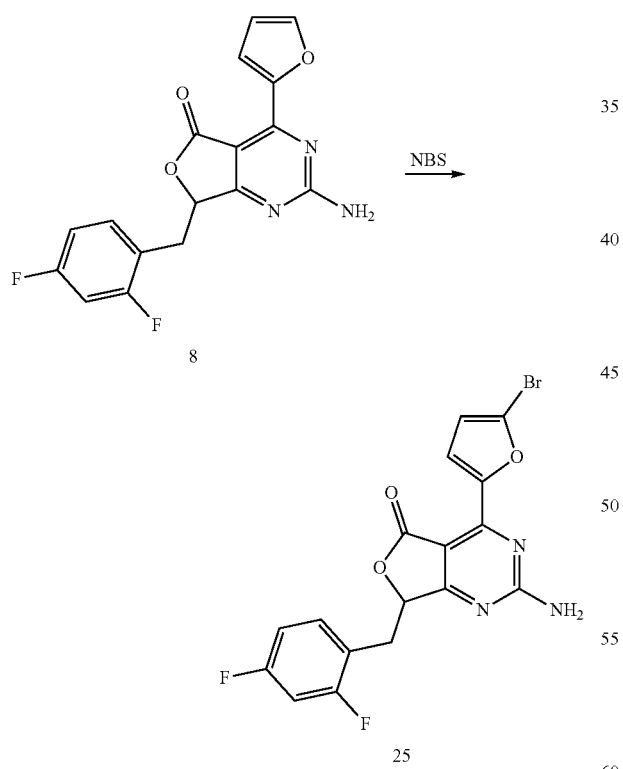

Synthesis of the Compound 25

Compound 8 (60 mg, 0.17 mmol) was dissolved in N,N-dimethylformamide (15 mL), N-bromosuccinimide (47 mg, 0.26 mmol) was added, the reaction mixture was stirred at room temperature for 12 hours. The reaction solution was then concentrated under reduced pressure, the residue was purified by HPLC (mobile phase: water (10 mM ammonium bicarbonate), acetonitrile; gradient: 15%-65% (initial mobile phase was 15% water-85% acetonitrile, at the end the mobile phase was 65% water-35% acetonitrile, the % refers to volume percentage) to give the compound 25 (26 mg, yield: 36.2%).

LC-MS (ESI): m/z=423 [M+H]$^+$.

$^1$H NMR (400 MHz, CDCl$_3$) δ: 8.49-8.48 (d, J=2.8 Hz, 1H), 7.25-7.24 (m, 1H), 6.82-6.79 (m, 2H), 6.59-6.58 (d, J=3.2 Hz, 1H), 5.92 (s, 2H), 5.38-5.35 (m, 1H), 3.53-3.49 (m, 1H), 3.03-2.99 (m, 1H) ppm Embodiment 26

2-amino-7-((2,4-difluorophenyl)methyl)-4-(5-methylfuran-2-yl)-5H,7H-furo[3,4-d]pyrimidin-5-one (Compound 26)

Synthetic Route

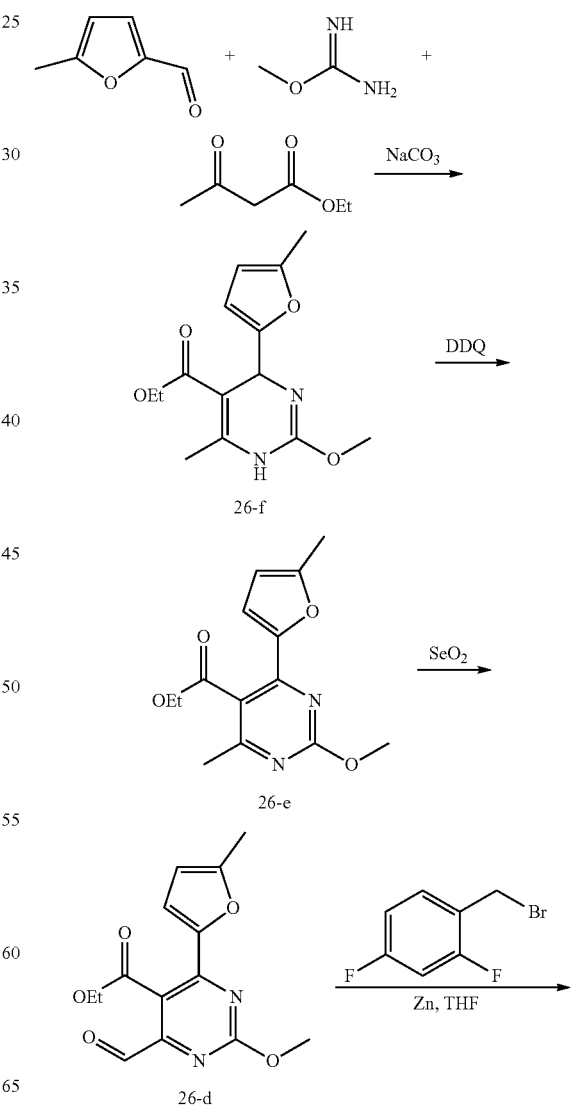

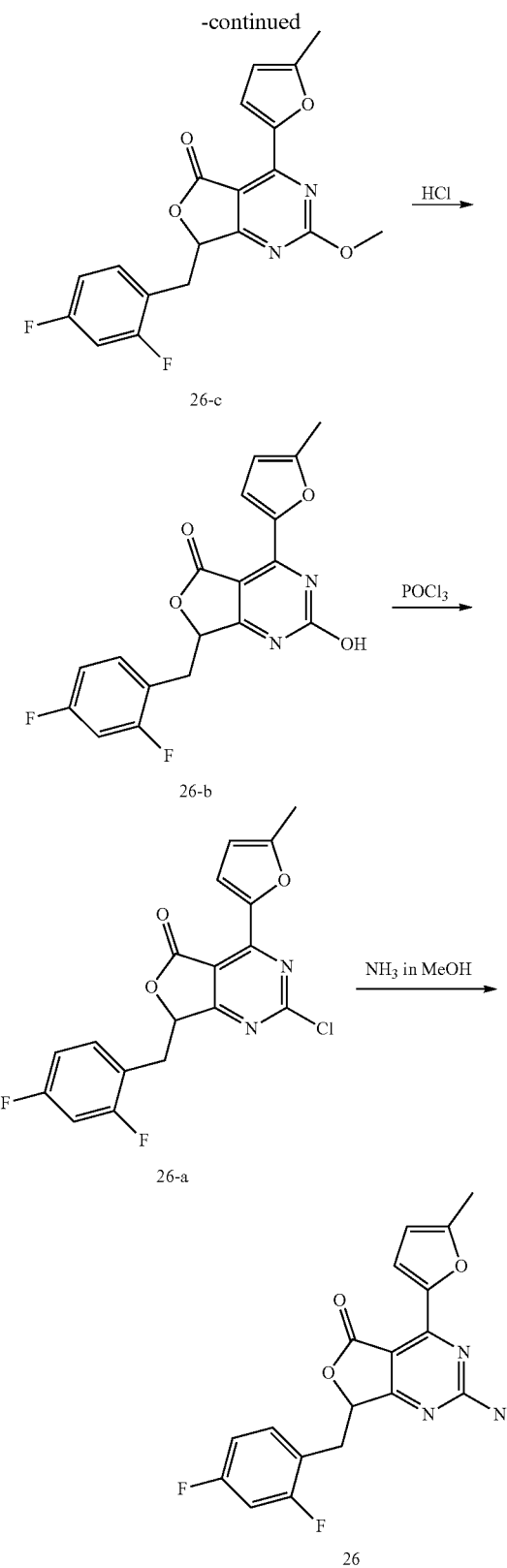

Synthesis of the Compound 26-f

Furfural (16.92 g, 153.68 mmol), O-methylisothiourea sulfate (26.46 g, 153.68 mmol) and ethyl acetoacetate (20 g, 153.68 mmol) were dissolved in anhydrous N,N-dimethyl-formamide (200 mL), sodium dicarbonate (19.37 g, 230.52 mmol) was added into the solution. Under nitrogen atmosphere, the reaction mixture was heated to 75° C., stirred for 16 hours and then cooled down to room temperature. The reaction mixture was added into EtOAc (200 mL), washed successively by water (200 mL×3) and saturated brine (200 mL), the combined organic phases were dried over anhydrous sodium sulfate, then concentrated under reduced pressure, and the residue was purified by silica gel chromatography (PE:EtOAc=10-3:1) to give the compound 26-f (32.38 g, yield: 75.7%).

Synthesis of the Compound 26-e

Compound 26-f (32.38 g, 116.35 mmol) was dissolved in DCM (700 mL), 2,3-dichloro-5,6-dicyanobenzoquinone (52.83 g, 232.7 mmol) was added at room temperature while stirring. The reaction mixture was stirred for 12 hours. After the reaction mixture was filtered, the residue was washed by EtOAc (150 mL×3), the filtrate was combined, then concentrated under reduced pressure, and the residue was purified by silica gel chromatography (PE:EtOAc=10:1) to give the compound 26-e (26.38 g, yield: 82.9%).

$^1$H NMR (500 MHz, CDCl$_3$) δ: 7.25-7.24 (d, J=3.5 Hz, 1H), 6.17-6.16 (d, J=3.0 Hz, 1H), 4.44-4.39 (m, 2H), 4.03 (s, 3H), 2.47 (s, 3H), 2.36 (s, 3H), 1.39-1.37 (t, 3H) ppm

Synthesis of the Compound 26-d

Compound 26-e (1.0 g, 3.62 mmol) was dissolved in a mixed solution of dioxane (20 mL) and EtOAc (1 mL), selenium dioxide (522 mg, 4.71 mmol) was added at room temperature, the mixture was heated to 120° C. and stirred for 6 hours. After cooling down to room temperature, the reaction mixture was filtered, the filter cake was washed with EtOAc (50 mL×3), the filtrate was combined, then concentrated under reduced pressure, and the residue was purified by silica gel chromatography (PE:EtOAc=10:1) to give the compound 26-d (561 mg, yield: 53.4%).

$^1$H NMR (500 MHz, CDCl$_3$) δ: 9.89 (s, 1H), 7.36-7.35 (d, J=3.5 Hz, 1H), 6.22-6.21 (d, J=3.0 Hz, 1H), 4.53-4.48 (q, 2H), 4.13 (s, 3H), 2.39 (s, 3H), 1.44-1.42 (t, 3H) ppm

Synthesis of the Compound 26-c

At room temperature, compound 26-d (642 mg, 3.1 mmol) was dissolved in anhydrous tetrahydrofuran (20 mL), zinc powder (203 mg, 3.1 mmol) and 2,4-difluorobenzyl bromide (300 mg, 1.03 mmol) were added into the reaction solution. The reaction mixture was heated to 55° C. and stirred for 1 hour. After cooling down to room temperature, saturated ammonium chloride solution (20 mL) was added to quench the reaction. After extraction with EtOAc (50 mL×2), the organic phases were combined and washed successively by water (50 mL) and saturated brine (50 mL), dried over anhydrous sodium sulfate. After concentration under reduced pressure, the residue was purified by silica gel chromatography (PE:EtOAc=5:1) to give a white solid 26-c (300 mg, yield: 91%). LC-MS (ESI): m/z=373[M+1]$^+$.

Synthesis of the Compound 26-b

Compound 26-c (300 mg, 0.81 mmol) was dissolved in 1,4-dioxane (20 mL), concentrated hydrochloric acid (0.5 mL) was added at room temperature. The reaction mixture was stirred at 100° C. for 4 hours and then cooled down to room temperature, a large amount of solid was precipitated, and then filtered, the residue was washed by water (20 mL×2), dried in vacuum to give a yellow solid 26-b (200 mg, yield: 70%). LC-MS (ESI): m/z=359[M+1]$^+$.

Synthesis of the Compound 26-a

Compound 26-b (200 mg, 0.56 mmol) was dissolved in phosphorus oxychloride (15 mL), N,N-dimethylaniline (0.02 mL) was added, the reaction mixture was stirred at 125° C. for 2 hours and then cooled down to room temperature. After concentration under reduced pressure, the residue was added into a mixture of ice and water (100 mL), and extracted with EtOAc (50 mL×2), the organic phases were combined and washed by water (30 mL) and saturated brine (20 mL), dried over anhydrous sodium sulfate. After concentration under reduced pressure, the residue was purified by silica gel chromatography (PE:EtOAc=5:1) to give a yellow solid 26-a (160 mg, yield: 75.9%).

LC-MS (ESI): m/z=377[M+1]⁺.

Synthesis of the Compound 26

Compound 26-a (160 mg, 0.43 mmol) was dissolved in tetrahydrofuran (15 mL), 7.0 M ammonia in methanol solution (5 mL, 35 mmol) was added at room temperature and stirred for 1 hour. The reaction mixture was then concentrated under reduced pressure, and the residue was purified by silica gel chromatography (DCM:EtOAc=15:1) to give the compound 26 (60 mg, yield: 39%). LC-MS (ESI): m/z=358[M+H]⁺.

$^1$H NMR (400 MHz, CDCl$_3$) δ: 8.49-8.48 (d, J=2.8 Hz, 1H), 7.25-7.24 (m, 1H), 6.81-6.79 (m, 2H), 6.28-6.27 (d, J=2.8 Hz, 1H), 5.83 (s, 2H), 5.35-5.33 (m, 1H), 3.53-3.49 (m, 1H), 3.01-2.96 (m, 1H), 2.48 (s, 3H) ppm Embodiment 27

2-amino-7-((2-fluorophenyl)methyl)-4-(5-methyl-furan-2-yl)-5H,7H-furo[3,4-d]pyrimidin-5-one (Compound 27)

Synthetic Route

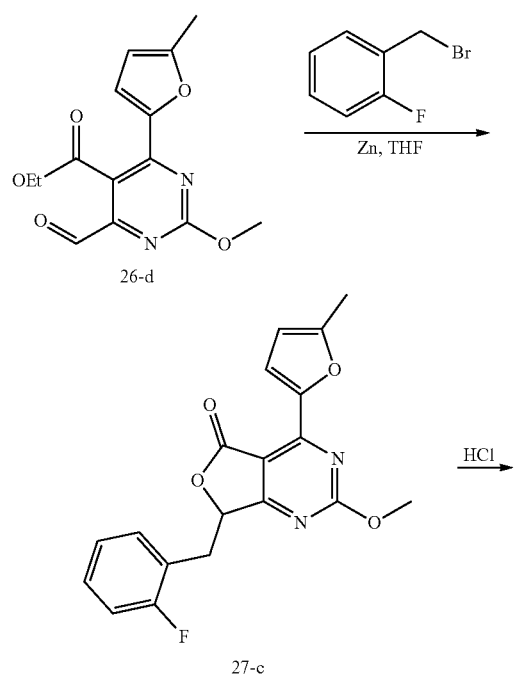

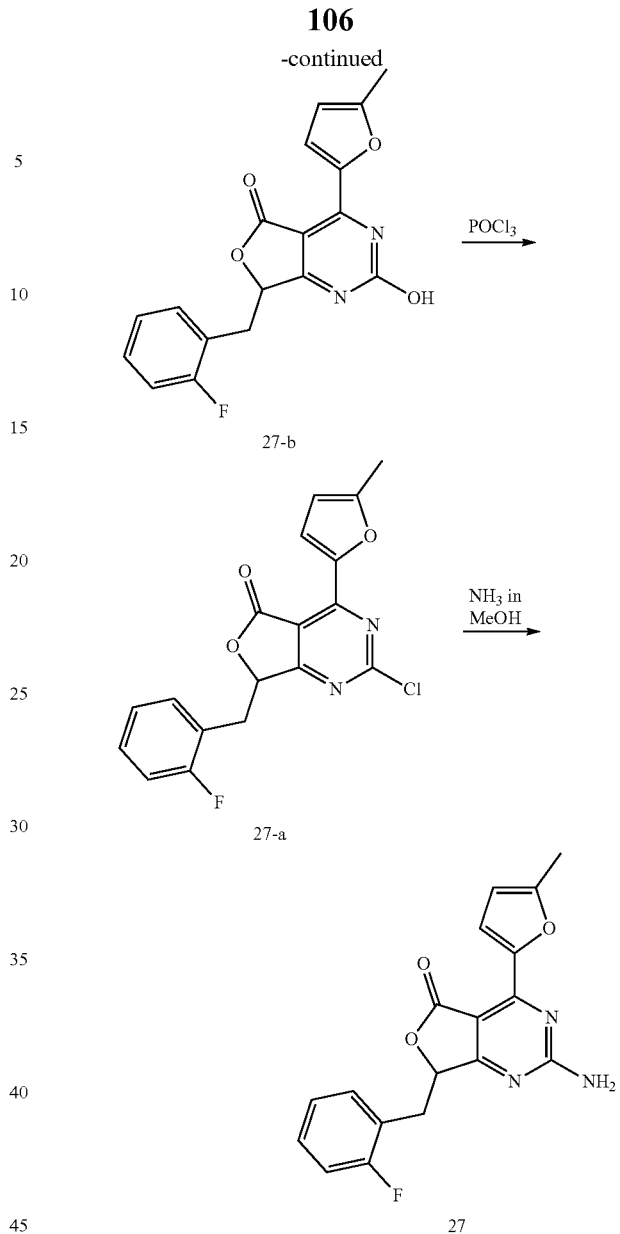

Synthesis of the Compound 27-c

At room temperature, compound 26-d (300 mg, 1.03 mmol) was dissolved in anhydrous tetrahydrofuran (20 mL), zinc powder (203 mg, 3.1 mmol) and 2-fluorobenzyl bromide (587 mg, 3.1 mmol) were added into the reaction solution. The reaction mixture was heated to 55° C. and stirred for 1 hour. After cooling down to room temperature, saturated ammonium chloride solution (20 mL) was added to quench the reaction. After extraction with EtOAc (50 mL×2), the organic phases were combined and washed successively by water (50 mL) and saturated brine (50 mL), dried over anhydrous sodium sulfate. After concentration under reduced pressure, the residue was purified by silica gel chromatography (PE:EtOAc=5:1) to give a white solid 27-c (340 mg, yield: 94%). LC-MS (ESI): m/z=355[M+1]⁺.

Synthesis of the Compound 27-b

Compound 27-c (340 mg, 0.96 mmol) was dissolved in 1,4-dioxane (15 mL), concentrated hydrochloric acid (0.5 mL) was added at room temperature. The reaction mixture was stirred at 100° C. for 4 hours and then cooled down to room temperature, a large amount of solid was precipitated, and then filtered, the residue was washed by water (20 mL×2), dried in vacuum to give a yellow solid 27-b (230 mg, yield: 70%). LC-MS (ESI): m/z=341[M+1]$^+$.

Synthesis of the Compound 27-a

Compound 27-b (230 mg, 0.68 mmol) was dissolved in phosphorus oxychloride (15 mL), N,N-dimethylaniline (0.02 mL) was added, the reaction mixture was stirred at 125° C. for 2 hours and then cooled down to room temperature. After concentration under reduced pressure, the residue was added into a mixture of ice and water (100 mL), and extracted with EtOAc (50 mL×2), the organic phases were combined and washed by water (30 mL) and saturated brine (20 mL), dried over anhydrous sodium sulfate. After concentration under reduced pressure, the residue was purified by silica gel chromatography (PE:EtOAc=5:1) to give a yellow solid 27-a (160 mg, yield: 65.7%).

LC-MS (ESI): m/z=359[M+1]$^+$.

Synthesis of the Compound 27

Compound 27-a (160 mg, 0.45 mmol) was dissolved in tetrahydrofuran (15 mL), 7.0 M ammonia in methanol solution (5 mL, 35 mmol) was added at room temperature, and stirred for 1 hour. The reaction mixture was then concentrated under reduced pressure, and the residue was purified by silica gel chromatography (DCM:EtOAc=15:1) to give the compound 27 (80 mg, yield: 52.4%).

LC-MS (ESI): m/z=340[M+H]$^+$.

$^1$H NMR (400 MHz, CDCl$_3$) δ: 8.49-8.48 (d, J=2.8 Hz, 1H), 7.32-7.28 (m, 1H), 7.25-7.21 (m, 1H), 7.08-7.01 (m, 2H), 6.28-6.27 (d, J=2.8 Hz, 1H), 5.79 (s, 2H), 5.39-5.37 (m, 1H), 3.58-3.54 (m, 1H), 3.02-2.97 (m, 1H), 2.48 (s, 3H) ppm Embodiment 28

2-amino-7-((2-(trifluoromethyl)phenyl)methyl)-4-(5-methylfuran-2-yl)-5H,7H-furo[3,4-d]pyrimidin-5-one (Compound 28)

Synthetic Route

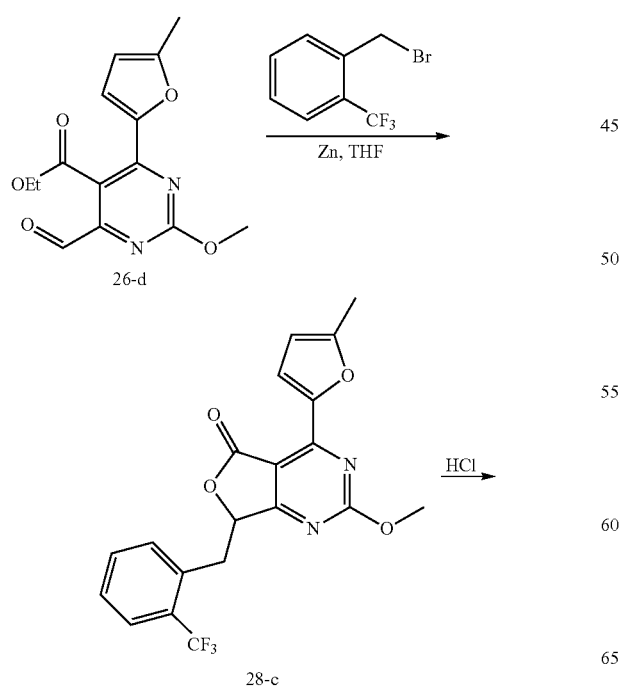

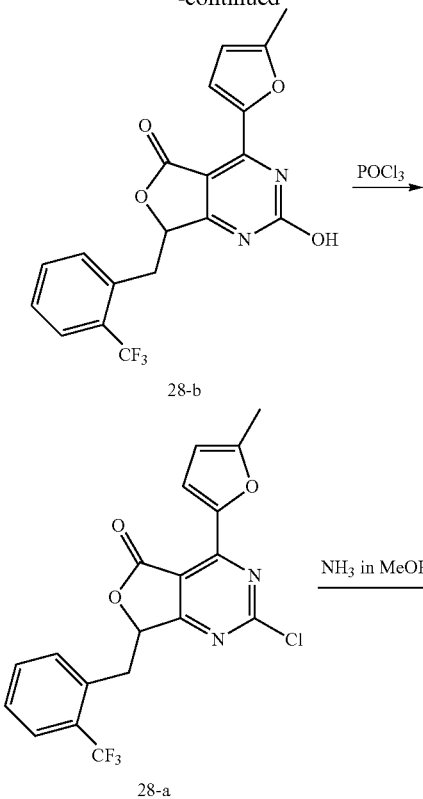

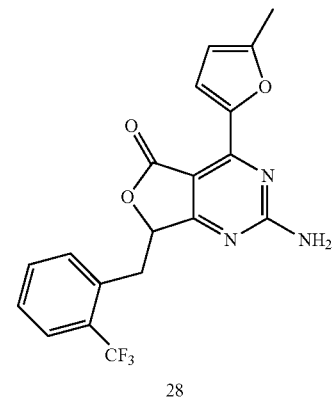

Synthesis of the Compound 28-c

At room temperature, compound 26-d (300 mg, 1.03 mmol) was dissolved in anhydrous tetrahydrofuran (20 mL), zinc powder (203 mg, 3.1 mmol) and 2-trifluoromethylbenzyl bromide (742 mg, 3.1 mmol) were added into the reaction solution. The reaction mixture was heated to 55° C. and stirred for 1 hour. After cooling down to room temperature, saturated ammonium chloride solution (20 mL) was added to quench the reaction. After extraction with EtOAc (50 mL×2), the organic phases were combined and washed successively by water (50 mL) and saturated brine (50 mL), dried over anhydrous sodium sulfate. After concentration under reduced pressure, the residue was purified by silica gel chromatography (PE:EtOAc=5:1) to give a white solid 28-c (340 mg, yield: 83%).

LC-MS (ESI): m/z=405[M+1]$^+$.

Synthesis of the Compound 28-b

Compound 28-c (340 mg, 0.84 mmol) was dissolved in 1,4-dioxane (15 mL), concentrated hydrochloric acid (0.5 mL) was added at room temperature. The reaction mixture was stirred at 100° C. for 4 hours and then cooled down to room temperature, a large amount of solid was precipitated, and then filtered, the residue was washed by water (20 mL×2), dried in vacuum to give a yellow solid 28-b (240 mg, yield: 73%).

LC-MS (ESI): m/z=391[M+1]$^+$.

Synthesis of the Compound 28-a

Compound 28-b (240 mg, 0.62 mmol) was dissolved in phosphorus oxychloride (15 mL), N,N-dimethylaniline (0.02 mL) was added, the reaction mixture was stirred at 125° C. for 2 hours and then cooled down to room temperature. After concentration under reduced pressure, the residue was added into a mixture of ice and water (100 mL), and extracted with EtOAc (50 mL×2), the organic phases were combined and washed by water (30 mL) and saturated brine (20 mL), dried over anhydrous sodium sulfate. After concentration under reduced pressure, the residue was purified by silica gel chromatography (PE:EtOAc=5:1) to give a yellow solid 28-a (216 mg, yield: 86%).

LC-MS (ESI): m/z=409[M+1]$^+$.

Synthesis of the Compound 28

Compound 28-a (216 mg, 0.53 mmol) was dissolved in tetrahydrofuran (15 mL), 7.0 M ammonia in methanol solution (5 mL, 35 mmol) was added at room temperature, and stirred for 15 mins. The reaction mixture was then concentrated under reduced pressure, and the residue was purified by silica gel chromatography (DCM:EtOAc=15:1) to give the compound 28 (140 mg, yield: 67.9%).

LC-MS (ESI): m/z=390[M+H]$^+$.

$^1$H NMR (400 MHz, CDCl$_3$) δ: 8.54-8.53 (d, J=2.8 Hz, 1H), 7.69-7.68 (d, J=6.4 Hz, 1H), 7.58-7.52 (m, 2H), 7.41-7.38 (t, J=5.4 Hz, 1H), 6.30-6.29 (m, 1H), 5.92 (s, 1H), 5.32-5.29 (m, 1H), 4.80 (s, 1H), 3.76-3.73 (m, 1H), 2.98-2.93 (m, 1H), 2.49 (s, 3H) ppm Embodiment 29

2-amino-7-((2,5-difluorophenyl)methyl)-4-(5-methylfuran-2-yl)-5H,7H-furo[3,4-d]pyrimidin-5-one (Compound 29)

Synthetic Route

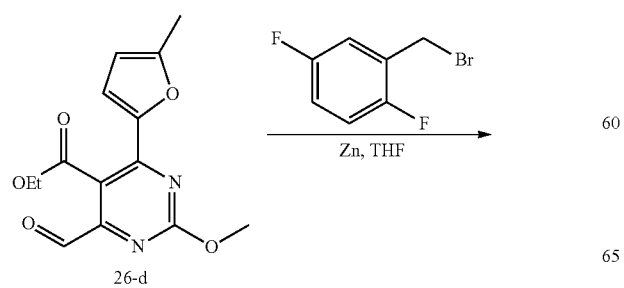

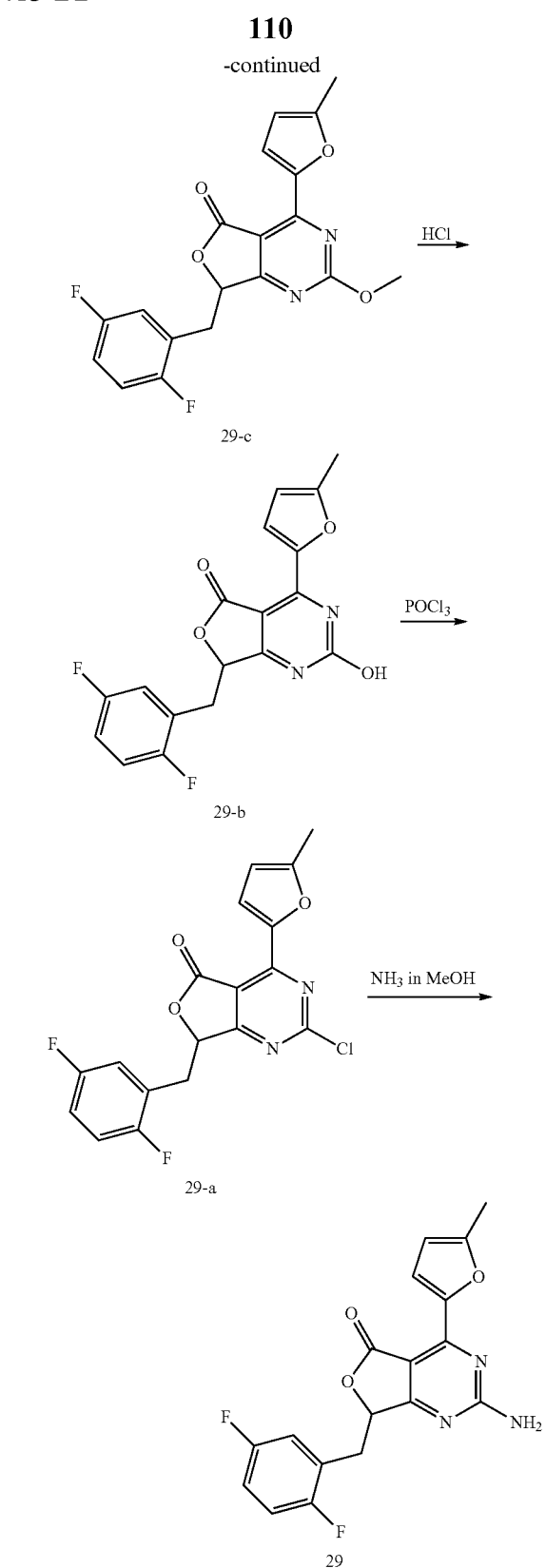

Synthesis of the Compound 29-c

At room temperature, compound 26-d (300 mg, 1.03 mmol) was dissolved in anhydrous tetrahydrofuran (20 mL), zinc powder (203 mg, 3.1 mmol) and 2,5-difluorobenzyl bromide (642 mg, 3.1 mmol) were added into the reaction solution. The reaction mixture was heated to 55° C. and stirred for 1 hour. After cooling down to room temperature, saturated ammonium chloride solution (20 mL) was added to quench the reaction. After extraction with EtOAc (50 mL×2), the organic phases were combined and washed successively by water (50 mL) and saturated brine (50 mL), dried over anhydrous sodium sulfate. After concentration under reduced pressure, the residue was purified by silica gel chromatography (PE:EtOAc=5:1) to give a white solid 29-c (305 mg, yield: 79%). LC-MS (ESI): m/z=373[M+1]$^+$.

Synthesis of the Compound 29-b

Compound 29-c (305 mg, 0.82 mmol) was dissolved in 1,4-dioxane (15 mL), concentrated hydrochloric acid (0.5 mL) was added at room temperature. The reaction mixture was stirred at 100° C. for 4 hours and then cooled down to room temperature, a large amount of solid was precipitated, and then filtered, the residue was washed by water (20 mL×2), dried in vacuum to give a yellow solid 29-b (290 mg, yield: 98%).

LC-MS (ESI): m/z=359[M+1]$^+$.

Synthesis of the Compound 29-a

Compound 29-b (290 mg, 0.81 mmol) was dissolved in phosphorus oxychloride (15 mL), N,N-dimethylaniline (0.02 mL) was added, the reaction mixture was stirred at 125° C. for 2 hours and then cooled down to room temperature. After concentration under reduced pressure, the residue was added into a mixture of ice and water (100 mL), and extracted with EtOAc (50 mL×2), the organic phases were combined and washed by water (30 mL) and saturated brine (20 mL), dried over anhydrous sodium sulfate. After concentration under reduced pressure, the residue was purified by silica gel chromatography (PE:EtOAc=5:1) to give a yellow solid 29-a (196 mg, yield: 64%).

LC-MS (ESI): m/z=377[M+1]$^+$.

Synthesis of the Compound 29

Compound 29-a (196 mg, 0.52 mmol) was dissolved in tetrahydrofuran (15 mL), 7.0 M ammonia in methanol solution (5 mL, 35 mmol) was added at room temperature, and stirred for 15 mins. The reaction mixture was then concentrated under reduced pressure, and the residue was purified by silica gel chromatography (DCM:EtOAc=15:1) to give the compound 29 (130 mg, yield: 70%).

LC-MS (ESI): m/z=358[M+H]$^+$.

$^1$H NMR (400 MHz, CDCl$_3$) δ: 8.51-8.50 (d, J=2.8 Hz, 1H), 7.05-6.97 (m, 2H), 6.94-6.90 (m, 1H), 6.29-6.28 (d, J=2.8 Hz, 1H), 5.85 (s, 2H), 5.36-5.34 (m, 1H), 3.55-3.51 (m, 1H), 2.97-2.92 (m, 1H), 2.49 (s, 3H) ppm Embodiment 30

2-amino-7-((5-chloro-2-fluorophenyl)methyl)-4-(5-methylfuran-2-yl)-5H,7H-furo[3,4-d]pyrimidin-5-one (Compound 30)

Synthetic Route

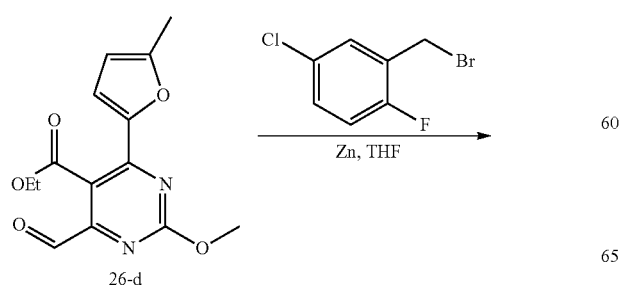

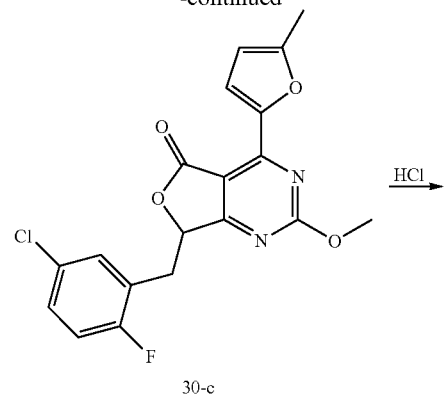

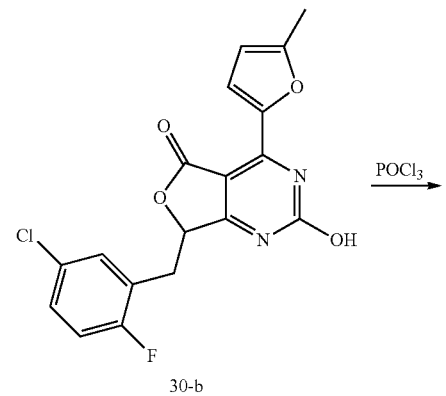

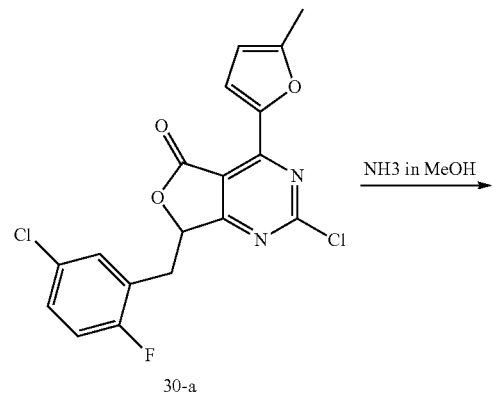

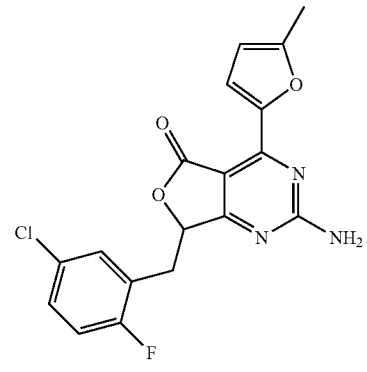

Synthesis of the Compound 30-c

At room temperature, compound 26-d (300 mg, 1.03 mmol) was dissolved in anhydrous tetrahydrofuran (20 mL), zinc powder (203 mg, 3.1 mmol) and 5-chloro-2-fluorobenzyl bromide (693 mg, 3.1 mmol) were added into the reaction solution. The reaction mixture was heated to 55° C. and stirred for 1 hour. After cooling down to room temperature, saturated ammonium chloride solution (20 mL) was added to quench the reaction. After extraction with EtOAc (50 mL×2), the organic phases were combined and washed successively by water (50 mL) and saturated brine (50 mL), dried over anhydrous sodium sulfate. After concentration under reduced pressure, the residue was purified by silica gel chromatography (PE:EtOAc=5:1) to give a white solid 30-c (360 mg, yield: 89%).

LC-MS (ESI): m/z=389[M+1]$^+$.

Synthesis of the Compound 30-b

Compound 30-c (360 mg, 0.89 mmol) was dissolved in 1,4-dioxane (15 mL), concentrated hydrochloric acid (0.5 mL) was added at room temperature. The reaction mixture was stirred at 100° C. for 4 hours and then cooled down to room temperature, a large amount of solid was precipitated, and then filtered, the residue was washed by water (20 mL×2), dried in vacuum to give a yellow solid 30-b (330 mg, yield: 95%).

LC-MS (ESI): m/z=375[M+1]$^+$.

Synthesis of the Compound 30-a

Compound 30-b (330 mg, 0.88 mmol) was dissolved in phosphorus oxychloride (15 mL), N,N-dimethylaniline (0.02 mL) was added, the reaction mixture was stirred at 125° C. for 2 hours and then cooled down to room temperature. After concentration under reduced pressure, the residue was added into a mixture of ice and water (100 mL), and extracted with EtOAc (50 mL×2), the organic phases were combined and washed by water (30 mL) and saturated brine (20 mL), dried over anhydrous sodium sulfate. After concentration under reduced pressure, the residue was purified by silica gel chromatography (PE:EtOAc=5:1) to give a yellow solid 30-a (202 mg, yield: 58%).

LC-MS (ESI): m/z=393[M+1]$^+$.

Synthesis of the Compound 30

Compound 30-a (202 mg, 0.52 mmol) was dissolved in tetrahydrofuran (15 mL), 7.0 M ammonia in methanol solution (2 mL, 14 mmol) was added at room temperature, and stirred for 15 mins. The reaction mixture was then concentrated under reduced pressure, and the residue was purified by silica gel chromatography (DCM:EtOAc=15:1) to give the compound 30 (131 mg, yield: 67.5%).

LC-MS (ESI): m/z=374[M+H]$^+$.

$^1$H NMR (400 MHz, CDCl$_3$) δ: 8.51-8.50 (d, J=2.8 Hz, 1H), 7.32-7.29 (m, 1H), 7.22-7.19 (m, 1H), 7.01-6.97 (t, J=7.2 Hz, 1H), 6.29-6.28 (d, J=2.8 Hz, 1H), 5.82 (s, 2H), 5.35-5.33 (m, 1H), 3.53-3.49 (m, 1H), 2.95-2.90 (m, 1H), 2.49 (s, 3H) ppm Embodiment 31

2-amino-7-((6-chloro-2-fluorophenyl)methyl)-4-(5-methylfuran-2-yl)-5H,7H-furo[3,4-d]pyrimidin-5-one (Compound 31)

Synthetic Route

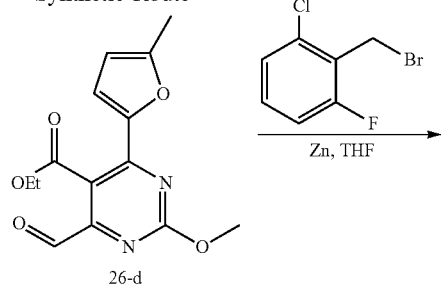

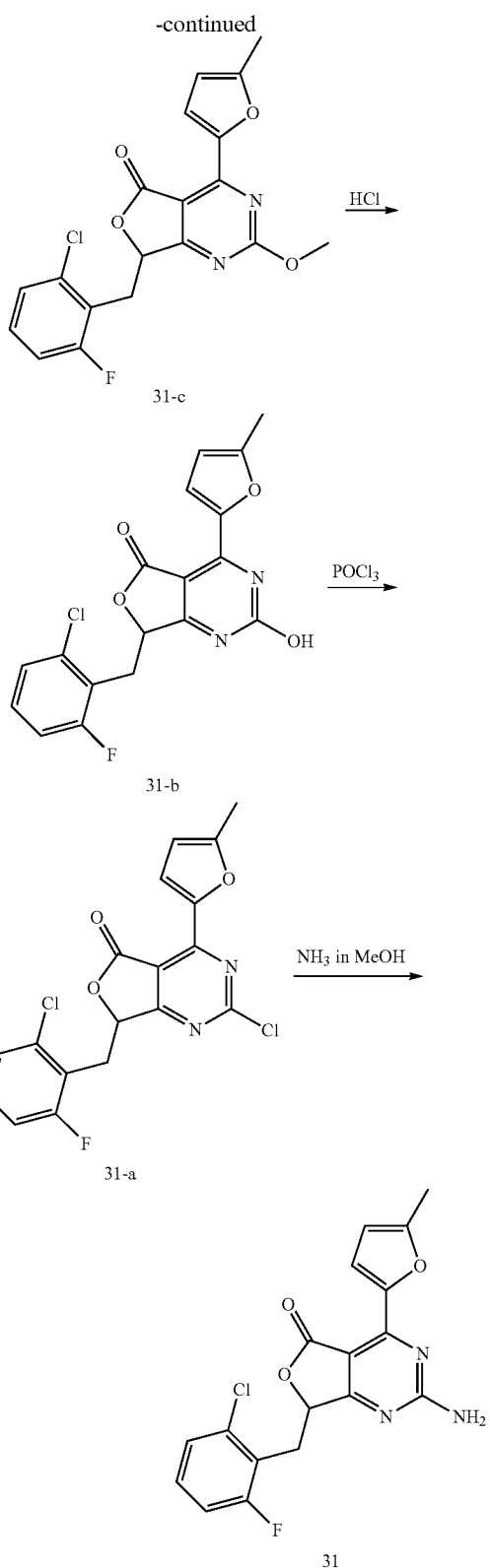

Synthesis of the Compound 31-c

At room temperature, compound 26-d (300 mg, 1.03 mmol) was dissolved in anhydrous tetrahydrofuran (20 mL), zinc powder (203 mg, 3.1 mmol) and 6-chloro-2-fluorobenzyl bromide (693 mg, 3.1 mmol) were added into the reaction solution. The reaction mixture was heated to 55° C. and stirred for 1 hour. After cooling down to room temperature, saturated ammonium chloride solution (20 mL) was added to quench the reaction. After extraction with EtOAc (50 mL×2), the organic phases were combined and washed successively by water (50 mL) and saturated brine (50 mL), dried over anhydrous sodium sulfate. After concentration under reduced pressure, the residue was purified by silica gel chromatography (PE:EtOAc=5:1) to give a white solid 31-c (325 mg, yield: 81%).

LC-MS (ESI): m/z=389[M+1]$^+$.

Synthesis of the Compound 31-b

Compound 31-c (325 mg, 0.84 mmol) was dissolved in 1,4-dioxane (15 mL), concentrated hydrochloric acid (0.5 mL) was added at room temperature. The reaction mixture was stirred at 100° C. for 4 hours and then cooled down to room temperature, a large amount of solid was precipitated, and then filtered, the residue was washed by water (20 mL×2), dried in vacuum to give a yellow solid 31-b (165 mg, yield: 53%). LC-MS (ESI): m/z=375[M+1]$^+$.

Synthesis of the Compound 31-a

Compound 31-b (165 mg, 0.44 mmol) was dissolved in phosphorus oxychloride (15 mL), N,N-dimethylaniline (0.02 mL) was added, the reaction mixture was stirred at 125° C. for 2 hours and then cooled down to room temperature. After concentration under reduced pressure, the residue was added into a mixture of ice and water (100 mL), and extracted with EtOAc (50 mL×2), the organic phases were combined and washed by water (30 mL) and saturated brine (20 mL), dried over anhydrous sodium sulfate. After concentration under reduced pressure, the residue was purified by silica gel chromatography (PE:EtOAc=5:1) to give a yellow solid 31-a (120 mg, yield: 69%).

LC-MS (ESI): m/z=393[M+1]$^+$.

Synthesis of the Compound 31

Compound 31-a (120 mg, 0.31 mmol) was dissolved in tetrahydrofuran (15 mL), 7.0 M ammonia in methanol solution (2 mL, 14 mmol) was added at room temperature, and stirred for 15 mins. The reaction mixture was then concentrated under reduced pressure, and the residue was purified by silica gel chromatography (DCM:EtOAc=15:1) to give the compound 31 (50 mg, yield: 43.2%).

LC-MS (ESI): m/z=374[M+H]$^+$.

$^1$H NMR (400 MHz, CDCl$_3$) δ: 8.55-8.54 (d, J=3.2 Hz, 1H), 7.23-7.21 (m, 2H), 7.04-7.00 (m, 1H), 6.29-6.28 (m, 1H), 5.74 (s, 2H), 5.43-5.40 (m, 1H), 3.52-3.48 (m, 1H), 3.25-3.23 (m, 1H), 2.49 (s, 3H) ppm Embodiment 32

2-amino-7-((4-fluoro-2-(trifluoromethyl)phenyl) methyl)-4-(5-methylfuran-2-yl)-5H,7H-furo[3,4-d] pyrimidin-5-one (Compound 32)

Synthetic Route

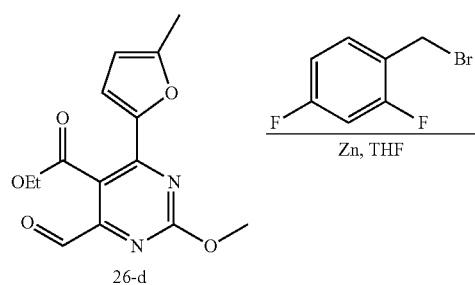

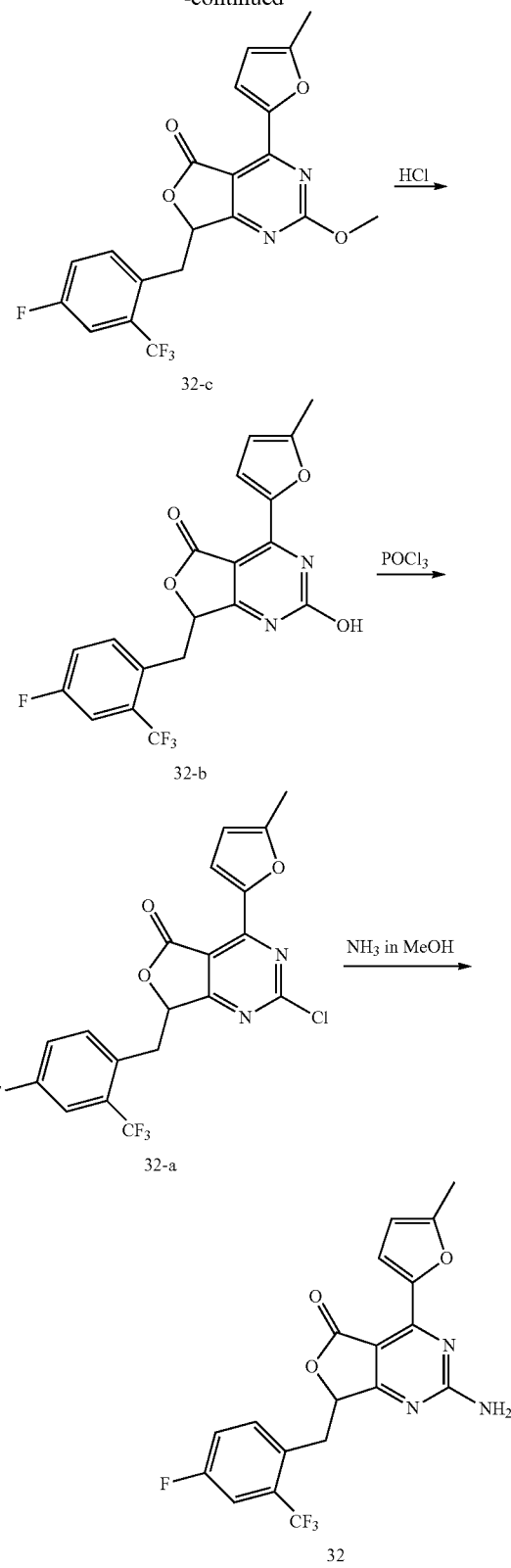

Synthesis of the Compound 32-c

At room temperature, compound 26-d (300 mg, 1.03 mmol) was dissolved in anhydrous tetrahydrofuran (20 mL), zinc powder (203 mg, 3.1 mmol) and 4-fluoro-2-trifluoromethylbenzyl bromide (798 mg, 3.1 mmol) were added into the reaction solution. The reaction mixture was heated to 55° C. and stirred for 1 hour. After cooling down to room temperature, saturated ammonium chloride solution (20 mL) was added to quench the reaction. After extraction with EtOAc (50 mL×2), the organic phases were combined and washed successively by water (50 mL) and saturated brine (50 mL), dried over anhydrous sodium sulfate. After concentration under reduced pressure, the residue was purified by silica gel chromatography (PE:EtOAc=5:1) to give a white solid 32-c (307 mg, yield: 70.6%).

LC-MS (ESI): m/z=423[M+1]$^+$.

Synthesis of the Compound 32-b

Compound 32-c (307 mg, 0.73 mmol) was dissolved in 1,4-dioxane (15 mL), concentrated hydrochloric acid (0.5 mL) was added at room temperature. The reaction mixture was stirred at 100° C. for 4 hours and then cooled down to room temperature, a large amount of solid was precipitated, and then filtered, the residue was washed by water (20 mL×2), dried in vacuum to give a yellow solid 32-b (220 mg, yield: 74%).

LC-MS (ESI): m/z=375[M+1]$^+$.

Synthesis of the Compound 32-a

Compound 32-b (220 mg, 0.54 mmol) was dissolved in phosphorus oxychloride (15 mL), N,N-dimethylaniline (0.02 mL) was added, the reaction mixture was stirred at 125° C. for 2 hours and then cooled down to room temperature. After concentration under reduced pressure, the residue was added into a mixture of ice and water (100 mL), and extracted with EtOAc (50 mL×2), the organic phases were combined and washed by water (30 mL) and saturated brine (20 mL), dried over anhydrous sodium sulfate. After concentration under reduced pressure, the residue was purified by silica gel chromatography (PE:EtOAc=5:1) to give a yellow solid 32-a (177 mg, yield: 77%).

LC-MS (ESI): m/z=427[M+1]$^+$.

Synthesis of the Compound 32

Compound 32-a (177 mg, 0.42 mmol) was dissolved in tetrahydrofuran (15 mL), 7.0 M ammonia in methanol solution (2 mL, 14 mmol) was added at room temperature, and stirred for 15 mins. The reaction mixture was then concentrated under reduced pressure, and the residue was purified by silica gel chromatography (DCM:EtOAc=15:1) to give the compound 32 (158 mg, yield: 92.4%).

LC-MS (ESI): m/z=408[M+H]$^+$.

$^1$H NMR (400 MHz, CDCl$_3$) δ: 8.53-8.52 (d, J=2.4 Hz, 1H), 7.58-7.55 (m, 1H), 7.42-7.39 (m, 1H), 7.26-7.23 (m, 1H), 6.30-6.29 (d, J=2.8 Hz, 1H), 5.81 (s, 2H), 5.28-5.25 (m, 1H), 3.73-3.69 (m, 1H), 2.96-2.90 (m, 1H), 2.49 (s, 3H) ppm Embodiment 33

(S)-7-benzyl-4-(furan-2-yl)-5,7-dihydrofuro[3,4-d]pyrimidin-2-amine (Compound 33)

Synthetic Route

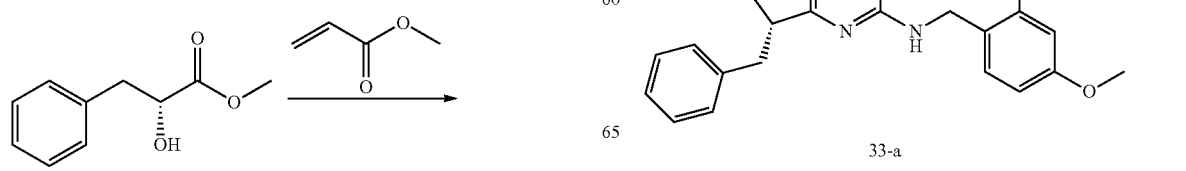

-continued

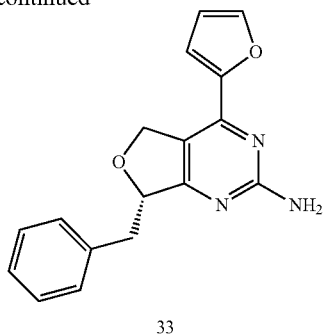

33

Synthesis of the Compound 33-f

Sodium hydride (1.08 g, 27.0 mmol) was suspended in anhydrous tetrahydrofuran (60 mL), (R)-3-phenyl-2-hydracrylic acid (3.24 g, 18.0 mmol) was added dropwise at 0° C. After the completion of the addition, the reaction mixture was further stirred at 0° C. for 30 mins, then methyl acrylate (2.22 g, 27.0 mmol) was added thereto. The reaction mixture was further stirred at room temperature for 3 hours, then the reaction was quenched by adding 0.5 M hydrochloric acid (30 mL). The mixture was extracted with EtOAc (50 mL×3). The organic phases were combined and washed by saturated brine (50 mL), dried over anhydrous sodium sulfate. After concentration under reduced pressure, the residue was purified by silica gel chromatography (PE:EtOAc=20:1-10:1) to give a colorless liquid product 33-f (2.8 g, yield: 66%).

Synthesis of the Compound 33-e

Urea (2.15 g, 36.0 mmol) and 35% concentrated hydrochloric acid (1.5 mL) were added into the compound 33-f (2.8 g, 12.0 mmol) in ethanol (50 mL) solution, and was heated and refluxed for reaction for 4 hours, then cooled down to room temperature, then concentrated under reduced pressure, the residue was added into EtOAc (100 mL), then washed successively by water (100 mL) and saturated brine (100 mL), dried over anhydrous sodium sulfate. After concentration under reduced pressure, the residue was purified by silica gel chromatography (PE:EtOAc=10:1-1:1) to give a pale yellow solid product 33-e (810 mg, yield: 25%). LC-MS (ESI): m/z=277 [M+1]$^+$.

Synthesis of the Compound 33-d

Compound 33-e (810 mg, 2.93 mmol) was dissolved in ethanol (20 mL) and tetrahydrofuran (10 mL) solution, potassium tert-butoxide (493 mg, 4.4 mmol) was added. The reaction mixture was stirred at 60° C. for 2 hours, then cooled down to room temperature. After concentration under reduced pressure, the residue was dissolved in water (15 mL), and 1 M hydrochloric acid was added dropwise slowly until pH<2, a white solid was precipitated. After filtration, the residue was dried in vacuum to give a white solid 33-d (550 mg, yield: 77%).

$^1$HNMR (500 MHz, DMSO-d$_6$) δ: 11.57 (s, 1H), 11.02 (s, 1H), 7.26-7.29 (m, 2H), 7.19-7.22 (m, 3H), 5.17-5.20 (m, 1H), 4.56-4.58 (m, 1H), 4.41-4.44 (m, 1H), 3.13-3.17 (m, 1H), 2.89-2.93 (m, 1H) ppm Synthesis of the Compound 33-c Compound 33-d (244 mg, 1.0 mmol) was suspended in phosphorus oxychloride (20 mL). The reaction mixture was stirred at 120° C. for 3 hours, then cooled down to room temperature. After concentration under reduced pressure, the residue was added into EtOAc (50 mL×2), then washed by water (20 mL) and saturated brine (20 mL) successively. After concentration under reduced pressure, the residue was purified by silica gel chromatography (PE:EtOAc=20:1-10:1) to give a white solid 33-c (260 mg, yield: 92%).

LC-MS (ESI): m/z=281 [M+1]$^+$.

Synthesis of the Compound 33-b

Compound 33-c (260 mg, 0.93 mmol) was dissolved in dry tetrahydrofuran (30 mL), 2-(tributylstannyl)furane (364 mg, 1.02 mmol) and palladium tetrakis(triphenyl)phosphine (107.4 mg, 0.093 mmol) were added. Under nitrogen atmosphere the reaction mixture was stirred at 60° C. for 16 hours, then cooled down to room temperature. After concentration under reduced pressure, the residue was purified by silica gel chromatography (PE:EtOAc=20:1-10:1) to give a pale yellow solid 33-b (240 mg, yield: 83%).

LC-MS (ESI): m/z=313 [M+1]$^+$.

Synthesis of the Compound 33-a

Compound 33-b (240 mg, 0.77 mmol) was dissolved in dioxane (20 mL), 2,4-dimethoxybenzylamine (385 mg, 2.30 mL) and di(isopropyl)ethylamine (296.7 mg, 2.3 mmol) were added. The reaction mixture was heated and refluxed for 4 hours, then cooled down to room temperature. After concentration under reduced pressure, the residue was purified by silica gel chromatography (PE:EtOAc=10:1-5:1) to give a pale yellow viscous product 33-a (150 mg, yield: 44%). LC-MS (ESI): m/z=444 [M+1]$^+$.

Synthesis of the Compound 33

Compound 33-a (150 mg, 0.33 mmol) was added into trifluoroacetic acid (10 mL), the reaction mixture was heated and refluxed for hours, then cooled down to room temperature. After concentration under reduced pressure, the residue was washed by saturated dicarbonate aqueous solution (20 mL), then extracted with EtOAc (20 mL×3). The organic phases were combined and then concentrated under reduced pressure, and the residue was purified by silica gel chromatography (PE:EtOAc=10:1-3:1) to give a white solid 33 (50 mg, yield: 50%).

LC-MS (ESI): m/z=294 [M+1]$^+$.

$^1$HNMR (500 MHz, CDCl$_3$) δ: 7.60 (s, 1H), 7.19-7.26 (m, 5H), 7.08 (d, J=3.5 Hz, 1H), 6.55-6.57 (m, 1H), 5.35 (brs, 2H), 5.21-5.23 (m, 1H), 5.16 (d, J=12.5 Hz, 1H), 5.08 (dd, J=12.5 Hz, 2.5 Hz, 1H), 3.30 (dd, J=14 Hz, 4.0 Hz, 1H), 2.96-3.01 (m, 1H) ppm

Embodiment 34
2-amino-9-((2,4-difluorophenyl)methyl)-6-(furan-2-yl)-8,9-dihydro-7H-purinyl-8-one (compound 34)
Synthetic Route
Synthesis of the Compound 34-e
2,4,6-Trihydro-5-nitropyrimidine (454 mg, 2.0 mmol) and diisopropylethylamine (516 mg, 4.0 mmol) were dissolved in anhydrous tetrahydrofuran (20 mL), 2,4-difluorobenzylamine (300 mg, 2.1 mmol) was added dropwise slowly at 0° C., stirred at 0° C. for 1 hour. After concentra-
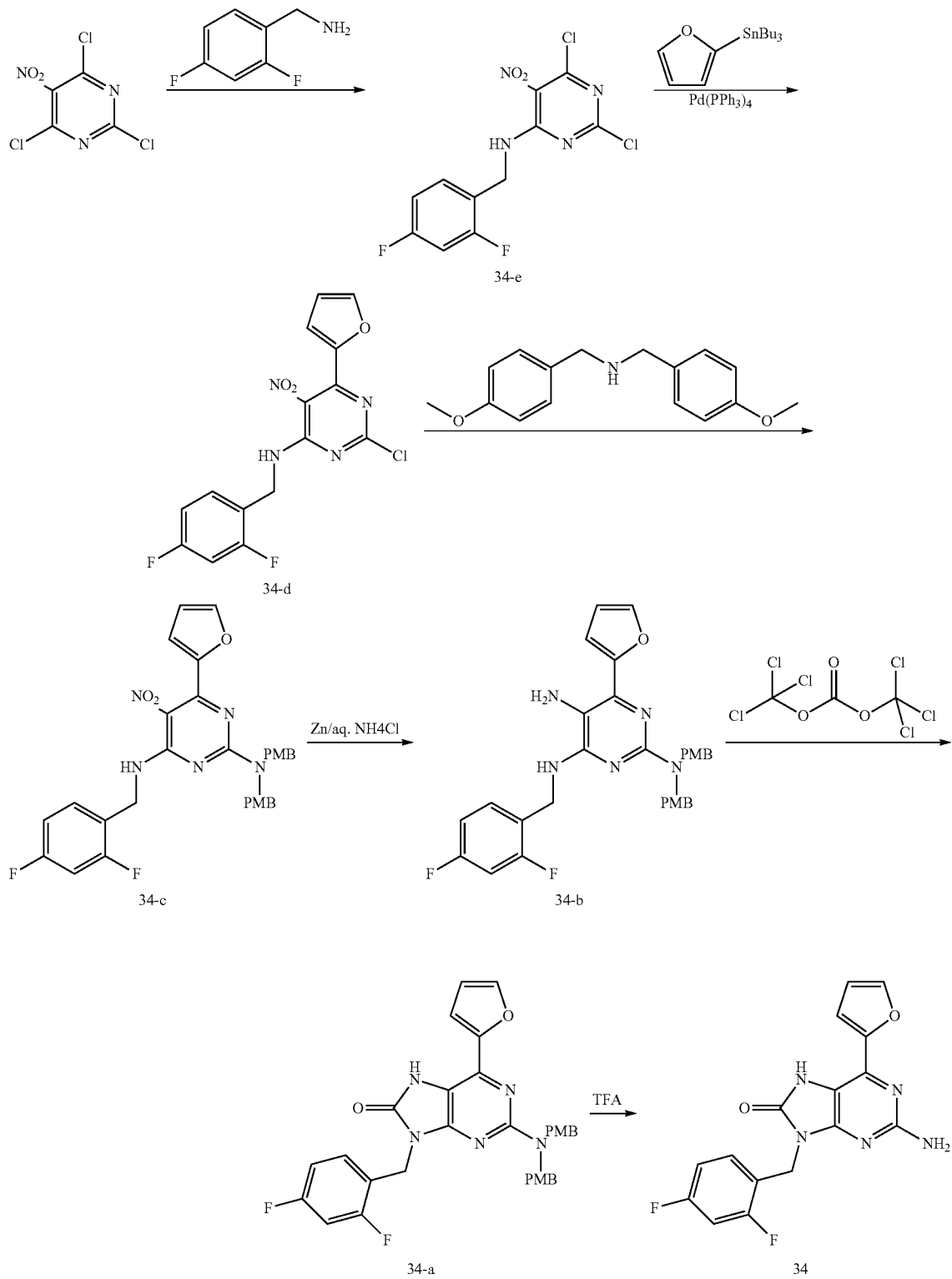

tion under reduced pressure, the residue was purified by silica gel chromatography (PE:EtOAc=15:1) to give a yellow solid product 34-e (547 mg, yield: 82%).

Synthesis of the Compound 34-d

Compound 34-e (200 mg, 0.60 mmol), 2-(tributylstannyl)furane (257 mg, 0.72 mmol), lithium chloride (50 mg, 1.2 mmol) and palladium tetrakis(triphenyl)phosphine (63 mg, 0.06 mmol) were added into dry tetrahydrofuran (10 mL). The reaction mixture was stirred at 25° C. for 18 hours under nitrogen atmosphere. After concentration under reduced pressure, the residue was purified by silica gel chromatography (PE:EtOAc=10:1) to give a yellow solid product 34-d (120 mg, yield: 55%).

LC-MS (ESI): m/z=367[M+1]$^+$.

Synthesis of the Compound 34-c

Compound 34-d (120 mg, 0.30 mmol), bis(p-methoxybenzyl)amine (168 mg, 0.65 mmol) and diisopropylethylamine (84 mg, 0.65 mmol) were added into dry tetrahydrofuran (10 mL). The reaction mixture was reacted at 60° C. for 5 hours, then cooled down to room temperature. The reaction solution was then concentrated, and the residue was purified by silica gel chromatography (PE:EtOAc=10:1) to give a yellow solid product 34-c (152 mg, yield: 78%).

LC-MS (ESI): m/z=588 [M+1]$^+$.

Synthesis of the Compound 34-b

Ammonium chloride (268 mg, 5.0 mmol) was dissolved in water (5 mL), zinc powder (163 mg, 2.5 mmol) and ethanol (10 mL) were added successively, and 34-c (120 mg, 0.30 mmol) in tetrahydrofuran (8 mL) solution was added dropwise while stirring at 0° C. After stirring for 1 hour at 0° C., the reaction was warmed to room temperature. The reaction solution was then concentrated under reduced pressure, the residue was diluted by water (20 mL), then extracted with EtOAc (20 mL), the organic phase were washed by saturated brine (20 mL), dried over anhydrous sodium sulfate, then concentrated under reduced pressure, and the residue was purified by silica gel chromatography (PE:EtOAc=5:1) to give a red solid product 34-b (120 mg, yield: 86%). LC-MS (ESI): m/z=558 [M+1]$^+$.

Synthesis of the Compound 34-a

Triphosgene (74 mg, 0.25 mmol) was added into 34-b (120 mg, 0.21 mmol) and diisopropylethylamine (387 mg, 3.0 mmol) in dry tetrahydrofuran (10 mL) solution at 0° C., stirred for 10 mins and then warmed to room temperature and stirred for further 1 hour. The reaction solution was then concentrated under reduced pressure, and the residue was purified by silica gel chromatography (PE:EtOAc=3:1) to give a pink solid product 34-a (75 mg, yield: 61%). LC-MS (ESI): m/z=584 [M+1]$^+$.

Synthesis of the Compound 34

Compound 34-a (38 mg, 0.065 mmol) was added into trifluoroacetic acid (4 mL). The reaction mixture was stirred at 80° C. for 5 hours, then cooled down to room temperature. The reaction solution was then concentrated under reduced pressure, and the residue was purified by silica gel chromatography (PE:EtOAc=2:1) to give a white solid product 34 (15 mg, yield: 67%).

LC-MS (ESI): m/z=344 [M+1]$^+$.

$^1$H NMR (500 MHz, CD$_3$OD) δ: 7.74 (s, 1H), 7.38 (s, 2H), 6.82-6.87 (m, 2H), 6.65 (s, 1H), 5.07 (s, 2H) ppm Embodiment 35

2-amino-9-((2,4-difluorophenyl)methyl)-6-(furan-2-yl)-7-methyl-8,9-dihydro-7H-purinyl-8-one (Compound 35)

Synthetic Route

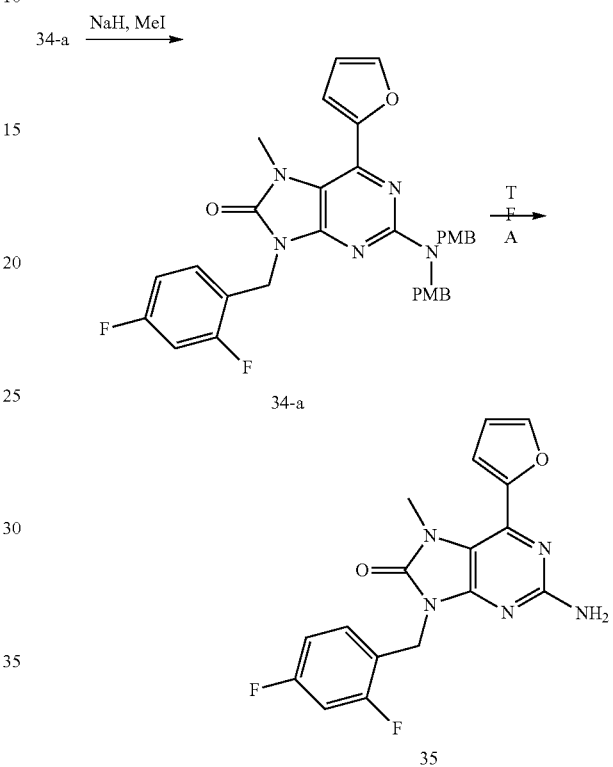

Synthesis of the Compound 35-a

60% Sodium hydride dispersed in mineral oil (8 mg, 0.2 mol) was suspended in dry N,N-dimethylformamide (4 mL), and then 34-a (36 mg, 0.061 mmol) in dry N,N-dimethylformamide (2 mL) was added dropwise to this suspension at 0° C. under nitrogen atmosphere, and further stirred at 0° C. for 1 hour. Methyl iodide (43 mg, 0.3 mmol) was added, then the reaction mixture was warmed to room temperature and continued to react for 1 hour. The reaction mixture was poured into half saturated ammonium chloride aqueous solution (20 mL), then extracted with EtOAc (20 mL×3). The organic phase were washed by saturated brine (20 mL), dried over anhydrous sodium sulfate, then concentrated under reduced pressure, and the residue was purified by silica gel chromatography (PE:EtOAc=2:1) to give a white solid product 35-a (33 mg, yield: 90%)).

LC-MS (ESI): m/z=344 [M+1]$^+$.

Synthesis of the Compound 35

Compound 35-a (33 mg, 0.055 mmol) was added into trifluoroacetic acid (4 mL). The reaction mixture was stirred at 80° C. for 4 hours, then cooled down to room temperature. The reaction solution was then concentrated, and the residue was purified by silica gel chromatography (PE:EtOAc=2:1) to give a white solid product 35 (18 mg, yield: 91%).

LC-MS (ESI): m/z=358 [M+1]$^+$.

¹H NMR (500 MHz, CD₃OD) δ: 7.60 (s, 1H), 7.31-7.36 (m, 1H), 7.10 (s, 1H), 6.80-6.83 (m, 2H), 6.58 (s, 1H), 5.09 (s, 2H), 3.58 (s, 3H) ppm Embodiment 36

2-amino-7-((2-(trifluoromethoxyl)phenyl)methyl)-4-(5-methylfuran-2-yl)-5H,7H-furo[3,4-d]pyrimidin-5-one (Compound 36)

Synthetic Route

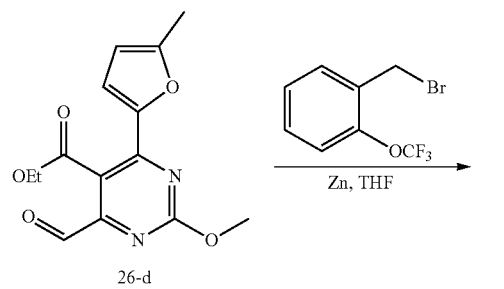

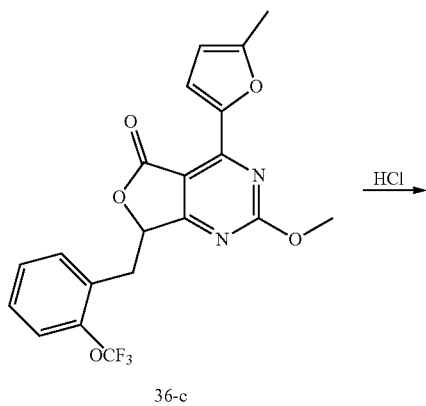

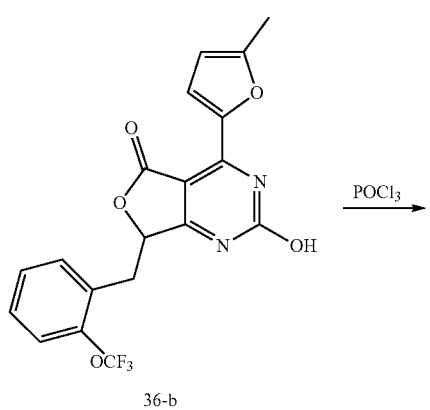

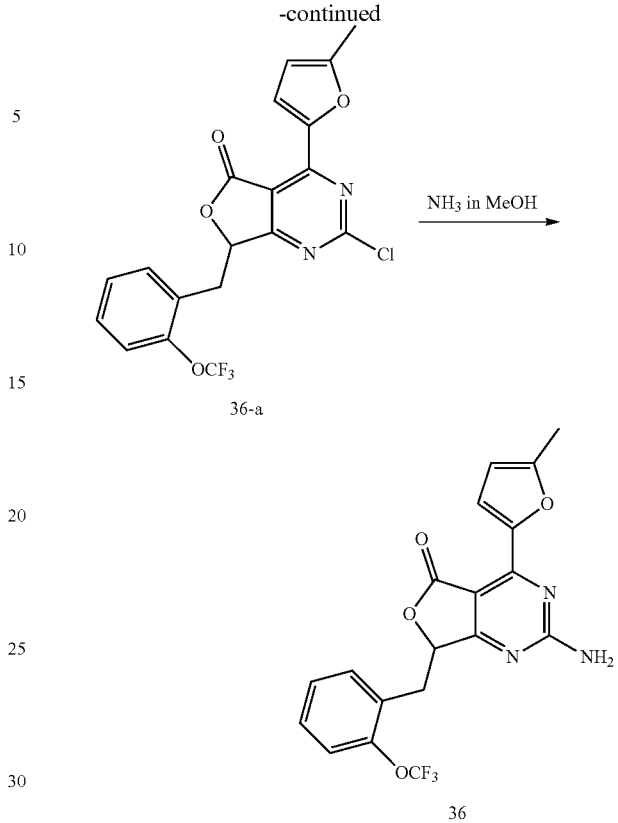

Synthesis of the Compound 36-c

At room temperature, compound 26-d (300 mg, 1.03 mmol) was dissolved in anhydrous tetrahydrofuran (20 mL), zinc powder (203 mg, 3.1 mmol) and 2-trifluoromethoxyl-benzyl bromide (791 mg, 3.1 mmol) were added into the reaction solution. The reaction mixture was heated to 55° C. and stirred for 1 hour. After cooling down to room temperature, saturated ammonium chloride solution (20 mL) was added to quench the reaction. After extraction with EtOAc (50 mL×2), the organic phases were combined and washed successively by water (50 mL) and saturated brine (50 mL), dried over anhydrous sodium sulfate. After concentration under reduced pressure, the residue was purified by silica gel chromatography (PE:EtOAc=5:1) to give a white solid 36-c (318 mg, yield: 73%). LC-MS (ESI): m/z=421[M+1]⁺.

Synthesis of the Compound 36-b

Compound 36-c (318 mg, 0.76 mmol) was dissolved in 1,4-dioxane (15 mL), concentrated hydrochloric acid (0.5 mL) was added at room temperature. The reaction mixture was stirred at 100° C. for 4 hours and then cooled down to room temperature, a large amount of solid was precipitated, and then filtered, the residue was washed by water (20 mL×2), dried in vacuum to give a yellow solid 36-b (254 mg, yield: 83%). LC-MS (ESI): m/z=407[M+1]⁺.

Synthesis of the Compound 36-a

Compound 36-b (254 mg, 0.63 mmol) was dissolved in phosphorus oxychloride (15 mL), N,N-dimethylaniline (0.02 mL) was added, the reaction mixture was stirred at 125° C. for 2 hours and then cooled down to room temperature. After concentration under reduced pressure, the residue was added into a mixture of ice and water (100 mL), and extracted with EtOAc (50 mL×2), the organic phases were combined and washed by water (30 mL) and saturated brine (20 mL), dried over anhydrous sodium sulfate. After concentration under reduced pressure, the residue was purified by silica gel chromatography (PE:EtOAc=5:1) to give a yellow solid 36-a (126 mg, yield: 50%).

LC-MS (ESI): m/z=425[M+1]+.

Synthesis of the Compound 36

Compound 36-a (126 mg, 0.30 mmol) was dissolved in tetrahydrofuran (15 mL), 7.0 M ammonia in methanol solution (2 mL, 14 mmol) was added at room temperature, and stirred for 15 mins. The reaction mixture was then concentrated under reduced pressure, and the residue was purified by silica gel chromatography (DCM:EtOAc=15:1) to give the compound 36 (80 mg, yield: 65.8%).

LC-MS (ESI): m/z=406[M+H]+.

$^1$H NMR (400 MHz, CDCl$_3$) δ: 8.50-8.49 (d, J=3.2 Hz, 1H), 7.44-7.41 (m, 1H), 7.31-7.29 (m, 1H), 7.26-7.23 (m, 2H), 6.28-6.27 (d, J=2.8 Hz, 1H), 5.78 (s, 2H), 5.37-5.35 (m, 1H), 3.60-3.57 (m, 1H), 3.03-2.98 (m, 1H), 2.48 (s, 3H) ppm Embodiment 37

2-amino-7-((2-(trifluoromethoxyl)phenyl)methyl)-4-(5-bromofuran-2-yl)-5H,7H-furo[3,4-d]pyrimidin-5-one (Compound 37)

Synthetic Route

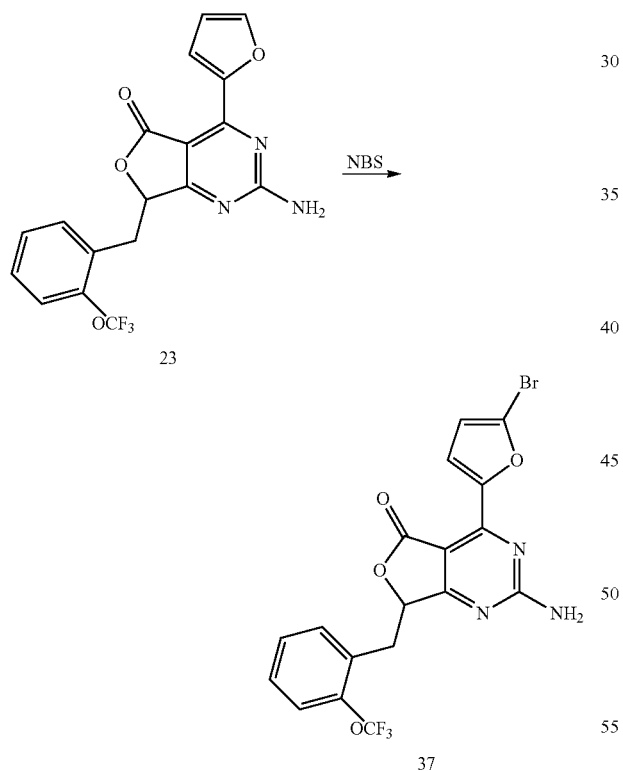

Synthesis of the Compound 37

Compound 23 (130 mg, 0.33 mmol) was dissolved in N,N-dimethylformamide (15 mL), N-bromosuccinimide (89 mg, 0.49 mmol) was added, the reaction mixture was stirred at room temperature for 12 hours. The reaction solution was then concentrated under reduced pressure, the residue was purified by HPLC (mobile phase: water (10 mM ammonium bicarbonate), acetonitrile; gradient: 15%-65% (initial mobile phase was 15% water-85% acetonitrile, at the end the mobile phase was 65% water-35% acetonitrile, the % refers to volume percentage) to give the compound 37 (70 mg, yield: 45.2%).

LC-MS (ESI): m/z=470 [M+H]+.

$^1$H NMR (400 MHz, CDCl$_3$) δ: 8.50-8.49 (d, J=3.2 Hz, 1H), 7.43-7.41 (m, 1H), 7.31-7.29 (m, 1H), 7.24-7.23 (m, 2H), 8.59-8.58 (d, J=3.2 Hz, 1H), 5.85 (s, 2H), 5.40-5.38 (m, 1H), 3.61-3.57 (m, 1H), 3.04-2.99 (m, 1H) ppm Embodiment 38

2-amino-7-((2-fluorophenyl)methylene)-4-(furan-2-yl)-6-methyl-5H,6H,7H-pyrrolo[3,4-d]pyrimidin-5-one (Compound 38)

Synthetic Route

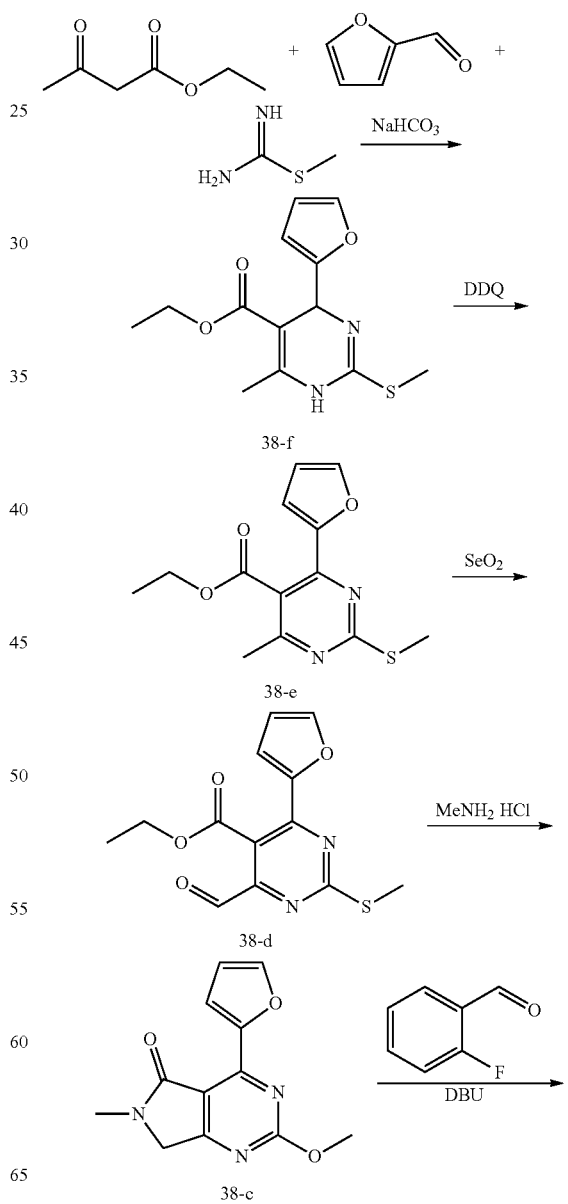

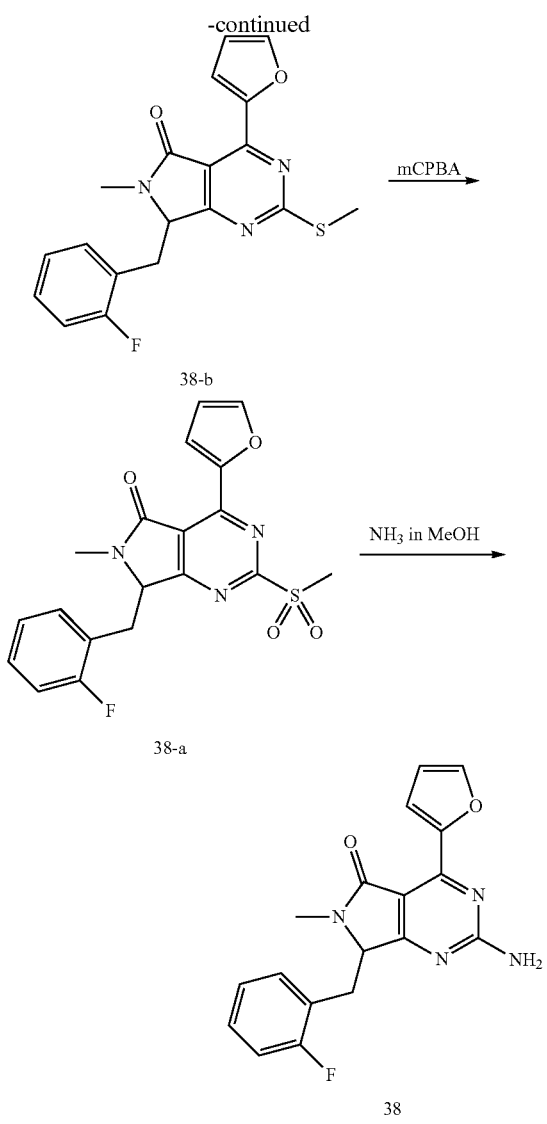

Synthesis of the Compound 38-f

Sodium dicarbonate (21.2 g, 200 mmol) was added into furfural (9.60 g, 100 mmol), S-methylisothiourea sulfate (20.7 g, 150 mmol) and ethyl acetoacetate (13.0 g, 100 mmol) in N,N-dimethylformyl (80 mL) solution. The reaction mixture was stirred at 80° C. for 6 hours, then cooled down to room temperature. After concentration under reduced pressure, water (100 mL) was added into the residue, then extracted with EtOAc (40 mL×3), the combined organic phases were washed by saturated brine (100 mL), dried over anhydrous sodium sulfate. After concentration under reduced pressure, the residue was purified by silica gel chromatography (PE:EtOAc=15:1) to give a yellow solid product 38-f (5.7 g, yield: 20%). LC-MS (ESI): m/z=281 [M+H]$^+$.

Synthesis of the Compound 38-e

In ice water bath, 2,3-dichloro-5,6-dicyanobenzoquinone (6.0 g, 26.4 mmol) was added in batches into compound 38-f (5.60 g, 20.0 mmol) in DCM (100 mL) solution, the reaction mixture was warmed to room temperature and further stirred for 8 hours. After filtration, the filter cake was washed by DCM (100 mL). Then the filtrate was concentrated under reduced pressure, and the residue was purified by silica gel chromatography (PE:EtOAc=12:1) to give a yellow solid product 38-e (4.10 g, yield: 74%)).

LC-MS (ESI): m/z=279 [M+H]$^+$.

Synthesis of the Compound 38-d

Compound 38-e (1.40 g, 5.0 mmol) was dissolved in 1,4-dioxane (60 mL), selenium dioxide (715 mg, 6.5 mmol) and glacial acetic acid (1.5 mL) were added. The reaction mixture was refluxed for 8 hours, then cooled down to room temperature. The reaction solution was then concentrated under reduced pressure, the residue was diluted by EtOAc (60 mL). After filtration, the filtrate was concentrated under reduced pressure, and the residue was purified by silica gel chromatography (PE:EtOAc=10:1-15:1) to give a yellow solid 38-d (0.98 g, yield: 70%).

LC-MS (ESI): m/z=293 [M+H]$^+$.

Synthesis of the Compound 38-c

Methylamine hydrochloride (680 mg, 10.0 mmol) and sodium acetate (820 mg, 10.0 mmol) were added into methanol (30 mL). The mixture was stirred at room temperature for 1 hour, and cooled down with ice water bath to 5° C., then compound 38-d (980 mg, 3.35 mmol) and DCM (30 mL) were added. After stirring for 30 mins, sodium cyanoborohydride (315 mg, 5.0 mmol) was added thereto, the reaction mixture was warmed to room temperature and further stirred for 16 hours. After concentration under reduced pressure, the residue was diluted by water (100 mL), extracted with DCM (50 mL×2). The organic phase were then concentrated under reduced pressure, and the residue was purified by silica gel chromatography (PE:EtOAc=2:1) to give a white solid product 38-c (560 mg, yield: 64%).

LC-MS (ESI): m/z=262 [M+H]$^+$.

Synthesis of the Compound 38-b 1,8-Diazabicycloundec-7-ene (60 mg, 0.4 mmol) was added into compound 38-c (261 mg, 1.0 mmol) and o-fluorobenzaldehyde (248 mg, 2.0 mmol) in dioxane (20 mL) solution. The mixture was refluxed under nitrogen atmosphere for 16 hours, then cooled down to room temperature. After concentration under reduced pressure, the residue was washed by EtOAc (20 mL×3), followed by filtration to give a brown solid 38-b (153 mg, yield: 41%), which was without further purification. LC-MS (ESI): m/z=368 [M+H]$^+$.

Synthesis of the Compound 38-a

80% m-Chloroperoxybenzoic acid (114 mg, 0.52 mmol) was added into compound 38-b (60 mg, 0.16 mmol) in DCM (20 mL) solution, stirred at room temperature for 16 hours. The reaction was quenched by adding saturated sodium thiosulfate solution (3 mL). After adding water (20 mL), the mixture was extracted with DCM (20 mL×3). The organic phase was then concentrated under reduced pressure, and the residue was purified by silica gel chromatography (PE:EtOAc=1:1) to give a pale yellow solid 38-a (40 mg, yield: 62%).

Synthesis of the Compound 38

7 N Ammonia in methanol solution (2 mL, 14 mmol) was added into compound 38-a (40 mg, 0.10 mmol) in tetrahydrofuran (5 mL) solution. The mixture was stirred to react at room temperature for 1 hour. After concentration under reduced pressure, the residue was purified by silica gel chromatography (PE:EtOAc=1:3) to give a white solid 38 (17 mg, yield: 50.4%).

LC-MS (ESI): m/z=337 [M+H]$^+$.

$^1$H NMR (500 MHz, CDCl$_3$) δ: 8.65 (d, J=8.0 Hz, 1H), 8.05-8.08 (m, 1H), 7.68-7.69 (m, 1H), 7.29-7.34 (m, 1H), 7.13-7.16 (m, 1H), 7.07-7.11 (m, 1H), 6.63 (dd, J=4.0 Hz, 2.0 Hz, 1H), 6.48 (s, 1H), 5.40 (brs, 2H), 3.37 (s, 3H) ppm Embodiment 39

2-amino-7-((2-(difluoromethoxyl)phenyl)methyl)-4-(5-methylfuran-2-yl)-5H,7H-furo[3,4-d]pyrimidin-5-one (Compound 39)

Synthetic Route

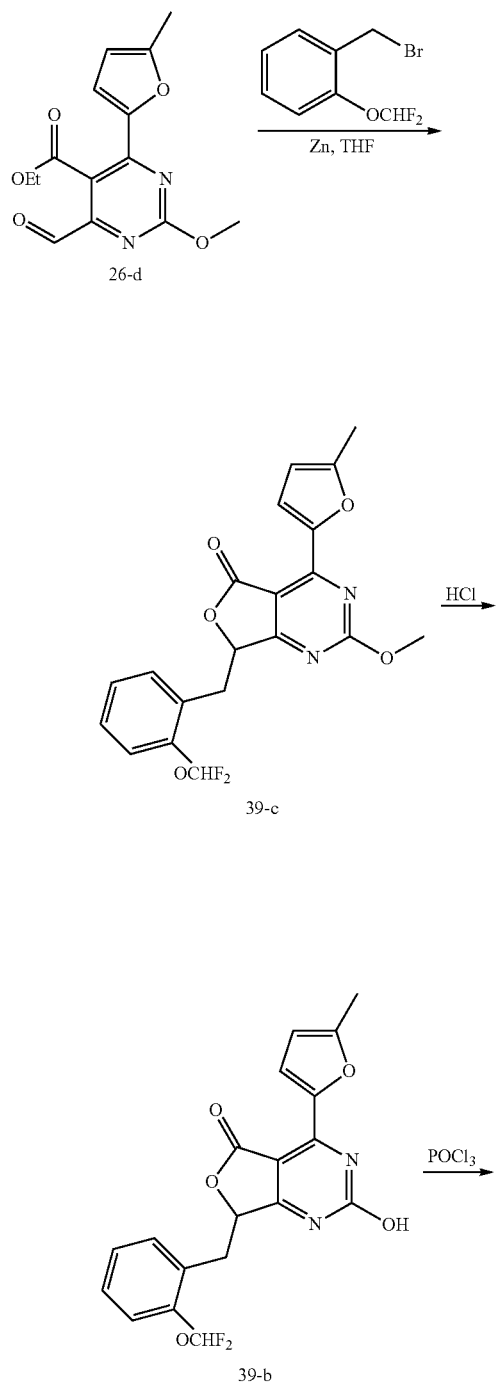

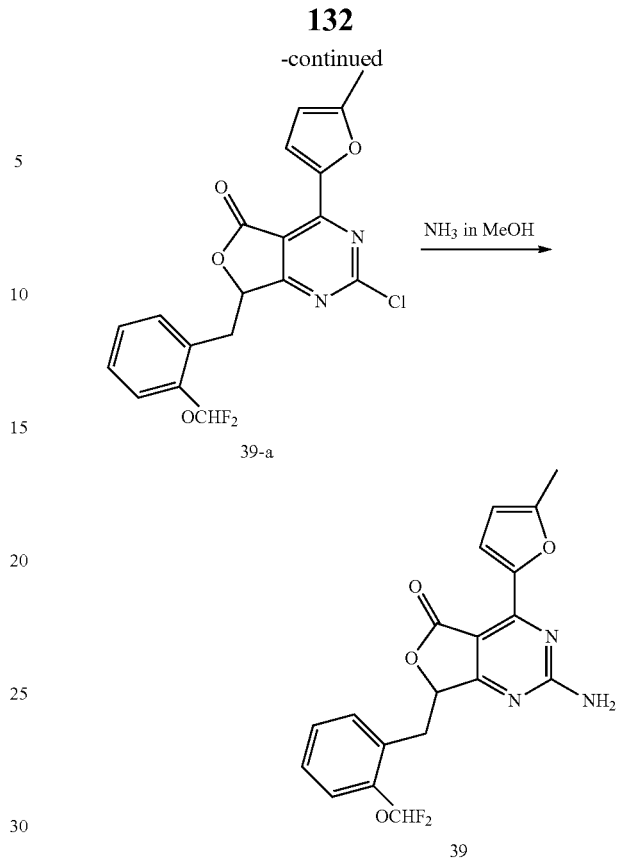

Synthesis of the Compound 39-c

At room temperature, compound 26-d (300 mg, 1.03 mmol) was dissolved in anhydrous tetrahydrofuran (20 mL), zinc powder (203 mg, 3.1 mmol) and 2-difluoromethoxyl benzyl bromide (736 mg, 3.1 mmol) were added into the reaction solution. The reaction mixture was heated to 55° C. and stirred for 1 hour. After cooling down to room temperature, saturated ammonium chloride solution (20 mL) was added to quench the reaction. After extraction with EtOAc (50 mL×2), the organic phases were combined and washed successively by water (50 mL) and saturated brine (50 mL), dried over anhydrous sodium sulfate. After concentration under reduced pressure, the residue was purified by silica gel chromatography (PE:EtOAc=5:1) to give a white solid 39-c (300 mg, yield: 72%).

LC-MS (ESI): m/z=403[M+1]$^+$.

Synthesis of the Compound 39-b

Compound 39-c (300 mg, 0.75 mmol) was dissolved in 1,4-dioxane (15 mL), concentrated hydrochloric acid (0.5 mL) was added at room temperature. The reaction mixture was stirred at 100° C. for 4 hours and then cooled down to room temperature, a large amount of solid was precipitated, and then filtered, the filter cake was washed by water (20 mL×2), dried in vacuum to give a yellow solid 39-b (260 mg, yield: 90%).

LC-MS (ESI): m/z=389[M+1]$^+$.

Synthesis of the Compound 39-a

Compound 39-b (260 mg, 0.673 mmol) was dissolved in phosphorus oxychloride (15 mL), N,N-dimethylaniline (0.02 mL) was added, the reaction mixture was stirred at 125° C. for 2 hours and then cooled down to room temperature. After concentration under reduced pressure, the residue was added into a mixture of ice and water (100 mL), and extracted with EtOAc (50 mL×2), the organic phases were combined and washed by water (30 mL) and saturated brine (20 mL), dried over anhydrous sodium sulfate. After concentration under reduced pressure, the residue was purified by silica gel chromatography (PE:EtOAc=5:1) to give a yellow solid 39-a (180 mg, yield: 66%).

LC-MS (ESI): m/z=407[M+1]$^+$.

Synthesis of the Compound 39

Compound 39-a (180 mg, 0.44 mmol) was dissolved in tetrahydrofuran (15 mL), 7.0 M ammonia in methanol solution (2 mL, 14 mmol) was added at room temperature, and stirred for 15 mins. The reaction mixture was then concentrated under reduced pressure, and the residue was purified by silica gel chromatography (DCM:EtOAc=15:1) to give the compound 39 (102 mg, yield: 59.9%). LC-MS (ESI): m/z=388[M+H]$^+$.

$^1$H NMR (400 MHz, CDCl$_3$) δ: 8.48-8.47 (d, J=3.2 Hz, 1H), 7.34-7.22 (m, 1H), 7.28-7.24 (m, 1H), 7.16-7.09 (m, 2H), 6.72-6.42 (3×s, 1H), 6.28-6.27 (d, J=2.8 Hz, 1H), 5.83 (s, 2H), 5.39-5.37 (m, 1H), 3.61-3.57 (m, 1H), 3.05-3.00 (m, 1H), 2.48 (s, 3H) ppm Embodiment 40

2-amino-9-((2-fluorophenyl)methyl)-6-(furan-2-yl)-7-methyl-8,9-dihydro-7H-purinyl-8-one (Compound 40)

Synthetic Route

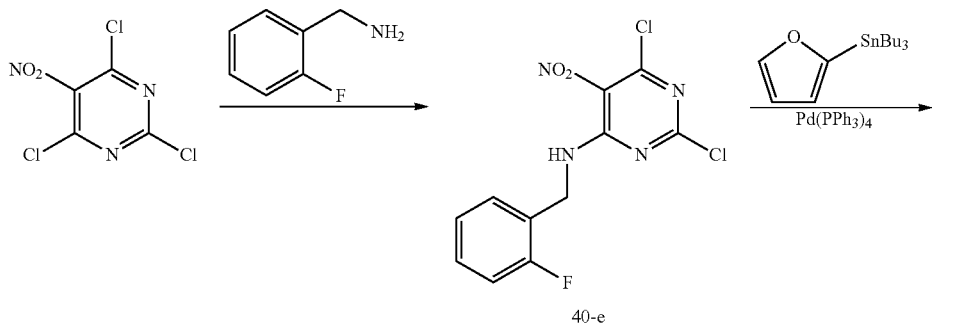

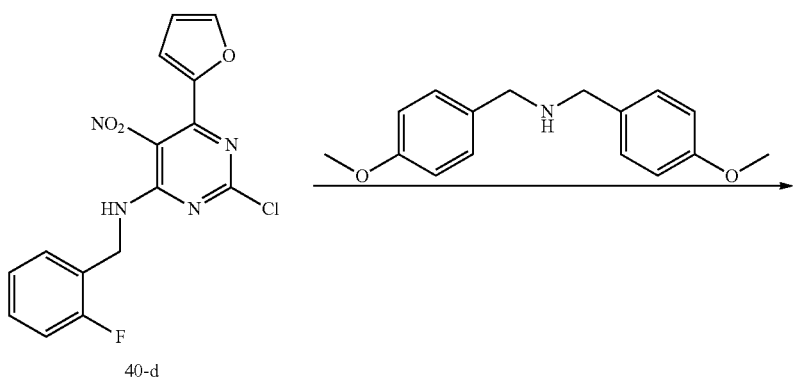

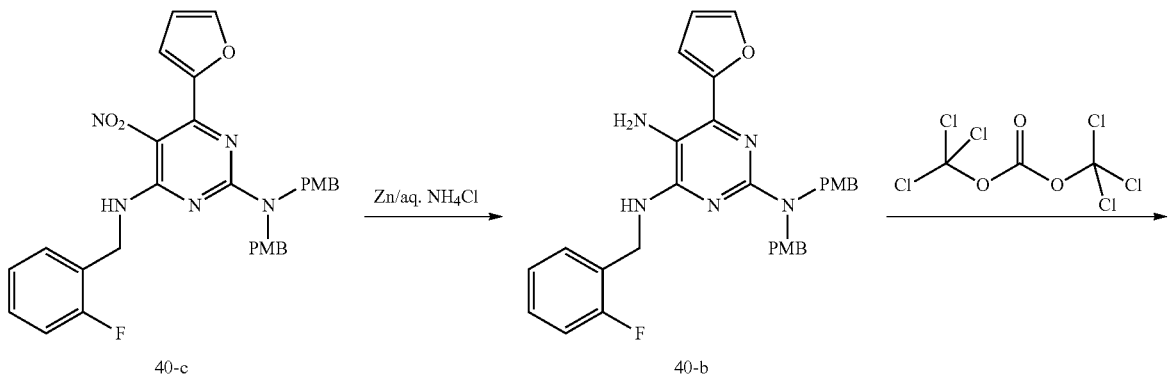

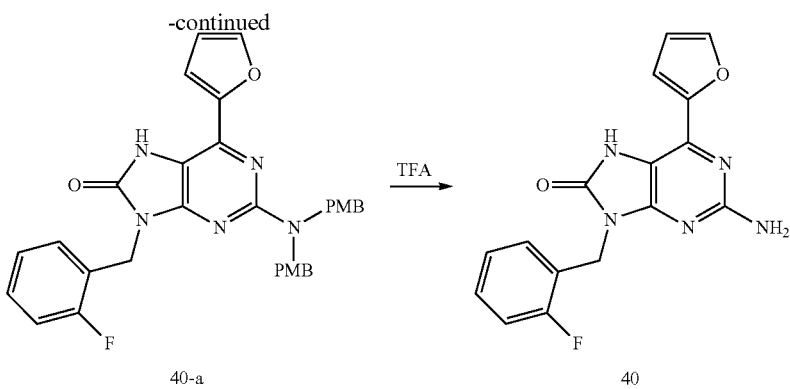

40-a → 40

Synthesis of the Compound 40-e 2,4,6-Trichloro-5-nitropyrimidine (500 mg, 2.19 mmol) was dissolved in anhydrous tetrahydrofuran (20 mL), 2-fluorobenzylamine (0.25 mL, 2.19 mmol) in anhydrous tetrahydrofuran (5 mL) solution was slowly added dropwise at 0° C., and then stirred at 0° C. for 1 hour. After concentration under reduced pressure, the residue was purified by silica gel chromatography (PE:EtOAc=6:1) to give a yellow solid product 40-e (584 mg, yield: 84%).

LC-MS (ESI): m/z=317[M+H]$^+$.

Synthesis of the Compound 40-d

Compound 40-e (390 mg, 1.23 mmol), tributyl-(2-furyl)stannane (0.7 mL, 2.2 mmol) and palladium tetrakis (triphenyl)phosphine (60 mg, 0.06 mmol) were added into dry tetrahydrofuran (10 mL). The reaction mixture was stirred at room temperature and under nitrogen atmosphere for 12 hours. The reaction solution was then concentrated, and the residue was purified by silica gel chromatography (PE:EtOAc=15:1) to give a yellow solid product 40-d (300 mg, yield: 70%).

LC-MS (ESI): m/z=349[M+1]$^+$.

Synthesis of the Compound 40-c

Compound 40-d (300 mg, 0.86 mmol), bis(p-methoxybenzyl)amine (444 mg, 1.7 mmol) and diisopropylethylamine (134 mg, 1.03 mmol) were added into dry tetrahydrofuran (15 mL). The reaction mixture was reacted at 60° C. for 5 hours, then cooled down to room temperature. The reaction solution was then concentrated, and the residue was purified by silica gel chromatography (PE:EtOAc=15:1) to give a yellow solid product 40-c (410 mg, yield: 84%).

LC-MS (ESI): m/z=570 [M+1]$^+$.

Synthesis of the Compound 40-b

Zinc powder (163 mg, 2.5 mmol) was added into saturated ammonium chloride solution (3 mL) and ethanol (3 mL), and 40-c (410 mg, 0.72 mmol) in tetrahydrofuran (10 mL) solution was add dropwise while stirring at 0° C. After stirring at 0° C. for 1 hour, the reaction was warmed to room temperature. The reaction solution was then concentrated under reduced pressure, the residue was diluted by water (20 mL), then extracted with EtOAc (20 mL), the organic phase was washed by saturated brine (20 mL), dried over anhydrous sodium sulfate, then concentrated under reduced pressure, and the residue was purified by silica gel chromatography (PE:EtOAc=5:1) to give a red solid product 40-b (300 mg, yield: 80%).

LC-MS (ESI): m/z=540 [M+1]$^+$.

Synthesis of the Compound 40-a

Triphosgene (315 mg, 1.06 mmol) was added into 40-b (300 mg, 0.88 mmol) and diisopropylethylamine (2 mL, 13.2 mmol) in dry tetrahydrofuran (10 mL) solution at 0° C., stirred for 10 mins and then warmed to room temperature and the reaction mixture was further stirred for 1 hour. The reaction solution was then concentrated under reduced pressure, and the residue was purified by silica gel chromatography (PE:EtOAc=6:1) to give a yellow oily product 40-a (210 mg, yield: 67%). LC-MS (ESI): m/z=584 [M+1]$^+$.

Synthesis of the Compound 40

Compound 40-a (120 mg, 0.21 mmol) was added into trifluoroacetic acid (3 mL). The reaction mixture was stirred at 85° C. for 2 hours, then cooled down to room temperature. The reaction solution was then concentrated under reduced pressure, and the residue was purified by silica gel chromatography (PE:EtOAc=2:1) to give a white solid product 40 (8 mg, yield: 11.6%).

LC-MS (ESI): m/z=326 [M+1]$^+$.

$^1$H NMR (400 MHz, DMSO-d$_6$) δ: 7.81 (s, 1H), 7.32-7.29 (m, 1H), 7.23-7.11 (m, 5H), 6.67-6.66 (m, 1H), 6.24 (s, 2H), 4.98 (s, 2H) ppm Embodiment 41

2-amino-9-((2-fluorophenyl)methyl)-6-(furan-2-yl)-7-methyl-8,9-dihydro-7H-purinyl-8-one (Compound 41)

Synthetic Route

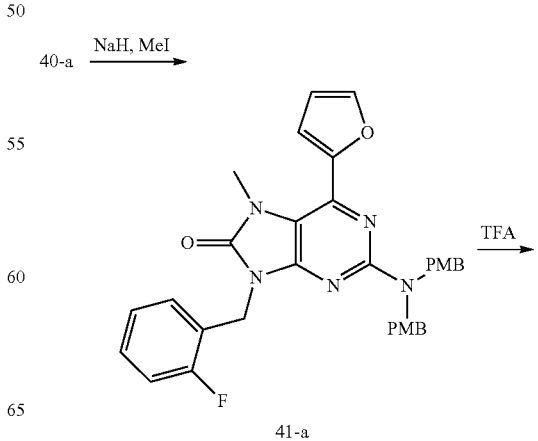

41-a

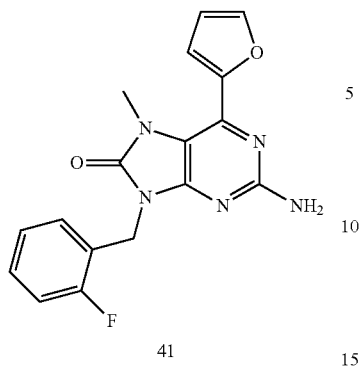

41

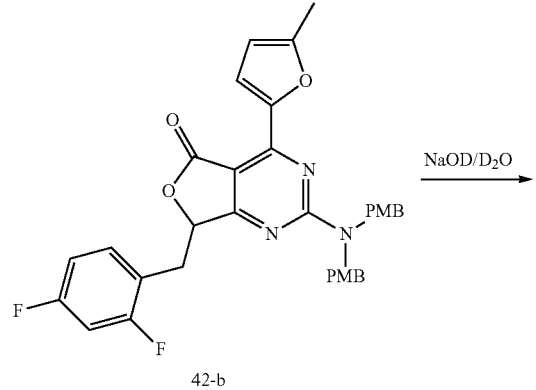

42-b

Synthesis of the Compound 41-a

60% Sodium hydride dispersed in mineral oil (15 mg, 0.56 mol) was suspended in dry N,N-dimethylformamide (10 mL), 40-a (210 mg, 0.37 mmol) in dry N,N-dimethylformamide (10 mL) solution was added dropwise into this suspension at 0° C. under nitrogen atmosphere, and further stirred at 0° C. for 1 hour. Methyl iodide (106 mg, 0.74 mmol) was added thereto, then warmed to room temperature and further stirred to react for 1 hour. The reaction mixture was poured into half saturated ammonium chloride aqueous solution (20 mL), then extracted with EtOAc (20 mL×3). The organic phase was washed by saturated brine (20 mL), dried over anhydrous sodium sulfate, then concentrated under reduced pressure, and the residue was purified by silica gel chromatography (PE:EtOAc=2:1) to give a white solid product 41-a (120 mg, yield: 55.9%)).

LC-MS (ESI): m/z=580 [M+1]$^+$.

Synthesis of the Compound 41

Compound 41-a (120 mg, 0.21 mmol) was added into trifluoroacetic acid (4 mL). The reaction mixture was stirred at 85° C. for 2 hours, then cooled down to room temperature. The reaction solution was then concentrated under reduced pressure, and the residue was purified by silica gel chromatography (PE:EtOAc=2:1) to give a white solid product 41 (8 mg, yield: 11.2%).

LC-MS (ESI): m/z=340 [M+1]$^+$.

$^1$H NMR (400 MHz, CDCl$_3$) δ: 7.60-7.59 (m, 1H), 7.27-7.28 (m, 1H), 7.25-7.24 (m, 1H), 7.10-7.04 (m, 3H), 6.59-6.58 (m, 1H), 5.15 (s, 2H), 4.78 (s, 2H), 3.58 (s, 3H) ppm Embodiment 42

2-amino-7-((2,4-difluorophenyl)methyl)-7-deuterium-4-(5-methylfuran-2-yl)-5H,7H-furo[3,4-d]pyrimidin-5-one (Compound 42)

Synthetic Route

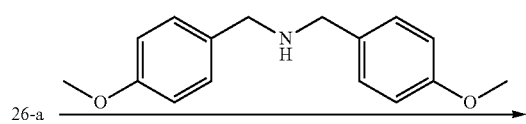

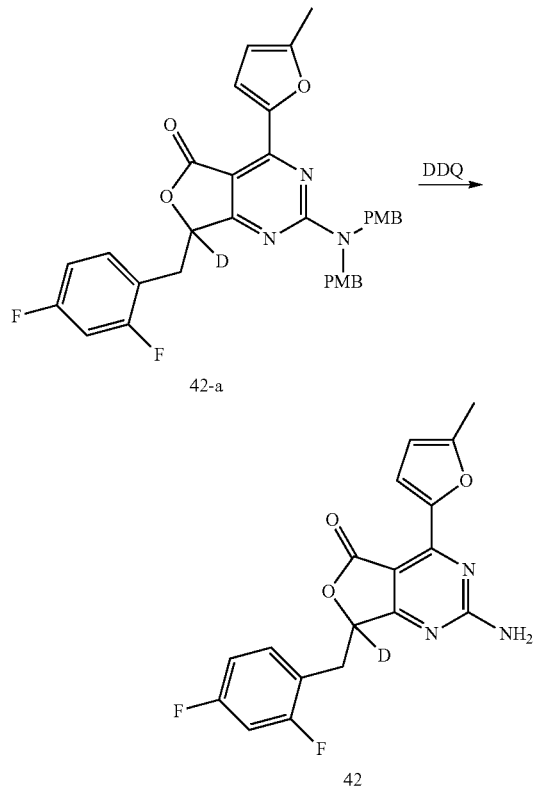

Synthesis of the Compound 42-b

At room temperature, bis(p-methoxybenzyl)amine (215.8 mg, 0.84 mmol) and diisopropylethylamine (271 mg, 2.1 mmol) were added into compound 26-a (300 mg, 0.79 mmol) in dioxane (20 mL) solution. The reaction mixture was heated to 110° C. and stirred for 4 hours, then cooled down to room temperature. Saturated ammonium chloride solution (20 mL) was added to quench the reaction. After extraction with EtOAc (50 mL×2), the organic phases were combined and washed by water (30 mL) and saturated brine (20 mL), dried over anhydrous sodium sulfate. After concentration under reduced pressure, the residue was purified by silica gel chromatography (PE:EtOAc=20:1-10:1) to give a yellow solid 42-b (320 mg, yield: 77%).

LC-MS (ESI): m/z=398 [M+1]$^+$.

Synthesis of the Compound 42-a

D$_2$O (5 mL) and 1 M deuterated sodium hydroxide solution (4 mL) was added into compound 42-b (260 mg, 0.43 mmol) in tetrahydrofuran (8 mL) solution. The reaction mixture was stirred at room temperature for 16 hours, then water (10 mL) was added and extracted with EtOAc (2×20 mL), the organic phases were combined and washed by saturated brine (10 mL) and water (10 mL), dried over anhydrous sodium sulfate. Then the solution was concentrated under reduced pressure to give a pale yellow solid 42-a (200 mg, yield: 76%), which was without further purification. LC-MS (ESI): m/z=599 [M+1]$^+$.

Synthesis of the Compound 42

Compound 42-a (200 mg, 0.33 mmol) was dissolved in DCM (30 mL), 2,3-dichloro-5,6-dicyanobenzoquinone (227 mg, 1.0 mmol) was added into the reaction mixture while stirring at room temperature, the reaction mixture was further stirred at room temperature for 3 days. The reaction mixture was filtered, and the filtrate was then concentrated under reduced pressure, the residue was purified by HPLC (mobile phase: water (10 mM ammonium bicarbonate), acetonitrile; gradient: 40%-70% (initial mobile phase was 40% water-60% acetonitrile, at the end the mobile phase was 70% water-30% acetonitrile, the % refers to volume percentage) to give the grayish white solid 42 (22 mg, yield: 19%). LC-MS (ESI): m/z=359 [M+1]$^+$.

$^1$H NMR (400 MHz, CDCl$_3$) δ: 8.51 (d, J=2.8 Hz, 1H), 7.30-7.26 (m, 1H), 6.84-6.78 (m, 2H), 6.30 (d, J=2.4 Hz, 1H), 5.85 (bs, 2H), 3.52 (d, J$_1$=11.6 Hz, 1H), 3.00 (d, J=12.0 Hz, 1H), 2.50 (s, 3H) ppm Embodiment 43

2-amino-7-((2-fluorophenyl)methyl)-7-methyl-4-(5-methylfuran-2-yl)-5H,7H-furo[3,4-d]pyrimidin-5-one (Compound 43)

Synthetic Route

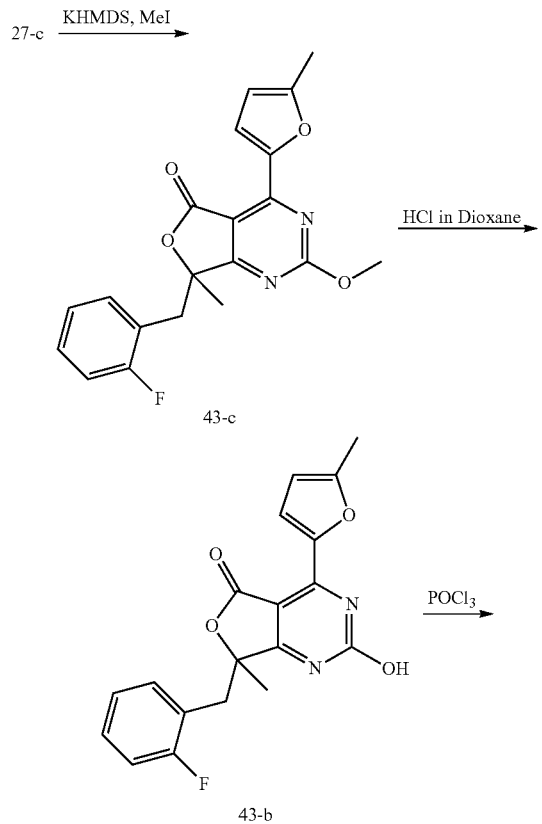

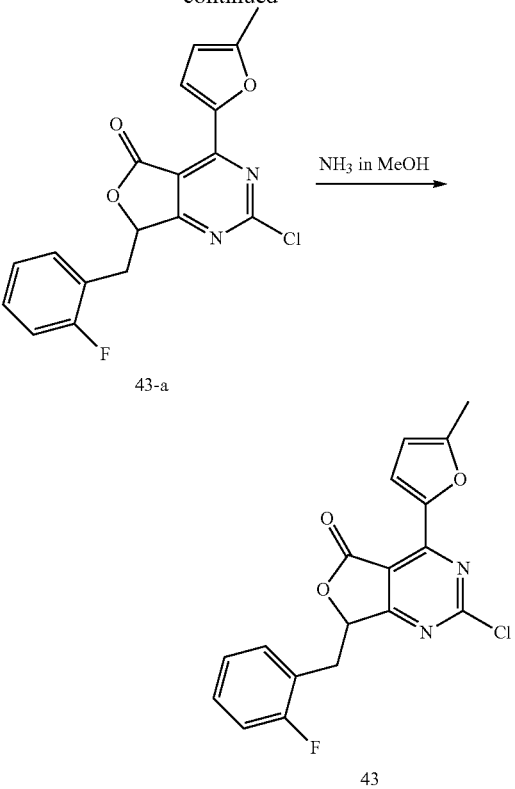

Synthesis of the Compound 43-c

Compound 27-c (190 mg, 0.53 mmol) was dissolved in tetrahydrofuran (15 mL), the reaction mixture was cooled down to −78° C., 1 M hexamethyldisilazide potassium solution (0.80 mL, 0.80 mmol) was added dropwise under nitrogen atmosphere, then stirred for 30 mins, methyl iodide (225.7 mg, 1.59 mmol) was then added dropwise. The reaction mixture was further stirred at this temperature for 1 hours, gradually warmed to room temperature, and then further stirred for 16 hours. The reaction was quenched by saturated ammonium chloride solution (50 mL). After extraction with EtOAc (50 mL×2), the organic phases were combined and washed by water (30 mL) and saturated brine (20 mL), dried over anhydrous sodium sulfate. Then the solution was concentrated under reduced pressure to give a yellow solid 43-c (210 mg), which was without further purification.

LC-MS (ESI): m/z=369 [M+1]$^+$.

Synthesis of the Compound 43-b

Compound 43-c (210 mg) was dissolved in dioxane (25 mL), concentrated hydrochloric acid (1.0 mL) was added into the reaction mixture under room temperature. The reaction mixture was stirred at 110° C. for 4 hours, then cooled down to room temperature. The reaction mixture was then concentrated under reduced pressure, methanol (20 mL) was added into the residue to give a suspension solution, followed by filtration, giving a pink solid 43-b (200 mg), which was without further purification. LC-MS (ESI): m/z=355 [M+1]$^+$. Synthesis of the compound 43-a Compound 43-b (300 mg) was dissolved in phosphorus oxychloride (20 mL), the reaction mixture was stirred at 110° C. for 3 hours, cooled down to room temperature. The reaction solution was then concentrated under reduced pressure, the residue was added into a mixture of ice and water (50 mL), and extracted with EtOAc (50 mL×2), the organic phases were combined and washed by water (30 mL) and saturated brine (20 mL), dried over anhydrous sodium sulfate. After concentration under reduced pressure, the residue was purified by silica gel chromatography (PE: EtOAc=30:1-10:1) to give a pale yellow solid 43-b (150 mg, yield: 50%). LC-MS (ESI): m/z=411 [M+1]$^+$.

Synthesis of the Compound 43

Compound 43-a (150 mg, 0.40 mmol) was dissolved in tetrahydrofuran (10 mL), 7 M ammonia in methanol solution (5 mL) was added into the reaction mixture at room temperature, and the reaction mixture was further stirred for 2 hours. The reaction solution was then concentrated under reduced pressure, the residue was purified by HPLC (mobile phase: water (10 mM ammonium bicarbonate), acetonitrile; gradient: 40%-70% (initial mobile phase was 40% water-60% acetonitrile, at the end the mobile phase was 70% water-30% acetonitrile, the % refers to volume percentage) to give the grayish white solid 43 (50 mg, yield: 35%).

LC-MS (ESI): m/z=454 [M+1]$^+$.

$^1$H NMR: (400 MHz, CDCl$_3$) δ: 8.46 (d, J=2.8 Hz, 1H), 7.74 (s, 1H), 7.24-7.16 (m, 2H), 7.03-6.95 (m, 2H), 6.27-6.26 (dd, J$_1$=0.8 Hz, J$_2$=2.8 Hz, 1H), 5.84 (bs, 2H), 3.40 (d, J=11.6 Hz, 1H), 3.16 (d, J=11.2 Hz, 1H), 2.48 (s, 3H), 1.65 (s, 3H) ppm Embodiment 44

2-amino-7-((2-fluorophenyl)methyl)-4-(furan-2-yl)-6-methyl-5H,6H,7H-pyrrolo[3,4-d]pyrimidin-5-one (Compound 44)

Synthetic Route

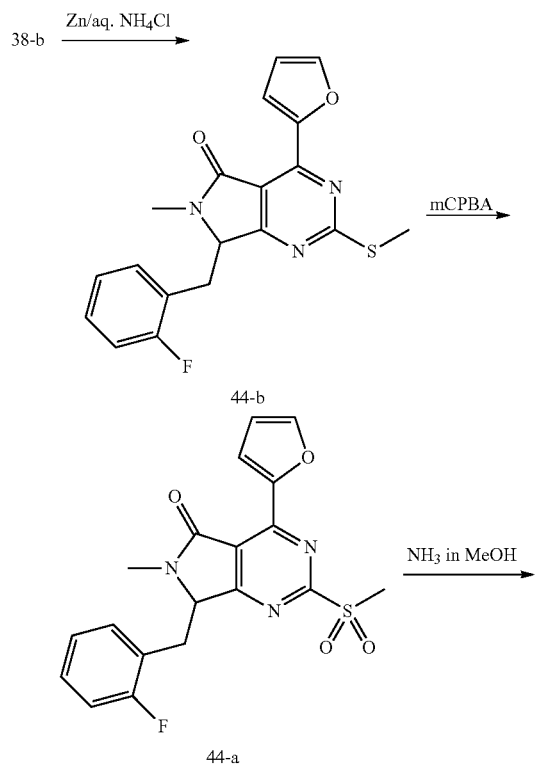

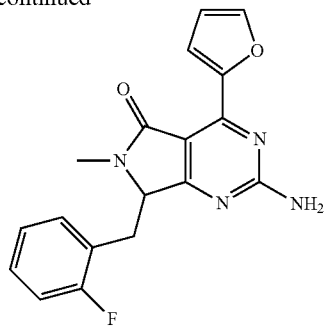

Compound 44-b

Compound 38-a (74 mg, 0.2 mmol) in tetrahydrofuran (4 mL) solution was added dropwise into the mixture of ammonium chloride (214 mg, 4.0 mmol) in water (5 mL), zinc powder (130 mg, 2.0 mmol) and ethanol (10 mL). After stirring for 4 hours, the reaction mixture was concentrated under reduced pressure, the residue was diluted by water (20 mL). After extraction with EtOAc (20 mL), the organic phase was washed by saturated brine (20 mL), then concentrated under reduced pressure, and the residue was purified by silica gel chromatography (PE:EtOAc=3:1) to give 44-b (55 mg, yield: 74%). LC-MS (ESI): m/z=370 [M+1]$^+$.

Synthesis of the Compound 44-a

80% m-Chloroperoxybenzoic acid (57 mg, 0.26 mmol) was added into compound 44-a (30 mg, 0.08 mmol) in DCM (10 mL) solution, the reaction mixture was stirred at room temperature for 16 hours. The reaction was quenched by adding saturated sodium thiosulfate solution (3 mL). After adding water (20 mL), the mixture was extracted with DCM (20 mL×3). After concentration under reduced pressure, the residue was purified by silica gel chromatography (PE: EtOAc=1:1) to give a pale yellow solid 44-a (28 mg, yield: 87%).

Synthesis of the Compound 44

7 N Ammonia in methanol solution (2 mL, 14 mmol) was added into compound 44-a (28 mg, 0.07 mmol) in tetrahydrofuran (5 mL) solution. The mixture was stirred at room temperature for 1 hour. After concentration under reduced pressure, the residue was purified by silica gel chromatography (PE:EtOAc=1:3) to give a white solid 44 (16 mg, yield: 68%).

LC-MS (ESI): m/z=339 [M+1]$^+$.

$^1$H NMR (500 MHz, CDCl$_3$) δ: 8.64 (d, J=8.5 Hz, 1H), 7.65 (d, J=1.0 Hz, 1H), 7.15-7.19 (m, 1H), 6.94-7.04 (m, 3H), 6.58 (dd, J=3.5 Hz, 2.0 Hz, 1H), 5.61 (brs, 2H), 4.53 (t, J=5.5 Hz, 1H), 3.47-3.50 (m, 1H), 3.14-3.18 (m, 1H), 3.00 (s, 3H) ppm Embodiment 45

2-amino-7-((2-trifluoromethoxylphenyl)methyl)-4-(furan-2-yl)-6-methyl-5H,6H,7H-pyrrolo[3,4-d]pyrimidin-5-one (Compound 45)

Synthetic Route

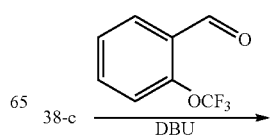

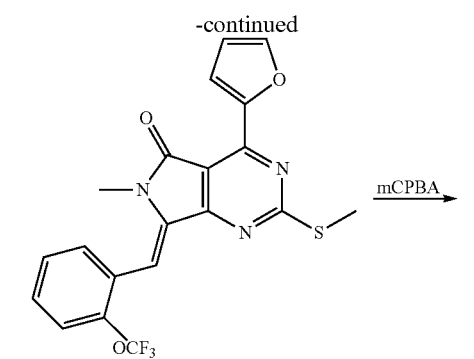

45-b

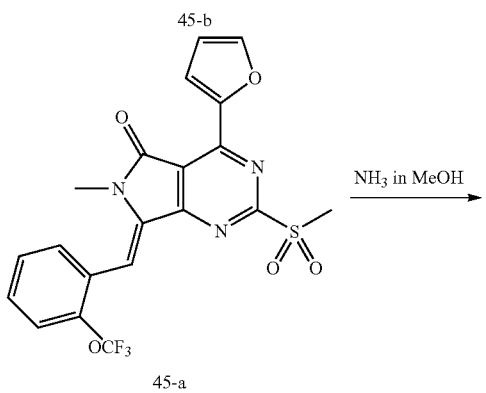

45-a

Synthesis of the Compound 45-b 1,8-diazabicycloundec-7-ene (87 mg, 0.58 mmol) was added into compound 38-c (300 mg, 1.15 mmol) and o-trifluoromethoxylbenzaldehyde (665 mg, 3.45 mmol) in dioxane (15 mL) solution. The mixture was stirred at 110° C. for 12 hours under nitrogen atmosphere, then cooled down to room temperature. After concentration under reduced pressure, the residue was purified by silica gel chromatography (PE:EtOAc=10:1) to give a yellow solid 45-b (50 mg, yield: 10%).

LC-MS (ESI): m/z=434 [M+H]$^+$.

Synthesis of the Compound 45-a

80% m-Chloroperoxybenzoic acid (80 mg, 0.46 mmol) was added into compound 45-b (50 mg, 0.12 mmol) in DCM (10 mL) solution, stirred at room temperature for 1 hour. The reaction was quenched by adding saturated sodium thiosulfate solution (3 mL). After adding water (20 mL), the mixture was extracted with DCM (20 mL×3). The organic phase was concentrated under reduced pressure to give a yellow solid 45-a (50 mg, yield: 93%), which was without further purification.

LC-MS (ESI): m/z=466 [M+H]$^+$.

Synthesis of the Compound 45

7 N Ammonia in methanol solution (2 mL, 14 mmol) was added into compound 45-a (50 mg, 0.10 mmol) in tetrahydrofuran (10 mL) solution. The mixture was stirred to react at room temperature for 1 hour. After concentration under reduced pressure, the residue was purified by silica gel chromatography (PE:EtOAc=1:3) to give a white solid 45 (17 mg, yield: 42.2%).

LC-MS (ESI): m/z=403 [M+H]$^+$.

$^1$H NMR (400 MHz, CDCl$_3$) δ: 8.64-8.63 (m, 1H), 7.71-7.70 (m, 1H), 7.42-7.39 (m, 1H), 7.36-7.32 (m, 3H), 7.08 (s, 1H), 6.65-6.64 (m, 1H), 5.61 (s, 2H), 2.98 (s, 3H) ppm Embodiment 46

2-amino-7-((2,4-difluorophenyl)methylene)-4-(furan-2-yl)-6-methyl-5H,6H,7H-pyrrolo[3,4-d]pyrimidin-5-one (Compound 46)

Synthetic Route

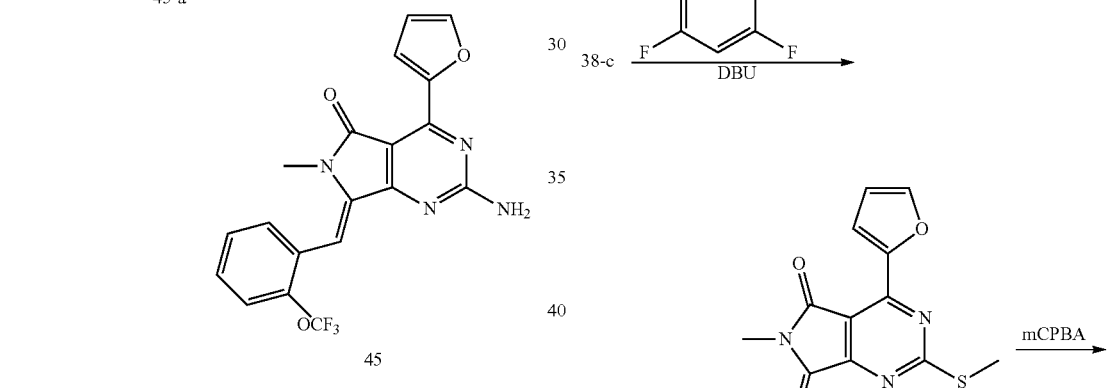

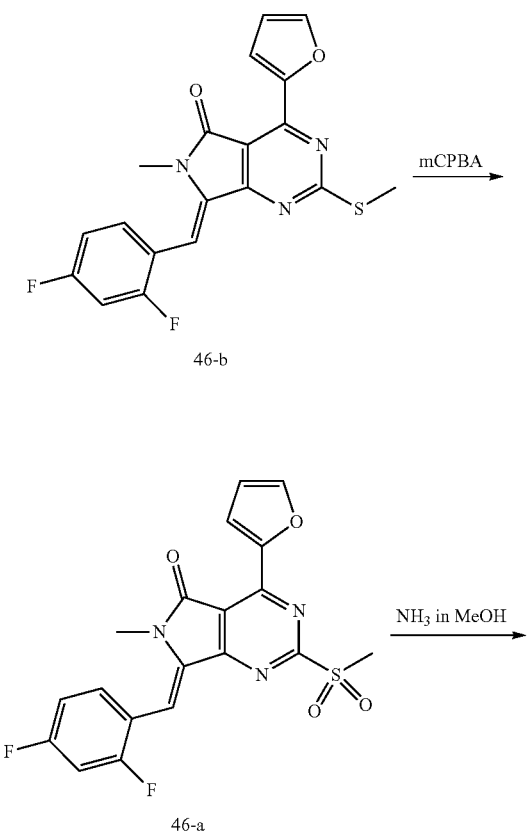

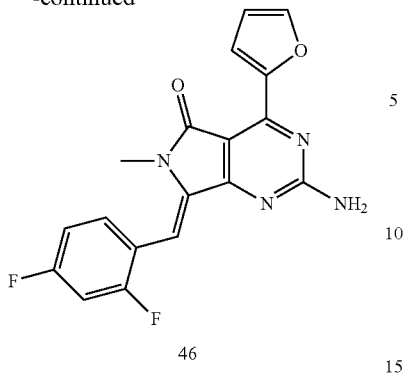

46

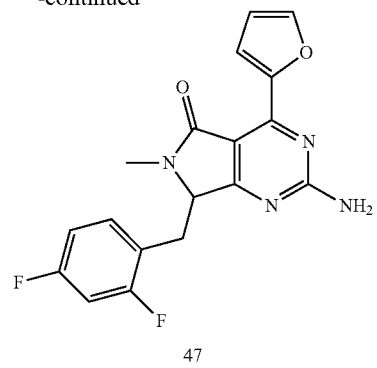

47

Synthesis of the Compound 46-b 1,8-Diazabicycloundec-7-ene (58 mg, 0.38 mmol) was added into compound 38-c (200 mg, 0.76 mmol) and 2,4-difluorobenzaldehyde (326 mg, 2.3 mmol) in dioxane (15 mL) solution. The mixture was stirred at 110° C. under nitrogen atmosphere for 12 hours, then cooled down to room temperature. After concentration under reduced pressure, the residue was purified by silica gel chromatography (PE:EtOAc=10:1) to give a yellow solid 46-b (135 mg, yield: 69%).

LC-MS (ESI): m/z=386 [M+H]$^+$.

Synthesis of the Compound 46-a

80% m-Chloroperoxybenzoic acid (242 mg, 1.4 mmol) was added into compound 46-b (135 mg, 0.35 mmol) in DCM (10 mL) solution, stirred at room temperature for 1 hour. The reaction was quenched by adding saturated sodium thiosulfate solution (3 mL). After adding water (20 mL), the mixture was extracted with DCM (20 mL×3). The organic phase was then concentrated under reduced pressure to give a yellow solid 46-a (210 mg), which was without need further purification.

LC-MS (ESI): m/z=418 [M+H]$^+$.

Synthesis of the Compound 46

7 N Ammonia in methanol solution (2 mL, 14 mmol) was added into compound 46-a (210 mg, 0.5 mmol) in tetrahydrofuran (10 mL) solution. The mixture was stirred to react at room temperature for 1 hour. After concentration under reduced pressure, the residue was washed by methanol (15 mL), followed by filtration, the residue was dried in vacuum to give the compound 46 (22 mg, yield: 12.3%).

LC-MS (ESI): m/z=355 [M+H]$^+$.

$^1$H NMR (400 MHz, CDCl$_3$) δ: 8.65-8.64 (m, 1H), 8.10-8.05 (m, 1H), 7.71-7.69 (m, 1H), 6.92-6.83 (m, 2H), 6.65-6.63 (m, 1H), 6.39 (s, 1H), 5.37 (s, 2H), 3.36 (s, 3H) ppm Embodiment 47

2-amino-7-((2,4-difluorophenyl)methyl)-4-(furan-2-yl)-6-methyl-5H,6H,7H-pyrrolo[3,4-d]pyrimidin-5-one (Compound 47)

Synthetic Route

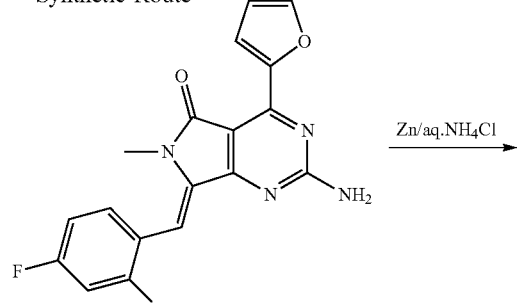

46

Synthesis of the Compound 47

Compound 46 (160 mg, 0.45 mmol) in tetrahydrofuran (10 mL) solution and zinc powder (294 mg, 4.5 mmol) was added into a mixed solution of ammonium chloride (481 mg, 8.9 mmol), water (2 mL) and ethanol (2 mL) at 0° C. After stirring for 1 hour, the mixture was warmed to room temperature. Water (20 mL) was added for dilution, then extracted with DCM (20 mL), the organic phase was washed by saturated brine (20 mL), then concentrated under reduced pressure, the residue was purified by HPLC (mobile phase: water (10 mM ammonium bicarbonate), acetonitrile; gradient: 30%-60% (initial mobile phase was 30% water-70% acetonitrile, at the end the mobile phase was 60% water-40% acetonitrile, the % refers to volume percentage) to give the 47 (8 mg, yield: 4.9%).

LC-MS (ESI): m/z=357 [M+1]$^+$.

$^1$H NMR (400 MHz, CDCl$_3$) δ: 8.64-8.63 (d, J=3.2 Hz, 1H), 7.65-7.64 (d, J=1.2 Hz, 1H), 6.98-6.93 (m, 1H), 6.77-6.67 (m, 2H), 6.59-6.58 (m, 1H), 5.35 (s, 2H), 4.49-4.78 (t, J=4.0 Hz, 1H), 3.43-3.39 (m, 1H), 3.21-3.17 (m, 1H), 3.04 (s, 3H) ppm Embodiment 48

2-amino-7-((2,4-difluorophenyl)methylene)-4-(5-methylfuran-2-yl)-6-methyl-5H,6H,7H-pyrrolo[3,4-d]pyrimidin-5-one (Compound 48)

Synthetic Route

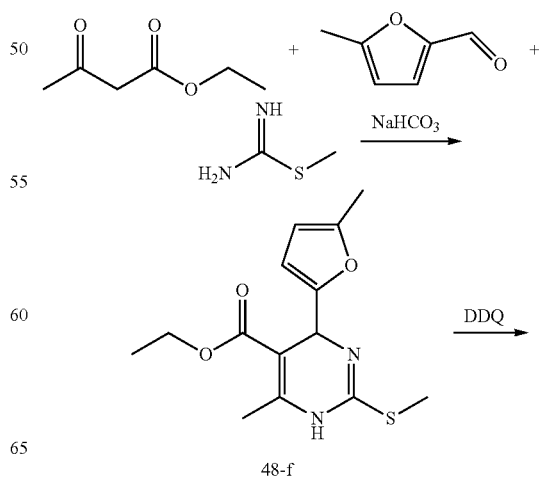

48-f

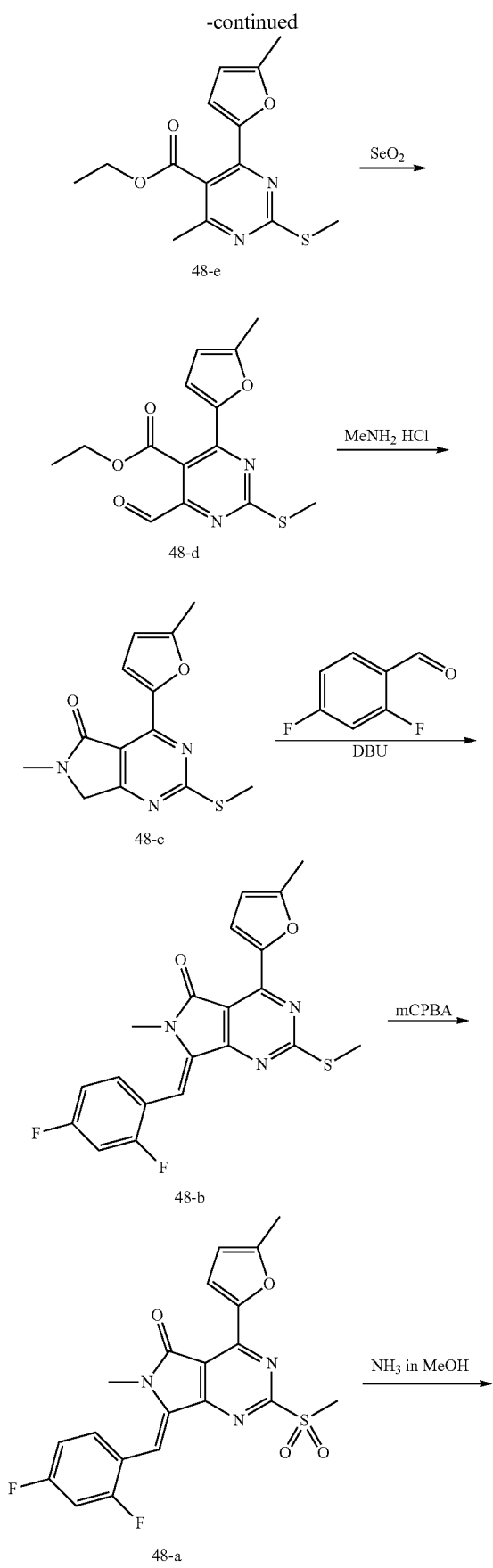

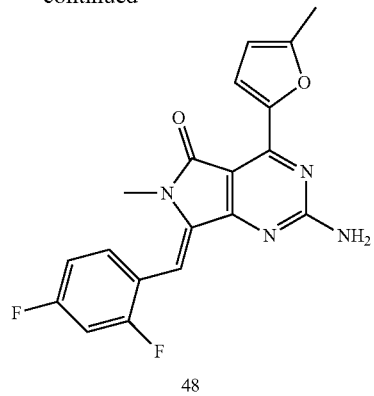

Synthesis of the Compound 48-f

Sodium dicarbonate (33.6 g, 400 mmol) was added into 5-methyl furfural (11.0 g, 100 mmol), S-methylisothiourea sulfate (16.68 g, 60 mmol) and ethyl acetoacetate (14.3 g, 110 mmol) in DMF (200 mL) solution. The reaction mixture was stirred at 70° C. for 3 hours, then cooled down to room temperature. After concentration under reduced pressure, water (100 mL) was added into the residue, and then extracted with EtOAc (500 mL×2), the combined organic phases were washed by water (200 mL) and saturated brine (100 mL), dried over anhydrous sodium sulfate. After concentration under reduced pressure, the residue was purified by silica gel chromatography (PE:EtOAc=6:1-3:1) to give a pale yellow solid 48-f (10.0 g, yield: 34%).

LC-MS (ESI): m/z=295 [M+H]$^+$.

Synthesis of the Compound 48-e

In ice water bath, 2,3-dichloro-5,6-dicyanobenzoquinone (9.26 g, 40.8 mmol) was added in batches into compound 48-f (10.0 g, 34 mmol) in DCM (300 mL) solution, the reaction mixture was warmed to room temperature and further stirred for 16 hours. After filtration, the residue was washed with DCM (50 mL). Then the filtrate was concentrated under reduced pressure, and the residue was purified by silica gel chromatography (PE:EtOAc=6:1-3:1) to give a yellow viscous product 48-e (5.10 g, yield: 52%)).

LC-MS (ESI): m/z=293 [M+H]$^+$.

Synthesis of the Compound 48-d

Compound 48-e (5.10 g, 5.0 mmol) was dissolved in 1,4-dioxane (60 mL), selenium dioxide (3.7 g, 33.4 mmol) and glacial acetic acid (1.5 mL) were added thereto. The reaction mixture was refluxed for 8 hours, then cooled down to room temperature. The reaction solution was then concentrated under reduce pressure, the residue was diluted by EtOAc (60 mL). After filtration, the filtrate was concentrated under reduced pressure, and the residue was purified by silica gel chromatography (PE:EtOAc=6:1-2:1) to give a yellow solid 48-d (4.0 g, yield: 58%).

LC-MS (ESI): m/z=307 [M+H]$^+$.

Synthesis of the Compound 48-c

Methylamine hydrochloride (1.76 g, 26.1 mmol), sodium acetate (3.56 g, 26.1 mmol) were added into methanol (30 mL). The mixture was stirred at room temperature for 1 hour, and cooled down with ice water bath to 0° C., then compound 48-d (2.0 g, 6.5 mmol) and DCM (10 mL) were added thereto. After stirring for 30 mins, sodium cyanoborohydride (0.61 g, 9.8 mmol) was added, the reaction mixture was warmed to room temperature and further stirred for 12 hours. After concentration under reduced pressure, the residue was diluted by water (100 mL), then extracted with DCM (50 mL×2), the combined organic phases were washed by water (100 mL) and saturated brine (100 mL). The organic phase was then concentrated under reduced pressure, and the residue was purified by silica gel chromatography (PE:EtOAc=10:1) to give a yellow solid 48-c (1.38 g, yield: 75%). LC-MS (ESI): m/z=276 [M+H]$^+$.

Synthesis of the Compound 48-b 1,8-Diazabicycloundec-7-ene (105 mg, 0.69 mmol) was added into compound 48-c (589 mg, 4.15 mmol) and 2,4-difluorobenzaldehyde (380 mg, 1.38 mmol) in dioxane (15 mL) solution. The mixture was refluxed under nitrogen atmosphere for 12 hours, then cooled down to room temperature. After concentration under reduced pressure, the residue was purified by silica gel chromatography (PE:EtOAc=10:1) to give a yellow solid 48-b (270 mg, yield: 50%). LC-MS (ESI): m/z=400 [M+H]$^+$.

Synthesis of the Compound 48-a

80% m-Chloroperoxybenzoic acid (427 mg, 2.71 mmol) was added into compound 48-b (270 mg, 0.67 mmol) in DCM (10 mL) solution, stirred at room temperature for 1 hour. The reaction was quenched by adding saturated sodium thiosulfate solution (10 mL). After adding water (20 mL), the mixture was extracted with DCM (20 mL×3), the combined organic phases were washed by water (20 mL) and saturated brine (20 mL), then the solution was concentrated under reduced pressure to give a yellow solid 48-a (40 mg, yield: 62%), which was without further purification. LC-MS (ESI): m/z=432 [M+H]$^+$.

Synthesis of the Compound 48

7 N Ammonia in methanol solution (2 mL, 14 mmol) was added into compound 48-a (400 mg, 0.93 mmol) in tetrahydrofuran (10 mL) solution. The mixture was stirred to react at room temperature for 1 hour. After concentration under reduced pressure, the residue was added into methanol (10 mL), a solid product was formed, filtered, the filter cake was washed by methanol (3 mL), then dried in vacuum to give the compound 48 (284 mg, yield: 80.1%).

LC-MS (ESI): m/z=369 [M+H]$^+$.

$^1$H NMR (400 MHz, CDCl$_3$) δ: 8.59-8.58 (m, 1H), 8.13-8.08 (m, 1H), 6.90-6.82 (m, 2H), 6.37 (s, 1H), 6.26-6.25 (m, 1H), 5.35 (s, 2H), 3.34 (s, 3H), 2.47 (s, 3H) ppm Embodiment 49

2-amino-7-((2,4-difluorophenyl)methyl)-4-(5-methylfuran-2-yl)-6-methyl-5H,6H,7H-pyrrolo[3,4-d]pyrimidin-5-one (Compound 49)

Synthetic Route

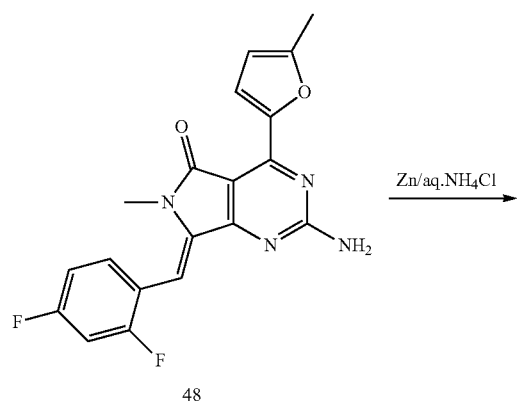

48

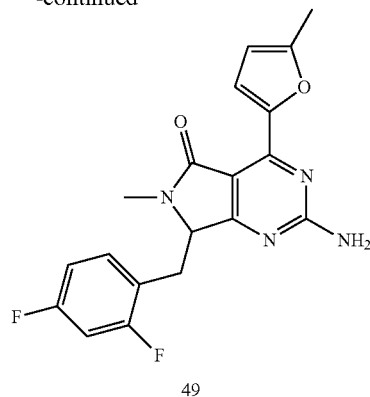

49

Synthesis of the Compound 49

Compound 48 (258 mg, 0.7 mmol) in tetrahydrofuran (10 mL) solution and zinc powder (458 mg, 7.1 mmol) were added into a mixed solution of ammonium chloride (760 mg, 14 mmol), water (3 mL) and ethanol (3 mL) at 9° C. After stirring for 1 hour, the mixture was warmed to room temperature. Then the mixture was diluted by water (20 mL), extracted with DCM (20 mL), the organic phase was washed by saturated brine (20 mL), then concentrated under reduced pressure, the residue was purified by thin layer chromatographic plate (PE:EtOAc=2:1) to give 49 (18 mg, yield: 6.9%).

LC-MS (ESI): m/z=371 [M+1]$^+$.

$^1$H NMR (400 MHz, CDCl$_3$) δ: 8.58-8.57 (d, J=2.8 Hz, 1H), 6.96-6.91 (m, 1H), 6.75-6.1 (m, 1H), 6.68-6.65 (m, 1H), 6.21-6.20 (m, 1H), 5.59 (s, 2H), 4.47-4.45 (t, J=4.0 Hz, 1H), 3.42-3.38 (m, 1H), 3.19-3.15 (m, 1H), 3.02 (s, 3H), 2.45 (s, 3H) ppm Embodiment 50

2-amino-7-((2-fluorophenyl)methylene)-4-(5-methylfuran-2-yl)-6-methyl-5H,6H,7H-pyrrolo[3,4-d]pyrimidin-5-one (Compound 50)

Synthetic Route

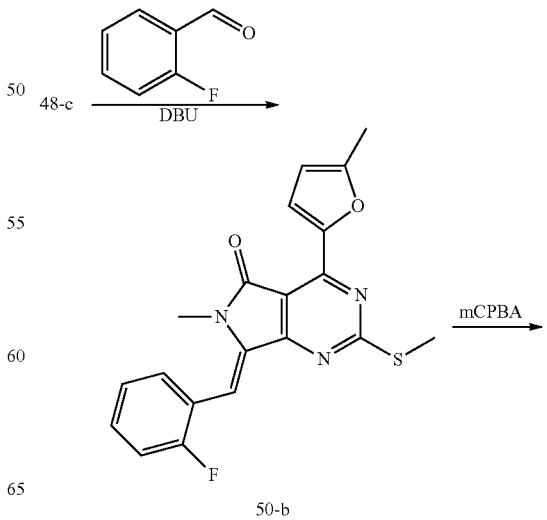

151

-continued

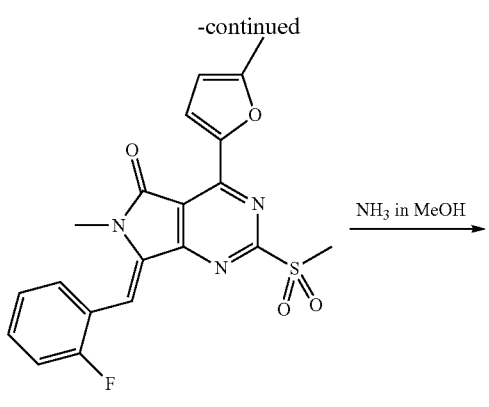

50-a

Synthesis of the Compound 50-b 1,8-Diazabicycloundec-7-ene (97 mg, 0.64 mmol) was added into compound 48-c (350 mg, 1.27 mmol) and 2-fluorobenzaldehyde (473 mg, 3.82 mmol) in dioxane (15 mL) solution. The mixture was refluxed under nitrogen atmosphere for 12 hours, then cooled down to room temperature. After concentration under reduced pressure, the residue was purified by silica gel chromatography (PE:EtOAc=10:1) to give a yellow solid 50-b (234 mg, yield: 48%). LC-MS (ESI): m/z=382 [M+H]$^+$.

Synthesis of the Compound 50-a

80% m-Chloroperoxybenzoic acid (424 mg, 2.64 mmol) was added into compound 50-b (234 mg, 0.61 mmol) in DCM (10 mL) solution, stirred at room temperature for 1 hour. The reaction was quenched by adding saturated sodium thiosulfate solution (10 mL). After adding water (20 mL), the mixture was extracted with DCM (20 mL×3), the combined organic phases were washed by water (20 mL) and saturated brine (20 mL), then the solution was concentrated under reduced pressure to give a yellow solid 50-a (330 mg), which was without further purification.

Synthesis of the Compound 50

7 N Ammonia in methanol solution (2 mL, 14 mmol) was added into compound 50-a (330 mg, 0.76 mmol) in tetrahydrofuran (10 mL) solution. The mixture was stirred to react at room temperature for 1 hour. After concentration under reduced pressure, the residue was added methanol (10 mL) and a solid was formed, filtered, the filter cake was washed by methanol (3 mL), then dried in vacuum to give the compound 50 (18 mg, yield: 8.4%).

LC-MS (ESI): m/z=351 [M+H]$^+$.

152

$^1$H NMR (400 MHz, CDCl$_3$) δ: 8.60-8.59 (d, J=2.8 Hz, 1H), 8.11-8.08 (m, 1H), 7.34-7.32 (m, 1H), 7.16-7.07 (m, 2H), 6.47 (s, 1H), 6.27-6.26 (m, 1H), 5.35 (s, 2H), 3.36 (s, 3H), 2.48 (s, 3H) ppm Embodiment 51

2-amino-7-((2-(trifluoromethyl)phenyl)methylene)-4-(5-methylfuran-2-yl)-6-methyl-5H,6H,7H-pyrrolo[3,4-d]pyrimidin-5-one (Compound 50)

Synthetic Route

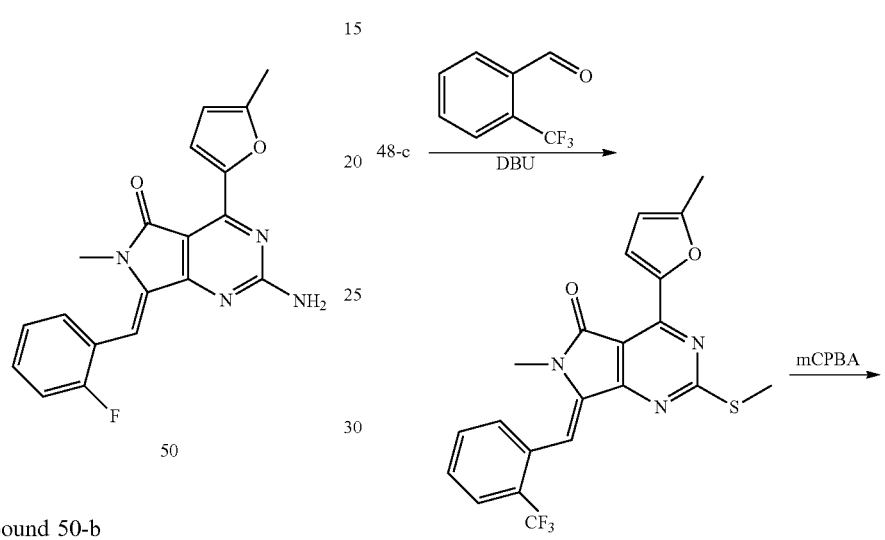

Synthesis of the Compound 51-b 1,8-Diazabicycloundec-7-ene (97 mg, 0.64 mmol) was added into compound 48-c (350 mg, 1.27 mmol) and 2-trifluoromethylbenzaldehyde (665 mg, 3.82 mmol) in dioxane (15 mL) solution. The mixture was refluxed under nitrogen atmosphere for 12 hours, then cooled down to room temperature. After concentration under reduced pressure, the residue was purified by silica gel chromatography (PE:EtOAc=10:1) to give a yellow solid 51-b (170 mg, yield: 31%). LC-MS (ESI): m/z=432 [M+H]$^+$.

Synthesis of the Compound 51-a

80% m-Chloroperoxybenzoic acid (272 mg, 1.58 mmol) was added into compound 51-b (170 mg, 0.39 mmol) in DCM (10 mL) solution, stirred at room temperature for 1 hour. The reaction was quenched by adding saturated sodium thiosulfate solution (10 mL). After adding water (20 mL), the mixture was extracted with DCM (20 mL×3), the combined organic phases were washed by water (20 mL) and saturated brine (20 mL), then the solution was concentrated under reduced pressure to give a yellow solid 51-a (248 mg), which was without further purification. LC-MS (ESI): m/z=464 [M+H]$^+$.

Synthesis of the Compound 51

7 N Ammonia in methanol solution (2 mL, 14 mmol) was added into compound 51-a (248 mg, 0.54 mmol) in tetrahydrofuran (10 mL) solution. The mixture was stirred to react at room temperature for 1 hour. After concentration under reduced pressure, the residue was added into methanol (10 mL) and a solid was formed, filtered, the filter cake was washed by methanol (3 mL), then dried in vacuum to give the compound 51 (18 mg, yield: 8.3%).

LC-MS (ESI): m/z=401 [M+H]$^+$.

$^1$H NMR (400 MHz, CDCl$_3$) δ: 8.58-8.57 (d, J=2.8 Hz, 1H), 7.82-7.81 (d, J=6.4 Hz, 1H), 7.70-7.69 (d, J=6.0 Hz, 1H), 7.52-7.49 (d, J=6.0 Hz, 1H), 7.44-7.41 (t, J=6.0 Hz, 1H), 6.60-6.59 (m, 1H), 6.26-6.25 (m, 1H), 5.23 (s, 2H), 3.34 (s, 3H), 2.48 (s, 3H) ppm Embodiment 52

2-amino-7-((2-(trifluoromethoxyl)phenyl)methylene)-4-(5-methylfuran-2-yl)-6-methyl-5H,6H,7H-pyrrolo[3,4-d]pyrimidin-5-one (Compound 52)

Synthetic Route

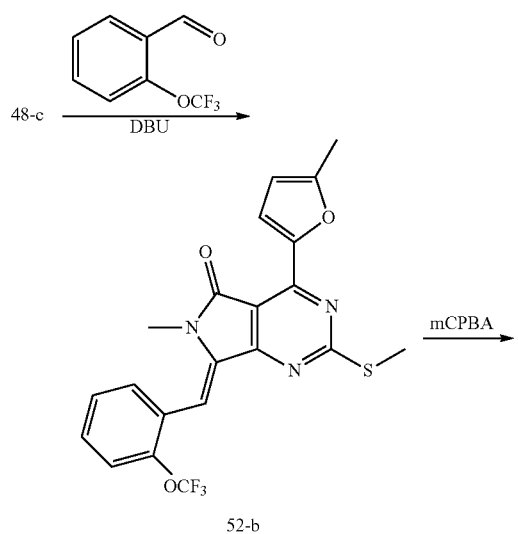

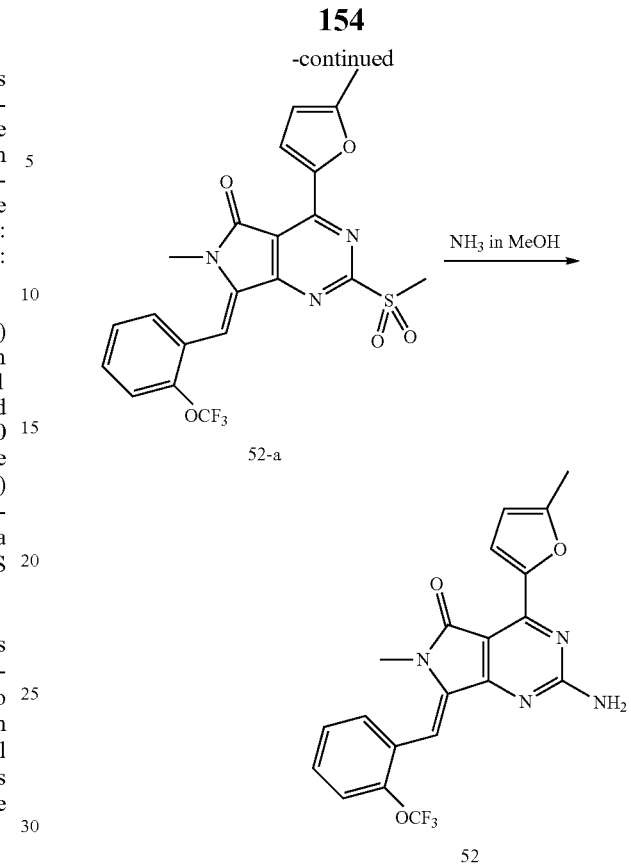

Synthesis of the Compound 52-b 1,8-Diazabicycloundec-7-ene (152 mg, 1.0 mmol) was added into compound 48-c (275 mg, 1.0 mmol) and 2-trifluoromethoxylbenzaldehyde (570 mg, 3.0 mmol) in dioxane (15 mL) solution. The mixture was heated to 120° C. under nitrogen atmosphere and stirred for 48 hours, then cooled down to room temperature. After concentration under reduced pressure, the residue was purified by silica gel chromatography (PE:EtOAc=15:1-10:1) to give a yellow solid 52-b (440 mg, yield: 98%). LC-MS (ESI): m/z=448 [M+H]$^+$.

Synthesis of the Compound 52-a

80% m-Chloroperoxybenzoic acid (519 mg, 3.0 mmol) was added into compound 52-b (440 mg, 1.0 mmol) in DCM (30 mL) solution, stirred at room temperature for 1 hour. Then the reaction was quenched by adding saturated sodium thiosulfate solution (30 mL). Water (50 mL) was added, then extracted with DCM (50 mL×3), the combined organic phases were washed by water (50 mL) and saturated brine (50 mL), then the solution was concentrated under reduced pressure to give a yellow solid 52-a (400 mg, yield: 82%), which was without further purification. LC-MS (ESI): m/z=440 [M+H]$^+$.

Synthesis of the Compound 52

7 N Ammonia in methanol solution (15 mL, 105 mmol) was added into compound 52-a (400 mg, 0.83 mmol) in tetrahydrofuran (15 mL) solution. The mixture was stirred to react at room temperature for 1 hour. After concentration under reduced pressure, the residue was added into methanol (3 mL), then a solid was formed, filtered, the filter cake was washed by methanol (3 mL), then dried in vacuum to give the compound 52 (300 mg, yield: 87%).

LC-MS (ESI): m/z=417 [M+H]$^+$.

¹H NMR: (400 MHz, CDCl₃) δ: 8.61 (d, J=2.4 Hz, 1H), 8.11-8.09 (m, 1H), 7.39-7.36 (m, 1H), 7.31-7.28 (m, 2H), 6.48 (s, 1H), 6.28 (d, J=2.8 Hz, 1H), 5.41 (bs, 2H), 3.36 (s, 3H), 2.50 (s, 3H) ppm Embodiment 53

2-amino-7-((2-(trifluoromethoxyl)phenyl)methyl)-4-(5-methylfuran-2-yl)-6-methyl-5H,6H,7H-pyrrolo[3,4-d]pyrimidin-5-one (Compound 53)

Synthetic Route

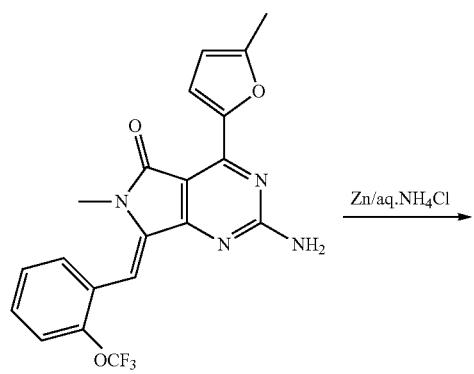

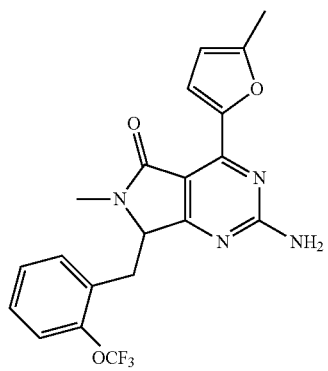

Synthesis of the Compound 53

Compound 52 (124.8 mg, 0.3 mmol) in tetrahydrofuran (10 mL) solution and zinc powder (195 mg, 3.0 mmol) were added into a mixed solution of ammonium chloride (321 mg, 6.0 mmol), water (3 mL) and ethanol (3 mL) at 9° C. After stirring for 1 hour, the mixture was heated to room temperature. Then the mixture was diluted by water (20 mL), extracted with DCM (20 mL), the organic phase was washed by saturated brine (20 mL), then concentrated under reduced pressure, the residue was purified by HPLC (mobile phase: water (10 mM ammonium bicarbonate), acetonitrile; gradient: 45%-75% (initial mobile phase was 45% water-55% acetonitrile, at the end the mobile phase was 75% water-25% acetonitrile, the % refers to volume percentage) to give a white solid 53 (30 mg, yield: 24%). LC-MS (ESI): m/z=419 [M+1]⁺.

¹H NMR: (400 MHz, CD₃OD) δ: 8.34 (d, J=2.8 Hz, 1H), 7.29-7.17 (m, 4H), 6.28-6.27 (m, 1H), 4.66 (t, J=4.0 Hz, 1H), 3.56-3.52 (m, 1H), 3.33-3.28 (m, 1H), 2.99 (s, 3H), 2.43 (s, 3H) ppm Embodiment 54

2-amino-7-((2-(trifluoromethyl)phenyl)methyl)-4-(5-methylfuran-2-yl)-6-methyl-5H,6H,7H-pyrrolo[3,4-d]pyrimidin-5-one (Compound 54)

Synthetic Route

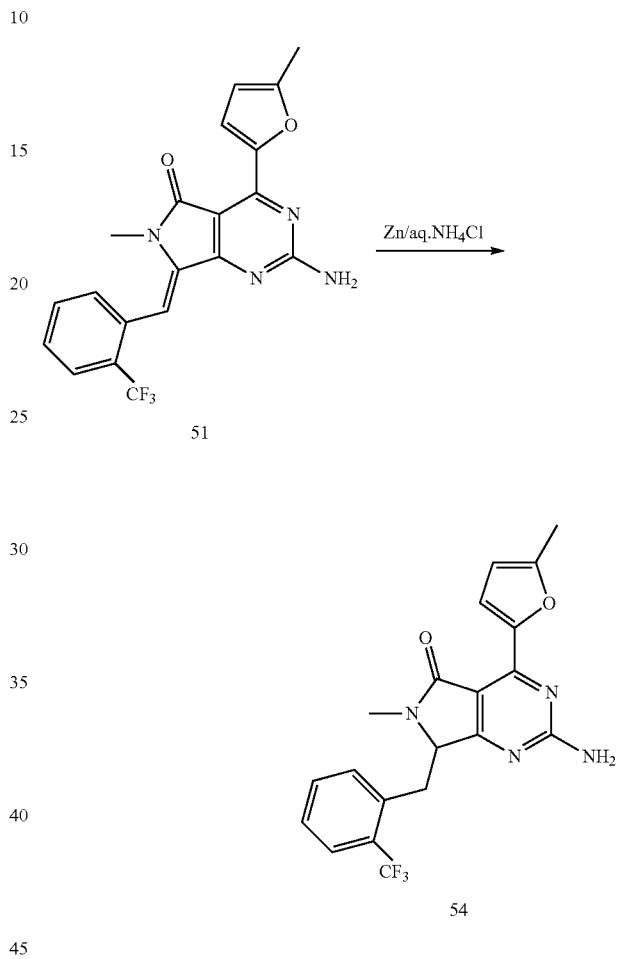

Synthesis of the Compound 54

Compound 51 (100 mg, 0.25 mmol) in tetrahydrofuran (10 mL) solution and zinc powder (163 mg, 2.5 mmol) were added into a mixed solution of ammonium chloride (268 mg, 5.0 mmol), water (3 mL) and ethanol (3 mL) at 9° C. After stirring for 1 hour, the mixture was warmed to room temperature. Then the mixture was diluted by water (20 mL), extracted with DCM (20 mL), the organic phase was washed by saturated brine (20 mL), then concentrated under reduced pressure, the residue was purified by thin layer chromatographic plate (PE:EtOAc=2:1) to give 54 (22 mg, yield: 21.8%). LC-MS (ESI): m/z=403 [M+1]⁺.

¹H NMR (400 MHz, CDCl₃) δ: 8.66-8.65 (d, J=2.8 Hz, 1H), 7.69-7.68 (d, J=6 Hz, 1H), 7.51-7.48 (m, 1H), 7.42-7.36 (m, 2H), 6.24-6.23 (m, 1H), 5.56 (s, 2H), 4.51-4.48 (m, 1H), 3.49-3.45 (m, 1H), 3.19-3.15 (m, 1H), 2.74 (s, 3H), 2.45 (s, 3H) ppm

157
Embodiment 55

2-amino-7-((2-fluorophenyl)methyl)-4-(5-methyl-furan-2-yl)-6-methyl-5H,6H,7H-pyrrolo[3,4-d]pyrimidin-5-one (Compound 55)

Synthetic Route

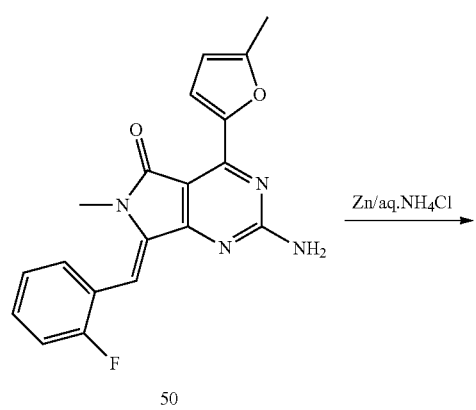

Synthesis of the Compound 55

Compound 50 (100 mg, 0.4 mmol) in tetrahydrofuran (10 mL) solution and zinc powder (262 mg, 4.0 mmol) were added into a mixed solution of ammonium chloride (428 mg, 8.0 mmol), water (3 mL) and ethanol (3 mL) at 0° C. The mixture was stirred for 1 hour and warmed to room temperature. Then the mixture was diluted by water (20 mL), extracted with DCM (20 mL), the organic phase was washed by saturated brine (20 mL), then concentrated under reduced pressure, the residue was purified by thin layer chromatographic plate (PE:EtOAc=2:1) to give 55 (15 mg, yield: 10.5%). LC-MS (ESI): m/z=353 [M+1]$^+$.

$^1$H NMR (400 MHz, CDCl$_3$) δ: 8.58-8.57 (d, J=2.8 Hz, 1H), 7.17-7.13 (m, 1H), 7.01-6.92 (m, 3H), 6.20-6.19 (m, 1H), 5.45 (s, 2H), 4.51-4.48 (m, 1H), 3.49-3.45 (m, 1H), 3.17-3.13 (m, 1H), 2.98 (s, 3H), 2.45 (s, 3H) ppm

158
Embodiment 56

2-amino-7-((2-(trifluoromethyl)-4-fluorophenyl) methylene)-4-(5-methylfuran-2-yl)-6-methyl-5H,6H, 7H-pyrrolo[3,4-d]pyrimidin-5-one (Compound 56)

Synthetic Route

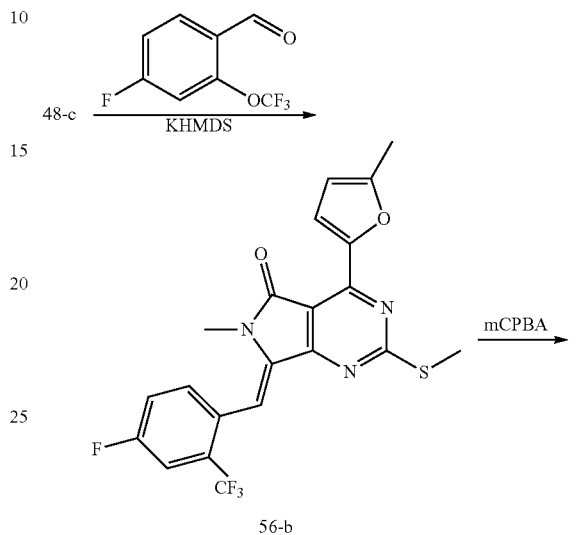

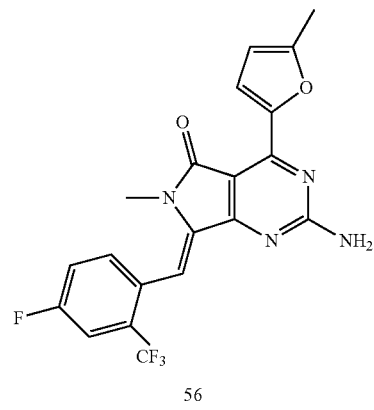

Synthesis of the Compound 56-b

Under nitrogen atmosphere, compound 48-c (275 mg, 1.0 mmol) in anhydrous tetrahydrofuran (20 mL) solution was added dropwise into 1 M potassium hexamethyldisilazide (1.5 mL, 1.5 mmol) in tetrahydrofuran solution at −78° C., the mixture was stirred for 1 hour, then 2-trifluoromethoxyl- 4-fluorobenzaldehyde (384 mg, 2.0 mmol) in anhydrous tetrahydrofuran (20 mL) solution was added dropwise, and further stirred for 1 hour. The reaction mixture was slowly warmed to room temperature, then added dropwise into saturated ammonium chloride (50 mL) solution, and extracted with EtOAc (50 mL×2). The organic phase was washed by saturated brine (50 mL), then concentrated under reduced pressure, and the residue was purified by silica gel chromatography (PE:EtOAc=10:1-15:1) to give a yellow solid 56-b (180 mg, yield: 40%). LC-MS (ESI): m/z=450 [M+H]$^+$.

Synthesis of the Compound 56-a

80% m-Chloroperoxybenzoic acid (150 mg, 0.86 mmol) was added into compound 56-b (130 mg, 0.29 mmol) in DCM (30 mL) solution, stirred at room temperature for 1 hour. The reaction was quenched by adding saturated sodium thiosulfate solution (10 mL). Water (30 mL) was added thereto, then extracted with DCM (30 mL×2), the combined organic phases were washed by water (30 mL) and saturated brine (30 mL), then the solution was concentrated under reduced pressure to give a yellow solid 56-a (150 mg, yield: 99%), which was without further purification. LC-MS (ESI): m/z=482 [M+H]$^+$.

Synthesis of the Compound 56

7 N Ammonia in methanol solution (5 mL, 35 mmol) was added into compound 56-a (150 mg, 0.31 mmol) in tetrahydrofuran (15 mL) solution. The mixture was stirred to react at room temperature for 1 hour. After concentration under reduced pressure, the residue was added into methanol (6 mL), then a solid was formed, filtered, the residue was washed by methanol (6 mL), then dried in vacuum to give the compound 56 (50 mg, yield: 39%).

LC-MS (ESI): m/z=419 [M+H]$^+$.

$^1$H NMR (400 MHz, CDCl$_3$) δ: 8.60 (d, J=3.2 Hz, 1H), 7.84-7.81 (m, 1H), 7.44-7.41 (m, 1H), 7.25-7.21 (m, 2H), 6.53 (s, 1H), 6.28 (d, J=2.4 Hz, 1H), 5.26 (bs, 2H), 3.35 (s, 3H), 2.50 (s, 3H) ppm Embodiment 57

2-amino-7-((2-(trifluoromethyl)-4-fluorophenyl) methyl)-4-(5-methylfuran-2-yl)-6-methyl-5H,6H,7H-pyrrolo[3,4-d]pyrimidin-5-one (Compound 57)

Synthetic Route

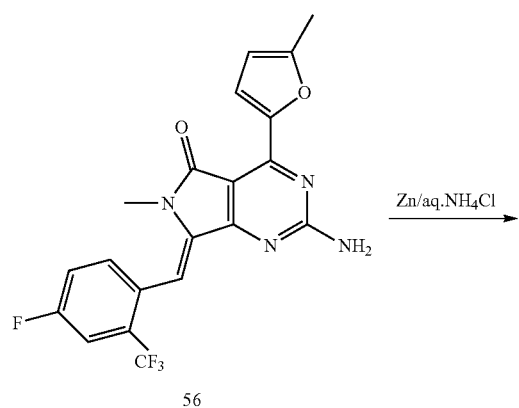

56

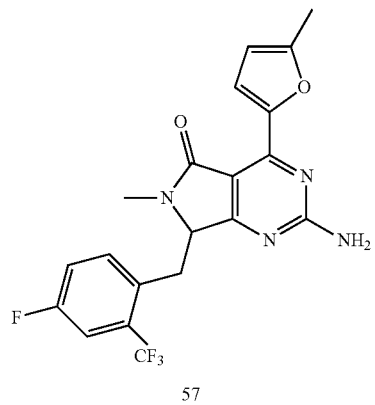

57

Synthesis of the Compound 57

Compound 56 (130 mg, 0.31 mmol) in tetrahydrofuran (10 mL) solution and zinc powder (201.5 mg, 3.1 mmol) were added into a mixed solution ammonium of chloride (331.7 mg, 6.2 mmol), water (4 mL) and ethanol (4 mL) at 0° C. The mixture was stirred for 1 hour and heated to room temperature. Then the mixture was diluted by water (20 mL), extracted with DCM (50 mL), the organic phase was washed by saturated brine (20 mL), then concentrated under reduced pressure, the residue was purified by HPLC (mobile phase: water (10 mM ammonium bicarbonate), acetonitrile; gradient: 45%-75% (initial mobile phase was 45% water-55% acetonitrile, at the end the mobile phase was 75% water-25% acetonitrile, the % refers to volume percentage) to give the 57 (13 mg, yield:11%). LC-MS (ESI): m/z=421 [M+1]$^+$.

Embodiment 58

4-((2-amino-6-methyl-4-(5-methylfuran-2-yl)-5-carbonyl-5H-pyrrolo[3,4-d]pyrimidin-7(6H)-ene) methyl)-N-oxide pyridine (Compound 58)

Synthetic Route

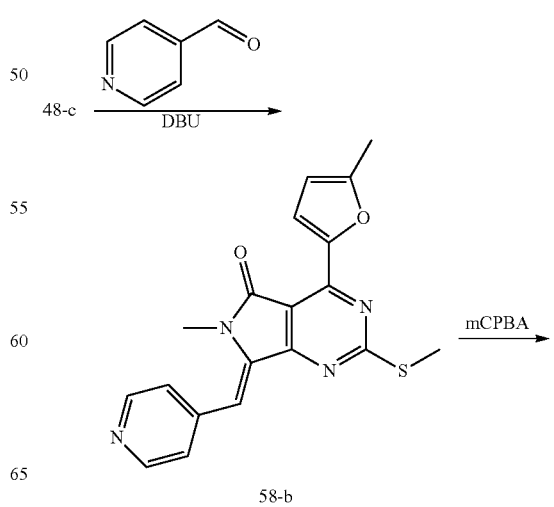

161

-continued

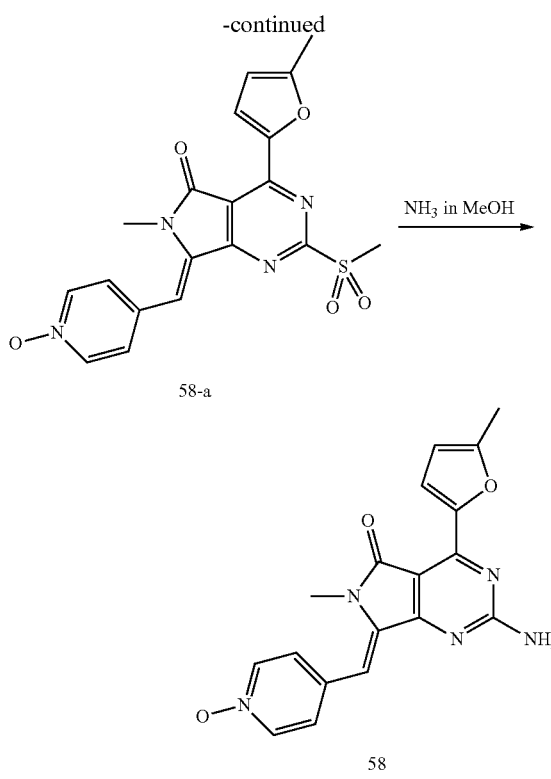

162

Embodiment 59

2-amino-6-methyl-4-(5-methylfuran-2-yl)-7-(pyridin-4-ylmethyl)-6,7-dihydro-5-carbonyl-5H-pyrrolo[3,4-d]pyrimidine (Compound 59)

Synthetic Route

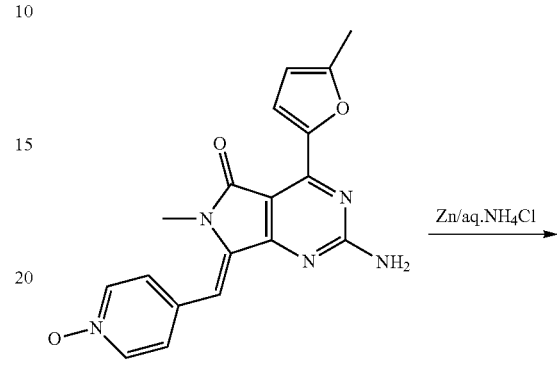

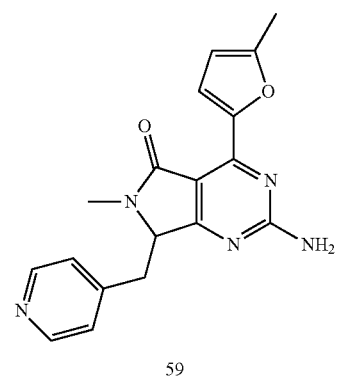

59

Synthesis of the Compound 58-b 1,8-Diazabicycloundec-7-ene (45 mg, 0.29 mmol) was added into compound 48-c (160 mg, 0.58 mmol) and 4-pyridinaldehyde (187 mg, 1.75 mmol) in dioxane (15 mL) solution. The mixture was heated to 110° C. under nitrogen atmosphere and stirred for 12 hours, then cooled down to room temperature. After concentration under reduced pressure, the residue was purified by silica gel chromatography (PE:EtOAc=10:1) to give a yellow solid 58-b (108 mg, yield: 49%). LC-MS (ESI): m/z=365 [M+H]$^+$.

Synthesis of the Compound 58-a

80% m-Chloroperoxybenzoic acid (205 mg, 1.18 mmol) was added into compound 58-b (108 mg, 0.3 mmol) in DCM (10 mL) solution, stirred at room temperature for 1 hour. The reaction was quenched by adding saturated sodium thiosulfate solution (10 mL). After adding water (20 mL), the mixture was extracted with DCM (20 mL×3), the combined organic phases were washed by water (20 mL) and saturated brine (20 mL), then the solution was concentrated under reduced pressure to give a yellow solid 58-a (200 mg), which was without need further purification. LC-MS (ESI): m/z=414 [M+H]$^+$.

Synthesis of the Compound 58

7 N Ammonia in methanol solution (2 mL, 14 mmol) was added into compound 58-a (200 mg, 0.48 mmol) in tetrahydrofuran (15 mL) solution. The mixture was stirred to react at room temperature for 1 hour. After concentration under reduced pressure, the residue was added into methanol (3 mL), then a solid was formed, filtered, the filter cake was washed by methanol (3 mL), then dried in vacuum to give the compound 58 (20 mg, yield: 11.9%).

LC-MS (ESI): m/z=350 [M+H]$^+$.

$^1$H NMR (400 MHz, CDCl$_3$) δ: 8.58-8.57 (d, J=2.8 Hz, 1H), 8.18-8.16 (d, J=5.6 Hz, 2H), 7.94-7.92 (d, J=5.6 Hz, 2H), 6.28-6.27 (m, 1H), 6.20 (s, 1H), 5.52 (s, 2H), 3.33 (s, 3H), 2.49 (s, 3H) ppm Synthesis of the Compound 59

Compound 58 (70 mg, 0.2 mmol) in tetrahydrofuran (10 mL) solution and zinc powder (131 mg, 2.0 mmol) were added into a mixed solution of ammonium chloride (215 mg, 4.0 mmol), water (2 mL) and ethanol (2 mL) at 0° C. The mixture was stirred for 1 hour and warmed to room temperature. Water (10 mL) was added for dilution, then extracted with DCM (10 mL), the organic phase was washed by saturated brine (10 mL), then concentrated under reduced pressure, the residue was purified by thin layer chromatographic plate (PE:EtOAc=2:1) to give 59 (7 mg, yield: 10.4%).

LC-MS (ESI): m/z=336 [M+1]$^+$.

$^1$H NMR (400 MHz, CDCl$_3$) δ: 8.54-8.53 (d, J=3.6 Hz, 1H), 8.41-8.39 (d, J=5.6 Hz, 2H), 6.96-6.94 (d, J=6.0 Hz, 2H), 6.20-6.19 (m, 1H), 5.47 (s, 2H), 4.52-4.48 (m, 1H), 3.33-3.31 (m, 1H), 3.26-3.25 (m, 1H), 3.05 (s, 3H), 2.44 (s, 3H) ppm

163

Embodiment 60

2-amino-6-(5-methylfuran-2-yl)-9-(2-(trifluoromethyl)phenyl)-8(9H)-carbonyl-7H-purine (Compound 60)

Synthetic Route

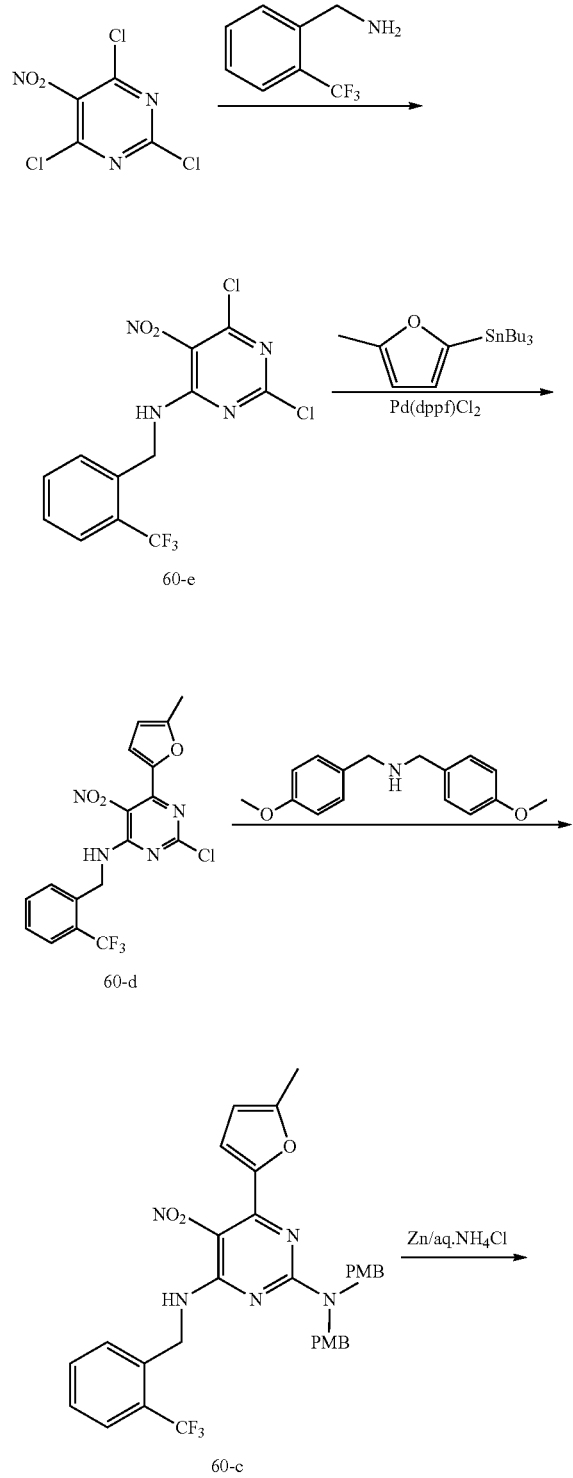

60-e 60-d

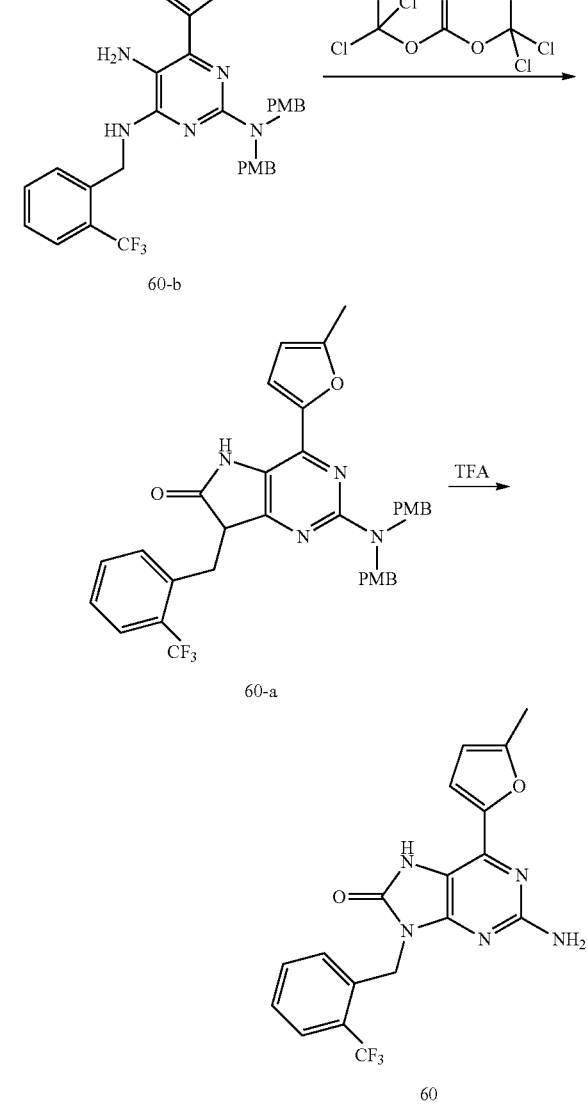

60-b 60-a

60

Synthesis of the Compound 60-e 2,4,6-Trihydro-5-nitropyrimidine (400 mg, 1.76 mmol) was dissolved in anhydrous tetrahydrofuran (20 mL), 2-trifluoromethyl-fluorobenzylamine (308 mg, 1.76 mmol) was added dropwise slowly at 0° C., and then stirred at 0° C. for 1 hour. After concentration under reduced pressure, the residue was purified by silica gel chromatography (PE: EtOAc=10:1) to give a yellow solid product 60-e (470 mg, yield: 73%).

LC-MS (ESI): m/z=367[M+1]$^+$.

Synthesis of the Compound 60-d

Compound 60-e (500 mg, 1.37 mmol), tributyl-(2-furyl)stannane (210 mg, 1.67 mmol), anhydrous potassium phosphate (890 mg, 4.2 mmol) and 1,1'-bisdiphenylphosphinoferrocene dichloropalladium (160 mg, 0.2 mmol) were added into dry tetrahydrofuran (10 mL). The reaction mixture was stirred at 80° C. for 18 hours under nitrogen atmosphere, then cooled down to room temperature. After concentration under reduced pressure, the residue was purified by silica gel chromatography (PE:EtOAc=10:1) to give a yellow solid product 60-d (120 mg, yield: 21%).

LC-MS (ESI): m/z=413[M+1]$^+$.

Synthesis of the Compound 60-c

Compound 60-d (120 mg, 0.29 mmol), bis(p-methoxybenzyl)amine (224 mg, 0.87 mmol) were added into dry tetrahydrofuran (10 mL). The reaction mixture was reacted at 50° C. for 5 hours, then cooled down to room temperature. The reaction solution was then concentrated under reduced pressure, and the residue was purified by silica gel chromatography (PE:EtOAc=10:1) to give a yellow solid product 360-c (120 mg, yield: 65%).

LC-MS (ESI): m/z=634 [M+1]$^+$.

Synthesis of the Compound 60-b

Ammonium chloride (40 mg, 0.75 mmol), zinc powder (50 mg, 0.75 mmol) and ethanol (3 mL) were added successively into compound 60-c (120 mg, 0.19 mmol) in water (3 mL) and ethanol (3 mL) solution at 0° C. while stirring. The reaction mixture was warmed to 80° C., and stirred for 1 hour, then cooled down to room temperature. The reaction solution was then concentrated under reduce pressure, the residue was diluted by water (50 mL) and extracted with EtOAc (50 mL), the organic phase was washed by saturated brine (20 mL), dried over anhydrous sodium sulfate, then the solution was concentrated under reduced pressure to give the a yellow solid 60-b (98 mg, yield: 85%), which was without further purification.

LC-MS (ESI): m/z=630 [M+1]$^+$.

Synthesis of the Compound 60-a

Triphosgene (24 mg, 0.08 mmol) was added into 60-b (98 mg, 0.16 mmol) and triethylamine (50 mg, 0.48 mmol) in dry tetrahydrofuran (5 mL) solution at 0° C., after stirring for 10 mins, the reaction mixture was then warmed to room temperature and further stirred for 3 hours. The reaction solution was then concentrated, the residue was diluted by adding water (5 mL), then filtered, the filter cake was dried in vacuum to give a pale brown solid 60-a (98 mg, yield: 96%), which was without further purification.

LC-MS (ESI): m/z=630 [M+1]$^+$.

Synthesis of the Compound 60

Compound 60-a (98 mg, 0.16 mmol) was added into trifluoroacetic acid (5 mL). The reaction mixture was stirred at 80° C. for 2 hours, then cooled down to room temperature. The reaction solution was then concentrated under reduced pressure, the residue was added into saturated potassium carbonate solution (30 mL) and DCM (50 mL), the organic phase was dried over anhydrous sodium sulfate, then concentrated under reduced pressure, the residue was purified by thin layer chromatographic plate (DCM:MeOH=10:1) to give a pale yellow solid 60 (15 mg, yield: 25%). LC-MS (ESI): m/z=390 [M+1]$^+$.

$^1$H-NMR (400 MHz, DMSO-d$_6$) δ: 11.3 (br, 1H), 7.80 (d, J=8 Hz, 1H), 7.61 (m, 1H), 7.51 (m, 1H), 7.13 (m, 1H), 7.06 (m, 1H), 6.36 (s, 1H), 5.12 (s, 2H), 2.43 (s, 3H) ppm Embodiment 61

2-amino-7-methyl-6-(5-methylfuran-2-yl)-9-(2-(trifluoromethyl)phenyl)-8(9H)-carbonyl-7H-purine (Compound 61)

Synthetic Route

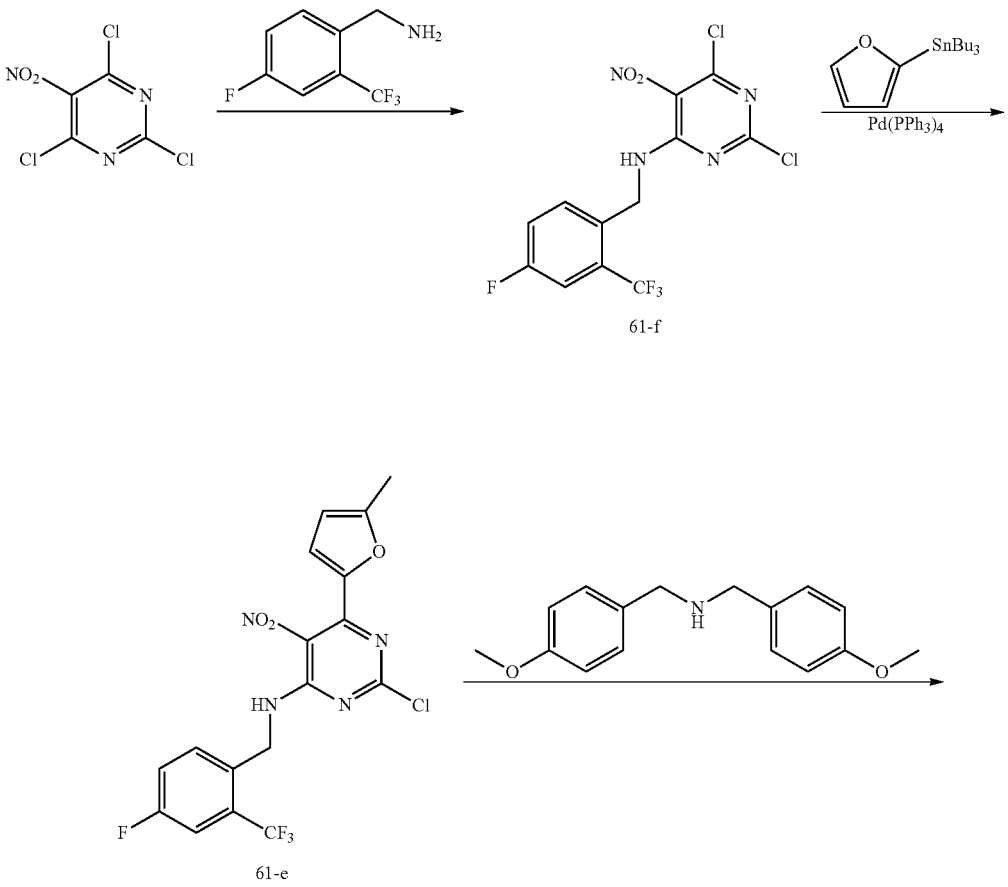

-continued
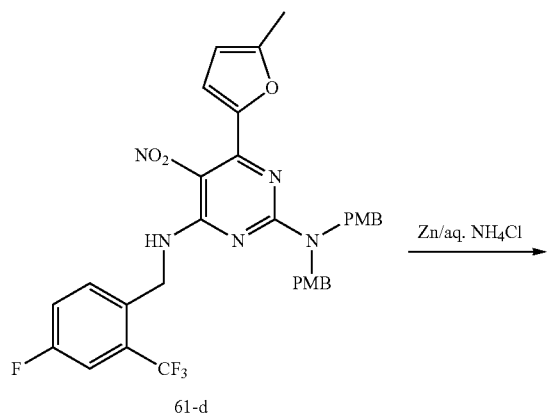
61-d
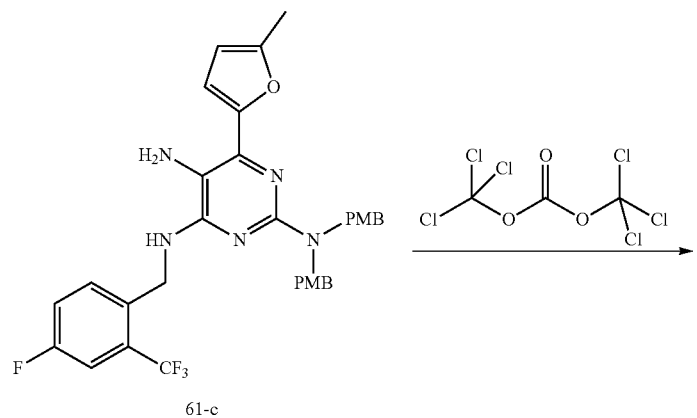
61-c
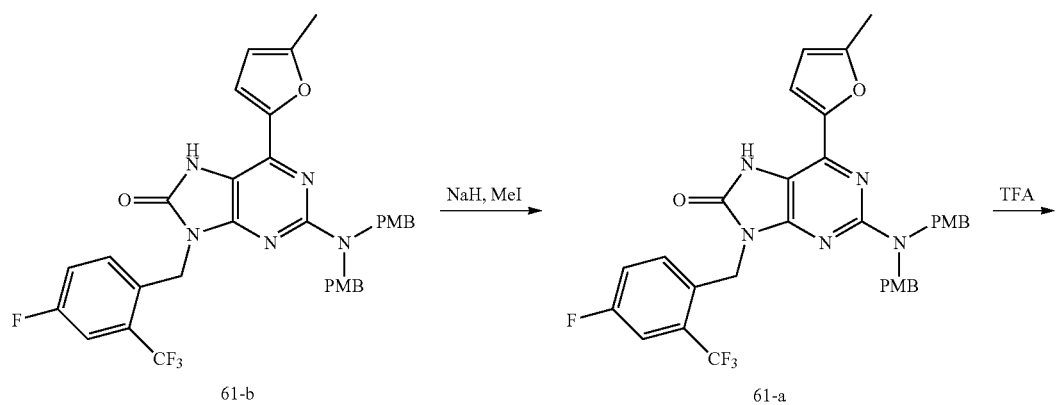
61-b        61-a
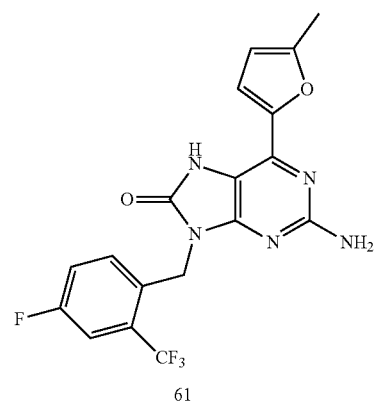
61

Synthesis of the Compound 61-f 2,4,6-Trihydro-5-nitropyrimidine (500 mg, 2.19 mmol) was dissolved in anhydrous tetrahydrofuran (20 mL), 2-trifluoromethyl-4-fluorobenzylamine (423 mg, 2.19 mmol) was added dropwise slowly at 0° C., and then stirred at 0° C. for 1 hour. After concentration under reduced pressure, the residue was purified by silica gel chromatography (PE:EtOAc=20:1) to give a yellow solid product 61-f (470 mg, yield: 58%). LC-MS (ESI): m/z=385[M+1]$^+$.

Synthesis of the Compound 61-e

Compound 61-f (470 mg, 1.22 mmol), tributyl-(2-furyl)stannane (123 mg, 0.98 mmol), potassium phosphate (780 mg, 3.67 mmol) and palladium tetrakis(triphenyl)phosphine (50 mg, 0.05 mmol) were added into dry toluene (20 mL). The reaction mixture was stirred at 80° C. under nitrogen atmosphere for 12 hours, then cooled down to room temperature. After concentration under reduced pressure, the residue was purified by silica gel chromatography (PE:EtOAc=20:1) to give a yellow solid product 61-e (160 mg, yield: 30%).

LC-MS (ESI): m/z=431[M+1]$^+$.

Synthesis of the Compound 61-d

Compound 61-e (160 mg, 0.37 mmol), bis(p-methoxybenzyl)amine (192 mg, 0.74 mmol) and diisopropylethylamine (58 mg, 0.45 mmol) were added into dry tetrahydrofuran (10 mL). The reaction mixture was reacted at 60° C. for 5 hours, then cooled down to room temperature. The reaction solution was then concentrated under reduced pressure, and the residue was purified by silica gel chromatography (PE:EtOAc=15:1) to give a yellow solid product 61-d (175 mg, yield: 72%).

LC-MS (ESI): m/z=652 [M+1]$^+$.

Synthesis of the Compound 61-c

Ammonium chloride (268 mg, 5.0 mmol) was dissolved in water (3 mL), zinc powder (171 mg, 2.6 mmol) and ethanol (3 mL) were added successively, and 61-d (170 mg, 0.26 mmol) in tetrahydrofuran (10 mL) solution was added dropwise while stirring at 0° C. After stirring at 0° C. for 1 hour, the reaction was warmed to room temperature. The reaction solution was then concentrated under reduced pressure, the residue was diluted by water (20 mL), then extracted with EtOAc (20 mL), the organic phase was washed by saturated brine (20 mL), dried over anhydrous sodium sulfate, then concentrated under reduced pressure, and the residue was purified by silica gel chromatography (PE:EtOAc=5:1) to give a black oily product 61-c (116 mg, yield: 72%).

LC-MS (ESI): m/z=622 [M+1]$^+$.

Synthesis of the Compound 61-b

Triphosgene (63 mg, 0.21 mmol) was added into 34-b (110 mg, 0.17 mmol) and diisopropylethylamine (0.5 mL, 2.65 mmol) in dry tetrahydrofuran (15 mL) solution at 0° C., the reaction mixture was stirred for 10 mins and heated to room temperature, then further stirred for 2 hours. The reaction solution was then concentrated under reduced pressure to give a yellow oily product 61-b (137 mg, yield: 61%), which was without further purification.

LC-MS (ESI): m/z=648 [M+1]$^+$.

Synthesis of the Compound 61-a

60% Sodium hydride dispersed in mineral oil (8 mg, 0.2 mol) was suspended in dry N,N-dimethylformamide (4 mL), 61-b (137 mg, 0.21 mmol) in dry N,N-dimethylformamide (10 mL) solution was added into this suspension dropwise at 0° C. under nitrogen atmosphere, and the reaction mixture was further stirred at 0° C. for 30 mins. Methyl iodide (60 mg, 0.42 mmol) was added, then warmed to room temperature and further stirred for 12 hours. The reaction mixture was poured into half saturated ammonium chloride water solution (20 mL), extracted with EtOAc (20 mL×3). The organic phase was washed by saturated brine (20 mL), dried over anhydrous sodium sulfate, then the solution was concentrated under reduced pressure to give a yellow solid 61-a (150 mg), which was without further purification.

LC-MS (ESI): m/z=662 [M+1]$^+$.

Synthesis of the Compound 61

Compound 61-a (150 mg, 0.23 mmol) was added into trifluoroacetic acid (3 mL). The reaction mixture was stirred at 85° C. for 2 hours, then cooled down to room temperature. The reaction solution was then concentrated under reduced pressure, the residue was purified by HPLC (mobile phase: water (10 mM ammonium bicarbonate), acetonitrile; gradient: 30%-60% (initial mobile phase was 30% water-70% acetonitrile, at the end the mobile phase was 60% water-40% acetonitrile, the % refers to volume percentage) to give the a white solid product 61 (26 mg, yield: 26.8%). LC-MS (ESI): m/z=422 [M+1]$^+$.

$^1$H NMR (400 MHz, CDCl$_3$) δ: 7.42-7.40 (m, 1H), 7.16-7.11 (m, 1H), 7.08-7.04 (m, 2H), 6.21-6.19 (m, 1H), 5.26 (m, 2H), 4.73 (s, 2H), 3.65 (s, 3H), 2.43 (s, 3H) ppm Effect Embodiment 1 evaluation experiment of the binding affinity IC$_{50}$ of the compound 1 to hA2A receptor.

Experimental procedure

1. Preparation of the test compound.
   1) The compound mother plate (1500 rpm, 1 minute) was centrifuged;
   2) 50 Nanoliters was transferred from the compound mother plate to the reaction plate by a nano-sound sonic pipetting system;
2. Preparation of buffer medium membrane, preparation of beads suspension;
   1) DMSO was added to the assay buffer, final concentration of DMSO was 1%;
   2) homogenized A2A receptor membrane was connected to a 1 mL syringe five times by a No. 26 needle (to avoid air bubbles);
   3) the buffer, A2A receptor membrane and ADA were mixed, and was let stand for 15 minutes at room temperature;
   4) SPA beads were added and mixed well with A2A receptor membrane;
3. Preparation of radioisotope buffer
4. Mix reaction reagents
   1) 20 μL of radioactive buffer solution was added into the reaction plate;
   2) 30 μL of membrane and scorpion suspension was added into the reaction plate;
   3) the plate was sealed and incubated for 1 hour at room temperature with vigorous mixing and shaking;
   4) the beads were precipitated for 4-5 minutes before reading.
   5) Reading with Microbeta;
5. Data processing Experimental Result The results of the binding affinity of the compounds of the present invention to the hA2A receptor according to the above experiments are as follows (Table 1):

TABLE 1

| IC$_{50}$ values of compound 1 binding affinity to hA2A receptor ||
|---|---|
| Compound | IC$_{50}$ (nM) |
| 1 | 79 |

Effect Embodiment 2

Evaluation experiment of the binding affinity IC$_{50}$ of the compounds 1-61 to hA2A receptor 1. Preparation of the reagents
   1) Detection buffer: 50 mM Tris-HCl pH 7.4, 10 mM MgCl$_2$, 1 mM EDTA, 1 µg/mL Adenosine Deaminase, and stored at 4° C. for use.
   2) Washing solution: 50 mM Tris-HCl pH 7.4, 154 mM NaCl, and stored at 4° C. for use.
   3) 0.5% PEI solution: 0.5 g PEI is dissolved in 100 mL ddH$_2$O, and stored at 4° C. for use.
2. Operation procedure
   1) Addition of compound: 250 nL of the compound was added to the Opti-plate with Echo 550, and sealed by sealing film.
   2) Membrane dilution: 1 mL assay buffer was added into 20 U A2A membrane, 0.75 uCi [3H]-CGS 21680 (final 25 nM), and 50 uL of which was added into the Opti-plate.
   3) Incubation: the above mixture was incubated for 90 minutes at 25° C.
   4) Preparation of the pre-filter plate: 100 uL of 0.5% PEI solution was added into UNIFILTER-96 GF/B filter plate, and soaked for 40 minutes at 4° C.
   5) Filtration:
      a. Cell Harvester transferred 500 uL of cleaning solution/empty cleaning UNIFILTER-96 GF/B filter plate 2 times. The mixed system in the Opti-plate was suspended and transfer to the UNIFILTER-96 GF/B filter plate.
      c. 500 uL cleaning solution/empty cleaning UNIFILTER-96 GF/B filter plate 9 times.
      d. Incubated for 10 minutes in a 55° C. incubator.
3. Readings
   40 uL of ULTIMA GOLD scintillation fluid was added to each well and the CPM (count per minute) value was read by TopCount.

Experimental Result

The results of the binding affinity of the compounds of the present invention to the hA2A receptor according to the above experiments are as follows (Table 2):

TABLE 2

Compounds for hA2A receptor binding affinity IC$_{50}$ values

| Compound | IC$_{50}$ (nM) | Compound | IC$_{50}$ (nM) |
| --- | --- | --- | --- |
| 1 | 14.7 | 2 | 39.3 |
| 3 | 159 | 4 | 249 |
| 5 | 40 | 6 | 157.3 |
| 7 | n.d. | 8 | 10.7 |
| 9 | n.d. | 10 | 114.4 |
| 11 | 32.1 | 12 | 99.8 |
| 13 | 152 | 14 | 218.2 |
| 15 | 274 | 16 | 15.7 |
| 17 | 29.2 | 18 | 73.7 |
| 19 | 31.1 | 20 | 298.9 |
| 21 | 105.8 | 22 | 47.3 |
| 23 | 3.9 | 24 | 917.8 |
| 25 | 18.6 | 26 | 32.1 |
| 27 | 21 | 28 | 11.2 |
| 29 | 252.3 | 30 | 94 |
| 31 | 38.4 | 32 | 19.9 |
| 33 | 274.8 | 34 | 39.2 |
| 35 | 30.1 | 36 | 28.1 |
| 37 | 67.4 | 38 | 6.1 |
| 39 | 127.7 | 40 | 106.3 |
| 41 | 43.5 | 42 | 87.4 |
| 43 | 992.4 | 44 | 64.6 |

TABLE 2-continued

Compounds for hA2A receptor binding affinity IC$_{50}$ values

| Compound | IC$_{50}$ (nM) | Compound | IC$_{50}$ (nM) |
| --- | --- | --- | --- |
| 45 | 11.6 | 46 | 8.7 |
| 47 | 16.4 | 48 | 13.2 |
| 49 | 32.1 | 50 | 7.3 |
| 51 | 4.7 | 52 | 3.6 |
| 53 | 56.2 | 54 | 34.7 |
| 55 | 29.3 | 56 | 3.4 |
| 57 | 152.1 | 58 | 21 |
| 59 | 178.7 | 60 | 176.9 |
| 61 | 212.8 | | | n.d.: no test.

Although the invention has been described with detailed embodiments, however, the man skilled in the art should understand that, the foregoing description are only illustration and examples, and various modifications and improvements could be made to the embodiments without departing from the principles and essences of the present disclosure. Therefor, the scope of the invention is defined by the appended claims.

What is claimed is:

1. An aminopyrimidine five-membered heterocyclic compound represented by formula I-1, a pharmaceutically acceptable salt, a tautomer, an enantiomer or a diastereomer or a prodrug thereof:

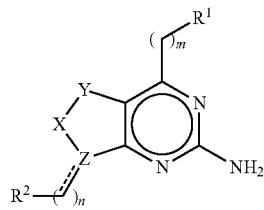

I-1 wherein, "$=\!=\!=\!=$" represents a single bond or a double bond;

when "$=\!=\!=\!=$" is a single bond, Z is N or CR$^5$; R$^5$ is H, D or C$_1$-C$_{20}$ alkyl;

when "$=\!=\!=\!=$" is double bond, Z is C;

X is O, CO or NR$^3$;

Y is CO, CH$_2$ or NR$^4$;

R$^1$ is selected from unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted tert-butyl, substituted or unsubstituted C$_6$-C$_{30}$ aryl or substituted or unsubstituted C$_2$-C$_{30}$ heteroaryl;

R$^2$ is selected from substituted or unsubstituted C$_1$-C$_{20}$ alkyl, substituted or unsubstituted C$_6$-C$_{30}$ aryl or substituted or unsubstituted C$_2$-C$_{30}$ heteroaryl;

the C$_2$-C$_{30}$ heteroaryl in the substituted or unsubstituted C$_2$-C$_{30}$ heteroaryl refers to a C$_2$-C$_{30}$ heteroaryl comprising 1-4 heteroatoms which is selected from the group consisting of N, O or S;

the substituent in the substituted ethyl, the substituted n-propyl, the substituted isopropyl, the substituted n-butyl, the substituted isobutyl, the substituted tert-butyl of R$^1$, the substituted C$_1$-C$_{20}$ alkyl group of R$^2$, the substituted C$_6$-C$_{30}$ aryl or the substituted C$_2$-C$_{30}$ heteroaryl of R$^1$ or R$^2$ is selected from one or more of the group consisting of one or more halogens, $C_1$-$C_{20}$ alkyl, halogenated $C_1$-$C_{20}$ alkyl, oxo, hydroxyl, amino,

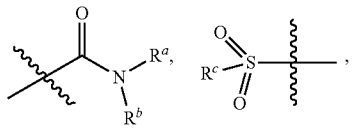

cyano, $C_1$-$C_{20}$ alkoxyl, halogenated $C_1$-$C_{20}$ alkoxyl and $C_1$-$C_{20}$ alkylthio; when the number of the substituent is more than one, the substituents are the same or different; wherein, each of $R^a$ and $R^b$ is independently H or $C_1$-$C_{20}$ alkyl; $R^c$ is $C_1$-$C_{20}$ alkyl;

$R^3$ is $C_1$-$C_{20}$ alkyl or $C_3$-$C_{30}$ cycloalkyl;

$R^4$ is H, $C_1$-$C_{20}$ alkyl or $C_3$-$C_{30}$ cycloalkyl;

m is 0, 1, 2 or 3;

n is 1, 2 or 3.

2. The aminopyrimidine five-membered heterocyclic compound represented by formula I-1 as defined in claim 1, the pharmaceutically acceptable salt, the tautomer, the enantiomer or the diastereomer or the prodrug thereof, wherein, the $C_1$-$C_{20}$ alkyl in the substituted or unsubstituted $C_1$-$C_{20}$ alkyl, the $C_1$-$C_{20}$ alkyl or the halogenated $C_1$-$C_{20}$ alkyl is $C_1$-$C_{10}$ alkyl;

the substituted or unsubstituted $C_6$-$C_{30}$ aryl is substituted or unsubstituted $C_6$-$C_{20}$ aryl;

the substituted or unsubstituted $C_2$-$C_{30}$ heteroaryl is substituted or unsubstituted $C_2$-$C_{20}$ heteroaryl comprising 1-4 heteroatoms selected from the group consisting of N, O and S;

the $C_1$-$C_{20}$ alkoxyl or the $C_1$-$C_{20}$ alkoxyl in halogenated $C_1$-$C_{20}$ alkoxyl is $C_1$-$C_{10}$ alkoxyl;

the $C_1$-$C_{20}$ alkylthio is $C_1$-$C_{10}$ alkylthio;

the halogen is selected from F, Cl, Br or I;

the $C_3$-$C_{30}$ cycloalkyl is $C_3$-$C_{10}$ cycloalkyl;

the halogenated $C_1$-$C_{20}$ alkyl is selected from

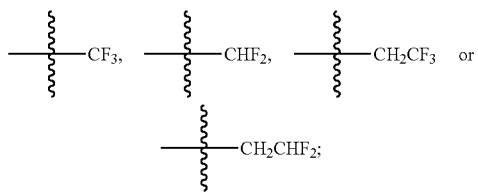

and the substituent in the substituted ethyl, the substituted n-propyl, the substituted isopropyl, the substituted n-butyl, the substituted isobutyl, the substituted tert-butyl of $R^1$, the substituted $C_1$-$C_{20}$ alkyl of $R^2$, the substituted $C_6$-$C_{30}$ aryl or the substituted $C_2$-$C_{30}$ heteroaryl of $R^1$ or $R^2$ is selected from one or more of the group consisting of one or more halogen, $C_1$-$C_{10}$ alkyl, halogenated $C_1$-$C_{10}$ alkyl, amino,

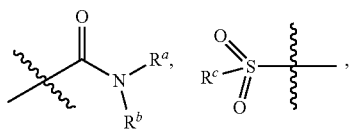

cyano, $C_1$-$C_{10}$ alkoxyl, halogenated $C_1$-$C_{10}$ alkoxyl and $C_1$-$C_{10}$ alkylthio.

3. The aminopyrimidine five-membered heterocyclic compound represented by formula I-1 as defined in claim 2, the pharmaceutically acceptable salt, the tautomer, the enantiomer or the diastereomer or the prodrug thereof, wherein, the $C_1$-$C_{10}$ alkyl is $C_1$-$C_4$ alkyl;

the substituted or unsubstituted $C_6$-$C_{20}$ aryl is substituted or unsubstituted phenyl, substituted or unsubstituted naphthyl, substituted or unsubstituted anthryl, or substituted or unsubstituted phenanthryl;

the substituted or unsubstituted $C_2$-$C_{20}$ heteroaryl comprising 1-4 heteroatoms is substituted or unsubstituted furanyl, substituted or unsubstituted thienyl, substituted or unsubstituted pyridinyl, or substituted or unsubstituted pyranyl;

the $C_1$-$C_{10}$ alkoxyl is $C_1$-$C_4$ alkoxyl;

the $C_1$-$C_{10}$ alkylthio is $C_1$-$C_4$ alkylthio;

the one or more halogen is F;

the $C_3$-$C_{10}$ cycloalkyl is $C_3$-$C_6$ cycloalkyl;

and, the number of halogenated atoms in the halogenated $C_1$-$C_{10}$ alkyl is 2 or 3.

4. The aminopyrimidine five-membered heterocyclic compound represented by formula I-1 as defined in claim 1, the pharmaceutically acceptable salt, the tautomer, the enantiomer or the diastereomer or the prodrug thereof, wherein, $R^1$ is

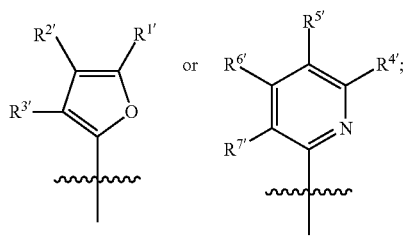

wherein, $R^{1'}$, $R^{2'}$, $R^{3'}$, $R^{4'}$, $R^{5'}$, $R^{6'}$ and $R^{7'}$ are the same or different, and independently selected from H, D, halogen or $C_1$-$C_{20}$ alkyl.

5. The aminopyrimidine five-membered heterocyclic compound represented by formula I-1 as defined in claim 1, the pharmaceutically acceptable salt, the tautomer, the enantiomer or the diastereomer or the prodrug thereof, wherein, $R^2$ is

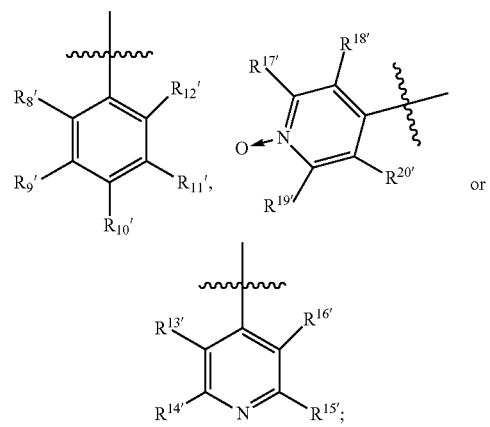

wherein, $R^{8'}$, $R^{9'}$, $R^{10'}$, $R^{11'}$, $R^{12'}$, $R^{13'}$, $R^{14'}$, $R^{15'}$, $R^{16'}$, $R^{17'}$, $R^{18'}$, $R^{19'}$, and $R^{20'}$ are the same or different, and independently selected from H, D, halogen, cyano,

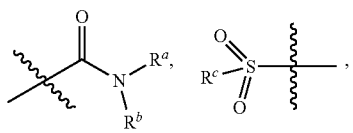

$C_1$-$C_{20}$ alkyl, halogenated $C_1$-$C_{20}$ alkyl, $C_1$-$C_{20}$ alkoxyl or halogenated $C_1$-$C_{20}$ alkoxyl;
m is 0 or 1;
n is 1;
when X is $NR^3$, $R^3$ is $C_1$-$C_{20}$ alkyl;
when Y is $NR^4$, $R^4$ is H or $C_1$-$C_{20}$ alkyl.

6. The aminopyrimidine five-membered heterocyclic compound represented by formula I-1 as defined in claim 1, the pharmaceutically acceptable salt, the tautomer, the enantiomer or the diastereomer or the prodrug thereof,
wherein the

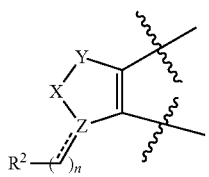

in formula I-1 is

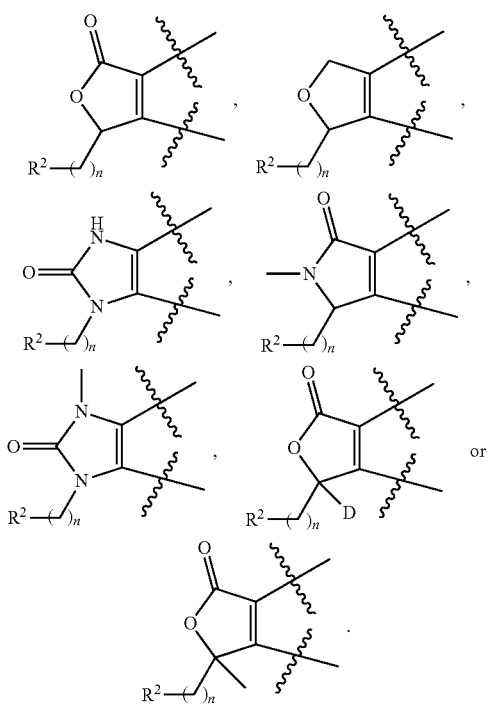

7. The aminopyrimidine five-membered heterocyclic compound represented by formula I-1 as defined in claim 1, the pharmaceutically acceptable salt, the tautomer, the enantiomer or the diastereomer or the prodrug thereof, wherein,
"----" represents a single bond or double bond;
when "----" is a single bond, Z is N or $CR^5$; $R^5$ is H, D or $C_1$-$C_{20}$ alkyl;
when "----" is a double bond, Z is C;
X is O, CO or $NR^3$; $R^3$ is $C_1$-$C_{20}$ alkyl;
Y is CO, $CH_2$ or $NR^4$; $R^4$ is H or $C_1$-$C_{20}$ alkyl;
each of $R^1$ and $R^2$ is independently selected from substituted or unsubstituted $C_6$-$C_{30}$ aryl or substituted or unsubstituted $C_2$-$C_{30}$ heteroaryl;
m is 0, 1, 2 or 3;
n is 1, 2 or 3.

8. The aminopyrimidine five-membered heterocyclic compound represented by formula I-1 as defined in claim 1, the pharmaceutically acceptable salt, the tautomer, the enantiomer or the diastereomer or the prodrug thereof, wherein,
"----" represents a single bond or double bond;
when "----" is a single bond, Z is N or $CR^5$; $R^5$ is H, D or $C_1$-$C_{20}$ alkyl;
when "----" is a double bond, Z is C;
X is O, CO or $NR^3$; $R^3$ is $C_1$-$C_{20}$ alkyl;
Y is CO, $CH_2$ or $NR^4$; $R^4$ is H or $C_1$-$C_{20}$ alkyl;
each of $R^1$ and $R^2$ is independently selected from substituted or unsubstituted $C_6$-$C_{20}$ aryl, or substituted or unsubstituted $C_2$-$C_{20}$ heteroaryl comprising 1-4 heteroatoms selected from N, O or S;
m is 0, 1, 2 or 3;
n is 1, 2 or 3.

9. The aminopyrimidine five-membered heterocyclic compound represented by formula I-1 as defined in claim 1, the pharmaceutically acceptable salt, the tautomer, the enantiomer or the diastereomer or the prodrug thereof, wherein,
"----" represents a single bond or double bond;
when "----" is a single bond, Z is N or $CR^5$; $R^5$ is H, D or $C_1$-$C_{20}$ alkyl;
when "----" is a double bond, Z is C;
X is O, CO or $NR^3$; $R^3$ is $C_1$-$C_{20}$ alkyl;
Y is CO, $CH_2$ or $NR^4$; $R^4$ is H or $C_1$-$C_{20}$ alkyl;
$R^2$ is substituted or unsubstituted $C_6$-$C_{20}$ aryl or substituted or unsubstituted $C_2$-$C_{20}$ heteroaryl comprising 1-4 heteroatoms selected from N, O or S;
$R^1$ is substituted or unsubstituted $C_2$-$C_{20}$ heteroaryl comprising 1-4 heteroatoms selected from N, O or S;
m is 0, 1, 2 or 3;
n is 1, 2 or 3.

10. The aminopyrimidine five-membered heterocyclic compound represented by formula I-1 as defined in claim 1, the pharmaceutically acceptable salt, the tautomer, the enantiomer or the diastereomer or the prodrug thereof, wherein,
"----" represents a single bond or double bond;
when "----" is single bond, Z is N or $CR^5$; $R^5$ is H or D;
when "----" is double bond, Z is C;
X is O, CO or $NR^3$; $R^3$ is $C_1$-$C_{20}$ alkyl;
Y is CO, $CH_2$ or $NR^4$; $R^4$ is H or $C_1$-$C_{20}$ alkyl;
$R^2$ is substituted or unsubstituted $C_6$-$C_{20}$ aryl or substituted or unsubstituted furanyl, thienyl, pyridinyl or pyranyl;
$R^1$ is substituted or unsubstituted furanyl, substituted or unsubstituted thienyl, substituted or unsubstituted pyridinyl, or substituted or unsubstituted pyranyl;
m is 0 or 1;
n is 1.

11. The aminopyrimidine five-membered heterocyclic compound represented by formula I-1 as defined in claim 1, the pharmaceutically acceptable salt, the tautomer, the enantiomer or the diastereomer or the prodrug thereof, wherein,
"----" represents a single bond or double bond;
when "----" is a single bond, Z is N or $CR^5$; $R^5$ is H or D;
when "----" is a double bond, Z is C;
X is O, CO or $NR^3$; $R^3$ is $C_1$-$C_{20}$ alkyl;
Y is CO, $CH_2$ or $NR^4$; $R^4$ is H or $C_1$-$C_{20}$ alkyl;

R¹ is

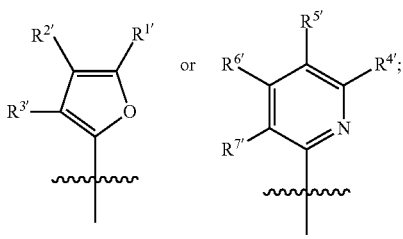

or wherein, $R^{1\prime}$, $R^{2\prime}$, $R^{3\prime}$, $R^{4\prime}$, $R^{5\prime}$, $R^{6\prime}$ and $R^{7\prime}$ are the same or different, and independently selected from H, D, halogen or $C_1$-$C_{20}$ alkyl;

R² is

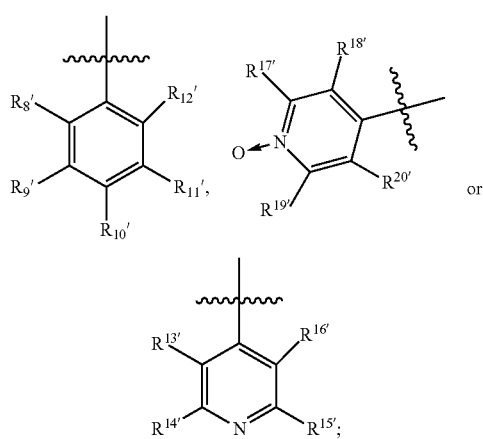

or wherein, $R^{8\prime}$, $R^{9\prime}$, $R^{10\prime}$, $R^{11\prime}$, $R^{12\prime}$, $R^{13\prime}$, $R^{14\prime}$, $R^{15\prime}$, $R^{16\prime}$, $R^{17\prime}$, $R^{18\prime}$ $R^{19\prime}$ and $R^{20\prime}$ are the same or different, and independently selected from H, D, halogen, cyano,

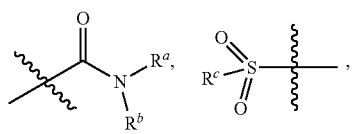

$C_1$-$C_{20}$ alkyl, halogenated $C_1$-$C_{20}$ alkyl, $C_1$-$C_{20}$ alkoxyl or halogenated $C_1$-$C_{20}$ alkoxyl;

m is 0 or 1;

n is 1.

12. The aminopyrimidine five-membered heterocyclic compound represented by formula I-1 as defined in claim 11, the pharmaceutically acceptable salt, the tautomer, the enantiomer or the diastereomer or the prodrug thereof, wherein, " ═══ " represents a single bond or double bond;

when " ═══ " is a single bond, Z is N or $CR^5$; $R^5$ is H or D;

when " ═══ " is a double bond, Z is C;

X is O, CO or $NR^3$; $R^3$ is $C_1$-$C_{20}$ alkyl;

Y is CO, $CH_2$ or $NR^4$; $R^4$ is H or $C_1$-$C_{20}$ alkyl;

R¹ is

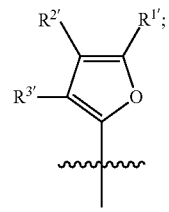

R² is

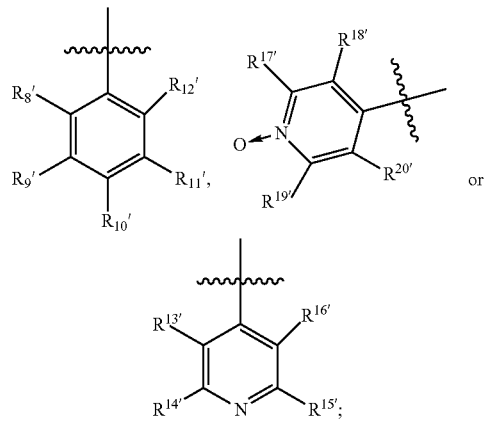

m is 0 or 1;

n is 1.

13. The aminopyrimidine five-membered heterocyclic compound represented by formula I-1 as defined in claim 1, the pharmaceutically acceptable salt, the tautomer, the enantiomer or the diastereomer or the prodrug thereof, wherein, " ═══ " represents a single bond or double bond;

when " ═══ " is a single bond, Z is N or $CR^5$; $R^5$ is H or D;

when " ═══ " is a double bond, Z is C;

X is O, CO or $NR^3$; $R^3$ is $C_1$-$C_{20}$ alkyl;

Y is CO, $CH_2$ or $NR^4$; $R^4$ is H or $C_1$-$C_{20}$ alkyl;

R¹ is

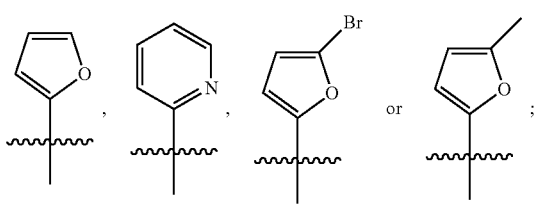

R² is

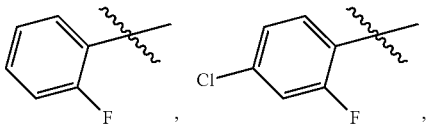

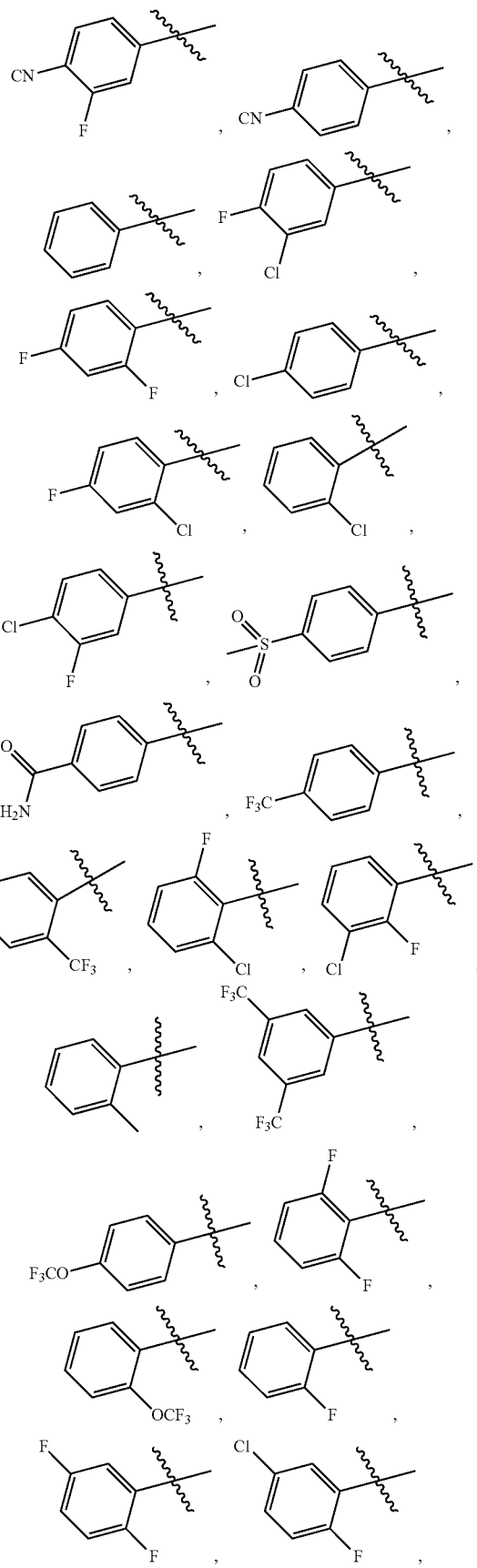
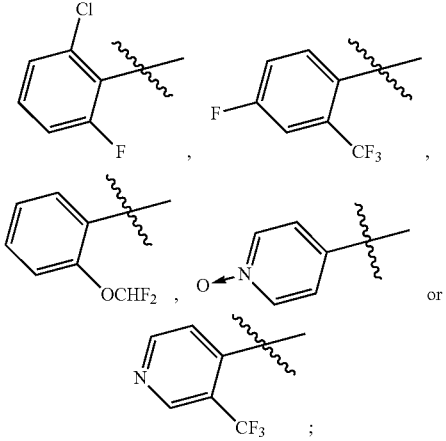

m is 0 or 1;

n is 1.

14. The aminopyrimidine five-membered heterocyclic compound represented by formula I-1 as defined in claim 1, the pharmaceutically acceptable salt, the tautomer, the enantiomer or the diastereomer or the prodrug thereof, wherein, " ---- " represents a single bond or a double bond;

when " ---- " is a single bond, Z is N or $CR^5$; $R^5$ is H or D;

when " ---- " is a double bond, Z is C;

X is O, CO or $NR^3$; $R^3$ is $C_1$-$C_{20}$ alkyl;

Y is CO, $CH_2$ or $NR^4$; $R^4$ is H or $C_1$-$C_{20}$ alkyl;

$R^1$ is

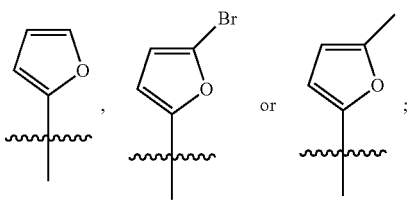

$R^2$ is

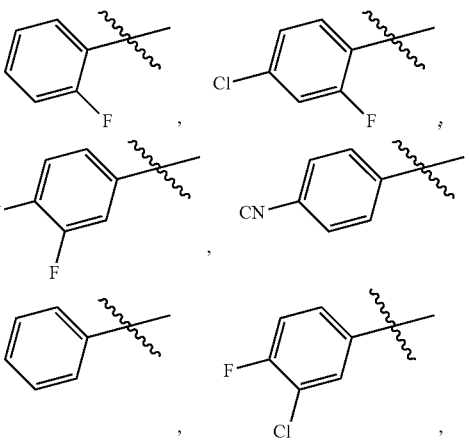

-continued
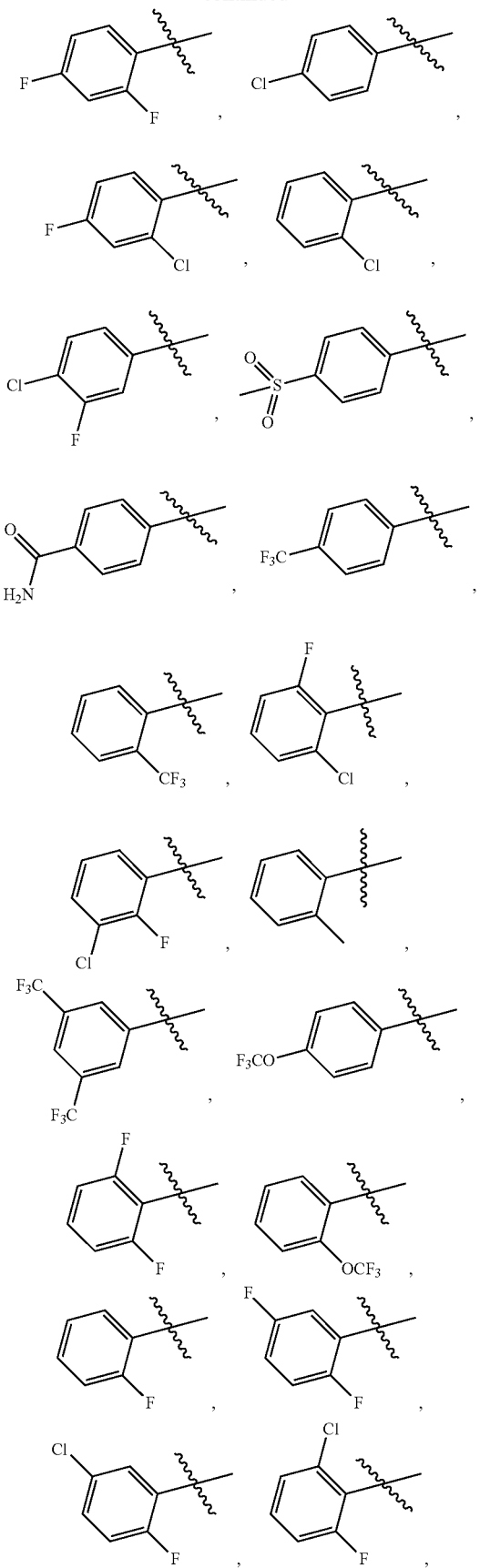
-continued
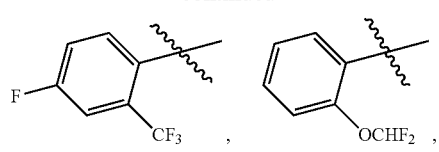
m is 0 or 1;
n is 1.
15. The aminopyrimidine five-membered heterocyclic compound represented by formula I-1 as defined in claim 1, is selected from the group consisting of
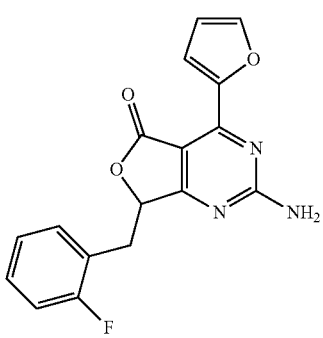
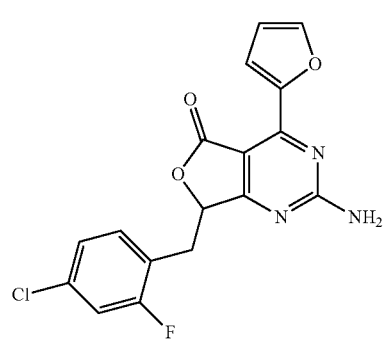
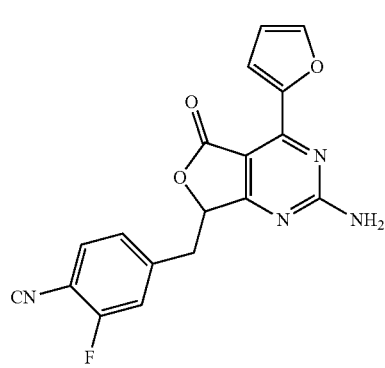

-continued
4
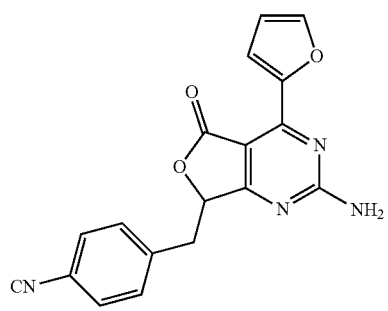
5
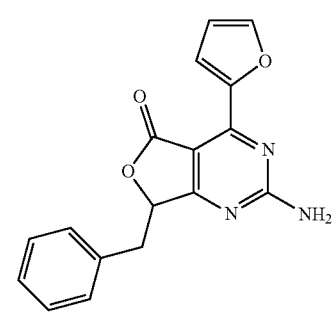
6
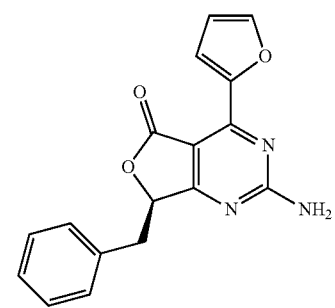
7
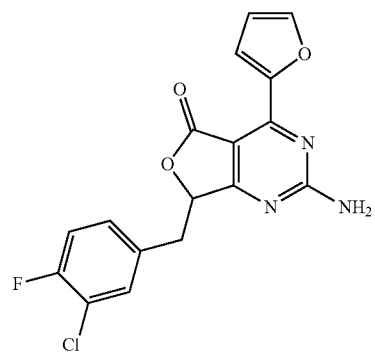
8
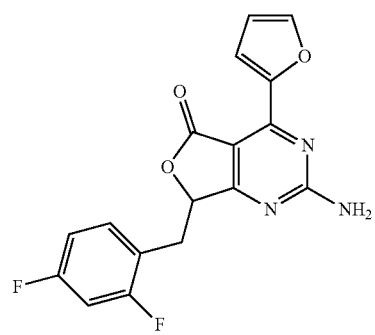
-continued
9
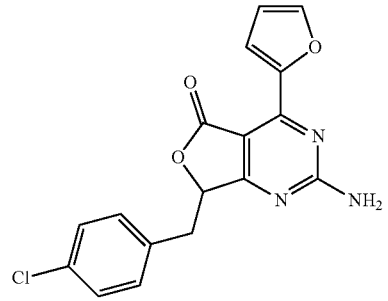
10
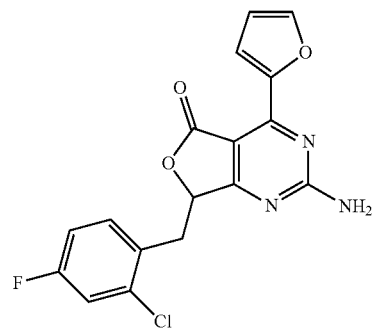
10
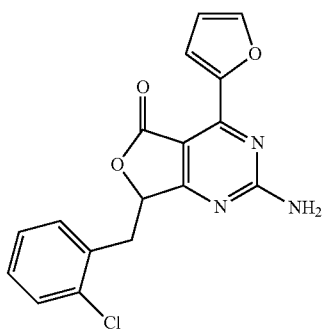
11
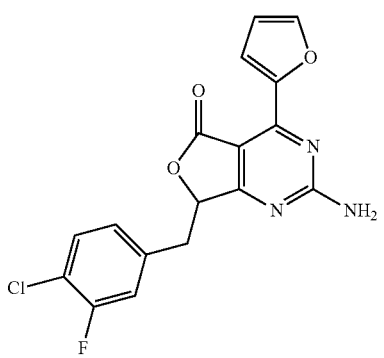
12
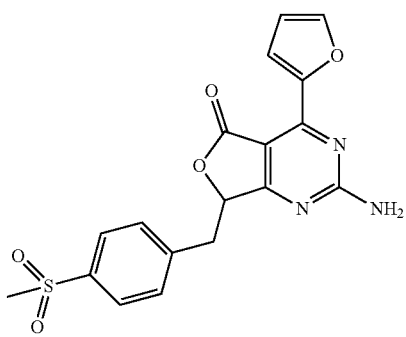

14
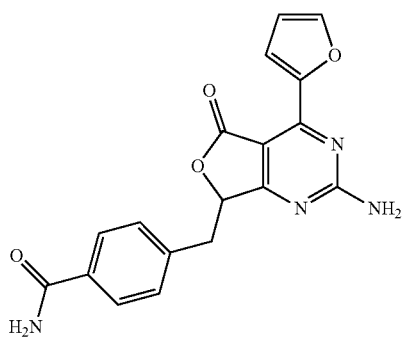
15
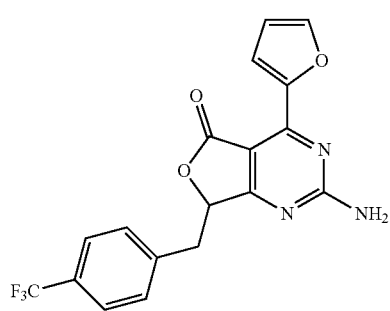
16
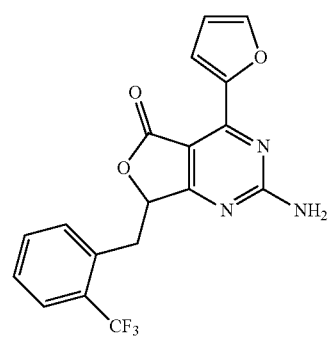
17
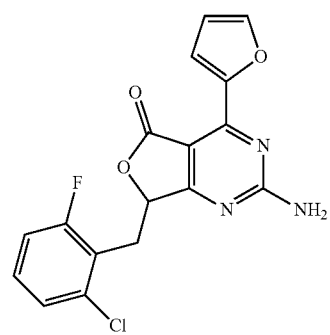
18
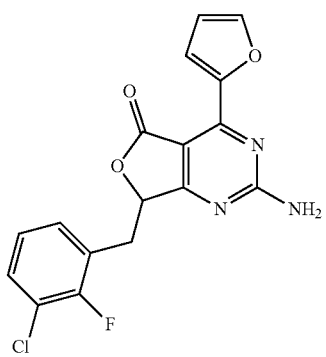
19
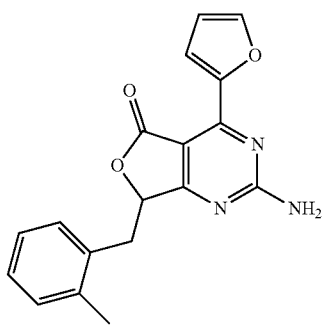
20
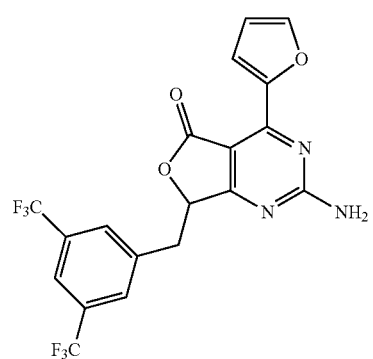
21
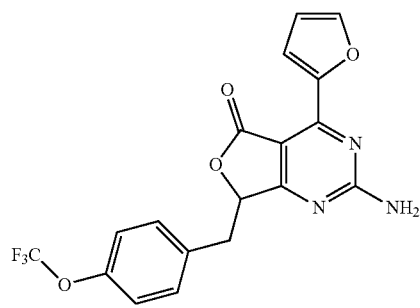

22 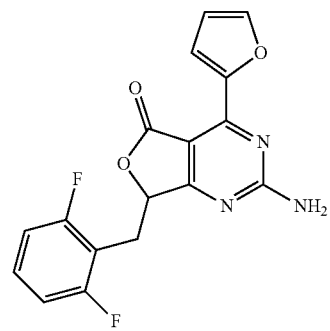
23 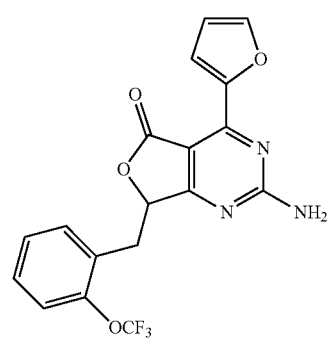
24 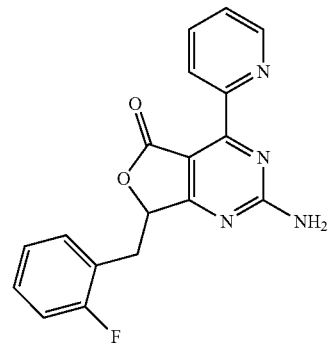
25 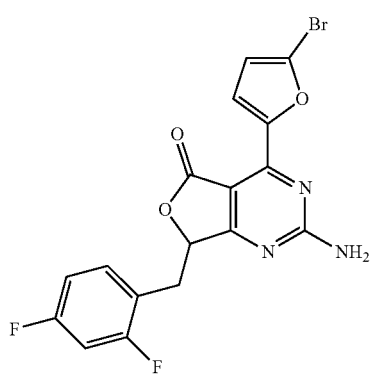
26 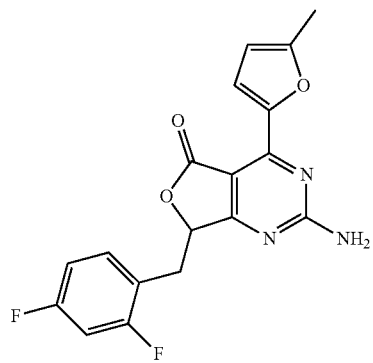
27 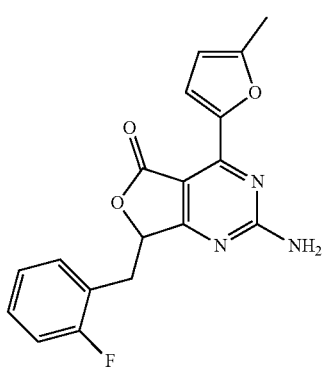
28 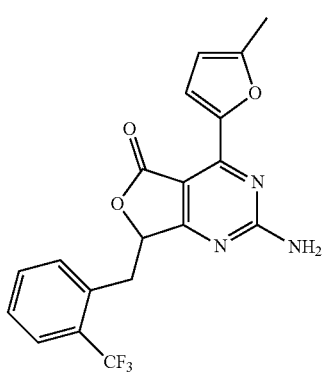
29 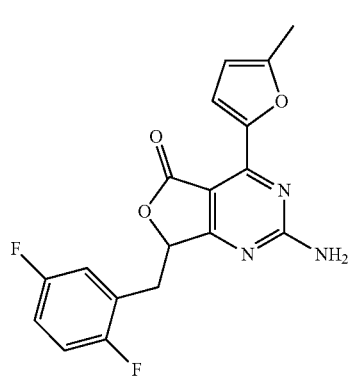

| 189 -continued | | 190 -continued | |
|---|---|---|---|
| 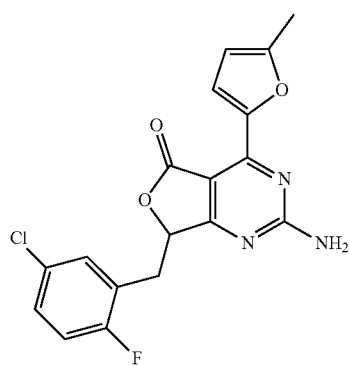 | 30 | 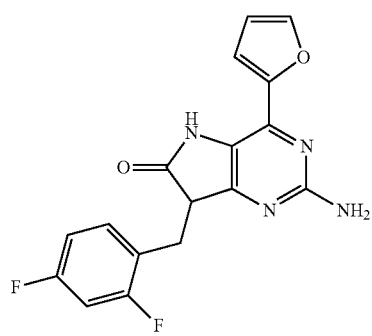 | 34 |
| 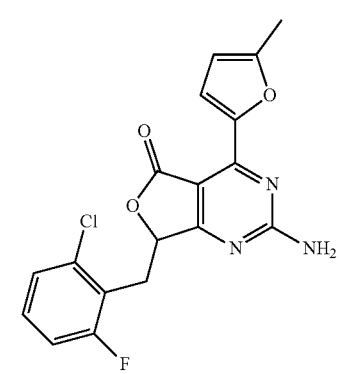 | 31 | 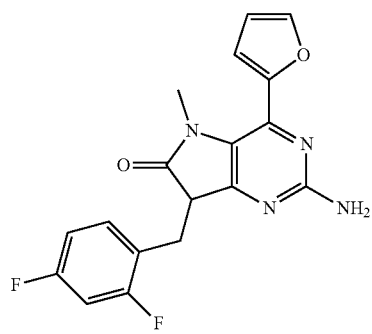 | 35 |
| 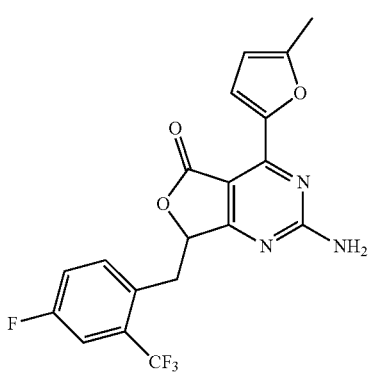 | 32 | 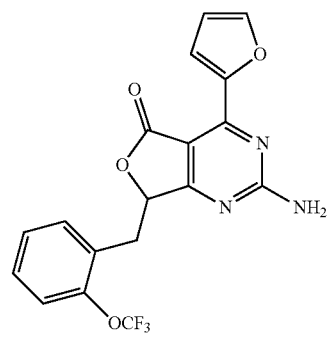 | 36 |
| 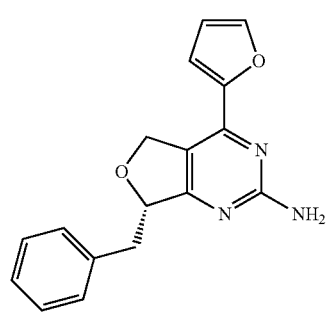 | 33 | 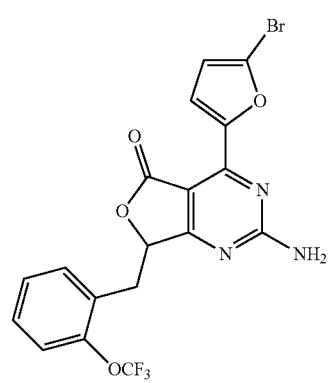 | 37 |

| 38 | 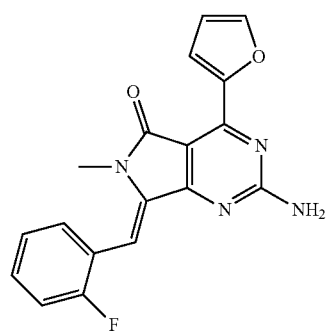 | 42 | 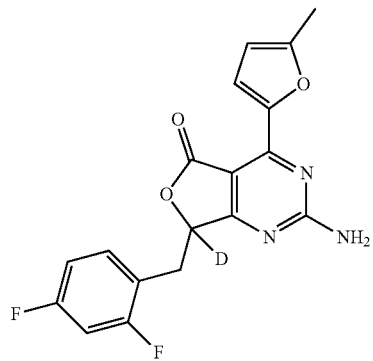 |
| 39 | 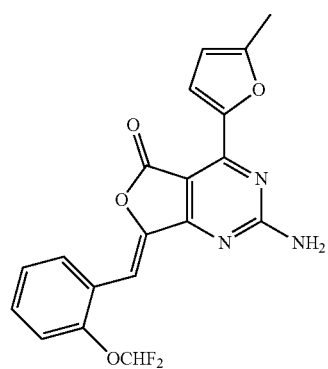 | 43 | 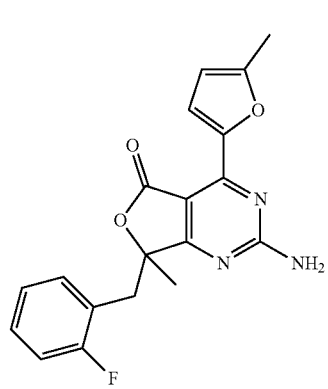 |
| 40 | 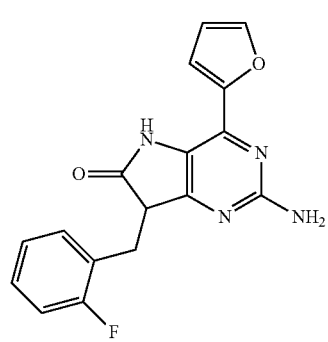 | 44 | 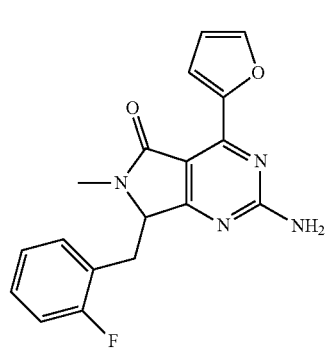 |
| 41 | 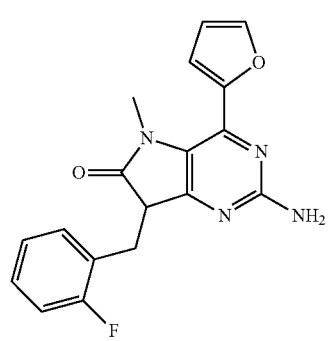 | 45 | 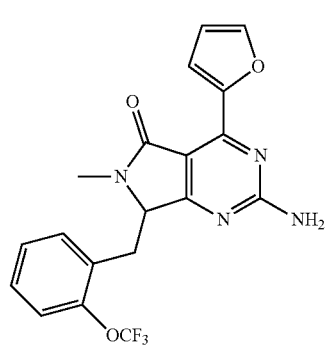 |

46
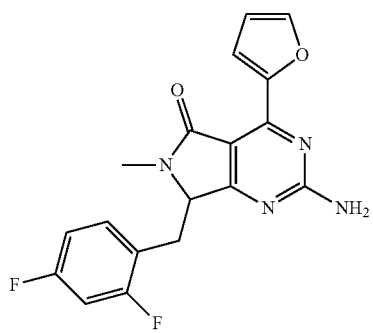
47
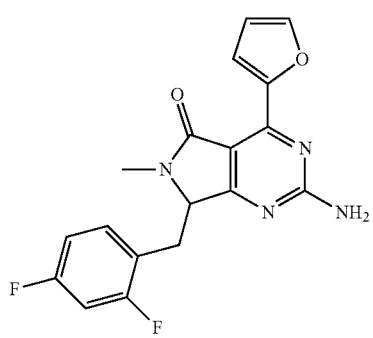
48
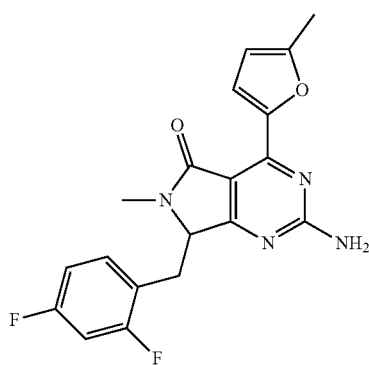
49
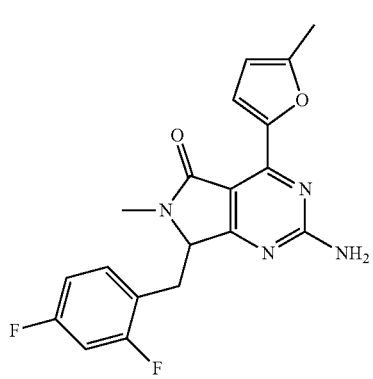
50
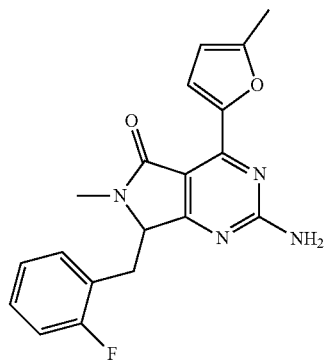
51
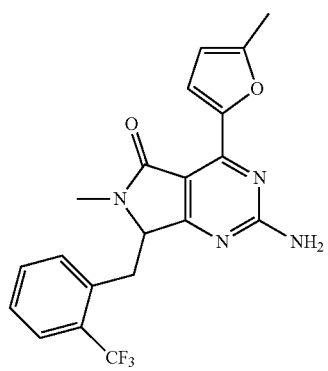
52
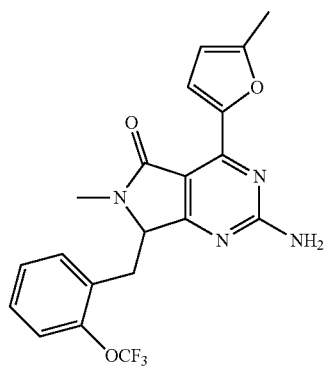
53
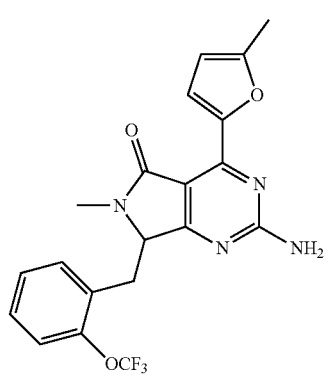

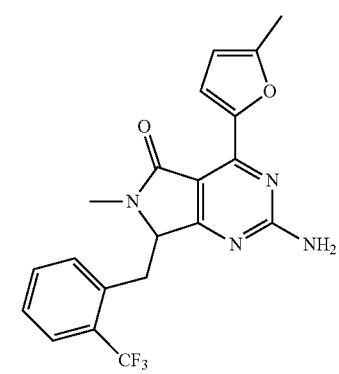

54

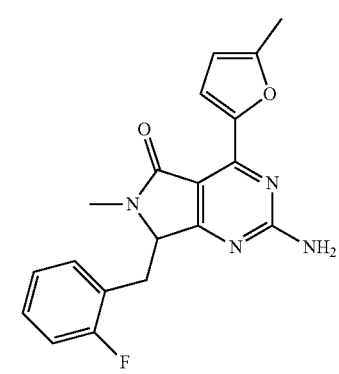

55

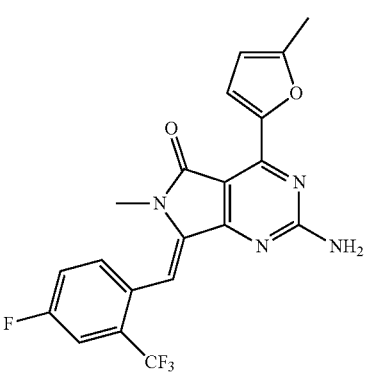

56

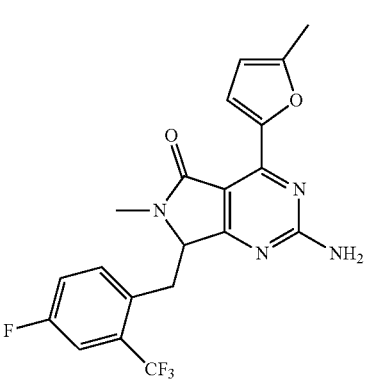

57

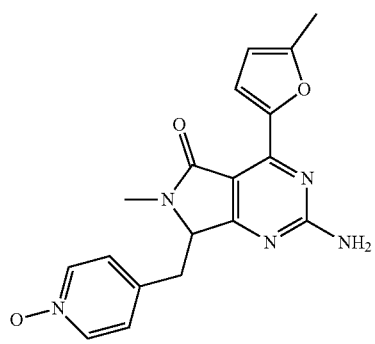

58

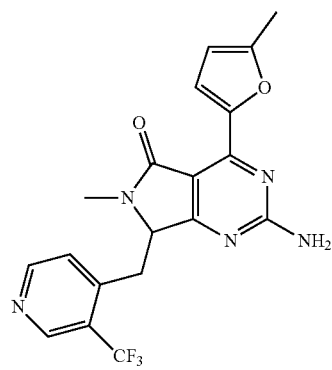

59

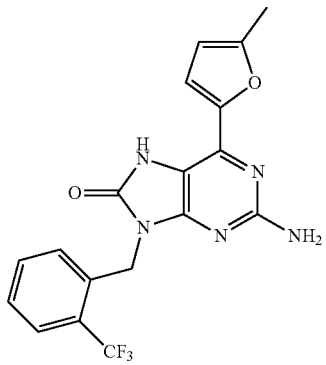

60 and

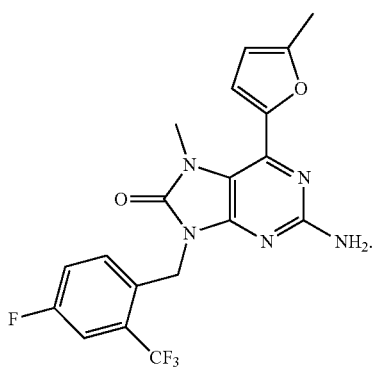

61

16. A method for preparing the aminopyrimidine five-membered heterocyclic compound represented by formula I-1 as defined in claim 1, comprising the steps below: in an organic solvent, carrying out a nucleophilic substitution reaction on a compound represented by formula I-A-1 with an aqueous ammonia solution or a solution of ammonia in methanol to obtain the aminopyrimidine five-membered heterocyclic compound represented by formula I-1 below;

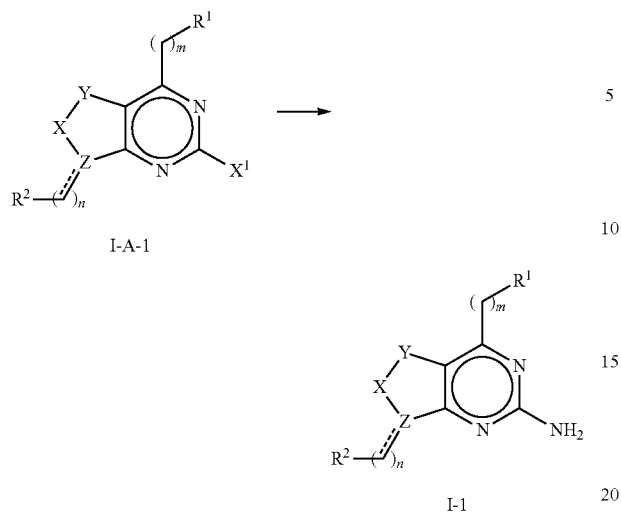

I-A-1

I-1 wherein, X, Y, Z, $R^1$, $R^2$, m and n are as defined in claim 1, $X^1$ is halogen or substituted sulfonyl, the substituent in substituted sulfonyl is $C_1$-$C_{20}$ alkyl.

17. A method for treating a patient in need of a medicament for mitigating and/or treating related diseases caused by adenosine A2A receptor, comprising administering to the patient a medicament comprising an effective amount of one or more of the aminopyrimidine five-membered heterocyclic compound represented by formula I-1 as defined in claim 1, the pharmaceutically acceptable salt, the tautomer, the enantiomer or the diastereomer or the prodrug thereof; wherein the related diseases caused by adenosine A2A receptor are selected from one or more of Parkinson's disease, Alzheimer's disease, depression, schizophrenia, epilepsy, Huntington's disease, myelofibrosis, leukemia, lymphoma, kidney cancer, liver cancer, stomach cancer, lung cancer, breast cancer, prostate cancer, pancreatic cancer, thyroid cancer, ovarian cancer, glioblastoma, skin cancer and melanoma, pneumonia, hepatitis, nephritis, myocarditis, septicopyemia, arthritis, asthma and atherosclerosis.

18. A method for antagonizing an A2A receptor in a patient, comprising administering to the patient a medicament comprising an effective amount of one or more of the aminopyrimidine five-membered heterocyclic compound represented by formula I-1 as defined in claim 1, the pharmaceutically acceptable salt, the tautomer, the enantiomer or the diastereomer or the prodrug thereof.

19. A pharmaceutical composition, comprising a mitigating and/or therapeutically effective amount of one or more of the aminopyrimidine five-membered heterocyclic compound represented by formula I-1 as defined in claim 1, the pharmaceutically acceptable salt, the tautomer, the enantiomer, the diastereomer and the prodrug thereof, and one or more of pharmaceutically acceptable carriers and/or diluents.

20. An intermediate of the aminopyrimidine five-membered heterocyclic compound represented by formula I-1 as defined in claim 1, the pharmaceutically acceptable salt, the tautomer, the enantiomer or the diastereomer and the prodrug thereof is selected from the group consisting of

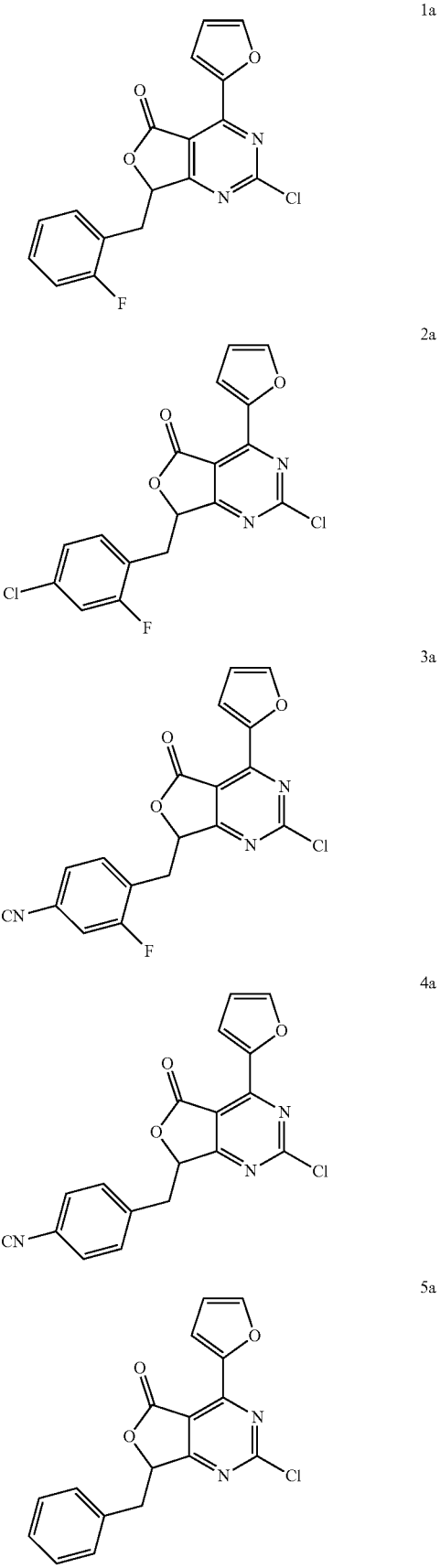

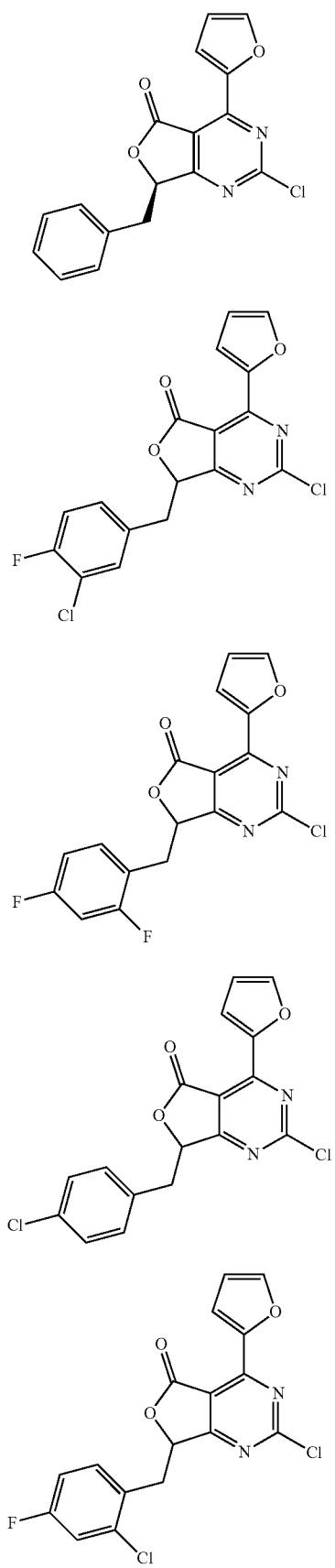
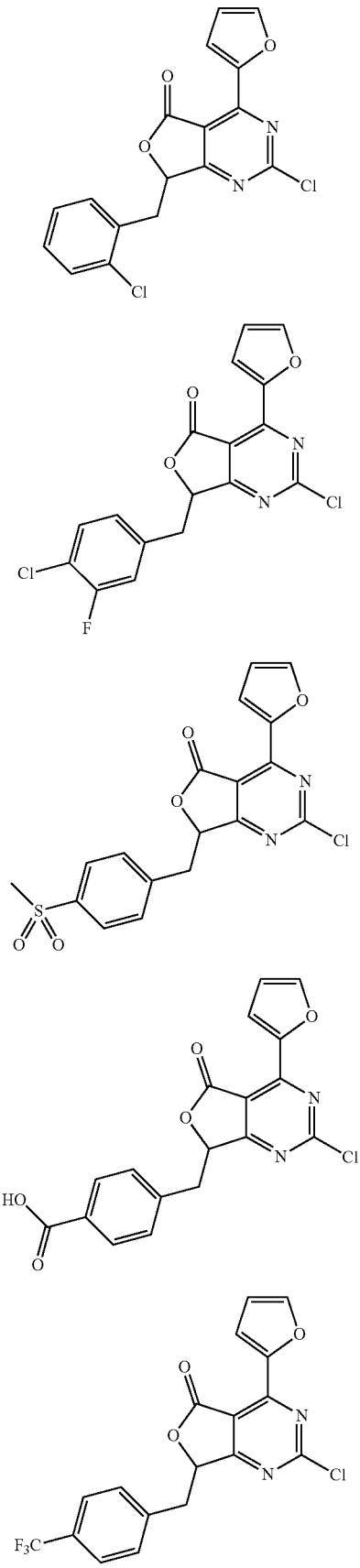

| 201 -continued | | 202 -continued | |
|---|---|---|---|
| 16a | 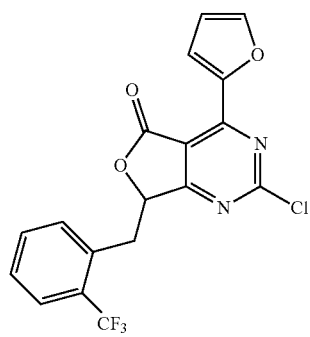 | 20a | 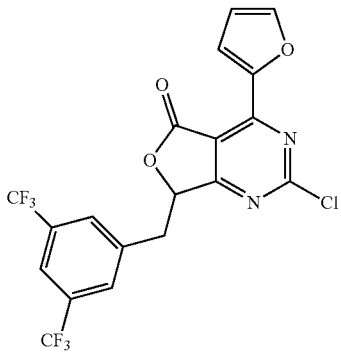 |
| 17a | 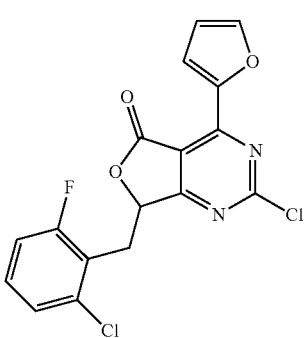 | 21a | 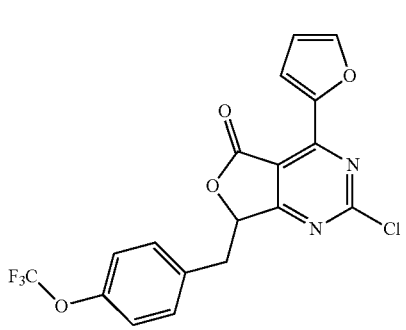 |
| 18a | 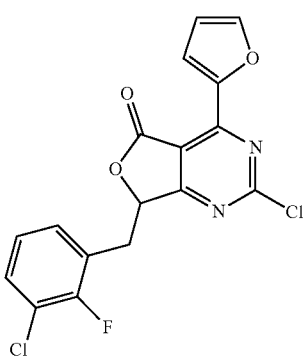 | 22a | 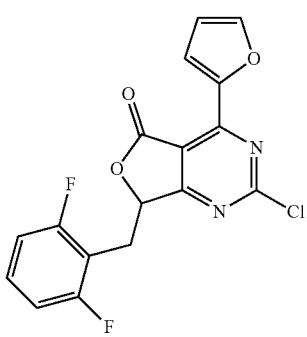 |
| 19a | 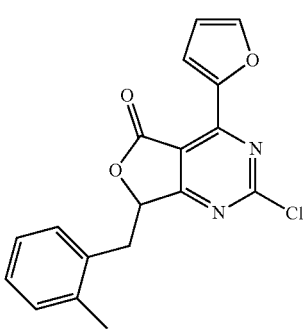 | 23a | 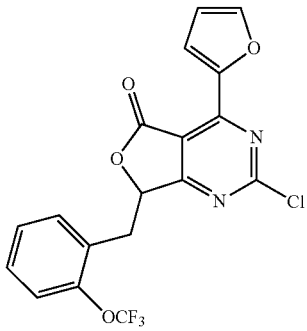 |

| 203 -continued | | 204 -continued | |
|---|---|---|---|
| 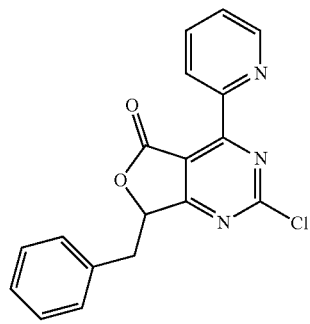 | 24a | 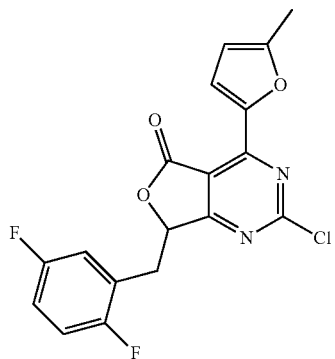 | 29a |
| 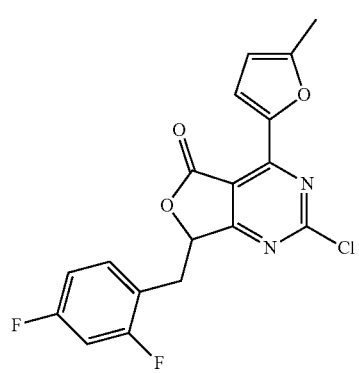 | 26a | 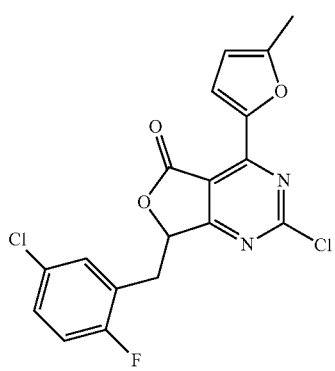 | 30a |
| 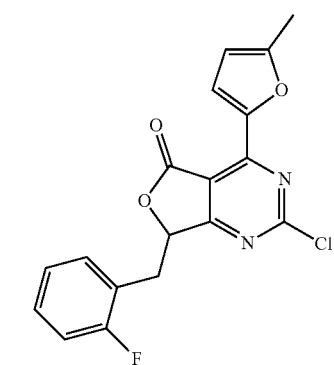 | 27a | 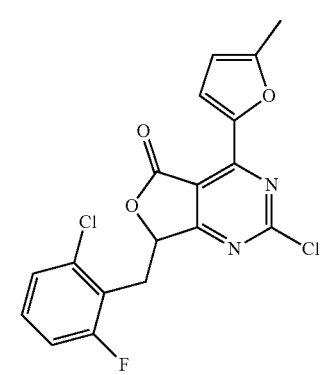 | 31a |
| 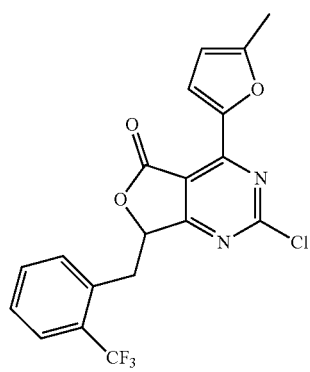 | 28a | 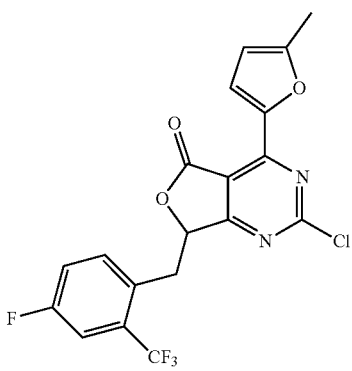 | 32a |

33a 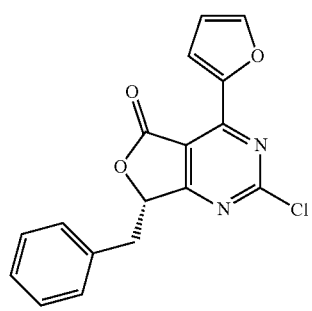
34a 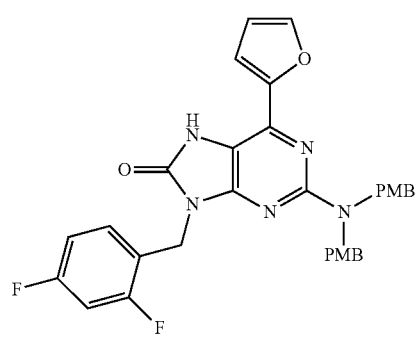
35a 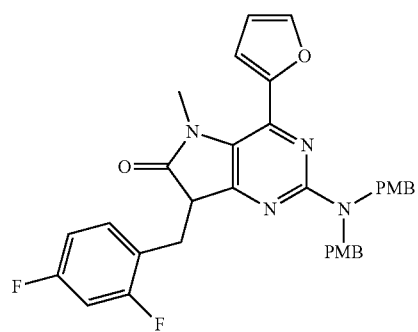
36a 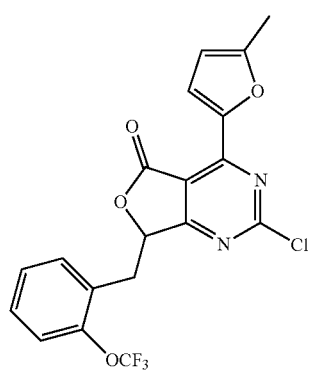
38a 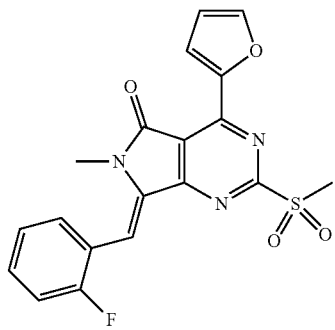
39a 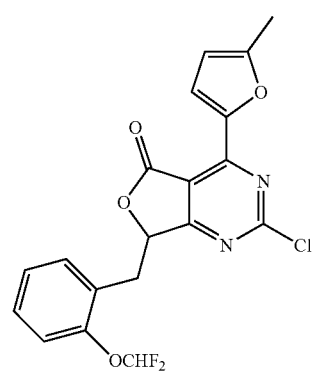
40a 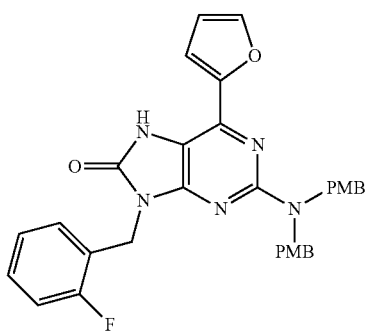
41a 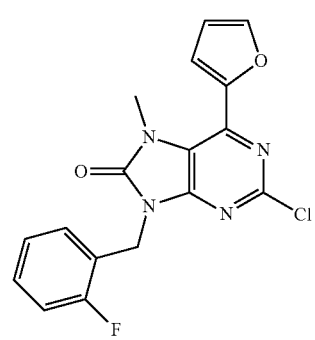

43a
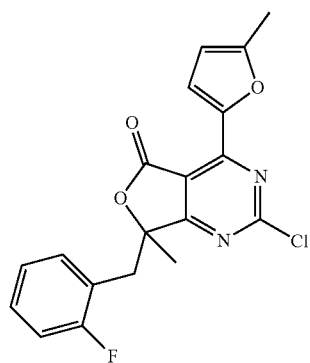
44a
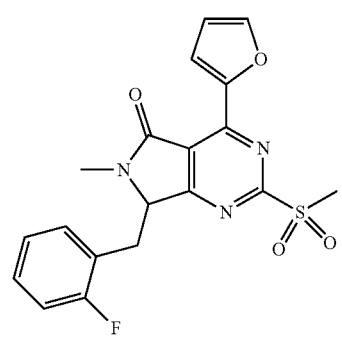
45a
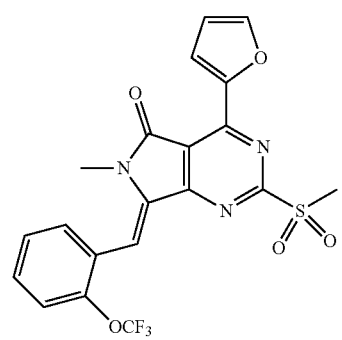
46a
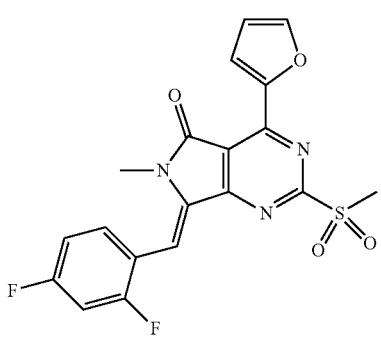
48a
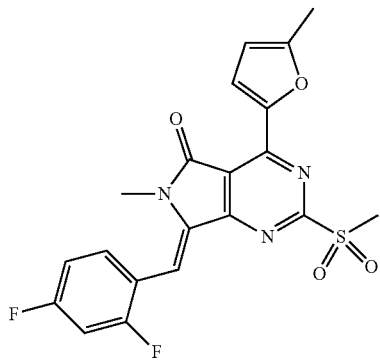
50a
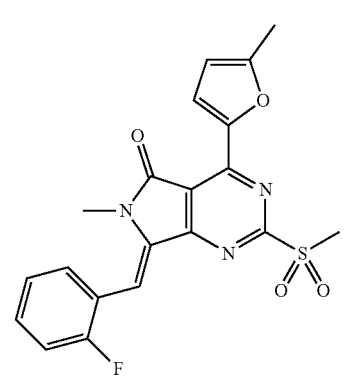
51a
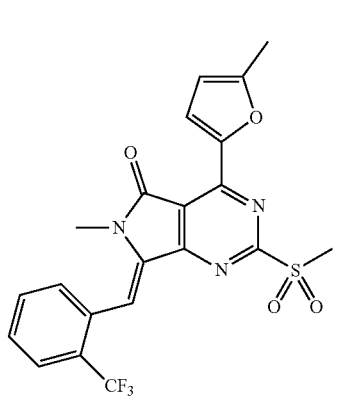
52a
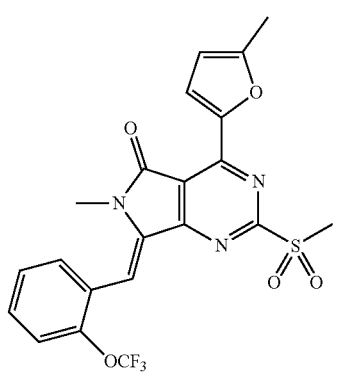

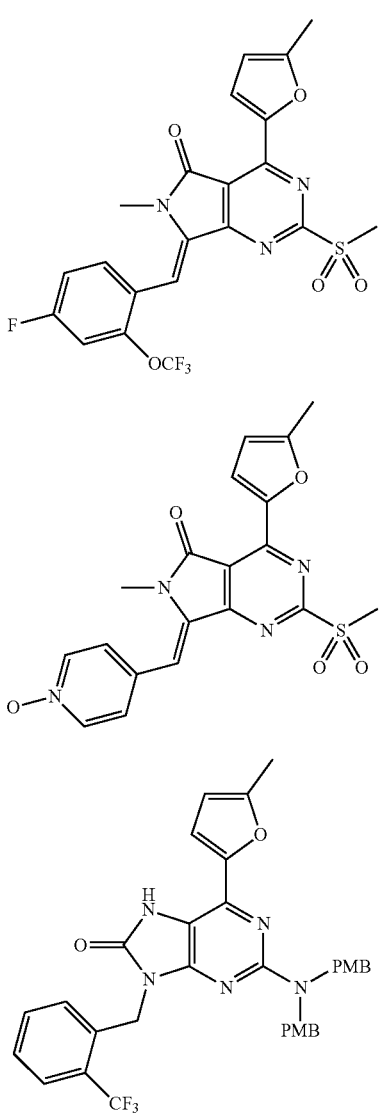

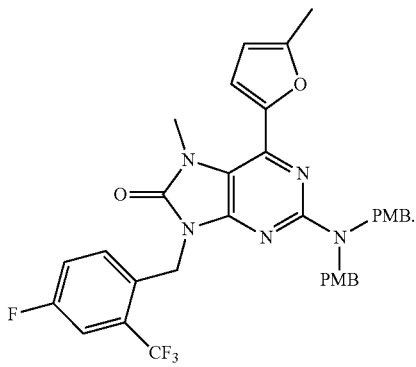

21. The aminopyrimidine five-membered heterocyclic compound represented by formula I-1 as defined in claim 10, the pharmaceutically acceptable salt, the tautomer, the enantiomer or the diastereomer or the prodrug thereof, wherein, $R^2$ is substituted or unsubstituted pyridinyl; and $R^1$ is substituted or unsubstituted furanyl.

22. The method for preparing the aminopyrimidine five-membered heterocyclic compound represented by formula I-1 as defined in claim 16, wherein, the substituent in substituted sulfonyl is $C_1$-$C_4$ alkyl.

23. The method for preparing the aminopyrimidine five-membered heterocyclic compound represented by formula I-1 as defined in claim 16, wherein, the substituent in substituted sulfonyl is methyl.

* * * * *